United States Patent [19]
Nakagawa et al.

[11] Patent Number: 5,438,054
[45] Date of Patent: * Aug. 1, 1995

[54] 2-(SUBSTITUTED PYRROLIDINYLTHIO) CARBAPENEM DERIVATIVES

[75] Inventors: Susumu Nakagawa; Norikazu Ohtake; Fumio Nakano; Koji Yamada; Ryosuke Ushijima; Satoshi Murase; Hiroshi Fukatsu, all of Okazaki, Japan

[73] Assignee: Banyu Pharmaceutical Co., Ltd., Tokyo, Japan

[ * ] Notice: The portion of the term of this patent subsequent to Dec. 13, 2011 has been disclaimed.

[21] Appl. No.: 208,046

[22] Filed: Mar. 9, 1994

Related U.S. Application Data

[63] Continuation of Ser. No. 25,804, Mar. 3, 1993, abandoned, which is a continuation of Ser. No. 674,971, Mar. 26, 1991, abandoned.

Foreign Application Priority Data

Mar. 27, 1990 [JP] Japan .................. 2-77431
Apr. 12, 1990 [JP] Japan .................. 2-96654
Dec. 27, 1990 [JP] Japan .................. 2-414637

[51] Int. Cl.$^6$ .................. A01N 43/00; A61K 31/395; C07D 487/04
[52] U.S. Cl. .................. 514/210; 540/350
[58] Field of Search .................. 514/210; 540/350

[56] References Cited

U.S. PATENT DOCUMENTS

| | | | |
|---|---|---|---|
| 4,921,852 | 5/1990 | Murata | 540/350 |
| 4,925,838 | 5/1990 | Murata | 540/350 |
| 4,933,333 | 6/1990 | Sunagawa et al. | 514/192 |

FOREIGN PATENT DOCUMENTS

| | | |
|---|---|---|
| 0126587 | 11/1984 | European Pat. Off. . |
| 0272455 | 6/1988 | European Pat. Off. . |
| 0280771 | 9/1988 | European Pat. Off. . |
| 0333175 | 9/1989 | European Pat. Off. . |
| 76339 | 6/1988 | Finland . |
| 81576 | 7/1990 | Finland . |
| 83419 | 3/1991 | Finland . |
| 83872 | 5/1991 | Finland . |
| 84070 | 6/1991 | Finland . |
| 84826 | 10/1991 | Finland . |
| 88037 | 12/1992 | Finland . |
| 88295 | 1/1993 | Finland . |
| 90238 | 9/1993 | Finland . |

OTHER PUBLICATIONS

Office Action in Finnish Patent Application No. 915026 (3 pages), with English Translation (4 pages).

*Primary Examiner*—Johann Richter
*Assistant Examiner*—Rebecca Cook
*Attorney, Agent, or Firm*—Oblon, Spivak, McClelland, Maier, & Neustadt

[57] ABSTRACT

Carbapenem compounds of formula I and their pharmaceutically acceptable salts and esters are provided:

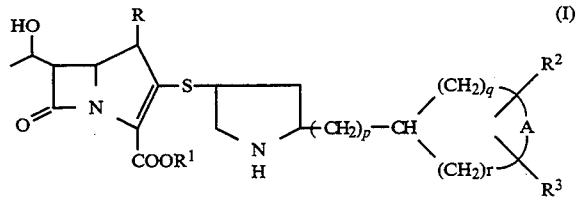

wherein R, $R^1$, $R^2$, $R^3$, p, q and r are as defined herein, which are useful as antibacterial agents.

19 Claims, No Drawings

2-(SUBSTITUTED PYRROLIDINYLTHIO) CARBAPENEM DERIVATIVES

This application is a Continuation of application Ser. No. 08/025,804, filed on Mar. 3, 1993, now abandoned; which in turn was an FWC of 07/674,971, filed on Mar. 26, 1991, now abandoned.

The present invention relates to novel carbapenem (7-oxo-1-azabicyclo[3.2.0]hept-2-en-2-carboxylic acid) compounds, and antibacterial agents containing such compounds as active ingredients, and a process for producing such compounds.

In recent years, new β-lactam antibiotic substances have been found in nature which have the same β-lactam rings as penicillin derivatives and as cephalosporin derivatives, but which have different basic structures.

For example, naturally derived carbapenem compounds such as thienamycin isolated from the fermentation of *Streptomyces cattleya* (J. Am. Chem. Soc., vol. 100, p.6491 (1978)), may be mentioned. Thienamycin has an excellent antibacterial spectrum and strong antibacterial activities over a wide range against gram positive bacteria and gram negative bacteria. Therefore, its development as a highly useful β-lactam agent has been expected. However, thienamycin itself is chemically unstable, and it has been reported that it is likely to be decomposed by a certain enzyme in vivo such as renal dehydropeptidase I (hereinafter referred to simply as DHP-I), whereby the antibacterial activities tend to decrease, and the recovery rate in the urine is low (Antimicrob. Agents Chemother., vol. 22, p.62 (1982); ditto, vol. 23, p.300 (1983)).

Merck & Co., Inc. have synthesized many thienamycin analogues with an aim to maintain the excellent antibacterial activities of thienamycin and to secure chemical stability. As a result, imipenem, (5R,6S,8R)-3-[[2-(formimidoylamino)ethyl]thio]-6-(1-hydroxyethyl)-7-oxo-1-azabicyclo[3.2.0]hept-2-en-2-carboxylic acid monohydrate, obtained by formimidation of the amino group of thienamycin, has been practically developed as a pharmaceutical product (J. Med. Chem., vol. 22, p. 1435 (1979)). Imipenem has antibacterial activities of an equal or higher level than thienamycin against various types of bacteria and has β-lactamase resistance. Especially against *Pseudomonas aeruginosa*, its antibacterial activities are superior to thienamycin by from 2 to 4 times. Further, the stability of imipenem in the solid form or in an aqueous solution is remarkably improved over thienamycin.

However, like thienamycin, imipenem is likely to be decomposed by DHP-I in the human kidney. Therefore, it can not be used for treatment of the urinary-tract infection. Further, it presents toxicity against the kidney due to the decomposition products. Therefore, imipenem can not be administered alone and is required to be used in combination with a DHP-I inhibitor like cilastatin (Antimicrob. Agents Chemother., vol. 12 (Suppl. D), p. 1 (1983)). In recent years, imipenem has been frequently used for the treatment and prevention of infectious diseases. Consequently, highly methicillin resistant *Staphylococcus aureus* which is resistant to imipenem and imipenem resistant *Pseudomonas aeruginosa* are increasing in the clinical field. Imipenem does not show adequate treating effects against these resistant bacteria.

As the prior art closest to the present invention, U.S. Pat. No. 4,933,333 may be mentioned. This publication discloses carbapenem compounds having a 2-(aminocarbonyl or N-mono- or N,N-di-lower alkylaminocarbonyl)pyrrolidin-4-ylthio group at the 2-position of the carbapenem structure, represented by meropenem, SM-7338: (4R,5S,6S,8R,2'S,4'S)-6-(1-hydroxyethyl)-4-methyl-3-[2-(N,N-dimethylaminocarbonyl)-pyrrolidin-4-ylthio]-7-oxo-1-azabicyclo[3.2.0-]hept-2-en-2-carboxylic acid, as a typical compound.

β-Lactam antibiotics exhibit selective toxicity against bacteria and show no substantial effects against animal cells. Therefore, they are widely used for treatment of infectious diseases caused by bacteria, as rare antibiotics having little side effects, and thus are highly useful drugs.

However, in recent years, highly methicillin resistant *Staphylococcus aureus* and resistant *Pseudomonas aeruginosa* have been isolated frequently from patients with the immunity decreased, as bacteria causing hardly curable infectious diseases. This is regarded as a clinically serious problem. Accordingly, it is strongly desired to develop an antibacterial agent having improved antibacterial activities against such resistant bacteria. Especially with respect to carbapenem compounds, it is desired to improve the antibacterial activities, to improve the stability against DHP-I, to reduce the toxicity against the kidney and to reduce side effects against the central nervous system.

The compounds disclosed in U.S. Pat. No. 4,933,333, particularly meropenem, have the stability against DHP-I substantially improved. However, the antibacterial activities against the above-mentioned highly methicillin resistant *Staphylococcus aureus* are not adequate, and a carbapenem compound having superior antibacterial activities, is desired.

The present inventors have made extensive researches with an aim to provide novel carbapenem compounds which have excellent antibacterial activities and which are resistant against DHP-I. As a result, they have found that carbapenem compounds of the present invention having, at the 2-position of the carbapenem structure, a group of the formula:

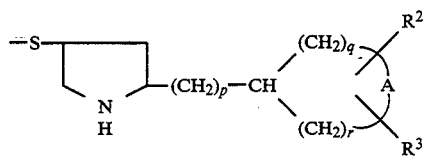

wherein each of $R^2$ and $R^3$ which may be the same or different, is a hydrogen atom, a lower alkyl group, a hydroxy lower alkyl group, a formimidoyl group, an acetoimidoyl group, $—COOR^4$, $—CON(R^5)R^6$, $—N(R^5)R^6$, $—CH_2COOR^4$, $—CH_2N(R^5)R^6$ or $—CH_2CON(R^5)R^6$ (wherein $R^4$ is a hydrogen atom or a lower alkyl group, each of $R^5$ and $R^6$ which may be the same or different, is a hydrogen atom or a lower alkyl group, or $R^5$ and $R^6$ form together with the adjacent nitrogen atom a heterocyclic group selected from the group consisting of an aziridinyl group, an azetidinyl group, a pyrrolidinyl group and a piperidyl group), A is $=NR^7$, $=N^+(R^7)R^8$, $—CON(R^7)—$, $—CON(R^7)CO—$, $—CON(R^7)CON(R^8)—$, $—N(R^7)CO(CH_2)_sN(R^8)—$, $—N(R^7)CO(CH_2)_sCON(R^8)—$, $—CON(R^7)N(R^8)—$ or $—N(R^7)(CH_2)_sN(R^8)—$ {wherein each of $R^7$ and $R^8$ which may be the same or different, is a hydrogen atom, a lower alkyl group, a hydroxy lower alkyl group, a formimidoyl group, an acetoimidoyl group, —COOR$^4$, —CON(R$^5$)R$^6$, —N(R$^5$)R$^6$, —CH$_2$COOR$^4$, —CH$_2$N(R$^5$)R$^6$ or —CH$_2$CON(R$^5$)R$^6$ (wherein R$^4$, R$^5$ and R$^6$ are as defined above), s is an integer of from 1 to 3}, p is an integer of from 0 to 3, and each of q and r which may be the same or different, is an integer of from 0 to 5, provided that q and r are not simultaneously 0 and q+r≦6, are novel compounds not disclosed any literatures, and that such compounds have strong antibacterial activities against gram positive bacteria such as Staphylococcus aureus and against gram negative bacteria including Pseudomonas aeruginosa and further exhibit excellent stability against DHP-I. The present invention has been accomplished on the basis of this discovery.

The present invention provides a compound of the formula:

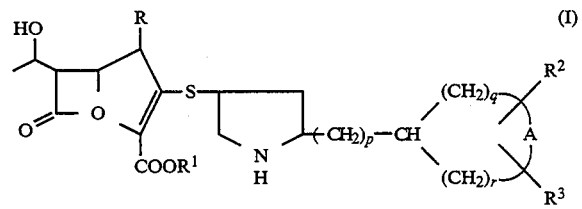

wherein R is a hydrogen atom or a methyl group, R$^1$ is a hydrogen atom or a negative charge, each of R$^2$ and R$^3$ which may be the same or different, is a hydrogen atom, a lower alkyl group, a hydroxy lower alkyl group, a formimidoyl group, an acetoimidoyl group, —COOR$^4$, —CON(R$^5$)R$^6$, —N(R$^5$)R$^6$, —CH$_2$COOR$^4$, —CH$_2$N(R$^5$)R$^6$ or —CH$_2$CON(R$^5$)R$^6$ (wherein R$^4$ is a hydrogen atom or a lower alkyl group, each of R$^5$ and R$^6$ which may be the same or different, is a hydrogen atom or a lower alkyl group, or R$^5$ and R$^6$ form together with the adjacent nitrogen atom a heterocyclic group selected from the group consisting of an aziridinyl group, an azetidinyl group, a pyrrolidinyl group and a piperidyl group), A is =NR$^7$, =N$^+$(R$^7$)R$^8$, —CON(R$^7$)—, —CON(R$^7$)CO—, —CON(R$^7$)CON(R$^8$)—, —N(R$^7$)CO(CH$_2$)$_s$N(R$^8$)—, —N(R$^7$)CO(CH$_2$)$_s$CON(R$^8$)—, —CON(R$^7$)N(R$^8$)— or —N(R$^7$)(CH$_2$)$_s$N(R$^8$)— {wherein each of R$^7$ and R$^8$ which may be the same or different, is a hydrogen atom, a lower alkyl group, a hydroxy lower alkyl group, a formimidoyl group an acetoimidoyl group, —COOR$^4$, —CON(R$^5$)R$^6$, —N(R$^5$)R$^6$, —CH$_2$COOR$^4$, —CH$_2$N(R$^5$)R$^6$ or —CH$_2$CON(R$^5$)R$^6$ (wherein R$^4$, R$^5$ and R$^6$ are as defined above), s is an integer of from 1 to 3}, p is an integer of from 0 to 3, and each of q and r which may be the same or different, is an integer of from 0 to 5, provided that q and r are not simultaneously 0 and q+r≦6; or a pharmaceutically acceptable salt or ester thereof.

The present invention also provides a process for producing the compound of the formula (I) or a pharmaceutically acceptable salt or ester thereof, which comprises reacting a compound of the formula:

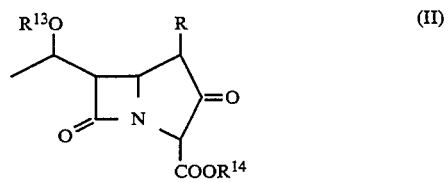

wherein R is as defined above, R$^{13}$ is a hydrogen atom or a hydroxyl-protecting group, and R$^{14}$ is a hydrogen atom or a carboxyl-protecting group, or a reactive derivative thereof, with a compound of the formula:

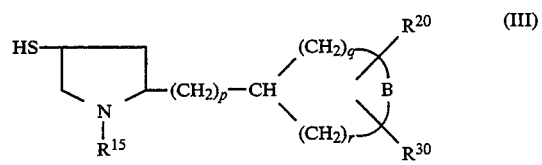

wherein R$^{15}$ is a hydrogen atom or an imino-protecting group, each of R$^{20}$ and R$^{30}$ which may be the same or different, is a hydrogen atom, a lower alkyl group, a hydroxy lower alkyl group which may be protected, a formimidoyl group which may be protected, an acetoimidoyl group which may be protected, —COOR$^{40}$, —CON(R$^{50}$)R$^{60}$, —N(R$^{50}$)R$^{60}$, —CH$_2$COOR$^{40}$, —CH$_2$N(R$^{50}$)R$^{60}$ or —CH$_2$CON(R$^{50}$)R$^{60}$ (wherein R$^{40}$ is a hydrogen atom, a lower alkyl group or a carboxyl-protecting group, and each of R$^{50}$ and R$^{60}$ which may be the same or different, is a hydrogen atom, a lower alkyl group, an amino-protecting group or an imino-protecting group, or R$^{50}$ and R$^{60}$ form together with the adjacent nitrogen atom a heterocyclic group selected from the group consisting of an aziridinyl group, an azetidinyl group, a pyrrolidinyl group and a piperidyl group), B is =NR$^{70}$, =N$^+$(R$^{70}$)R$^{80}$, —CON(R$^{70}$)—, —CON(R$^{70}$)CO—, —CON(R$^{70}$)CON(R$^{80}$)—, —N(R$^{70}$)CO(CH$_2$)$_s$N(R$^{80}$)—, —N(R$^{70}$)CO(CH$_2$)$_s$CON(R$^{80}$)—, —CON(R$^{70}$)N(R$^{80}$)— or —N(R$^{70}$)(CH$_2$)$_s$N(R$^{80}$)— {wherein each of R$^{70}$ and R$^{80}$ which may be the same or different is a hydrogen atom, a lower alkyl group, a hydroxy lower alkyl group which may be protected, a formimidoyl group which may be protected, an acetoimidoyl group which may be protected, an imino-protecting group, —COOR$^{40}$, —CON(R$^{50}$)R$^{60}$, —N(R$^{50}$)R$^{60}$, —CH$_2$COOR$^{40}$, —CH$_2$N(R$^{50}$)R$^{60}$ or —CH$_2$CON(R$^{50}$)R$^{60}$ (wherein R$^{40}$, R$^{50}$ and R$^{60}$ are as defined above), and s is an integer of from 1 to 3}, and p, q and r are as defined above, to obtain a compound of the formula:

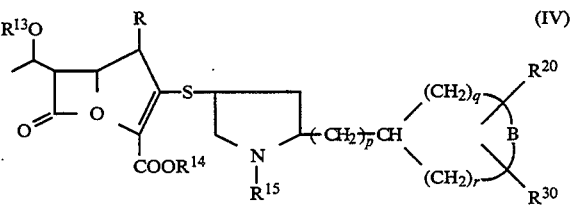

wherein R, R$^{13}$, R$^{14}$, R$^{15}$, R$^{20}$, R$^{30}$, B, p, q and r are as defined above, and if necessary, removing any protecting group of the compound of the formula (IV).

Further, the present invention provides an antibacterial agent comprising an antibacterially effective amount of the compound of the formula (I) or a pharmaceutically acceptable salt or ester thereof, and a pharmaceutically acceptable carrier or diluent.

Now, the present invention will be described in detail with reference to the preferred embodiments. Firstly, the symbols and terms used in this specification will be explained.

The compound of the present invention has a basic structure of the formula:

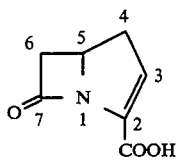

which is systematically referred to as a 7-oxo-1-azabicyclo[3.2.0]hept-2-en-2-carboxylic acid. For the convenience sake, in this specification, this basic structure will be referred to as a 1-carbapen-2-em-3-carboxylic acid by putting the numbers based on a commonly widely used carbapenem of the formula:

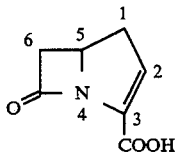

The present invention includes optical isomers based on the asymmetrical carbon atoms at the 1-position, 5-position, 6-position and 8-position of the carbapenem structure and stereoisomers. Among these isomers, preferred is a compound of a (5R,6S,8R) configuration i.e. a compound having a steric configuration of (5R,6S) (5,6-trans) like thienamycin and in which the carbon atom at the 8-position takes a R-configuration, or a compound of a (1R,5S,6S,8R) configuration in a case where a methyl group is present at the 1-position.

Also with respect to the 2-(alicyclic heteroring-substituted or alicyclic heteroring lower alkyl)pyrrolidin-4-ylthio group, the present invention includes isomers based on the asymmetrical carbon atoms at the 2-position and 4-position of the pyrrolidine structure and in the side chain at the 2-position. Among these isomers, preferred are compounds of (2'S,4'S) configuration and (2'R,4'R) configuration when p is 0, and compounds of (2'R,4'S) configuration and (2'S,4'R) configuration when p is an integer of from 1 to 3.

Further, with respect to the alicyclic heterocyclic group at the 2-position of the pyrrolidine structure, there exist isomers based on asymmetrical carbons, and the present invention includes such isomers as well.

The lower alkyl group means a linear or branched alkyl group having from 1 to 6 carbon atoms, such as a methyl group, an ethyl group, a propyl group, an isopropyl group, a butyl group, a sec-butyl group, a tert-butyl group, a pentyl group or a hexyl group, preferably a methyl group, an ethyl group or a tert-butyl group.

The hydroxy lower alkyl group means a hydroxyalkyl group having the above mentioned lower alkyl group substituted with a hydroxyl group, such as a hydroxymethyl group, a hydroxyethyl group, a hydroxypropyl group or a hydroxybutyl group, preferably a hydroxymethyl group or a hydroxyethyl group.

The lower alkyl carbamoyl group means a carbamoyl group substituted by the above mentioned lower alkyl group, such as an N-methylcarbamoyl group, an N-ethylcarbamoyl group or an N-propylcarbamoyl group, preferably an N-methylcarbamoyl group.

The di-lower alkyl carbamoyl group means a carbamoyl group di-substituted by the above mentioned lower alkyl group, such as an N,N-dimethyl carbamoyl group, an N,N-diethyl carbamoyl group or an N-ethyl-N-methylcarbamoyl group, preferably an N,N-dimethylcarbamoyl group.

The carboxyl-protecting group may, for example, be a lower alkyl group such as a methyl group, an ethyl group, a propyl group, an isopropyl group or a tert-butyl group; a halogenated lower alkyl group such as a 2,2,2-trichloroethyl group or a 2,2,2-trifluoroethyl group; a lower alkanoyloxyalkyl group such as an acetoxymethyl group, a propionyloxymethyl group, a pivaloyloxymethyl group, a 1-acetoxyethyl group or a 1-propionyloxyethyl group; a lower alkoxycarbonyloxyalkyl group such as a 1-(methoxycarbonyloxy)ethyl group, a 1-(ethoxycarbonyloxy)ethyl group or a 1-(isopropoxycarbonyloxy)ethyl group; a lower alkenyl group such as a 2-propenyl group, a 2-chloro-2-propenyl group, a 3-methoxycarbonyl-2-propenyl group, a 2-methyl-2-propenyl group, a 2-butenyl group or a cinnamyl group; an aralkyl group such as a benzyl group, a p-methoxybenzyl group, a 3,4-dimethoxybenzyl group, an o-nitrobenzyl group, a p-nitrobenzyl group, a benzhydryl group or a bis(p-methoxyphenyl)methyl group; a (5-substituted 2-oxo-1,3-dioxol-4-yl)methyl group such as a (5-methyl-2-oxo-1,3-dioxol-4-yl)methyl group; a lower alkylsilyl group such as a trimethylsilyl group or a tert-butyldimethylsilyl group; an indanyl group, a phthalidyl group or a methoxymethyl group. Particularly preferred are a 2-propenyl group, a p-nitrobenzyl group, a p-methoxybenzyl group, a benzhydryl group and a tert-butyldimethylsilyl group.

The hydroxyl-protecting group may, for example, be a lower alkylsilyl group such as a trimethylsilyl group or a tert-butyldimethylsilyl group; a lower alkoxymethyl group such as a methoxymethyl group or a 2-methoxyethoxymethyl group; a tetrahydropyranyl group; an aralkyl group such as a benzyl group, a p-methoxybenzyl group, a 2,4-dimethoxybenzyl group, an o-nitrobenzyl group, a p-nitrobenzyl group or a trityl group; an acyl group such as a formyl group or an acetyl group; a lower alkoxycarbonyl group such as a tert-butoxycarbonyl group, a 2-iodoethoxycarbonyl group or a 2,2,2-trichloroethoxycarbonyl group; an alkenyloxycarbonyl group such as a 2-propenyloxycarbonyl group, a 2-chloro-2-propenyloxycarbonyl group, a 3-methoxycarbonyl-2-propenyloxycarbonyl group, a 2-methyl-2-propenyloxycarbonyl group, a 2-butenyloxycarbonyl group or a cinnamyloxycarbonyl group; or an aralkyloxycarbonyl group such as a benzyloxycarbonyl group, a p-methoxybenzyloxycarbonyl group, an o-nitrobenzyloxycarbonyl group or a p-nitrobenzyloxycarbonyl group. Particularly preferred are a 2-propenyloxycarbonyl group, a p-nitrobenzyloxycarbonyl group and a tert-butyldimethylsilyl group.

The amino- or imino-protecting group may, for example, be an aralkylidene group such as a benzylidene group, a p-chlorobenzylidene group, a p-nitrobenzylidene group, a salicylidene group, an α-naphthylidene group or a β-naphthylidene group; an aralkyl group such as a benzyl group, a p-methoxybenzyl group, a 3,4-dimethoxybenzyl group, an o-nitrobenzyl group, a p-nitrobenzyl group, a benzhydryl group, a bis(p-methoxyphenyl)methyl group or a trityl group; a lower alkanoyl group such as a formyl group, an acetyl group, a propionyl group, a butyryl group, an oxalyl group, a succinyl group, or a pivaloyl-group; a halogenated lower alkanoyl group such as a chloroacetyl group, a dichloroacetyl group, a trichloroacetyl group or a trifluoroacetyl group; an arylalkanoyl group such as a phenylacetyl group or a phenoxyacetyl group; a lower alkoxycarbonyl group such as a methoxycarbonyl group, an ethoxycarbonyl group, a propoxycarbonyl group or a tert-butoxycarbonyl group; a halogenated lower alkoxycarbonyl group such as a 2-iodoethoxycarbonyl group or a 2,2,2-trichloroethoxycarbonyl group; an alkenyloxycarbonyl group such as a 2-propenyloxycarbonyl group, a 2-chloro-2-propenyloxycarbonyl group, a 3-methoxycarbonyl-2-propenyloxycarbonyl group, a 2-methyl-2-propenyloxycarbonyl group, a 2-butenyloxycarbonyl group or a cinnamyloxycarbonyl group; an aralkyloxycarbonyl group such as a benzyloxycarbonyl group, an o-nitrobenzyloxycarbonyl group, a p-nitrobenzyloxycarbonyl group or a phenethyloxycarbonyl group; or a lower alkylsilyl group such as a trimethylsilyl group or a tert-butyldimethylsilyl group. Particularly preferred are a 2-propenyloxycarbonyl group, a tert-butoxycarbonyl group and a p-nitrobenzyloxycarbonyl group.

The alicyclic heterocyclic group on the pyrrolidin-4-ylthio group as the side chain at the 2-position of the carbapenem structure, is substituted at the 2-position of the pyrrolidine ring and has a structure of the formula:

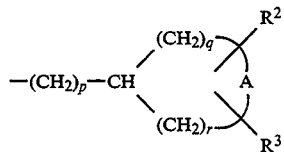

wherein each of $R^2$ and $R^3$ which may be the same or different, is a hydrogen atom, a lower alkyl group, a hydroxy lower alkyl group, a formimidoyl group, an acetoimidoyl group, —COOR$^4$, —CON(R$^5$)R$^6$, —N(R$^5$)R$^6$, —CH$_2$COOR$^4$, —CH$_2$N(R$^5$)R$^6$ or —CH$_2$CON(R$^5$)R$^6$ (wherein R$^4$ is a hydrogen atom or a lower alkyl group, each of R$^5$ and R$^6$ which may be the same or different, is a hydrogen atom or a lower alkyl group, or R$^5$ and R$^6$ form together with the adjacent nitrogen atom a heterocyclic group selected from the group consisting of an aziridinyl group, an azetidinyl group, a pyrrolidinyl group and a piperidyl group), A is =NR$^7$, =N$^+$(R$^7$)R$^8$, —CON(R$^7$)—, —CON(R$^7$)CO—, —CON(R$^7$)CON(R$^8$)—, —N(R$^7$)CO(CH$_2$)$_s$N(R$^8$)—, —N(R$^7$)CO(CH$_2$)$_s$CON(R$^8$)—, —CON(R$^7$)N(R$^8$)— or —N(R$^7$)(CH$_2$)$_s$N(R$^8$)— {wherein each of R$^7$ and R$^8$ which may be the same or different, is a hydrogen atom, a lower alkyl group, a hydroxy lower alkyl group, a formimidoyl group, an acetoimidoyl group, —COOR$^4$, —CON(R$^5$)R$^6$, —N(R$^5$)R$^6$, —CH$_2$COOR$^4$, —CH$_2$N(R$^5$)R$^6$ or —CH$_2$CON(R$^5$)R$^6$ (wherein R$^4$, R$^5$ and R$^6$ are as defined above), s is an integer of from 1 to 3}, p is an integer of from 0 to 3, and each of q and r which may be the same or different, is an integer of from 0 to 5, provided that q and r are not simultaneously 0 and q+r≦6. R$^2$ (or R$^{20}$) and R$^3$ (or R$^{30}$) may be the same or different and may be substituted at any optional positions on carbon atoms constituting said alicyclic heteroring. Each of R$^2$ and R$^3$ is preferably a hydrogen atom, a lower alkyl group, a hydroxy lower alkyl group, —CON(R$^5$)R$^6$ or —N(R$^5$)R$^6$ (wherein R$^5$ and R$^6$ are as defined above). Particularly preferred among them is a hydrogen atom, a carbamoyl group, a lower alkyl carbamoyl group, a di-lower alkyl carbamoyl group or an amino-group.

A represents a partial Structure of said alicyclic heterocyclic group.

A is preferably =NR$^7$, =N$^+$(R$^7$)R$^8$, —CON(R$^7$)—, —CON(R$^7$)CO—, —CON(R$^7$)CON(R$^8$)—, —N(R$^7$)COCH$_2$N(R$^8$)—, —CON(R$^7$)N(R$^8$)— or —N(R$^7$)(CH$_2$)$_2$N(R$^8$)— (wherein R$^7$ and R$^8$ are as defined above). Among them, =NR$^7$, =N$^+$(R$^7$)R$^8$, or —CON(R$^7$)— (wherein R$^7$ and R$^8$ are as defined above) is preferable. Particularly preferred among them is =NH, =NMe, =N$^+$ME$_2$ or —CONH—.

p is an integer of from 0 to 3, preferably 0 or 1, more preferably 0.

When p is 0, said alicyclic heterocyclic group may be a substituent selected from the group consisting of an aziridinyl group, an azetidinyl group, a 2-carbamoylazetidinyl group, a 2-oxoazetidinyl group, an N-methyl-2-oxoazetidinyl group, a pyrrolidinyl group, an N-methylpyrrolidinyl group, an N,N-dimethylpyrrolidinio group, a 2-oxopyrrolidinyl group, a 2,5-dioxopyrrolidinyl group, an N-(2-hydroxyethyl)pyrrolidinyl group, a 2,5-dioxo-N-methylpyrrolidinyl group, a 2-carbamoylpyrrolidinyl group, a 2-(N-methylcarbamoyl)pyrrolidinyl group, a 2-(N,N-dimethylcarbamoyl)pyrrolidinyl group, a 3-amino-2-oxopyrrolidinyl group, a pyrazolidinyl group, a 3-oxopyrazolidinyl group, an imidazolidinyl group, a 2,4-dioxoimidazolidinyl group, a piperazinyl group, a 2-oxopiperazinyl group, a piperidyl group, an N-methylpiperidyl group, an N,N-dimethylpiperidinio group, a 2-oxopiperidyl group, a 2,6-dioxopiperidyl group, a 2-carbamoyl piperidyl group, a hexahydroazepinyl group, an N-methylhexahydroazepinyl group, an N,N-dimethylhexahydroazepinio group, a hexahydro-2-oxoazepinyl group, a 2,7-dioxohexahydroazepinyl group, a 2-carbamoylhexahydroazepinyl group, a hexahydro-1H-1,4-diazepinyl group, a hexahydro-2-oxo-1H-1,4-diazepinyl group, an octahydroazocinyl group, an N-methyloctahydroazocinyl group and an N,N-dimethyloctahydroazocinio group. Particularly preferred among them is a substituent selected from the group consisting of a 2-oxoazetidinyl group, a pyrrolidinyl group, an N,N-dimethylpyrrolidinio group, a 2-carbamoylpyrrolidinyl group, a 3-amino-2-oxopyrrolidinyl group, a 2-oxopyrrolidinyl group, a piperidyl group and a 2-oxopiperidyl group.

When p is 1, it may be a substituent selected from the group consisting of an aziridinylmethyl group, an azetidinylmethyl group, a 2-carbamoylazetidinylmethyl group, a 2-oxoazetidinylmethyl group, an N-methyl-2-oxoazetidinylmethyl group, a pyrrolidinylmethyl group, an N-methylpyrrolidinylmethyl group, an N,N-dimethylpyrrolidiniomethyl group, a 2-oxopyrrolidinylmethyl group, a 2,5-dioxopyrrolidinylmethyl group, an N-(2-hydroxyethyl)pyrrolidinylmethyl group, a 2,5-dioxo-N-methylpyrrolidinylmethyl group, a 2-carbamoylpyrrolidinylmethyl group, a 2-(N-methylcarbamoyl)pyrrolidinylmethyl group, a 2-(N,N-dimethylcarbamoyl)pyrrolidinylmethyl group, a 3-amino-2-oxopyrrolidinylmethyl group, a pyrazolidinylmethyl group, a 3-oxopyrazolidinylmethyl group, an imidazolidinylmethyl group, a 2,4-dioxoimidazolidinylmethyl group, a piperazinylmethyl group, a 2-oxopiperazinylmethyl group, a piperidylmethyl group, an N-methylpiperidylmethyl group, an N,N-dimethylpiperidiniomethyl group, a 2-oxopiperidylmethyl group, a 2,6-dioxopiperidylmethyl group, a 2-carbamoylpiperidylmethyl group, a hexahydroazepinylmethyl group, an N-methylhexahydroazepinylmethyl group, an N,N-dimethylhexahydroazepiniomethyl group, a hexahydro-2-oxoazepinylmethyl group, a 2,7-dioxohexahydroazepinylmethyl group, a 2-carbamoylhexahydroazepinylmethyl group, a hexahydro-1H-1,4-diazepinylmethyl group, a hexahydro-2-oxo-1H-1,4-diazepinylmethyl group, an octahydroazocinylmethyl group, an N-methyloctahydroazocinylmethyl group and an N,N-dimethyloctahydroazociniomethyl group. Particularly preferred among them is a substituent selected from the group consisting of a 2-oxoazetidinylmethyl group, a pyrrolidinylmethyl group, an N,N-dimethylpyrrolidiniomethyl group, a 2-carbamoylpyrrolidinylmethyl group, a 3-amino-2-oxopyrrolidinylmethyl group, a 2-oxopyrrolidinylmethyl group, a piperidylmethyl group and a 2-oxopiperidylmethyl group.

$R^1$ is a hydrogen atom or a negative charge. When the alicyclic heterocyclic group substituted at the 2-position of the pyrrolidine ring has a quaternary ammonium structure, $R^1$ represents a negative charge forming a pair with the ammonium ion, whereby the compound of the formula (I) forms an intramolecular salt.

The salt of the compound of the formula (I) is a common pharmaceutically acceptable salt and may, for example, be a salt at the carboxyl group at the 3-position of the carbapenem structure, or at the pyrrolidine base or the base of the alicyclic heterocyclic group in the side chain at the 2-position of the carbapenem structure.

The basic addition salt at said carboxyl group includes, for example, an alkali metal salt such as a sodium salt or a potassium salt; an alkaline earth metal salt such as a calcium salt or a magnesium salt; an ammonium salt; an aliphatic amine salt such as a trimethylamine salt, a triethylamine salt, a dicyclohexylamine salt, an ethanolamine salt, a diethanolamine salt, a triethanolamine salt or a procaine salt; an aralkylamine salt such as an N,N'-dibenzylethylenediamine salt; an aromatic heterocyclic amine salt such as a pyridine salt, a picoline salt, a quinoline salt or an isoquinoline salt; a quaternary ammonium salt such as a tetramethylammonium salt, a tetraethylammonium salt, a benzyltrimethylammonium salt, a benzyltriethylammonium salt, a benzyltributylammonium salt, a methyltrioctylammonium salt or a tetrabutylammonium salt; and a basic amino acid salt such as an arginine salt or a lysine salt.

The acid addition salt at the pyrrolidine base or at the base of the alicyclic heterocyclic group includes, for example, an inorganic salt such as a hydrochloride, a sulfate, a nitrate, a phosphate, a carbonate, a hydrogencarbonate or a perchlorate; an organic salt such as an acetate, a propionate, a lactate, a maleate, a fumarate, a tartrate, a malate, a succinate or an ascorbate; a sulfonate such as a methanesulfonate, an isethionate, a benzenesulfonate or a p-toluenesulfonate; and an acidic amino acid salt such as an aspartate or a glutamate.

The non-toxic ester of the compound of the formula (I) means a common pharmaceutically acceptable ester at the carboxyl group at the 3-position of the carbapenem structure. For example, it includes an ester with an alkanoyloxymethyl group such as an acetoxymethyl group or a pivaloyloxymethyl group, an ester with an alkoxycarbonyloxyalkyl group such as a 1-(ethoxycarbonyloxy)ethyl group, an ester with a phthalidyl group and an ester with a (5-substituted-2-oxo-1,3-dioxol-4-yl)methyl group such as a (5-methyl-2-oxo-1,3-dioxol-4-yl)methyl group.

The compound of the formula (I) of the present invention includes a compound of the formula:

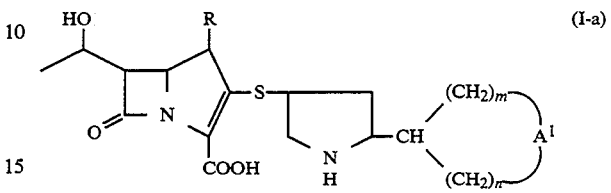

(I-a)

wherein R is a hydrogen atom or a methyl group, $A^1$ is $=NR^9$, $-CON(R^{10})-$ or $-CON(R^{10})CO-$ (wherein $R^9$ is a hydrogen atom, a lower alkyl group, a formimidoyl group or an acetoimidoyl group, and $R^{10}$ is a hydrogen atom or a lower alkyl group), and each of m and n which may be the same or different, is an integer of from 0 to 3, provided that m and n are not simultaneously 0, a compound of the formula:

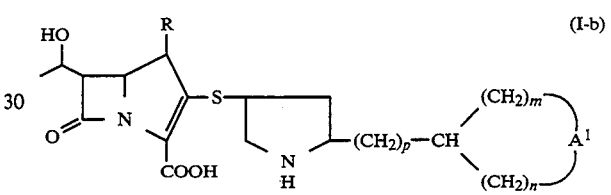

(I-b)

wherein R is a hydrogen atom or a methyl group, A is $=NR^9$, $-CON(R^{10})-$ or $-CON(R^{10})CO-$ (wherein $R^9$ is a hydrogen atom, a lower alkyl group, a formimidoyl group or an acetoimidoyl group, $R^{10}$ is a hydrogen atom or a lower alkyl group), and each of m, n and p which may be the same or different, is an integer of from 0 to 3, provided that m and n are not simultaneously 0, and a compound of the formula:

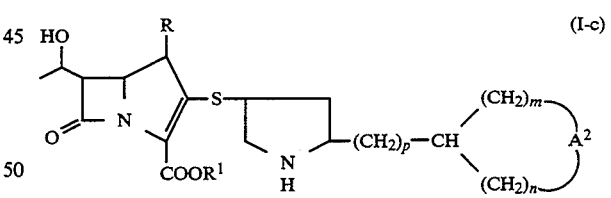

(I-c)

wherein R is a hydrogen atom or a methyl group, $R^1$ is a hydrogen atom or a negative charge, $A^2$ is $=NR^9$, $=N^+(R^{11})R^{12}$, $-CON(R^{10})-$ or $-CON(R^{10})CO-$ (wherein $R^9$ is a hydrogen atom, a lower alkyl group, a formimidoyl group or an acetoimidoyl group, $R^{10}$ is a hydrogen atom or a lower alkyl group, and each of $R^{11}$ and $R^{12}$ which may be the same or different, is a lower alkyl group), and each of m, n and p which may be the same or different, is an integer of from 0 to 3, provided that m and n are not simultaneously 0.

Among the compounds of the formulas (I-a) and (I-b), those wherein $A^1$ is $-CON(R^{10})-$ or $=NR^9$, are preferred.

Among the compounds of the formula (I-c), those therein $A^2$ is $=NR^9$, $=N^+(R^{11})R^{12}$, or $-CON(R^{10})-$, are preferred.

Specific examples of the compound of the formula (I) include, for example, the following compounds.

TABLE 1

| No. | $R^1$ | $R^3$ group | No. | $R^1$ | $R^3$ group |
|---|---|---|---|---|---|
| 1 | H | HN- (4-membered ring) | 13 | H | pyrrolidine-NH |
| 2 | H | MeN- (4-membered ring) | 14 | H | pyrrolidine-NMe |
| 3 | H | HN=CHN- (4-membered ring) | 15 | H | pyrrolidine-N-CH=NH |
| 4 | H | Me(HN=)CN- (4-membered ring) | 16 | H | pyrrolidine-N-C(=NH)Me |
| 5 | H | -NH (azetidine) | 17 | H | piperidine-HN |
| 6 | H | -NMe (azetidine) | 18 | H | piperidine-MeN |
| 7 | H | -NCH=NH | 19 | H | piperidine-HN=HCN |
| 8 | H | -NC(=NH)Me | 20 | H | piperidine-NH |
| 9 | H | HN (pyrrolidine) | 21 | H | piperidine-NMe |

TABLE 1-continued

[Structure: carbapenem core with HO-CH(Me)- at C6, COOR¹ at C2, S-linked pyrrolidine with -CH((CH₂)q-R², (CH₂)r-R³)A substituent]

| No. | R¹ | -CH((CH₂)q-R², A, (CH₂)r-R³) | No. | R¹ | -CH((CH₂)q-R², A, (CH₂)r-R³) |
|---|---|---|---|---|---|
| 10 | H | (pyrrolidine with MeN) | 22 | H | (piperidine with NCH=NH) |
| 11 | H | (pyrrolidine with HN=HCN) | 23 | H | (piperidine with NH) |
| 12 | H | (pyrrolidine with Me(HN=)CN) | 24 | H | (piperidine with NMe) |

TABLE 2

| No. | R¹ | -CH((CH₂)q-R², A, (CH₂)r-R³) | No. | R¹ | -CH((CH₂)q-R², A, (CH₂)r-R³) |
|---|---|---|---|---|---|
| 25 | H | (piperidine with NCH=NH) | 39 | H | (piperidinone with NMe, =O) |
| 26 | H | (β-lactam with HN, =O) | 40 | H | (piperidinone with =O, NH) |
| 27 | H | (β-lactam with MeN, =O) | 41 | H | (piperidinone with =O, NMe) |
| 28 | H | (β-lactam with O=, NH) | 42 | H | (piperidinone with =O, NH) |
| 29 | H | (β-lactam with O=, NMe) | 43 | H | (piperidinone with =O, NMe) |

TABLE 2-continued
| No. | R¹ | (structure) | No. | R¹ | (structure) |
|---|---|---|---|---|---|
| 30 | H | 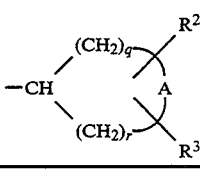 | 44 | H |  |
| 31 | H | 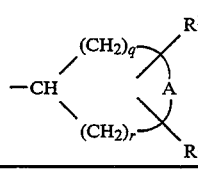 | 45 | H | 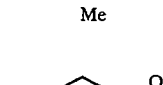 |
| 32 | H | 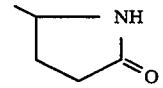 | 46 | H | 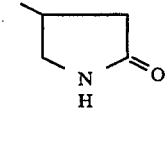 |
| 33 | H | 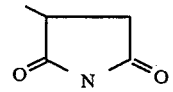 | 47 | H | 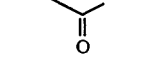 |
| 34 | H | 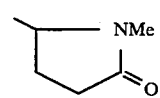 | 48 | H | 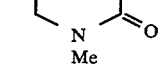 |
| 35 | H | 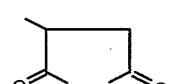 | 49 | H | 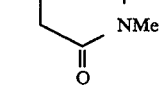 |
| 36 | H | 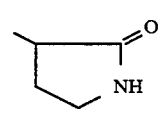 | 50 | H | 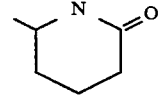 |
| 37 | H | 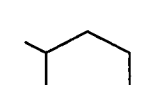 | 51 | H | 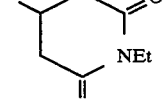 |
| 38 | H |  | 52 | H | 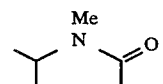 |

TABLE 3
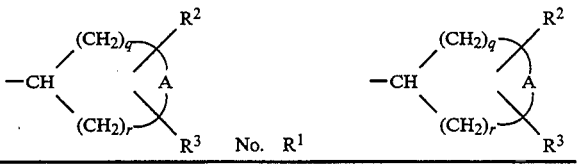

TABLE 3-continued

| No. | R¹ | (structure) | No. | R¹ | (structure) |
|---|---|---|---|---|---|
| 63 | Negative charge | 4-methyl-N,N-dimethylpyrrolidinium | 76 | H | 5-methyl-2-amino-piperidine-2-carboxamide |
| 64 | Negative charge | 4-methyl-N,N-dimethyl-2-carbamoylpyrrolidinium | 77 | H | 5-methyl-2-(N-methylamino)-piperidine-2-carboxamide |
| 65 | Negative charge | 4-methyl-N,N-dimethyl-2-(N-methylcarbamoyl)pyrrolidinium | 78 | Negative charge | 5-methyl-N,N-dimethyl-2-carbamoylpiperidinium |

TABLE 4

| No. | R¹ | (structure) | No. | R¹ | (structure) |
|---|---|---|---|---|---|
| 79 | H | 3-amino-4-methyl-2-pyrrolidinone | 90 | H | 5-methyl-2-piperazinone |
| 80 | H | 3-amino-4-methyl-2-pyrrolidinone (isomer) | 91 | H | 5-methyl-4-methyl-2-piperazinone |
| 81 | H | 3-amino-5-methyl-2-piperidinone | 92 | H | 5-methyl-2,3-piperazinedione |
| 82 | H | 4-amino-5-methyl-2-piperidinone | 93 | H | 5-methyl-piperazine-2-carboxamide |
| 83 | H | 3-amino-5-methyl-2-piperidinone (isomer) | 94 | H | 5-methyl-piperazine-3-carboxamide |

TABLE 4-continued

| No. | R¹ | (structure) | No. | R¹ | (structure) |
|---|---|---|---|---|---|
| 84 | H | 4-amino-methyl-piperidinone (H₂N, NH, C=O) | 95 | H | 1,4-diazepane (methyl-substituted) |
| 85 | H | 2-methylpiperazine | 96 | H | methyl-1,4-diazepan-2-one |
| 86 | H | 1-methyl-3-methylpiperazine (Me on N) | 97 | H | methyl-1,4-diazepane-2,3-dione |
| 87 | H | 4-methyl-2-methylpiperazine | 98 | H | methyl-1,4-diazepane-2-carboxamide (CONH₂) |
| 88 | H | 1,4-dimethyl-2-methylpiperazine | 99 | H | methyl-hydantoin (HN, NH, C=O) |
| 89 | H | 5-methylpiperazin-2-one | 100 | H | methyl-pyrazolidinone (HN–N, C=O) |

TABLE 5

| No. | R¹ | (structure) | No. | R¹ | (structure) |
|---|---|---|---|---|---|
| 101 | H | methyl-pyrazolidinone | 112 | H | 3-methyl-1-(2-hydroxyethyl)piperidine (N–CH₂CH₂OH) |
| 102 | H | azetidine-N-CH₂CONH₂ | 113 | H | 4-(2-hydroxyethylamino)cyclohexyl (NCH₂CH₂OH) |

TABLE 5-continued
| No. | R¹ | (structure) | No. | R¹ | (structure) |
|---|---|---|---|---|---|
| 103 | H | 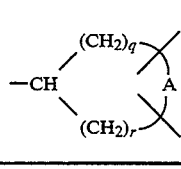 NCH₂CONMe | 114 | Negative charge | 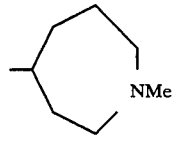 +N(Me)Me |
| 104 | H | 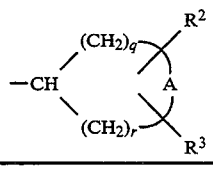 N-CH₂CONH₂ | 115 | H | 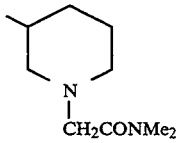 NH |
| 105 | H |  N-CH₂CONMe₂ | 116 | H | 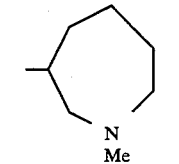 NH |
| 106 | H | 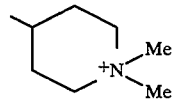 N-CH₂CONH₂ | 117 | H | 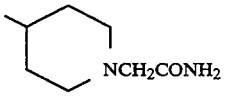 NMe |
| 107 | H | 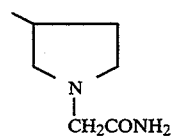 N-CH₂CONMe₂ | 118 | H | 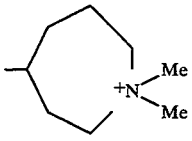 N-Me |
| 108 | H | 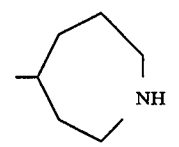 NCH₂CONH₂ | 119 | Negative charge | 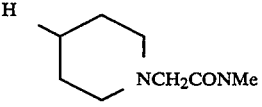 +N(Me)Me |
| 109 | H | 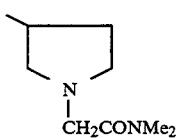 NCH₂CONMe | 120 | Negative charge | 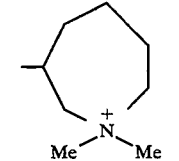 +N(Me)Me |
| 110 | H | 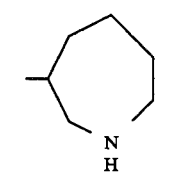 NCH₂CH₂OH | 121 | H | 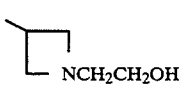 NH |

TABLE 5-continued
| | | (CH₂)_q — A — (CH₂)_r with R² and R³, attached via —CH— | | | |
|---|---|---|---|---|---|
| No. | R¹ | | No. | R¹ | |
| 111 | H | 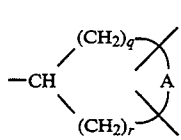 | 122 | H | 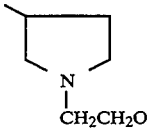 |
TABLE 6
| No. | R¹ | | No. | R¹ | |
|---|---|---|---|---|---|
| 123 | H | 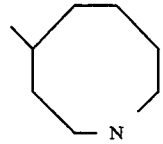 | 127 | Negative charge | 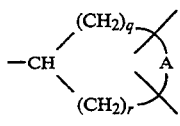 |
| 124 | H | 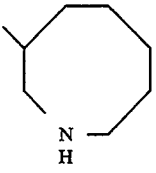 | 128 | Negative charge | 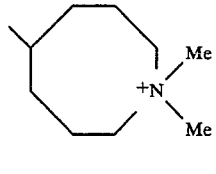 |
| 125 | H | 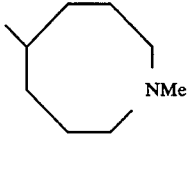 | 129 | Negative charge | 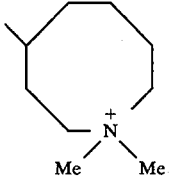 |
| 126 | H | 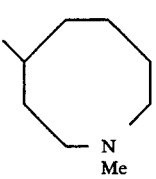 | | | |

TABLE 7

| No. | R¹ | R²/R³ group | No. | R¹ | R²/R³ group |
|---|---|---|---|---|---|
| 130 | H | HN (azetidine) | 142 | H | pyrrolidine NH |
| 131 | H | MeN (azetidine) | 143 | H | pyrrolidine NMe |
| 132 | H | HN=CHN (azetidine) | 144 | H | pyrrolidine N–CH=NH |
| 133 | H | Me(HN=)CN (azetidine) | 145 | H | pyrrolidine N–C(=NH)Me |
| 134 | H | NH (azetidine) | 146 | H | HN (piperidine) |
| 135 | H | NMe (azetidine) | 147 | H | MeN (piperidine) |
| 136 | H | NCH=NH (azetidine) | 148 | H | HN=HCN (piperidine) |
| 137 | H | NC(=NH)Me (azetidine) | 149 | H | NH (piperidine) |
| 138 | H | HN (pyrrolidine) | 150 | H | NMe (piperidine) |
| 139 | H | MeN (pyrrolidine) | 151 | H | NCH=NH (piperidine) |

TABLE 7-continued

[Structure: carbapenem core with HO-CH(CH3)- group, β-lactam ring, COOR¹, S-linked pyrrolidine with CH substituent bearing (CH2)q-A-R² and (CH2)r-R³ ring]

| No. | R¹ | –CH<(CH2)q–A–R² / (CH2)r–R³> | No. | R¹ | –CH<(CH2)q–A–R² / (CH2)r–R³> |
|---|---|---|---|---|---|
| 140 | H | HN=HCN (cyclopentane with amidino) | 152 | H | piperidine (NH) |
| 141 | H | Me(HN=)CN (cyclopentane with N-Me amidino) | 153 | H | piperidine (NMe) |

TABLE 8

| No. | R¹ | –CH<(CH2)q–A–R² / (CH2)r–R³> | No. | R¹ | –CH<(CH2)q–A–R² / (CH2)r–R³> |
|---|---|---|---|---|---|
| 154 | H | cyclohexane-NCH=NH | 168 | H | piperidinone, NMe |
| 155 | H | β-lactam, HN, =O | 169 | H | δ-valerolactam NH |
| 156 | H | β-lactam, MeN, =O | 170 | H | δ-valerolactam NMe |
| 157 | H | β-lactam, O=, NH | 171 | H | 6-membered lactam NH |
| 158 | H | β-lactam, O=, NMe | 172 | H | 6-membered lactam NMe |
| 159 | H | γ-butyrolactam NH | 173 | H | succinimide (N-H) |

TABLE 8-continued

| No. | R¹ | structure | No. | R¹ | structure |
|---|---|---|---|---|---|
| 160 | H | -CH2-CH(NMe)-C(=O)- (pyrrolidinone w/ NMe side chain) | 174 | H | N-methyl succinimide |
| 161 | H | 5-membered lactam (γ-butyrolactam, NH) | 175 | H | glutarimide (NH) |
| 162 | H | 5-membered lactam (NMe) | 176 | H | N-methyl glutarimide |
| 163 | H | pyrrolidin-2-one (NH) | 177 | H | glutarimide variant (NH) |
| 164 | H | pyrrolidin-2-one (NMe) | 178 | H | glutarimide variant (NMe) |
| 165 | H | piperidin-2-one (NH) | 179 | H | glutarimide variant (NEt) |
| 166 | H | piperidin-2-one (NMe) | 180 | H | azetidine-CONH2 (NH) |
| 167 | H | piperidin-2-one (NH, different position) | 181 | H | azetidine-CONH2 (NMe) |

TABLE 9

| No. | R¹ | structure | No. | R¹ | structure |
|---|---|---|---|---|---|
| 182 | H | azetidine with CONH2 and NCH=NH | 195 | Negative charge | pyrrolidinium with N(Me)2 and CONMe2 |

TABLE 9-continued

| No. | R¹ | structure | No. | R¹ | structure |
|---|---|---|---|---|---|
| 183 | H | pyrrolidine-2-CONH₂, NH | 196 | Negative charge | pyrrolidine-3-CONH₂, N⁺(Me)₂ |
| 184 | H | pyrrolidine-2-CONHMe, NH | 197 | Negative charge | pyrrolidine-2-CONH₂, N⁺(Me)₂ |
| 185 | H | pyrrolidine-2-CONMe₂, NH | 198 | H | pyrrolidine-2-CONH₂, N–CH=NH |
| 186 | H | pyrrolidine-2-CONH₂, N-Me | 199 | H | pyrrolidine-3-CONH₂, N–CH=NH |
| 187 | H | pyrrolidine-2-CONMe₂, N-Me | 200 | H | pyrrolidine-2-CONH₂, N–CH=NH |
| 188 | H | pyrrolidine-3-CONH₂, NH | 201 | H | piperidine-2-CONH₂, NH |
| 189 | H | pyrrolidine-3-CONH₂, N-Me | 202 | H | piperidine-2-CONH₂, N-Me |
| 190 | H | pyrrolidine-2-CONH₂, NH | 203 | Negative charge | piperidine, N⁺(Me)₂ |
| 191 | H | pyrrolidine-2-CONH₂, N-Me | 204 | Negative charge | piperidine-2-CONH₂, N⁺(Me)₂ |
| 192 | Negative charge | pyrrolidine, N⁺(Me)₂ | 205 | H | piperidine-2-CONH₂, NH |

TABLE 9-continued
| No. | R¹ | | No. | R¹ | |
|---|---|---|---|---|---|
| 193 | Negative charge | 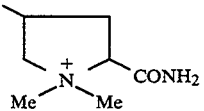 | 206 | H | 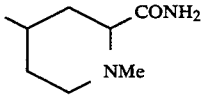 |
| 194 | Negative charge | 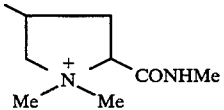 | 207 | Negative charge | 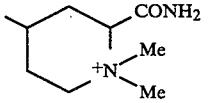 |
TABLE 10
| No. | R¹ | | No. | R¹ | |
|---|---|---|---|---|---|
| 208 | H | 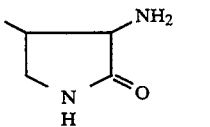 | 219 | H | 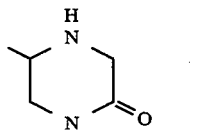 |
| 209 | H | 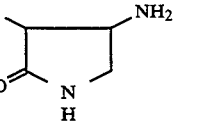 | 220 | H | 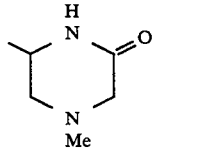 |
| 210 | H | 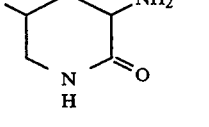 | 221 | H | 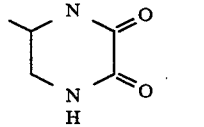 |
| 211 | H | 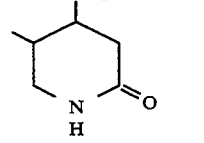 | 222 | H | 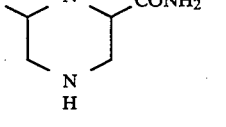 |
| 212 | H | 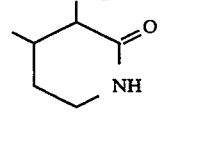 | 223 | H | 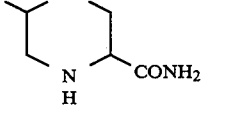 |
| 213 | H | 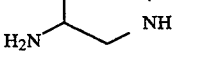 | 224 | H | 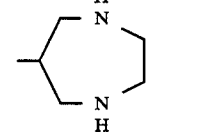 |

TABLE 10-continued

| No. | R¹ | (structure) | No. | R¹ | (structure) |
|---|---|---|---|---|---|
| 214 | H | piperazine (3-yl, NH, NH) | 225 | H | 1,4-diazepan-5-one (NH, NH, C=O) |
| 215 | H | 3-methylpiperazine (NMe top, NH bottom) | 226 | H | 2,3-dioxo-1,4-diazepane |
| 216 | H | 3-methyl... piperazine (NH, NMe) | 227 | H | 1,4-diazepane-2-carboxamide (CONH₂) |
| 217 | H | 1,4-dimethylpiperazine (NMe, NMe) | 228 | H | hydantoin (HN, NH, C=O) |
| 218 | H | piperazin-2-one (NH, NH, =O) | 229 | H | pyrazolidin-3-one (HN, NH, =O) |

TABLE 11

| No. | R¹ | (structure) | No. | R¹ | (structure) |
|---|---|---|---|---|---|
| 230 | H | pyrazolidinone | 241 | H | 1-(2-hydroxyethyl)piperidine (N-CH₂CH₂OH) |
| 231 | H | NCH₂CONH₂ | 242 | H | NCH₂CH₂OH |
| 232 | H | NCH₂CONMe | 243 | Negative charge | ⁺N(Me)₂ (N,N-dimethylpiperidinium) |

TABLE 11-continued
| No. | R¹ | (structure) | No. | R¹ | (structure) |
|---|---|---|---|---|---|
| 233 | H | 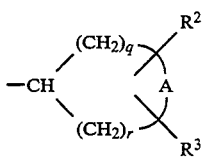 | 244 | H | 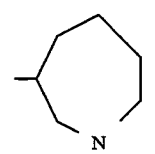 |
| 234 | H | 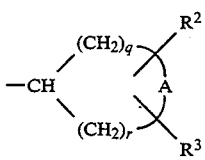 | 245 | H | 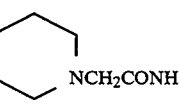 |
| 235 | H | 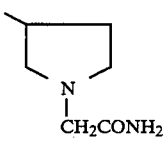 | 246 | H | 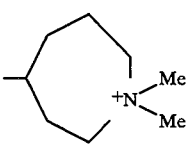 |
| 236 | H | 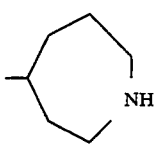 | 247 | H | 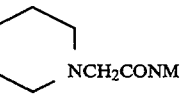 |
| 237 | H | 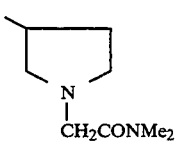 | 248 | Negative charge | 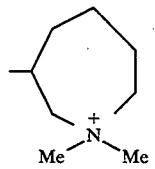 |
| 238 | H | 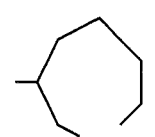 | 249 | Negative charge | 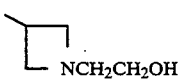 |
| 239 | H | 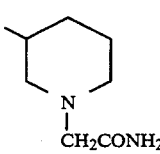 | 250 | H | 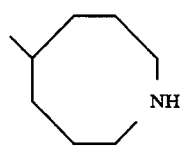 |
| 240 | H | 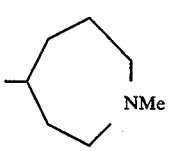 | 251 | H | 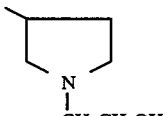 |

TABLE 12

| No. | R¹ | structure | No. | R¹ | structure |
|---|---|---|---|---|---|
| 252 | H | azocane (NH) | 256 | Negative charge | azocanium N⁺Me₂ |
| 253 | H | azocane-CH₂NMe | 257 | Negative charge | azocane-CH₂N⁺Me₂ |
| 254 | H | azocane N-Me | 258 | Negative charge | azocane N⁺Me₂ |
| 255 | H | azocane N-Me (isomer) | | | |

TABLE 13

| No. | R¹ | structure | No. | R¹ | structure |
|---|---|---|---|---|---|
| 259 | H | azetidine (HN) | 271 | H | pyrrolidine (NH) |
| 260 | H | azetidine (MeN) | 272 | H | pyrrolidine (NMe) |

TABLE 13-continued

[Structure: carbapenem core with 1-hydroxyethyl group, attached via S to a pyrrolidine (NH) bearing a -CH₂-CH< group with (CH₂)q-R² and (CH₂)r-R³ branches connected through A]

| No. | R¹ | substituent | No. | R¹ | substituent |
|---|---|---|---|---|---|
| 261 | H | azetidine with HN=CHN | 273 | H | pyrrolidine N-CH=NH |
| 262 | H | azetidine with Me(HN=)CN | 274 | H | pyrrolidine N-C(=NH)Me |
| 263 | H | azetidine-NH | 275 | H | piperidine HN |
| 264 | H | azetidine-NMe | 276 | H | piperidine MeN |
| 265 | H | azetidine-NCH=NH | 277 | H | piperidine HN=HCN |
| 266 | H | azetidine-NC(=NH)Me | 278 | H | piperidine NH |
| 267 | H | pyrrolidine HN | 279 | H | piperidine NMe |
| 268 | H | pyrrolidine MeN | 280 | H | piperidine NCH=NH |
| 269 | H | pyrrolidine HN=HCN | 281 | H | piperidine NH |
| 270 | H | pyrrolidine Me(HN=)CN | 282 | H | piperidine NMe |

TABLE 14
| No. | R¹ | ![structure] | No. | R¹ | ![structure] |
|---|---|---|---|---|---|
| 283 | H | 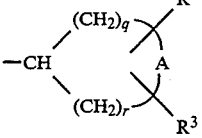 | 297 | H | 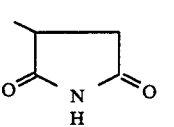 |
| 284 | H | 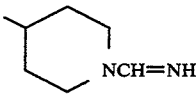 | 298 | H | 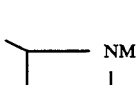 |
| 285 | H | 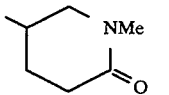 | 299 | H |  |
| 286 | H | 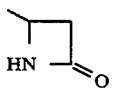 | 300 | H | 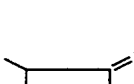 |
| 287 | H | 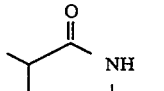 | 301 | H | 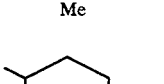 |
| 288 | H | 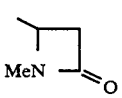 | 302 | H | 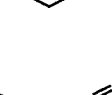 |
| 289 | H | 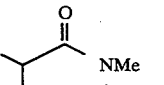 | 303 | H | 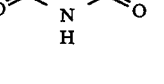 |
| 290 | H | 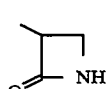 | 304 | H | 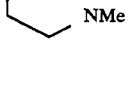 |
| 291 | H | 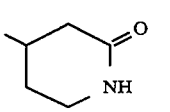 | 305 | H | 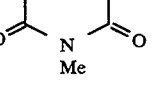 |
| 292 | H | 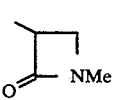 | 306 | H | 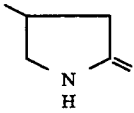 |
| 293 | H | 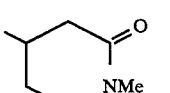 | 307 | H | 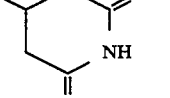 |

TABLE 14-continued
| No. | R¹ | (structure) | No. | R¹ | (structure) |
|---|---|---|---|---|---|
| 294 | H | 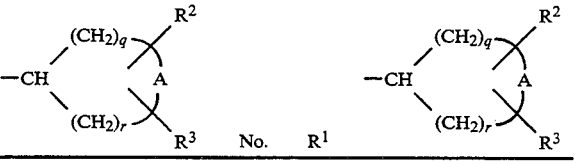 | 308 | H | 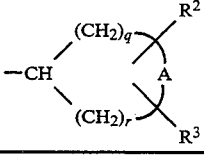 |
| 295 | H | 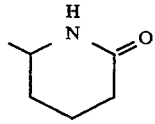 | 309 | H | 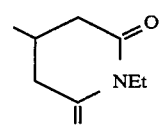 |
| 296 | H | 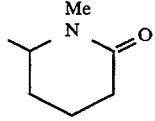 | 310 | H | 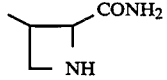 |
TABLE 15
| No. | R¹ | (structure) | No. | R¹ | (structure) |
|---|---|---|---|---|---|
| 311 | H | 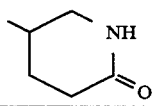 | 324 | Negative charge | 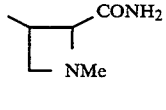 |
| 312 | H |  | 325 | Negative charge | 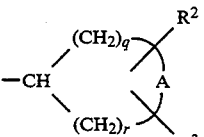 |
| 313 | H | 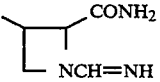 | 326 | Negative charge | 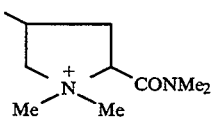 |
| 314 | H | 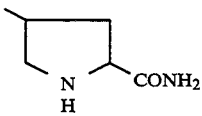 | 327 | H | 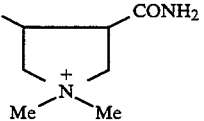 |
| 315 | H | 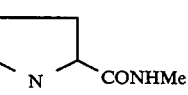 | 328 | H | 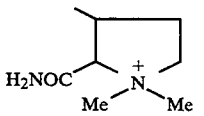 |
| 316 | H | 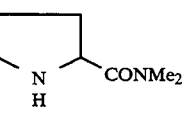 | 329 | H | 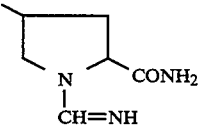 |

TABLE 15-continued

| No. | R¹ | (structure) | No. | R¹ | (structure) |
|---|---|---|---|---|---|
| 317 | H | pyrrolidine-3-CONH₂, NH | 330 | H | piperidine-2-CONH₂, NH |
| 318 | H | pyrrolidine-3-CONH₂, N-Me | 331 | H | piperidine-2-CONH₂, N-Me |
| 319 | H | pyrrolidine-2-CONH₂, NH | 332 | Negative charge | N,N-dimethylpiperidinium |
| 320 | H | pyrrolidine-2-CONH₂, N-Me | 333 | Negative charge | N,N-dimethylpiperidinium-2-CONH₂ |
| 321 | Negative charge | N,N-dimethylpyrrolidinium | 334 | H | 2-CONH₂ azepane, NH |
| 322 | Negative charge | N,N-dimethylpyrrolidinium-2-CONH₂ | 335 | H | 2-CONH₂ azepane, N-Me |
| 323 | Negative charge | N,N-dimethylpyrrolidinium-2-CONHMe | 336 | Negative charge | N,N-dimethyl azepanium-2-CONH₂ |

TABLE 16

| No. | R¹ | (structure) | No. | R¹ | (structure) |
|---|---|---|---|---|---|
| 337 | H | 3-NH₂ pyrrolidin-2-one, NH | 348 | H | piperazin-2-one |

TABLE 16-continued

| No. | R¹ | structure | No. | R¹ | structure |
|---|---|---|---|---|---|
| 338 | H | 3-methyl-4-amino-pyrrolidin-2-one | 349 | H | 5-methyl-3-oxo-piperazine |
| 339 | H | 5-methyl-3-amino-piperidin-2-one | 350 | H | 5-methyl-2,3-dioxo-piperazine |
| 340 | H | 5-methyl-4-amino-piperidin-2-one | 351 | H | 5-methyl-piperazine-3-carboxamide |
| 341 | H | 3-methyl-2-amino-piperidin-6-one | 352 | H | 5-methyl-piperazine-2-carboxamide |
| 342 | H | 4-methyl-5-amino-piperidin-2-one | 353 | H | 6-methyl-1,4-diazepane |
| 343 | H | 5-methyl-piperazine | 354 | H | 6-methyl-3-oxo-1,4-diazepane |
| 344 | H | 5-methyl-4-N-methyl-piperazine | 355 | H | 6-methyl-2,3-dioxo-1,4-diazepane |
| 345 | H | 5-methyl-1-N-methyl-piperazine | 356 | H | 6-methyl-1,4-diazepane-2-carboxamide |
| 346 | H | 5-methyl-1,4-N,N-dimethyl-piperazine | 357 | H | 5-methyl-hydantoin |

TABLE 16-continued

| | | $-CH\underset{(CH_2)_r}{\overset{(CH_2)_q}{\diagup}}\underset{R^3}{\overset{R^2}{\diagdown}}A$ | | | $-CH\underset{(CH_2)_r}{\overset{(CH_2)_q}{\diagup}}\underset{R^3}{\overset{R^2}{\diagdown}}A$ |
|---|---|---|---|---|---|
| No. | R¹ | | No. | R¹ | |
| 347 | H | 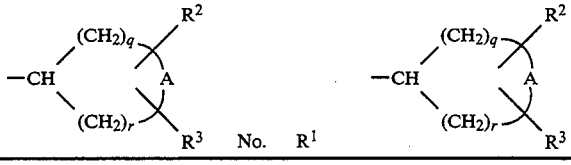 | 358 | H | 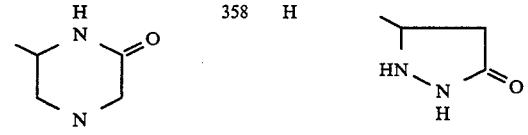 |

TABLE 17

| | | $-CH\underset{(CH_2)_r}{\overset{(CH_2)_q}{\diagup}}\underset{R^3}{\overset{R^2}{\diagdown}}A$ | | | $-CH\underset{(CH_2)_r}{\overset{(CH_2)_q}{\diagup}}\underset{R^3}{\overset{R^2}{\diagdown}}A$ |
|---|---|---|---|---|---|
| No. | R¹ | | No. | R¹ | |
| 359 | H | 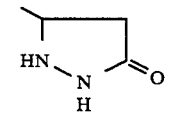 | 370 | H | 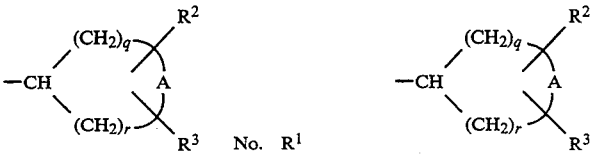 |
| 360 | H | 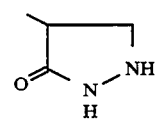 | 371 | H | 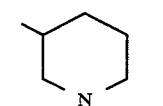 |
| 361 | H | 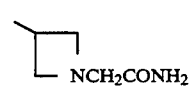 | 372 | Negative charge | 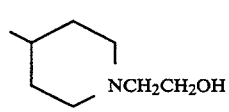 |
| 362 | H | 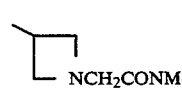 | 373 | H | 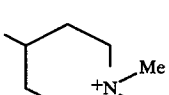 |
| 363 | H | 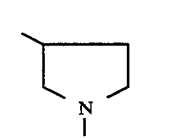 | 374 | H | 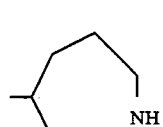 |
| 364 | H | 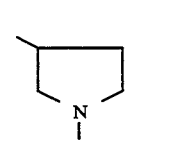 | 375 | H | 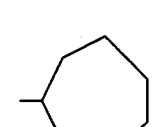 |
| 365 | H | 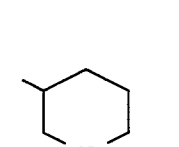 | 376 | H | 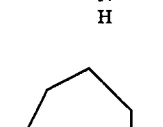 |

TABLE 17-continued

| No. | R¹ | (structure) | No. | R¹ | (structure) |
|---|---|---|---|---|---|
| 366 | H | cyclohexyl-NCH$_2$CONH$_2$ | 377 | Negative charge | azepane-N$^+$(Me)(Me) |
| 367 | H | cyclohexyl-NCH$_2$CONMe | 378 | Negative charge | azepane-N$^+$(Me)(Me) |
| 368 | H | azetidine-NCH$_2$CH$_2$OH | 379 | H | azocane-NH |
| 369 | H | pyrrolidine-N-CH$_2$CH$_2$OH | 380 | H | azocane-NH |

TABLE 18

| No. | R¹ | (structure) | No. | R¹ | (structure) |
|---|---|---|---|---|---|
| 381 | H | azocane-NH | 385 | Negative charge | azocane-N$^+$(Me)(Me) |
| 382 | H | azocane-NMe | 386 | Negative charge | azocane-N$^+$(Me)(Me) |
| 383 | H | azocane-NMe | 387 | Negative charge | azocane-N$^+$(Me)(Me) |

TABLE 18-continued
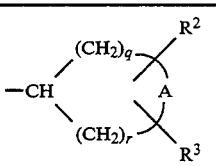
| No. | R¹ | 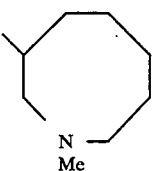 | No. | R¹ | |
|---|---|---|---|---|---|
| 384 | H | (N-Me azocane, methyl on ring) | | | |
TABLE 19
(carbapenem-pyrrolidine-thio core structure with substituent chain)
| No. | R¹ | | No. | R¹ | |
|---|---|---|---|---|---|
| 388 | H |  HN | 400 | H | 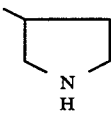 N-H |
| 389 | H | MeN | 401 | H | N-Me |
| 390 | H | 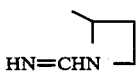 HN=CHN | 402 | H | 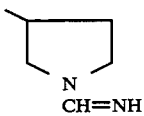 N-CH=NH |
| 391 | H | 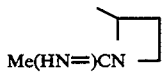 Me(HN=)CN | 403 | H | 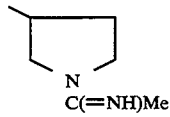 N-C(=NH)Me |
| 392 | H |  NH | 404 | H | 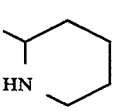 HN |
| 393 | H | 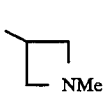 NMe | 405 | H | 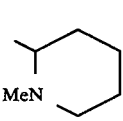 MeN |
| 394 | H |  NCH=NH | 406 | H | 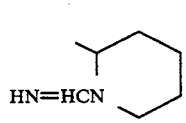 HN=HCN |

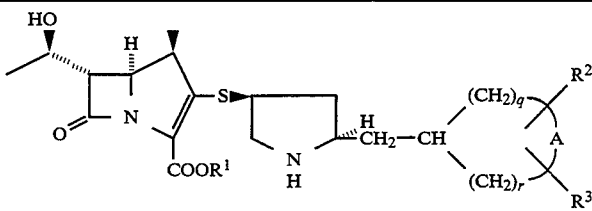

TABLE 20-continued
| No. | R¹ | structure | No. | R¹ | structure |
|---|---|---|---|---|---|
| 415 | H | 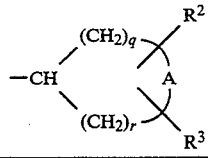 | 429 | H | 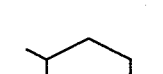 |
| 416 | H | 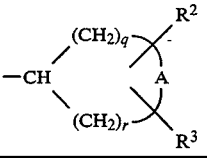 | 430 | H | 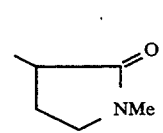 |
| 417 | H |  | 431 | H | 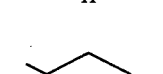 |
| 418 | H | 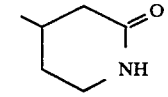 | 432 | H |  |
| 419 | H | 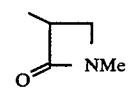 | 433 | H |  |
| 420 | H | 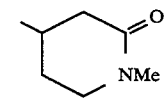 | 434 | H | 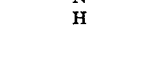 |
| 421 | H |  | 435 | H | 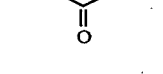 |
| 422 | H |  | 436 | H | 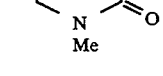 |
| 423 | H |  | 437 | H | 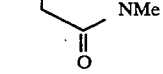 |
| 424 | H | 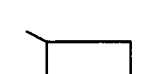 | 438 | H | 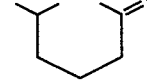 |

TABLE 20-continued

| No. | R¹ | (structure) | No. | R¹ | (structure) |
|---|---|---|---|---|---|
| 425 | H | 4-methylpiperidin-2-one ring (NH, C=O) | 439 | H | azetidine with CONH₂ and NMe |

TABLE 21

| No. | R¹ | (structure) | No. | R¹ | (structure) |
|---|---|---|---|---|---|
| 440 | H | azetidine with CONH₂ and NCH=NH | 453 | Negative charge | pyrrolidinium N⁺(Me)(Me) with CONMe₂ |
| 441 | H | pyrrolidine-2-carboxamide (NH), CONH₂ | 454 | Negative charge | pyrrolidinium N⁺(Me)(Me) with CONH₂ |
| 442 | H | pyrrolidine (NH) with CONHMe | 455 | Negative charge | pyrrolidinium N⁺(Me)(Me) with H₂NOC |
| 443 | H | pyrrolidine (NH) with CONMe₂ | 456 | H | pyrrolidine with CONH₂, N–CH=NH |
| 444 | H | pyrrolidine (NMe) with CONH₂ | 457 | H | pyrrolidine with CONH₂, N–CH=NH |
| 445 | H | pyrrolidine (NMe) with CONMe₂ | 458 | H | pyrrolidine with H₂NOC, N–CH=NH |
| 446 | H | pyrrolidine (NH) with CONH₂ | 459 | H | piperidine (NH) with CONH₂ |
| 447 | H | pyrrolidine (NMe) with CONH₂ | 460 | H | piperidine (NMe) with CONH₂ |

TABLE 21-continued

| No. | R¹ | structure | No. | R¹ | structure |
|---|---|---|---|---|---|
| 448 | H | pyrrolidine with H₂NOC, NH | 461 | Negative charge | N-methylpiperidinium, N⁺Me₂ |
| 449 | H | pyrrolidine with H₂NOC, N-Me | 462 | Negative charge | piperidinium with CONH₂, N⁺Me₂ |
| 450 | Negative charge | pyrrolidinium N⁺Me₂ | 463 | H | piperidine with CONH₂, NH |
| 451 | Negative charge | pyrrolidinium with CONH₂, N⁺Me₂ | 464 | H | piperidine with CONH₂, NMe |
| 452 | Negative charge | pyrrolidinium with CONHMe, N⁺Me₂ | 465 | Negative charge | piperidinium with CONH₂, N⁺Me₂ |

TABLE 22

| No. | R¹ | structure | No. | R¹ | structure |
|---|---|---|---|---|---|
| 466 | H | pyrrolidinone with NH₂ | 477 | H | piperazinone |
| 467 | H | pyrrolidinone with NH₂ | 478 | H | N-methylpiperazinone |
| 468 | H | piperidinone with NH₂ | 479 | H | piperazine-2,3-dione |

TABLE 22-continued

| No. | R¹ | (structure) | No. | R¹ | (structure) |
|---|---|---|---|---|---|
| 469 | H | 4-amino-5-methyl-piperidin-2-one | 480 | H | 5-methyl-piperazine-2-carboxamide |
| 470 | H | 2-amino-propanoyl-piperidine | 481 | H | 5-methyl-piperazine-2-carboxamide |
| 471 | H | 4-amino-3-methyl-piperidin-2-one | 482 | H | 5-methyl-1,4-diazepane |
| 472 | H | 3-methyl-piperazine | 483 | H | 6-methyl-1,4-diazepan-2-one |
| 473 | H | 1-methyl-3-methyl-piperazine | 484 | H | 6-methyl-1,4-diazepane-2,3-dione |
| 474 | H | 4-methyl-piperazine | 485 | H | 6-methyl-1,4-diazepane-2-carboxamide |
| 475 | H | 1,4-dimethyl-piperazine | 486 | H | hydantoin methyl derivative |
| 476 | H | 5-methyl-piperazin-2-one | 487 | H | 5-methyl-pyrazolidin-3-one |

TABLE 23

| No. | R¹ | structure | No. | R¹ | structure |
|---|---|---|---|---|---|
| 488 | H | 4-methyl-pyrazolidin-3-one (via CH₂) | 499 | H | 3-methylpiperidine N-CH₂CH₂OH |
| 489 | H | azetidine N-CH₂CONH₂ | 500 | H | 4-methylpiperidine N-CH₂CH₂OH |
| 490 | H | azetidine N-CH₂CONMe | 501 | Negative charge | 4-methyl-1,1-dimethylpiperidinium |
| 491 | H | pyrrolidine N-CH₂CONH₂ | 502 | H | 4-methylazepane NH |
| 492 | H | pyrrolidine N-CH₂CONMe₂ | 503 | H | 3-methylazepane NH |
| 493 | H | 3-methylpiperidine N-CH₂CONH₂ | 504 | H | 4-methylazepane N-Me |
| 494 | H | 3-methylpiperidine N-CH₂CONMe₂ | 505 | H | 3-methylazepane N-Me |
| 495 | H | 4-methylpiperidine N-CH₂CONH₂ | 506 | Negative charge | 4-methyl-1,1-dimethylazepanium |
| 496 | H | 4-methylpiperidine N-CH₂CONMe | 507 | Negative charge | 3-methyl-1,1-dimethylazepanium |

TABLE 23-continued
| | | (CH₂)q—A—R² / (CH₂)r—R³ attached to —CH— | | | | (CH₂)q—A—R² / (CH₂)r—R³ attached to —CH— |
|---|---|---|---|---|---|---|
| No. | R¹ | | | No. | R¹ | |
| 497 | H | 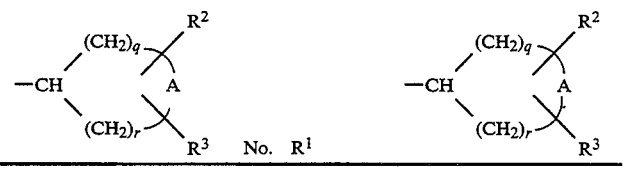 NCH₂CH₂OH | | 508 | H |  NH |
| 498 | H | 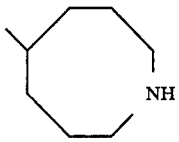 N—CH₂CH₂OH | | 509 | H | 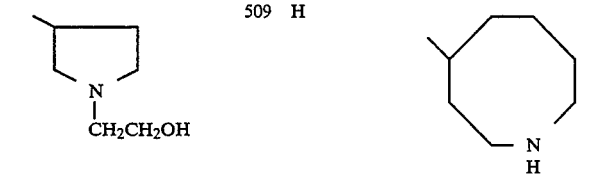 NH |
TABLE 24
| | | (CH₂)q—A—R² / (CH₂)r—R³ attached to —CH— | | | | (CH₂)q—A—R² / (CH₂)r—R³ attached to —CH— |
|---|---|---|---|---|---|---|
| No. | R¹ | | | No. | R¹ | |
| 510 | H | 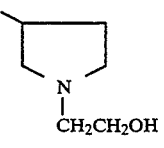 NH | | 514 | Negative charge | 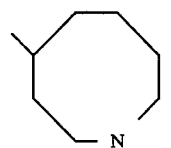 +N(Me)(Me) |
| 511 | H | 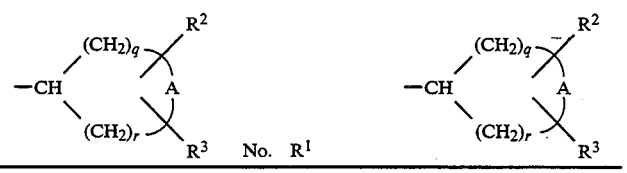 NMe | | 515 | Negative charge | 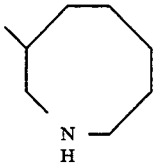 +N(Me)(Me) |
| 512 | H | 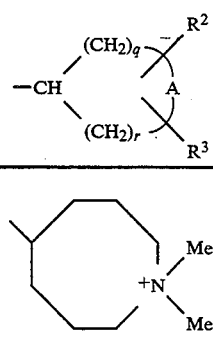 N—Me | | 516 | Negative charge | 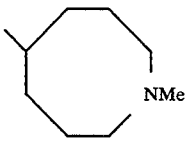 +N(Me)(Me) |
| 513 | H | 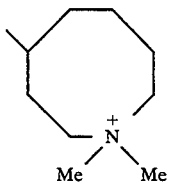 N—Me | | | | |

TABLE 25
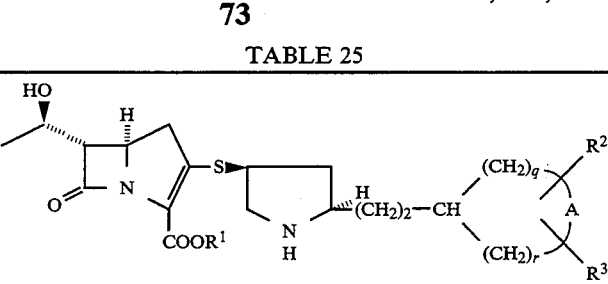
| No. | R¹ | (structure) | No. | R¹ | (structure) |
|---|---|---|---|---|---|
| 517 | H | HN⟨ring⟩ | 529 | H | ⟨ring⟩NH |
| 518 | H | MeN⟨ring⟩ | 530 | H | ⟨ring⟩NMe |
| 519 | H | HN=CHN⟨ring⟩ | 531 | H | ⟨ring⟩N-CH=NH |
| 520 | H | Me(HN=)CN⟨ring⟩ | 532 | H | ⟨ring⟩N-C(=NH)Me |
| 521 | H | ⟨ring⟩NH | 533 | H | HN⟨ring⟩ |
| 522 | H | ⟨ring⟩NMe | 534 | H | MeN⟨ring⟩ |
| 523 | H | ⟨ring⟩NCH=NH | 535 | H | HN=HCN⟨ring⟩ |
| 524 | H | ⟨ring⟩NC(=NH)Me | 536 | H | ⟨ring⟩NH |
| 525 | H | HN⟨ring⟩ | 537 | H | ⟨ring⟩NMe |
| 526 | H | MeN⟨ring⟩ | 538 | H | ⟨ring⟩NCH=NH |

TABLE 25-continued

[Structure: carbapenem core with HO-CH(CH₃)- group, COOR¹, linked via S to pyrrolidine-NH, with -(CH₂)₂-CH< bearing (CH₂)q-A(R²)-(CH₂)r-R³ ring]

| No. | R¹ | -CH<(CH₂)q-A(R²)/(CH₂)r-R³ | No. | R¹ | -CH<(CH₂)q-A(R²)/(CH₂)r-R³ |
|---|---|---|---|---|---|
| 527 | H | cyclopentane with HN=HCN | 539 | H | piperidine NH |
| 528 | H | cyclopentane with Me(HN=)CN | 540 | H | piperidine NMe |

TABLE 26

| No. | R¹ | ring | No. | R¹ | ring |
|---|---|---|---|---|---|
| 541 | H | cyclohexane with NCH=NH | 555 | H | piperidine NMe, with =O |
| 542 | H | β-lactam HN, =O | 556 | H | δ-lactam NH, =O |
| 543 | H | β-lactam MeN, =O | 557 | H | δ-lactam NMe, =O |
| 544 | H | β-lactam O=, NH | 558 | H | δ-lactam NH, =O (isomer) |
| 545 | H | β-lactam O=, NMe | 559 | H | δ-lactam NMe, =O (isomer) |
| 546 | H | γ-lactam NH, =O | 560 | H | succinimide (O=, NH, =O) |

TABLE 26-continued
| No. | R¹ | structure | No. | R¹ | structure |
|---|---|---|---|---|---|
| 547 | H | 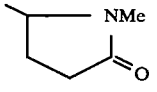 | 561 | H | 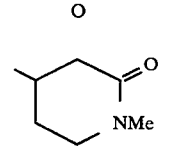 |
| 548 | H | 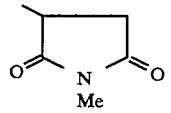 | 562 | H | 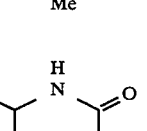 |
| 549 | H | 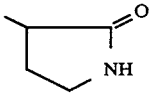 | 563 | H | 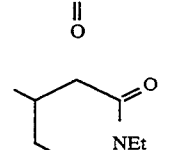 |
| 550 | H | 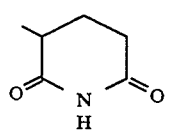 | 564 | H | 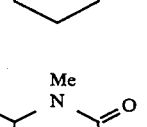 |
| 551 | H | 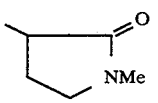 | 565 | H | 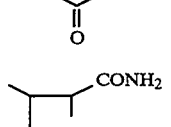 |
| 552 | H | 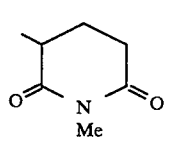 | 566 | H | 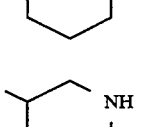 |
| 553 | H | 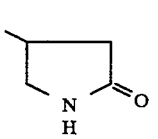 | 567 | H | 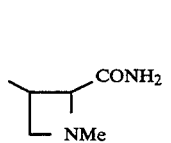 |
| 554 | H | 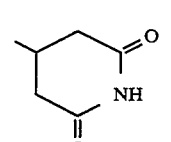 | 568 | H | 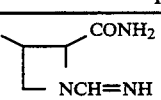 |
TABLE 27
| No. | R¹ | structure | No. | R¹ | structure |
|---|---|---|---|---|---|
| 569 | H | 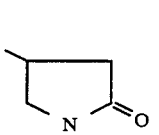 | 582 | Negative charge | 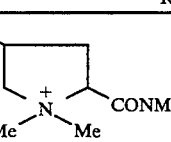 |

TABLE 27-continued

| No. | R¹ | (structure) | No. | R¹ | (structure) |
|---|---|---|---|---|---|
| 570 | H | pyrrolidine-2-CONH₂, NH | 583 | Negative charge | pyrrolidinium-3-CONH₂, N⁺(Me)(Me) |
| 571 | H | pyrrolidine-2-CONHMe, NH | 584 | Negative charge | pyrrolidinium-2-CONH₂ (H₂NOC-), N⁺(Me)(Me) |
| 572 | H | pyrrolidine-2-CONMe₂, NH | 585 | H | pyrrolidine-2-CONH₂, N-CH=NH |
| 573 | H | pyrrolidine-2-CONH₂, N-Me | 586 | H | pyrrolidine-3-CONH₂, N-CH=NH |
| 574 | H | pyrrolidine-2-CONMe₂, N-Me | 587 | H | pyrrolidine-2-CONH₂ (H₂NOC-), N-CH=NH |
| 575 | H | pyrrolidine-3-CONH₂, NH | 588 | H | piperidine-2-CONH₂, NH |
| 576 | H | pyrrolidine-3-CONH₂, N-Me | 589 | H | piperidine-2-CONH₂, N-Me |
| 577 | H | pyrrolidine-2-CONH₂ (H₂NOC-), NH | 590 | Negative charge | piperidinium, N⁺(Me)(Me) |
| 578 | H | pyrrolidine-2-CONH₂ (H₂NOC-), N-Me | 591 | Negative charge | piperidinium-2-CONH₂, N⁺(Me)(Me) |
| 579 | Negative charge | pyrrolidinium, N⁺(Me)(Me) | 592 | H | piperidine-2-CONH₂, NH |

TABLE 27-continued

| No. | R¹ | structure | No. | R¹ | structure |
|---|---|---|---|---|---|
| 580 | Negative charge | pyrrolidinium N,N-diMe, CONH₂ | 593 | H | piperidine NMe, CONH₂ |
| 581 | Negative charge | pyrrolidinium N,N-diMe, CONHMe | 594 | Negative charge | piperidinium N,N-diMe, CONH₂ |

TABLE 28

| No. | R¹ | structure | No. | R¹ | structure |
|---|---|---|---|---|---|
| 595 | H | 3-amino-pyrrolidin-2-one | 606 | H | piperazin-2-one |
| 596 | H | 3-amino-4-methyl-pyrrolidin-2-one | 607 | H | 4-methyl-piperazin-2-one |
| 597 | H | 3-amino-piperidin-2-one | 608 | H | piperazine-2,3-dione |
| 598 | H | 4-amino-piperidin-2-one | 609 | H | piperazine-2-carboxamide |
| 599 | H | 3-amino-piperidin-2-one (isomer) | 610 | H | piperazine-2-carboxamide (isomer) |
| 600 | H | 4-amino-piperidin-2-one (isomer) | 611 | H | 1,4-diazepane |

TABLE 28-continued

| No. | R¹ | structure | No. | R¹ | structure |
|---|---|---|---|---|---|
| 601 | H | piperazine (3-Me, NH) | 612 | H | 1,4-diazepan-2-one (methyl-substituted) |
| 602 | H | piperazine (3-Me, N-Me top) | 613 | H | 1,4-diazepane-2,3-dione |
| 603 | H | piperazine (3-Me, N-Me bottom) | 614 | H | 1,4-diazepane with CONH₂ |
| 604 | H | piperazine (N,N'-diMe) | 615 | H | imidazolidin-2-one (Me-substituted) |
| 605 | H | piperazin-2-one (Me-substituted) | 616 | H | pyrazolidin-3-one (Me-substituted) |

TABLE 29

| No. | R¹ | structure | No. | R¹ | structure |
|---|---|---|---|---|---|
| 617 | H | pyrazolidin-3-one | 628 | H | N-(2-hydroxyethyl)piperidine (3-Me) |
| 618 | H | azetidine-NCH₂CONH₂ | 629 | H | N-(2-hydroxyethyl)cyclohexylamine |
| 619 | H | azetidine-NCH₂CONMe | 630 | Negative charge | 4-Me-piperidinium N⁺Me₂ |

TABLE 29-continued
| No. | R¹ | (structure) | No. | R¹ | (structure) |
|---|---|---|---|---|---|
| 620 | H | 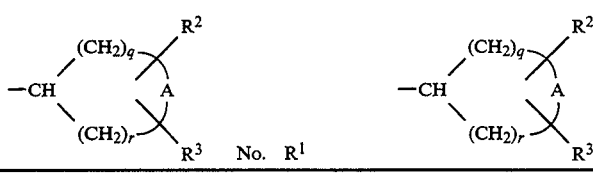 pyrrolidine N-CH₂CONH₂ | 631 | H | 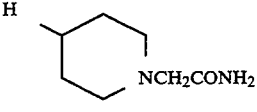 azepane NH |
| 621 | H | 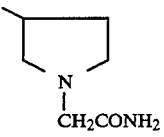 pyrrolidine N-CH₂CONMe₂ | 632 | H | 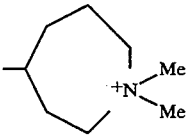 azepane NH |
| 622 | H | 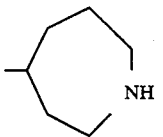 piperidine N-CH₂CONH₂ | 633 | H | 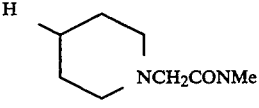 azepane NMe |
| 623 | H | 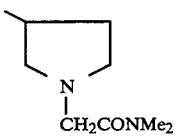 piperidine N-CH₂CONMe₂ | 634 | H | 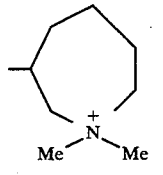 azepane N-Me |
| 624 | H | 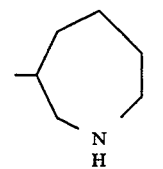 NCH₂CONH₂ | 635 | Negative charge | 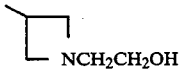 +N(Me)₂ |
| 625 | H | 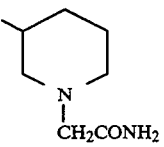 NCH₂CONMe | 636 | Negative charge | 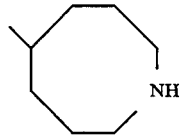 +N(Me)₂ |
| 626 | H | 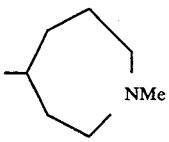 NCH₂CH₂OH | 637 | H | 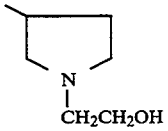 NH |
| 627 | H | 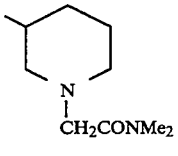 pyrrolidine N-CH₂CH₂OH | 638 | H | 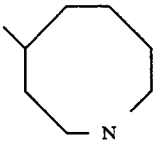 NH |

TABLE 30

Structure: -CH with (CH2)q-R2 and (CH2)r-R3 branches connected through A

| No. | R¹ | Structure | No. | R¹ | Structure |
|-----|----|-----------|----|----|-----------|
| 639 | H | 8-membered ring with NH | 643 | Negative charge | 8-membered ring with N⁺(Me)₂ |
| 640 | H | 8-membered ring with NMe | 644 | Negative charge | 8-membered ring with N⁺(Me)₂ |
| 641 | H | 8-membered ring with N-Me | 645 | Negative charge | 8-membered ring with N⁺(Me)₂ |
| 642 | H | 8-membered ring with N-Me | | | |

TABLE 31

Structure: Carbapenem core with HO-CH(CH₃)- group, β-lactam ring fused to pyrroline with COOR¹, S linked to pyrrolidine (NH), connected via (CH₂)₂-CH to ring bearing (CH₂)q-R² and (CH₂)r-R³ through A.

| No. | R¹ | Structure | No. | R¹ | Structure |
|-----|----|-----------|----|----|-----------|
| 646 | H | 4-membered ring with HN | 658 | H | 5-membered ring with NH |
| 647 | H | 4-membered ring with MeN | 659 | H | 5-membered ring with N-Me |

TABLE 31-continued

| No. | R¹ | [structure] | No. | R¹ | [structure] |
|---|---|---|---|---|---|
| 648 | H | HN=CHN (azetidine) | 660 | H | pyrrolidine N-CH=NH |
| 649 | H | Me(HN=)CN (azetidine) | 661 | H | pyrrolidine N-C(=NH)Me |
| 650 | H | azetidine-NH | 662 | H | piperidine HN |
| 651 | H | azetidine-NMe | 663 | H | piperidine MeN |
| 652 | H | azetidine-NCH=NH | 664 | H | piperidine HN=HCN |
| 653 | H | azetidine-NC(=NH)Me | 665 | H | piperidine NH |
| 654 | H | pyrrolidine HN | 666 | H | piperidine NMe |
| 655 | H | pyrrolidine MeN | 667 | H | piperidine NCH=NH |
| 656 | H | pyrrolidine HN=HCN | 668 | H | piperidine NH |
| 657 | H | pyrrolidine Me(HN=)CN | 669 | H | piperidine NMe |

TABLE 32
| No. | R¹ | | No. | R¹ | |
|---|---|---|---|---|---|
| 670 | H | 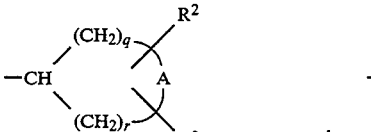 | 684 | H | 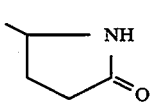 |
| 671 | H | 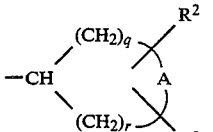 | 685 | H | 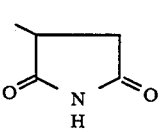 |
| 672 | H | 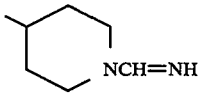 | 686 | H | 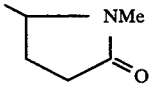 |
| 673 | H | 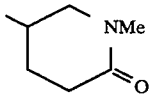 | 687 | H | 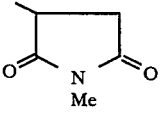 |
| 674 | H | 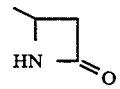 | 688 | H | 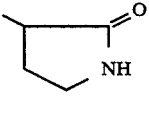 |
| 675 | H | 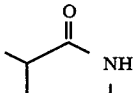 | 689 | H | 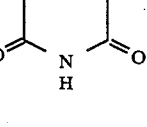 |
| 676 | H | 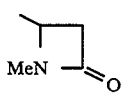 | 690 | H | 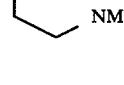 |
| 677 | H | 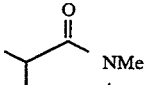 | 691 | H | 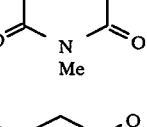 |
| 678 | H | 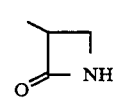 | 692 | H | 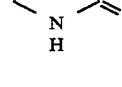 |
| 679 | H | 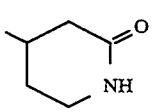 | 693 | H | 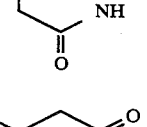 |
| 680 | H | 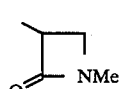 | 694 | H | 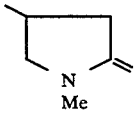 |

TABLE 32-continued

| No. | R¹ | structure | No. | R¹ | structure |
|---|---|---|---|---|---|
| 681 | H | 6-methyl-piperidin-2-one | 695 | H | 5-methyl-N-ethyl-glutarimide-like |
| 682 | H | 1,6-dimethyl-piperidin-2-one | 696 | H | azetidine-2-carboxamide |
| 683 | H | 5-methyl-piperidin-2-one (NH-C=O) | 697 | H | 1-methyl-azetidine-2-carboxamide |

TABLE 33

| No. | R¹ | structure | No. | R¹ | structure |
|---|---|---|---|---|---|
| 698 | H | azetidine-2-carboxamide, N-CH=NH | 711 | Negative charge | 1,1-dimethyl-pyrrolidinium-2-CONMe₂ |
| 699 | H | pyrrolidine-2-CONH₂, NH | 712 | Negative charge | 1,1-dimethyl-pyrrolidinium-3-CONH₂ |
| 700 | H | pyrrolidine-2-CONHMe, NH | 713 | Negative charge | 1,1-dimethyl-pyrrolidinium-2-CONH₂ |
| 701 | H | pyrrolidine-2-CONMe₂, NH | 714 | H | pyrrolidine-2-CONH₂, N-CH=NH |
| 702 | H | 1-methyl-pyrrolidine-2-CONH₂ | 715 | H | pyrrolidine-3-CONH₂, N-CH=NH |
| 703 | H | 1-methyl-pyrrolidine-2-CONMe₂ | 716 | H | pyrrolidine-2-CONH₂, N-CH=NH |

TABLE 33-continued

| No. | R¹ | —CH<(CH₂)q / (CH₂)r>A<R²/R³ | No. | R¹ | —CH<(CH₂)q / (CH₂)r>A<R²/R³ |
|---|---|---|---|---|---|
| 704 | H | pyrrolidine-3-CONH₂ (NH) | 717 | H | piperidine-2-CONH₂ (NH) |
| 705 | H | pyrrolidine-3-CONH₂ (NMe) | 718 | H | piperidine-2-CONH₂ (NMe) |
| 706 | H | H₂NOC-pyrrolidine-2 (NH) | 719 | Negative charge | N,N-dimethylpiperidinium |
| 707 | H | H₂NOC-pyrrolidine-2 (NMe) | 720 | Negative charge | N,N-dimethyl-2-CONH₂-piperidinium |
| 708 | Negative charge | N,N-dimethylpyrrolidinium | 721 | H | 2-CONH₂-piperidine (NH) |
| 709 | Negative charge | N,N-dimethyl-2-CONH₂-pyrrolidinium | 722 | H | 2-CONH₂-piperidine (NMe) |
| 710 | Negative charge | N,N-dimethyl-2-CONHMe-pyrrolidinium | 723 | Negative charge | N,N-dimethyl-2-CONH₂-piperidinium |

TABLE 34

| No. | R¹ | —CH<(CH₂)q / (CH₂)r>A<R²/R³ | No. | R¹ | —CH<(CH₂)q / (CH₂)r>A<R²/R³ |
|---|---|---|---|---|---|
| 724 | H | 3-NH₂-pyrrolidin-2-one (NH) | 735 | H | piperazin-2-one (NH, NH) |

TABLE 34-continued
| No. | R¹ | structure | No. | R¹ | structure |
|---|---|---|---|---|---|
| 725 | H | 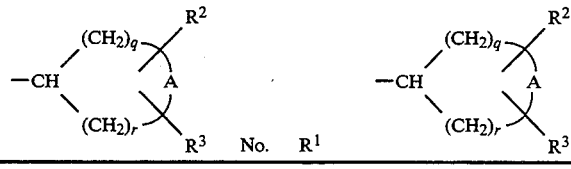 | 736 | H | 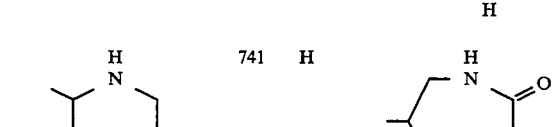 |
| 726 | H | 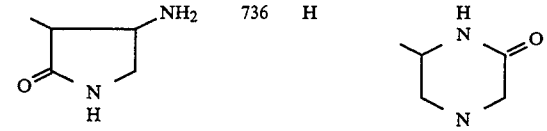 | 737 | H | 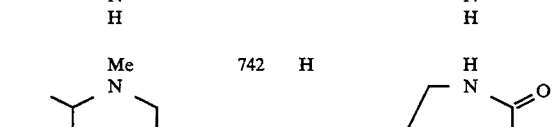 |
| 727 | H | | 738 | H | |
| 728 | H | 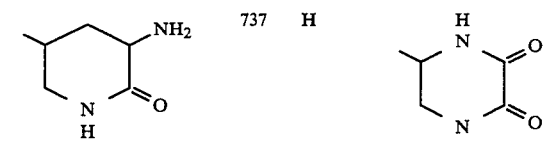 | 739 | H | 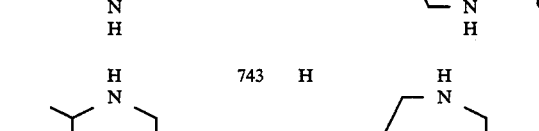 |
| 729 | H | 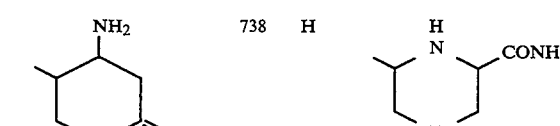 | 740 | H | 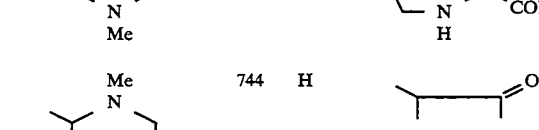 |
| 730 | H | | 741 | H | |
| 731 | H | 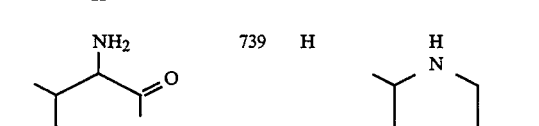 | 742 | H |  |
| 732 | H | | 743 | H | |
| 733 | H | 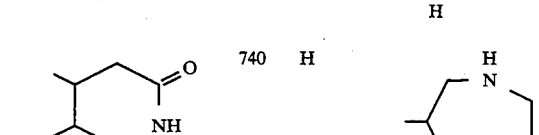 | 744 | H |  |

TABLE 34-continued

| No. | R¹ | (structure) | No. | R¹ | (structure) |
|---|---|---|---|---|---|
| 734 | H | 6-methyl-piperazin-2-one (attached via ring carbon) | 745 | H | 5-methyl-pyrazolidin-3-one (attached via ring carbon) |

TABLE 35

| No. | R¹ | (structure) | No. | R¹ | (structure) |
|---|---|---|---|---|---|
| 746 | H | 5-methyl-pyrazolidin-3-one | 757 | H | 3-methyl-1-(2-hydroxyethyl)piperidine |
| 747 | H | azetidine-N-CH₂CONH₂ | 758 | H | 4-methyl-1-(2-hydroxyethyl)piperidine |
| 748 | H | azetidine-NCH₂CONMe | 759 | Negative charge | 4-methyl-1,1-dimethylpiperidinium (+NMe₂) |
| 749 | H | pyrrolidine-N-CH₂CONH₂ | 760 | H | hexahydroazepine (NH) |
| 750 | H | pyrrolidine-N-CH₂CONMe₂ | 761 | H | hexahydroazepine (NH) isomer |
| 751 | H | piperidine-N-CH₂CONH₂ | 762 | H | N-methyl hexahydroazepine |
| 752 | H | piperidine-N-CH₂CONMe₂ | 763 | H | N-methyl hexahydroazepine isomer |

TABLE 35-continued

| No. | R¹ | (structure) | No. | R¹ | (structure) |
|---|---|---|---|---|---|
| 753 | H | cyclohexyl-NCH₂CONH₂ | 764 | Negative charge | azocane ring with +N(Me)Me |
| 754 | H | cyclohexyl-NCH₂CONMe | 765 | Negative charge | azocane ring with +N(Me)Me |
| 755 | H | cyclobutyl-NCH₂CH₂OH | 766 | H | azocane ring with NH |
| 756 | H | pyrrolidine N-CH₂CH₂OH | 767 | H | azocane ring with NH |

TABLE 36

| No. | R¹ | (structure) | No. | R¹ | (structure) |
|---|---|---|---|---|---|
| 768 | H | azocane with NH | 772 | Negative charge | azocane with +N(Me)Me |
| 769 | H | azocane with NMe | 773 | Negative charge | azocane with +N(Me)Me |
| 770 | H | azocane with N-Me | 774 | Negative charge | azocane with +N(Me)Me |

TABLE 36-continued

| No. | R¹ | ![structure](−CH with (CH₂)q, A, (CH₂)r, R², R³) |
|-----|----|----|
| 771 | H | 8-membered ring with N-Me |

TABLE 37

[Structure: carbapenem with HO-CH(Me)- group, COOR¹, S-pyrrolidine-(CH₂)₃-CH with (CH₂)q-A-(CH₂)r bearing R² and R³]

| No. | R¹ | R³ ring | No. | R¹ | R³ ring |
|-----|----|---------|-----|----|---------|
| 775 | H | azetidine, HN | 787 | H | pyrrolidine, NH |
| 776 | H | azetidine, MeN | 788 | H | pyrrolidine, N-Me |
| 777 | H | azetidine, HN=CHN | 789 | H | pyrrolidine, N-CH=NH |
| 778 | H | azetidine, Me(HN=)CN | 790 | H | pyrrolidine, N-C(=NH)Me |
| 779 | H | azetidine, NH | 791 | H | piperidine, HN |
| 780 | H | azetidine, NMe | 792 | H | piperidine, MeN |
| 781 | H | azetidine, NCH=NH | 793 | H | piperidine, HN=HCN |

TABLE 37-continued

[Structure of parent compound with substituents R¹, R², R³, A, (CH₂)q, (CH₂)r]

| No. | R¹ | substituent | No. | R¹ | substituent |
|---|---|---|---|---|---|
| 782 | H | —CH<(CH₂)-NC(=NH)Me ring | 794 | H | piperidine-NH |
| 783 | H | pyrrolidine HN | 795 | H | piperidine-NMe |
| 784 | H | pyrrolidine MeN | 796 | H | piperidine-NCH=NH |
| 785 | H | pyrrolidine HN=HCN | 797 | H | piperidine-NH |
| 786 | H | pyrrolidine Me(HN=)CN | 798 | H | piperidine-NMe |

TABLE 38

| No. | R¹ | substituent | No. | R¹ | substituent |
|---|---|---|---|---|---|
| 799 | H | cyclohexyl-NCH=NH | 813 | H | piperidinone-NMe |
| 800 | H | β-lactam HN,O | 814 | H | piperidinone NH |
| 801 | H | β-lactam MeN,O | 815 | H | piperidinone NMe |

TABLE 38-continued

| No. | R¹ | structure | No. | R¹ | structure |
|---|---|---|---|---|---|
| 802 | H | (2-oxo-azetidin-3-yl, NH) | 816 | H | (4-methyl-2-oxo-piperidin-... NH) |
| 803 | H | (2-oxo-1-methyl-azetidin-3-yl, NMe) | 817 | H | (4-methyl-2-oxo-piperidin-... NMe) |
| 804 | H | (3-amino-butanoyl, NH) | 818 | H | (succinimide, NH) |
| 805 | H | (3-methylamino-butanoyl, NMe) | 819 | H | (N-methyl succinimide, NMe) |
| 806 | H | (4-amino-butanoyl, NH) | 820 | H | (glutarimide, NH) |
| 807 | H | (4-methylamino-butanoyl, NMe) | 821 | H | (N-methyl glutarimide, NMe) |
| 808 | H | (pyrrolidin-2-one, NH) | 822 | H | (4-methyl-glutarimide, NH) |
| 809 | H | (1-methyl-pyrrolidin-2-one, NMe) | 823 | H | (N-methyl-4-methyl-glutarimide, NMe) |
| 810 | H | (piperidin-2-one, NH) | 824 | H | (N-ethyl-4-methyl-glutarimide, NEt) |
| 811 | H | (1-methyl-piperidin-2-one, NMe) | 825 | H | (β-amino, CONH₂) |

TABLE 38-continued
| No. | R¹ | (structure) | No. | R¹ | (structure) |
|---|---|---|---|---|---|
| 812 | H | 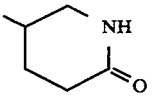 | 826 | H | 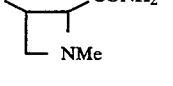 |
TABLE 39
| No. | R¹ | (structure) | No. | R¹ | (structure) |
|---|---|---|---|---|---|
| 827 | H | 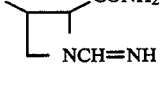 | 840 | Negative charge | 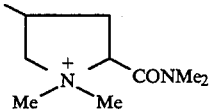 |
| 828 | H | 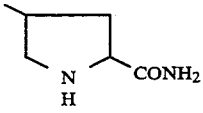 | 841 | Negative charge | 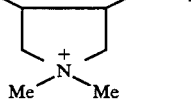 |
| 829 | H | 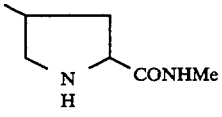 | 842 | Negative charge | 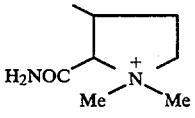 |
| 830 | H | 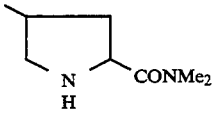 | 843 | H | 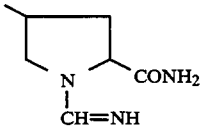 |
| 831 | H | 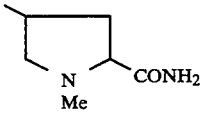 | 844 | H | 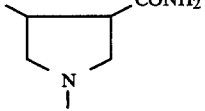 |
| 832 | H | 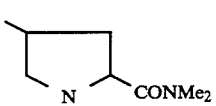 | 845 | H | 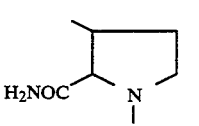 |
| 833 | H | 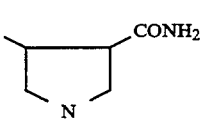 | 846 | H | 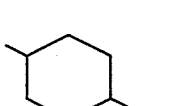 |
| 834 | H | 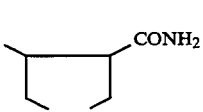 | 847 | H | 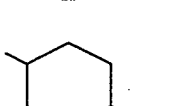 |

TABLE 39-continued

| No. | R¹ | structure | No. | R¹ | structure |
|---|---|---|---|---|---|
| 835 | H | 3-methyl pyrrolidine-2-carboxamide (H₂NOC, NH) | 848 | Negative charge | 3-methyl-N,N-dimethylpiperidinium |
| 836 | H | 3-methyl-1-methyl pyrrolidine-2-carboxamide (H₂NOC, NMe) | 849 | Negative charge | 5-methyl-N,N-dimethyl-2-carboxamide piperidinium |
| 837 | Negative charge | 3-methyl-N,N-dimethyl pyrrolidinium | 850 | H | 5-methyl-2-carboxamide piperidine (NH) |
| 838 | Negative charge | 3-methyl-N,N-dimethyl-2-carboxamide pyrrolidinium | 851 | H | 5-methyl-2-carboxamide-N-methylpiperidine |
| 839 | Negative charge | 3-methyl-N,N-dimethyl-2-(N-methylcarboxamide) pyrrolidinium (CONHMe) | 852 | Negative charge | 5-methyl-2-carboxamide-N,N-dimethylpiperidinium |

TABLE 40

| No. | R¹ | structure | No. | R¹ | structure |
|---|---|---|---|---|---|
| 853 | H | 3-amino-4-methyl-pyrrolidin-2-one | 864 | H | 5-methylpiperazin-2-one |
| 854 | H | 4-amino-3-methyl-pyrrolidin-2-one | 865 | H | 6-methyl-4-methyl-piperazin-2-one |
| 855 | H | 3-amino-5-methyl-piperidin-2-one | 866 | H | 6-methyl-piperazine-2,3-dione |

TABLE 40-continued

| No. | R¹ | structure | No. | R¹ | structure |
|---|---|---|---|---|---|
| 856 | H | 4-amino-5-methyl-piperidin-2-one | 867 | H | 5-methyl-piperazine-2-carboxamide |
| 857 | H | 3-amino-4-methyl-piperidin-2-one | 868 | H | 5-methyl-piperazine-2-carboxamide (isomer) |
| 858 | H | 4-amino-3-methyl-piperidin-2-one (variant) | 869 | H | 6-methyl-1,4-diazepane |
| 859 | H | 2-methyl-piperazine | 870 | H | 6-methyl-1,4-diazepan-2-one |
| 860 | H | 1,2-dimethyl-piperazine | 871 | H | 6-methyl-1,4-diazepane-2,3-dione |
| 861 | H | 1,3-dimethyl-piperazine | 872 | H | 6-methyl-1,4-diazepane-2-carboxamide |
| 862 | H | 1,4-dimethyl-2-methyl-piperazine | 873 | H | 5-methyl-imidazolidine-2,4-dione |
| 863 | H | 5-methyl-piperazin-2-one | 874 | H | 5-methyl-pyrazolidin-3-one |

TABLE 41
| No. | R¹ | (structure) | No. | R¹ | (structure) |
|---|---|---|---|---|---|
| 875 | H | 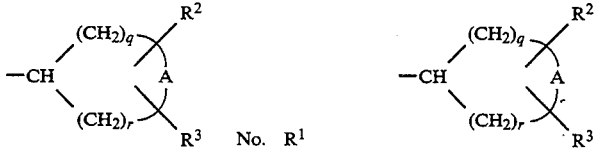 | 886 | H | 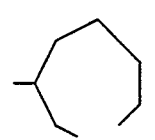 |
| 876 | H | 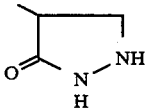 | 887 | H | 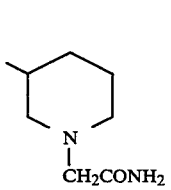 |
| 877 | H | 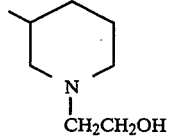 | 888 | Negative charge | 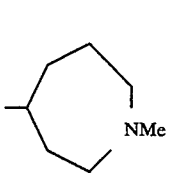 |
| 878 | H | 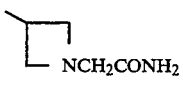 | 889 | H | 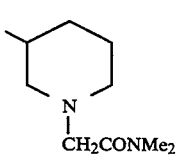 |
| 879 | H | 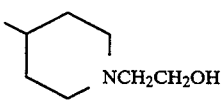 | 890 | H | 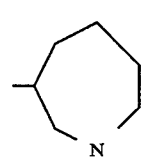 |
| 880 | H | 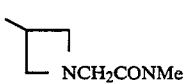 | 891 | H | 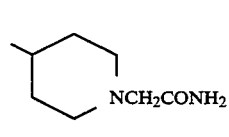 |
| 881 | H | 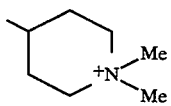 | 892 | H | 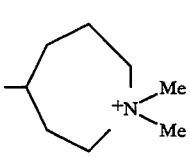 |
| 882 | H | 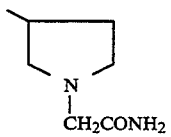 | 893 | Negative charge | 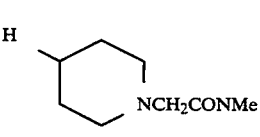 |
| 883 | H | 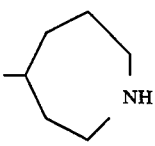 | 894 | Negative charge | 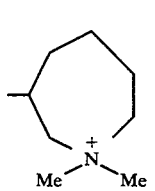 |

TABLE 41-continued
| No. | R¹ | | No. | R¹ | |
|---|---|---|---|---|---|
| 884 | H | 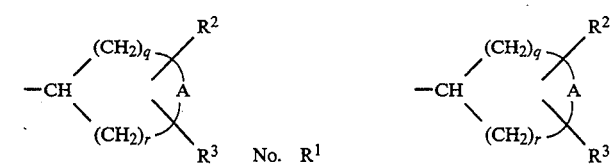 | 895 | H | 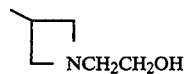 |
| 885 | H | 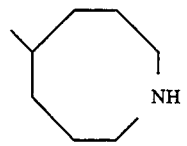 | 896 | H | 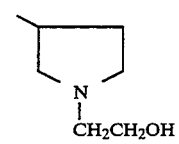 |
TABLE 42
| No. | R¹ | | No. | R¹ | |
|---|---|---|---|---|---|
| 897 | H | 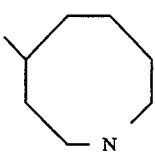 | 901 | Negative charge | 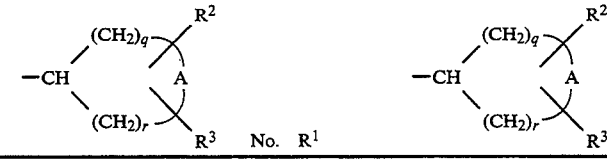 |
| 898 | H | 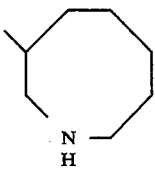 | 902 | Negative charge | 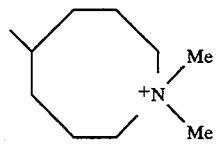 |
| 899 | H | 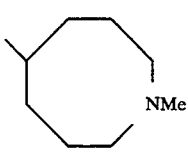 | 903 | Negative charge | 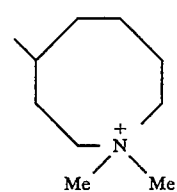 |
| 900 | H | 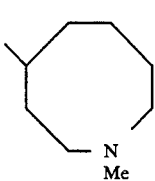 | | | |

TABLE 43

[Structure: carbapenem with HO-CH(Me)- group, core β-lactam fused ring with S-pyrrolidine substituent bearing -(CH2)3-CH< connecting to a ring system with (CH2)q and (CH2)r arms, A bridge, R2 and R3 substituents, and COOR1]

| No. | R¹ | -CH<(CH2)q/(CH2)r ring (R²/A/R³) | No. | R¹ | -CH<(CH2)q/(CH2)r ring (R²/A/R³) |
|-----|----|----|-----|----|----|
| 904 | H | (ring with HN) | 916 | H | (ring with NH) |
| 905 | H | (ring with MeN) | 917 | H | (ring with N-Me) |
| 906 | H | (ring with HN=CHN) | 918 | H | (ring with N-CH=NH) |
| 907 | H | (ring with Me(HN=)CN) | 919 | H | (ring with N-C(=NH)Me) |
| 908 | H | (ring with NH) | 920 | H | (ring with HN) |
| 909 | H | (ring with NMe) | 921 | H | (ring with MeN) |
| 910 | H | (ring with NCH=NH) | 922 | H | (ring with HN=HCN) |
| 911 | H | (ring with NC(=NH)Me) | 923 | H | (ring with NH) |
| 912 | H | (ring with HN) | 924 | H | (ring with NMe) |
| 913 | H | (ring with MeN) | 925 | H | (ring with NCH=NH) |

TABLE 43-continued
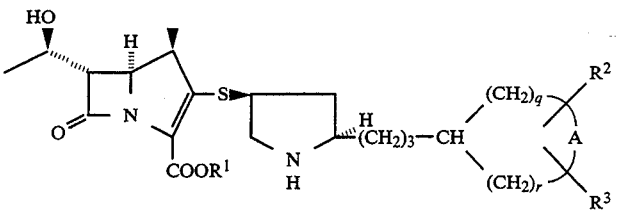
| No. | R¹ | (structure) | No. | R¹ | (structure) |
|---|---|---|---|---|---|
| 914 | H | HN=HCN-cyclopentyl | 926 | H | piperidine-NH |
| 915 | H | Me(HN=)CN-cyclopentyl | 927 | H | piperidine-NMe |
TABLE 44
| No. | R¹ | (structure) | No. | R¹ | (structure) |
|---|---|---|---|---|---|
| 928 | H | cyclohexyl-NCH=NH | 942 | H | NMe, C=O |
| 929 | H | HN–C(=O) (azetidinone) | 943 | H | piperidinone (O, NH) |
| 930 | H | MeN–C(=O) | 944 | H | piperidinone (O, NMe) |
| 931 | H | O=C–NH | 945 | H | piperidinone (NH, =O) |
| 932 | H | O=C–NMe | 946 | H | piperidinone (NMe, =O) |
| 933 | H | NH, C=O | 947 | H | succinimide (O=,N-H,=O) |

TABLE 44-continued

| No. | R¹ | structure | No. | R¹ | structure |
|---|---|---|---|---|---|
| 934 | H | —CH₂CH₂C(O)NMe (chain) | 948 | H | N-methylsuccinimide |
| 935 | H | γ-butyrolactam (NH) | 949 | H | glutarimide (NH) |
| 936 | H | N-methyl γ-butyrolactam | 950 | H | N-methylglutarimide |
| 937 | H | 2-pyrrolidinone (NH) | 951 | H | glutarimide-type (NH) |
| 938 | H | N-methyl-2-pyrrolidinone | 952 | H | N-methyl diketone amide |
| 939 | H | δ-valerolactam (NH) | 953 | H | N-ethyl diketone amide |
| 940 | H | N-methyl-δ-valerolactam | 954 | H | azetidine-CONH₂ (NH) |
| 941 | H | 4-piperidinone amide | 955 | H | N-methyl azetidine-CONH₂ |

TABLE 45

| No. | R¹ | structure | No. | R¹ | structure |
|---|---|---|---|---|---|
| 956 | H | azetidine-CONH₂ with NCH=NH | 969 | Negative charge | N,N-dimethyl pyrrolidinium-CONMe₂ |

TABLE 45-continued

| No. | R¹ | structure | No. | R¹ | structure |
|---|---|---|---|---|---|
| 957 | H | pyrrolidine-2-CONH₂, NH | 970 | Negative charge | pyrrolidine-3-CONH₂, N⁺(Me)₂ |
| 958 | H | pyrrolidine-2-CONHMe, NH | 971 | Negative charge | pyrrolidine-2-CONH₂ (H₂NOC-), N⁺(Me)₂ |
| 959 | H | pyrrolidine-2-CONMe₂, NH | 972 | H | pyrrolidine-2-CONH₂, N-CH=NH |
| 960 | H | pyrrolidine-2-CONH₂, N-Me | 973 | H | pyrrolidine-3-CONH₂, N-CH=NH |
| 961 | H | pyrrolidine-2-CONMe₂, N-Me | 974 | H | pyrrolidine-2-CONH₂ (H₂NOC-), N-CH=NH |
| 962 | H | pyrrolidine-3-CONH₂, NH | 975 | H | piperidine-2-CONH₂, NH |
| 963 | H | pyrrolidine-3-CONH₂, N-Me | 976 | H | piperidine-2-CONH₂, N-Me |
| 964 | H | pyrrolidine-2-CONH₂ (H₂NOC-), NH | 977 | Negative charge | piperidine, N⁺(Me)₂ |
| 965 | H | pyrrolidine-2-CONH₂ (H₂NOC-), N-Me | 978 | Negative charge | piperidine-2-CONH₂, N⁺(Me)₂ |
| 966 | Negative charge | pyrrolidine, N⁺(Me)₂ | 979 | H | piperidine-2-CONH₂, NH |

TABLE 45-continued

| No. | R¹ | (structure) | No. | R¹ | (structure) |
|---|---|---|---|---|---|
| 967 | Negative charge | pyrrolidinium with N⁺(Me)(Me) and CONH₂ | 980 | H | cyclohexane with NMe and CONH₂ |
| 968 | Negative charge | pyrrolidinium with N⁺(Me)(Me) and CONHMe | 981 | Negative charge | piperidinium with N⁺(Me)(Me) and CONH₂ |

TABLE 46

| No. | R¹ | (structure) | No. | R¹ | (structure) |
|---|---|---|---|---|---|
| 982 | H | 3-amino-2-pyrrolidinone | 993 | H | piperazin-2-one |
| 983 | H | 4-amino-3-methyl-2-pyrrolidinone | 994 | H | 4-methyl-piperazin-2-one |
| 984 | H | 3-amino-2-piperidinone | 995 | H | piperazine-2,3-dione |
| 985 | H | 4-amino-2-piperidinone | 996 | H | piperazine-2-carboxamide |
| 986 | H | 3-amino-2-piperidinone isomer | 997 | H | piperazine-2,5-dicarboxamide |
| 987 | H | 4-amino-2-piperidinone isomer | 998 | H | 1,4-diazepane |

TABLE 46-continued

| No. | R¹ | structure | No. | R¹ | structure |
|---|---|---|---|---|---|
| 988 | H | piperazine (3-Me, NH, NH) | 999 | H | 1,4-diazepan-2-one (Me-substituted) |
| 989 | H | piperazine (3-Me, N-Me, NH) | 1000 | H | 1,4-diazepane-2,3-dione (Me-substituted) |
| 990 | H | piperazine (3-Me, NH, N-Me) | 1001 | H | 1,4-diazepane-2-CONH₂ (Me-substituted) |
| 991 | H | piperazine (3-Me, N-Me, N-Me) | 1002 | H | hydantoin (Me-substituted) |
| 992 | H | piperazin-2-one (6-Me) | 1003 | H | pyrazolidin-3-one (5-Me) |

TABLE 47

| No. | R¹ | structure | No. | R¹ | structure |
|---|---|---|---|---|---|
| 1004 | H | pyrazolidin-3-one | 1015 | H | 3-Me-piperidine, N—CH₂CH₂OH |
| 1005 | H | azetidine-N—CH₂CONH₂ | 1016 | H | 4-Me-piperidine, N—CH₂CH₂OH |
| 1006 | H | azetidine-N—CH₂CONMe | 1017 | Negative charge | 4-Me-piperidinium, N⁺(Me)₂ |

TABLE 47-continued

| No. | R¹ | [ring structure] | No. | R¹ | [ring structure] |
|---|---|---|---|---|---|
| 1007 | H | pyrrolidine N-CH₂CONH₂ | 1018 | H | azepane NH |
| 1008 | H | pyrrolidine N-CH₂CONMe₂ | 1019 | H | azepane NH |
| 1009 | H | piperidine N-CH₂CONH₂ | 1020 | H | azepane NMe |
| 1010 | H | piperidine N-CH₂CONMe₂ | 1021 | H | azepane N-Me |
| 1011 | H | piperidine NCH₂CONH₂ | 1022 | Negative charge | azepane ⁺N(Me)₂ |
| 1012 | H | piperidine NCH₂CONMe | 1023 | Negative charge | azepane ⁺N(Me)₂ |
| 1013 | H | azetidine NCH₂CH₂OH | 1024 | H | azocane NH |
| 1014 | H | pyrrolidine N-CH₂CH₂OH | 1025 | H | azocane NH |

TABLE 48

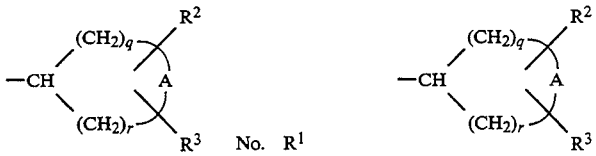

| No. | R¹ | | No. | R¹ | |
|---|---|---|---|---|---|
| 1026 | H | 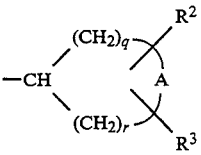 | 1030 | Negative charge | 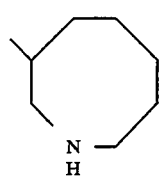 |
| 1027 | H | 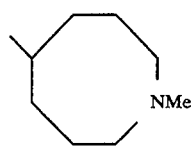 | 1031 | Negative charge | 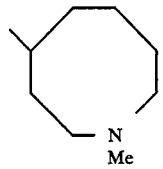 |
| 1028 | H | 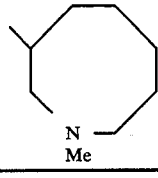 | 1032 | Negative charge | 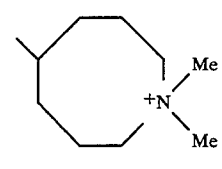 |
| 1029 | H | 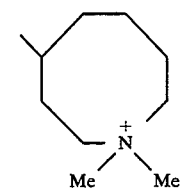 | | | |

Among the above compounds, preferred are compounds identified by compound Nos. 5, 7, 9, 13, 14, 20, 23, 24, 26, 27, 28, 32, 34, 44, 45, 54, 63, 79, 85, 89, 90, 95, 96, 99, 100, 114, 115, 117, 119, 121, 122, 124, 125, 127, 128, 130, 132, 134, 136, 138, 140, 142, 143, 144, 149, 152, 153, 155, 156, 157, 159, 161, 163, 167, 171, 173, 174, 180, 183, 192, 201, 205, 208, 214, 218, 224, 225, 227, 228, 229, 233, 237, 239, 240, 242, 243, 244, 245, 246, 247, 248, 249, 250, 251, 252, 253, 254, 255, 256, 257, 258, 263, 265, 267, 271, 273, 278, 281, 282, 284, 286, 290, 292, 302, 312, 313, 314, 343, 353, 354, 357, 372, 373, 375, 377, 379, 380, 382, 383, 385, 386, 388, 389, 390, 392, 393, 394, 396, 398, 400, 401, 402, 407, 410, 411, 413, 415, 417, 419, 421, 431, 438, 441, 450, 459, 463, 466, 472, 476, 482, 483, 485, 486, 495, 497, 498, 500, 501, 502, 503, 504, 505, 506, 507, 508, 509, 510, 511, 512, 513, 514, 515 and 516.

Among them, particularly preferred are as follows:

34  (5R,6S)-6-[(R)-1-hydroxyethyl]-2-[(2S,4S)-2-(2-pyrrolidon-4-yl)pyrrolidin-4-ylthio]-1-carbapen-2-em-3-carboxylic acid, 134 (1R,5S,6S)-2-[(2S,4S)-2-(azetidin-3-yl)pyrrolidin-4-ylthio]-6-[(R)-1-hydroxyethyl]-1-methyl-1-carbapen-2-em-3-carboxylic acid, 136 (1R,5S,6S)-2-[(2S,4S)-2-(N-formimidoylazetidin-3-yl)pyrrolidin-4-ylthio]-6-[(R)-1-hydroxyethyl]-1-methyl-1-carbapen-2-em-3-carboxylic acid, 138 (1R,5S,6S)-6-[(R)-1-hydroxyethyl]-1-methyl-2-[(2S,4S)-2-(pyrrolidin-2-yl)pyrrolidin-4-ylthio]-1-carbapen-2-em-3-carboxylic acid, 142 (1R,5S,6S)-6-[(R)-1-hydroxyethyl]-1-methyl-2-[(2S,4S)-2-(pyrrolidin-3-yl)pyrrolidin-4-ylthio]-1-carbapen-2-em-3-carboxylic acid, 143 (1R,5S,6S)-6-[(R)-1-hydroxyethyl]-1-methyl-2-[(2S,4S)-2-(N-methylpyrrolidin-3-yl)pyrrolidin-4-ylthio]-1-carbapen-2-em-3-carboxylic acid, 144 (1R,5S,6S)-2-[(2S,4S)-2-(N-formimidoylpyrrolidin-3-yl)pyrrolidin-4-ylthio]-6-[(R)-1-hydroxyethyl]-1-methyl-1-carbapen-2-em-3-carboxylic acid, 149 (1R,5S,6S)-6-[(R)-1-hydroxyethyl]-1-methyl-2-[(2S,4S)-2-(piperidin-3-yl)pyrrolidin-4-ylthio]-1-carbapen-2-em-3-carboxylic acid, 152 (1R,5S,6S)-6-[(R)-1-hydroxyethyl]-1-methyl-2-[(2S,4S)-2-(piperidin-4-yl)pyrrolidin-4-ylthio]-1-carbapen-2-em-3-carboxylic acid, 153 (1R,5S,6S)-6-[(R)-1-hydroxyethyl]-1-methyl-2-[(2S,4S)-2-(N-methylpiperidin-4-yl)pyrrolidin-4-ylthio]-1-carbapen-2-em-3-carboxylic acid, 155 (1R,5S,6S)-2-[(2S,4S)-2-(2-azetidinon-4-yl)pyrrolidin-4-ylthio]-6-[(R)-1-hydroxyethyl]-1-methyl-1-carbapen-2-em-3-carboxylic acid, 157 (1R,5S,6S)-2-[(2S,4S)-2-(2-azetidinon-3-yl)pyrrolidin-4-ylthio]-6-[(R)-1-hydroxyethyl]-1-methyl-1-carbapen-2-em-3-carboxylic acid, 159 (1R,5S,6S)-6-[(R)-1-hydroxyethyl]-1-methyl-2-[(2S,4S)-2-(2-pyrrolidon-5-yl)pyrrolidin-4-ylthio]-1-carbapen-2-em-3-carboxylic acid, 161 (1R,5S,6S)-6-[(R)-1-hydroxyethyl]-1-methyl-2-[(2S,4S)-2-(2-pyrrolidon-3-yl)pyrrolidin-4-ylthio]-1-carbapen-2-em-3-carboxylic acid, 163 (1R,5S,6S)-6-[(R)-1-hydroxyethyl]-1-methyl-2-[(2S,4S)-2-(2-pyrrolidon-4-yl)pyrrolidin-4-ylthio]-1-carbapen-2-em-3-carboxylic acid, 183 (1R,5S,6S)-2-[(2S,4S)-2-(2-carbamoylpyrrolidin-4-yl)pyrrolidin-4-ylthio]-6-[(R)-1-hydroxyethyl]-1-methyl-1-carbapen-2-em-3-carboxylic acid, 192 (1R,5S,6S)-2-[(2S,4S)-2-(N,N-dimethyl-3-pyrrolidinio)pyrrolidin-4-ylthio]-6-[(R)-1-hydroxyethyl]-1-methyl-1-carbapen-2-em-3-carboxylic acid, 208 (1R,5S,6S)-2-[(2S,4S)-2-(3-amino-2-pyrrolidon-4-yl)pyrrolidin-4-ylthio]-6-[(R)-1-hydroxyethyl]-1-methyl-1-carbapen-2-em-3-carboxylic acid, 214 (1R,5S,6S)-6-[(R)-1-hydroxyethyl]-1-methyl-2-[(2S,4S)-2-(2-piperazinyl)pyrrolidin-4-ylthio]-1-carbapen-2-em-3-carboxylic acid, 218 (1R,5S,6S)-6-[(R)-1-hydroxyethyl]-1-methyl-2-[(2S,4S)-2-(3-oxopiperazin-5-yl)pyrrolidin-4-ylthio]-1-carbapen-2-em-3-carboxylic acid, 224 (1R,5S,6S)-2-[(2S,4S)-2-(hexahydro-1H-1,4-diazepin-6-yl)pyrrolidin-4-ylthio]-6-[(R)-1-hydroxyethyl]-1-methyl-1-carbapen-2-em-3-carboxylic acid, 225 (1R,5S,6S)-2-[(2S,4S)-2-(hexahydro-2-oxo-1H-1,4-diazepin-6-yl)pyrrolidin-4-ylthio]-6-[(R)-1-hydroxyethyl]-1-methyl-1-carbapen-2-em-3-carboxylic acid, 240 (1R,5S,6S)-6-[(R)-1-hydroxyethyl]-2-[(2S,4S)-2-[N-(2-hydroxyethyl)pyrrolidin-3-yl]pyrrolidin-4-ylthio]-1-methyl-1-carbapen-2-em-3-carboxylic acid, 243 (1R,5S,6S)-2-[(2S,4S)-2-(N,N-dimethyl-4-piperidinio)pyrrolidin-4-ylthio]-1-carbapen-2-em-3-carboxylate, 244 (1R,5S,6S)-2-[(2S,4S)-2-(hexahydroazepin-4-yl)pyrrolidin-4-ylthio]-6-[(R)-1-hydroxyethyl]-1-methyl-1-carbapen-2-em-3-carboxylic acid, 246 (1R,5S,6S)-6-[(R)-1-hydroxyethyl]-1-methyl-2-[(2S,4S)-2-(N-methylhexahydroazepin-4-yl)pyrrolidin-4-ylthio]-1-carbapen-2-em-3-carboxylic acid, 248 (1R,5S,6S)-2-[(2S,4S)-2-(N,N-dimethylhexahydro-4-azepinio)pyrrolidin-4-ylthio]-6-[(R)-1-hydroxyethyl]-1-methyl-1-carbapen-2-em-3-carboxylate, 250 (1R,5S,6S)-6-[(R)-1-hydroxyethyl]-1-methyl-2-[(2S,4S)-2-(octahydroazocin-5-yl)pyrrolidin-4-ylthio]-1-carbapen-2-em-3-carboxylic acid, 251 (1R,5S,6S)-6-[(R)-1-hydroxyethyl]-1-methyl-2-[(2S,4S)-2-(octahydroazocin-4-yl)pyrrolidin-4-ylthio]-1-carbapen-2-em-3-carboxylic acid, 253 (1R,5S,6S)-6-[(R)-1-hydroxyethyl]-1-methyl-2-[(2S,4S)-2-(N-methyloctahydroazocin-5-yl)pyrrolidin-4-ylthio]-1-carbapan-2-em-3-carboxylic acid, 254 (1R,5S,6S)-6-[(R)-1-hydroxyethyl]-1-methyl-2-[(2S,4S)-2-(N-methyloctahydroazocin-4-yl)pyrrolidin-4-ylthio]-1-carbapen-2-em-3-carboxylic acid, 256 (1R,5S,6S)-2-[(2S,4S)-2-(N,N-dimethyloctahydro-5-azocinio)pyrrolidin-4-ylthio]-6-[(R)-1-hydroxyethyl]-1-methyl-1-carbapen-2-em-3-carboxylate, 257 (1R,5S,6S)-2-[(2S,4S)-2-(N,N-dimethyloctahydro-4-azocinio)pyrrolidin-4-ylthio]-6-[(R)-1-hydroxyethyl]-1-methyl-1-carbapen-2-em-3-carboxylate, 290 (5R,6S)-6-[(R)-1-hydroxyethyl]-2-[(2R,4S)-2-(2-pyrrolidon-3-ylmethyl)pyrrolidin-4-ylthio]-1-carbapen-2-em-3-carboxylic acid, 392 (1R,5S,6S)-2-[(2R,4S)-2-(azetidin-3-ylmethyl)pyrrolidin-4-ylthio]-6-[(R)-1-hydroxyethyl]-1-methyl-1-carbapen-2-em-3-carboxylic acid, 394 (1R,5S,6S)-2-[(2R,4S)-2-(N-formimidoylazetidin-3-ylmethyl)pyrrolidin-4-ylthio]-6-[(R)-1-hydroxyethyl]-1-methyl-1-carbapen-2-em-3-carboxylic acid, 400 (1R,5S,6S)-6-[(R)-1-hydroxyethyl]-1-methyl-2-[(2R,4S)-2-(pyrrolidin-3-ylmethyl)pyrrolidin-4-ylthio]-1-carbapen-2-em-3-carboxylic acid, 401 (1R,5S,6S)-6-[(R)-1-hydroxyethyl]-1-methyl-2-[(2R,4S)-2-(N-methylpyrrolidin-3-ylmethyl)pyrrolidin-4-ylthio]-1-carbapen-2-em-3-carboxylic acid, 402 (1R,5S,6S)-2-[(2R,4S)-2-(N-formimidoylpyrrolidin-3-ylmethyl)pyrrolidin-4-ylthio]-6-[(R)-1-hydroxyethyl]-1-methyl-1-carbapen-2-em-3-carboxylic acid, 413 (1R,5S,6S)-2-[(2R,4S)-2-(2-azetidinon-4-ylmethyl)pyrrolidin-4-ylthio]-6-[(R)-1-hydroxyethyl]-1-methyl-1-carbapen-2-em-3-carboxylic acid, 415 (1R,5S,6S)-2-[(2R,4S)-2-(2-azetidinon-3-ylmethyl)pyrrolidin-4-ylthio]-6-[(R)-1-hydroxyethyl]-1-methyl-1-carbapen-2-em-3-carboxylic acid, 417 (1R,5S,6S)-6-[(R)-1-hydroxyethyl]-1-methyl-2-[(2R,4S)-2-(2-pyrrolidon-5-ylmethyl)pyrrolidin-4-ylthio]-1-carbapen-2-em-3-carboxylic acid, 419 (1R,5S,6S)-6-[(R)-1-hydroxyethyl]-1-methyl-2-[(2R,4S)-2-(2-pyrrolidon-3-ylmethyl)pyrrolidin-4-ylthio]-1-carbapen-2-em-3-carboxylic acid, 421 (1R,5S,6S)-6-[(R)-1-hydroxyethyl]-1-methyl-2-[(2R,4S)-2-(2-pyrrolidon-4-ylmethyl)pyrrolidin-4-ylthio]-1-carbapen-2-em-3-carboxylic acid, 441 (1R,5S,6S)-2-[(2R,4S)-2-(2-carbamoylpyrrolidin-4-ylmethyl)pyrrolidin-4-ylthio]-6-[(R)-1-hydroxyethyl]-1-methyl-1-carbapen-2-em-3-carboxylic acid, 450 (1R,5S,6S)-2-[(2R,4S)-2-(N,N-dimethyl-3-pyrrolidiniomethyl)pyrrolidin-4-ylthio]-6-[(R)-1-hydroxyethyl]-1-methyl-1-carbapen-2-em-3-carboxylic acid, 466 (1R,5S,6S)-2-[(2R,4S)-2-(3-amino-2-pyrrolidon-4-ylmethyl)pyrrolidin-4-ylthio]-6-[(R)-1-hydroxyethyl]-1-methyl-1-carbapen-2-em-3-carboxylic acid, 476 (1R,5S,6S)-6-[(R)-1-hydroxyethyl]-1-methyl-2-[(2R,4S)-2-(3-oxopiperazin-5-ylmethyl)pyrrolidin-4-ylthio]-1-carbapen-2-em-3-carboxylic acid, and 498 (1R,5S,6S)-6-[(R)-1-hydroxyethyl]-2-[(2R,4S)-2-[N-(2-hydroxyethyl)pyrrolidin-3-ylmethyl]pyrrolidin-4-ylthio]-1-methyl-1-carbapen-2-em-3-carboxylic acid.

Especially preferred are compounds No. 142 i.e. (1R,5S,6S)-6-[(R)-1-hydroxyethyl]-1-methyl-2-[(2S,4S)-2-(pyrrolidin-3-yl)pyrrolidin-4-ylthio]-1-carbapen-2-em-3-carboxylic acid and No. 152 i.e. (1R,5S,6S)-6-[(R)-1-hydroxyethyl]-1-methyl-2-[(2S,4S)-2-(piperidin-4-yl)pyrrolidin-4-ylthio]-1-carbapen-2-em-3-carboxylic acid.

Now, the process for producing the compound of the present invention will be described.

An activating reagent is reacted to a compound of the formula:

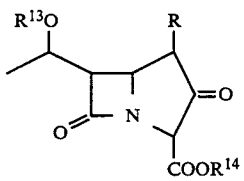

wherein R is a hydrogen atom or a methyl group, $R^{13}$ is a hydrogen atom or a hydroxyl-protecting group, and $R^{14}$ is a hydrogen atom or a carboxyl-protecting group in an inert organic solvent in the presence of a base to form a reactive derivative of the formula (II'):

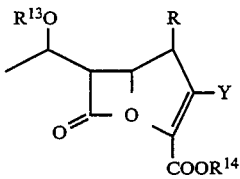

wherein R, $R^{13}$ and $R^{14}$ are as defined above, and Y is a leaving group.

The inert organic solvent to be used for the reaction may, for example, be diethyl ether, tetrahydrofuran, dioxane, benzene, toluene, chlorobenzene, methylene chloride, chloroform, carbon tetrachloride, dichloroethane, trichloroethylene, acetone, ethyl acetate, acetonitrile, N,N-dimethylformamide, hexamethylphosphoric triamide-or a mixture of such solvents. Particularly preferred are acetonitrile and benzene.

The base to be used for the reaction may, for example, be a tertiary aliphatic amine such as trimethylamine, triethylamine, N,N-diisopropylethylamine, N-methylmorpholine, N-methylpyrrolidine, N-methylpiperidine, N,N-dimethylaniline, 1,8-diazabicyclo[5.4.0]undec-7-ene (DBU) or 1,5-diazabicyclo[4.3.0]non-5-ene (DBN); or an aromatic amine such as pyridine, 4-dimethylaminopyridine, picoline, lutidine, quinoline or isoquinoline. Particularly preferred are N,N-diisopropylethylamine and triethylamine.

The activating reagent to be used for the reaction may, for example, be an acid anhydride such as trifluoroacetic anhydride, methanesulfonic anhydride, trifluoromethanesulfonic anhydride or p-toluenesulfonic anhydride; or an acid chloride such as methanesulfonyl chloride, p-toluenesulfonyl chloride or diphenyl chlorophosphate. Particularly preferred is diphenyl chlorophosphate.

In the formula (II'), Y is a leaving group such as a trifluoroacetoxy group, a methanesulfonyloxy group, a trifluoromethanesulfonyloxy group, a p-toluenesulfonyloxy group or a diphenoxyphosphoryloxy group. Particularly preferred is a diphenoxyphosphoryloxy group.

For the reaction, from 1 to 3 mols, preferably from 1 to 1.5 mols, of the base and from 1 to 1.2 mols of the activating reagent are used per mol of the compound of the formula (II).

The reaction is conducted usually within a temperature range of from $-40°$ to $50°$ C., preferably from $-20°$ to $20°$ C., and usually completed quantitatively in from 0.5 to 3 hours.

After completion of the reaction, the reaction product is treated in accordance with a usual method to obtain the reactive derivative (II') of the compound of the formula (II) quantitatively.

The reaction of the reactive derivative of the formula (II') with a compound of the formula:

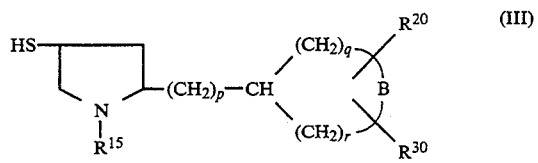

wherein $R^{15}$ is a hydrogen atom or an imino-protecting group, each of $R^{20}$ and $R^{30}$ which may be the same or different, is a hydrogen atom, a lower alkyl group, a hydroxy lower alkyl group which may be protected, a formimidoyl group which may be protected, an acetoimidoyl group which may be protected $-COOR^{40}$, $-CON(R^{50})R^{60}$, $-N(R^{50})R^{60}$, $-CH_2COOR^{40}$, $-CH_2N(R^{50})R^{60}$ or $-CH_2CON(R^{50})R^{60}$ (wherein $R^{40}$ is a hydrogen atom, a lower alkyl group or a carboxyl-protecting group, and each of $R^{50}$ and $R^{60}$ which may be the same or different, is a hydrogen atom, a lower alkyl group, an amino-protecting group or an imino-protecting group, or $R^{50}$ and $R^{60}$ form together with the adjacent nitrogen atom a heterocyclic group selected from the group consisting of an aziridinyl group, an azetidinyl group, a pyrrolidinyl group and a piperidyl group), B is $=NR^{70}$, $=N^+(R^{70})R^{80}$, $-CON(R^{70})-$, $-CON(R^{70})CO-$, $-CON(R^{70})CON(R^{80})-$, $-N(R^{70})CO(CH_2)_sN(R^{80})-$, $-N(R^{70})CO(CH_2)_sCON(R^{80})-$, $-CON(R^{70})N(R^{80})-$ or $-N(R^{70})(CH_2)_sN(R^{80})-$ {wherein each of $R^{70}$ and $R^{80}$ which may be the same or different is a hydrogen atom, a lower alkyl group, a hydroxy lower alkyl group which may be protected, a formimidoyl group which may be protected, an acetoimidoyl group which may be protected, an imino-protecting group, $-COOR^{40}$, $-CON(R^{50})R^{60}$, $-N(R^{50})R^{60}$, $-CH_2COOR^{40}$, $-CH_2N(R^{50})R^{60}$ or $-CH_2CON(R^{50})R^{60}$ (wherein $R^{40}$, $R^{50}$ and $R^{60}$ are as defined above), and s is an integer of from 1 to 3}, and p, q and r are as defined above, is conducted using the above mentioned inert organic solvent and base to form a compound of the formula:

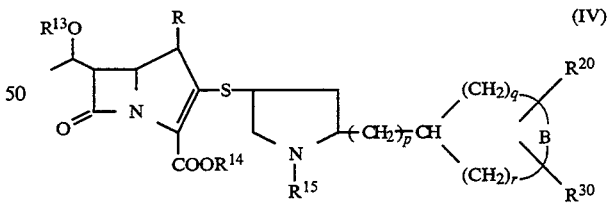

wherein R, $R^{13}$, $R^{14}$, $R^{15}$, $R^{20}$, $R^{30}$, B, p, q and r are as defined above.

The reaction is conducted using from 1 to 2 mols, preferably from 1 to 1.5 mols, of the base and from 1 to 1.2 mols of the compound of the formula (III), per mol of the reactive derivative of the formula (II'). The reaction is conducted usually within a temperature range of from $-40°$ to $50°$ C., preferably from $-20°$ to $20°$ C., and the reaction is completed usually in from 0.5 to 3 hours.

Further, the compound of the formula (IV) can be prepared in one step from the compound of the formula (II). Namely, without isolating the reactive derivative of the formula (II') prepared from the compound of the formula (II), the compound of the formula (III) is reacted thereto in the same reaction system to prepare the compound of the formula (IV) efficiently. To conduct the production in one step, from 2 to 4 mols, preferably from 2.5 to 3.5 mols, of the base is employed per mol of the compound of the formula (II).

After completion of the reaction, usual treatment is conducted to obtain a crude product of the formula (IV), which may be subjected to a reaction for removing a protecting group without purification. However, it is preferred to purify the crude product (IV) by crystallization or by column chromatography by means of e.g. silica gel.

From the compound of the formula (IV) thus obtained, a compound of the formula (I) can be obtained, if necessary, by conducting a reaction for removing a protecting group for a hydroxyl group, an amino or imino group and a carboxyl group.

For the removal of the protecting groups, the method varies depending upon the type of the protecting groups. However, the removal can be conducted in accordance with conventional methods, for example, by solvolysis, by chemical reduction or by hydrogenation.

For example, when in the above formula (IV), the protecting group for the hydroxyl group and/or for the amino or imino group is an aralkyloxycarbonyl group such as a benzyloxycarbonyl group or a p-nitrobenzyloxycarbonyl group, and the protecting group for the carboxyl group is an aralkyl group such as a benzyl group, a p-nitrobenzyl group or a benzhydryl group, such protecting groups can be removed by catalytic hydrogenation by means of a platinum catalyst such as platinum oxide, platinum wire or platinum black, or a palladium catalyst such as palladium black, palladium oxide, palladium-carbon or palladium hydroxide-carbon.

As a solvent to be used for such a catalytic hydrogenation reaction, methanol, ethanol, tetrahydrofuran, dioxane, acetic acid or a solvent mixture of such an organic solvent with water or with a buffer solution of e.g. a phosphate, may be used.

The reaction can be completed in from 0.5 to 4 hours at a temperature within a range of from 0° to 50° C. under hydrogen gas stream of from 1 to 4 atm.

When in the above formula (IV), the protecting group for the hydroxyl group and/or the amino or imino group is an allyloxycarbonyl group, and the protecting group for the carboxyl group is an allyl group, such protecting groups can be removed by reacting an organo-soluble palladium complex catalyst in an inert organic solvent containing an allyl group-capturing agent (method by W. McCombie et al., J. Org. Chem., vol. 47, p. 587–590 (1982) and method by F. Guibé, the same literature, vol. 52, p. 4,984–4,993 (1987)).

The solvent useful for the reaction includes, for example, water, acetone, diethyl ether, tetrahydrofuran, dioxane, ethyl acetate, acetonitrile, methylene chloride, chloroform and a solvent mixture thereof.

The palladium compound complex useful for this reaction includes, for example, palladium-carbon, palladium hydroxide-carbon, palladium(II) chloride, palladium(II) acetate, tetrakis(triphenylphosphine)palladium (O), tetrakis(triphenoxyphosphine)palladium (O), tetrakis(triethoxyphosphine)palladium (O), bis[ethylenebis(diphenylphosphine)]palladium (O), tetrakis[tri(2-furyl)phosphine]palladium (O), bis(triphenylphosphine)palladium(II) chloride and bis(triphenylphosphine)palladium(II) acetate.

The allyl group-capturing agent may, for example, be dimedone, formic acid, acetic-acid, ammonium formate, sodium formate, sodium 2-ethylhexanoate, potassium 2-ethylhexanoate, pyrrolidine, piperidine and tributyltin hydride.

The reaction is conducted usually within a temperature range of from $-10°$ to 50° C., preferably from 0° to 30° C. using from 0.01 to 0.5 mol of the catalyst and from 1 to 6 mols of the nucleophilic agent relative to 1 mol of the compound of the formula (IV), and the reaction is completed usually in from 0.5 to 3 hours.

Further, when in the above formula (IV), the protecting group for the hydroxyl group and/or the amino or imino group is an o-nitrobenzyloxycarbonyl group, and the protecting group for the carboxyl group is an o-nitrobenzyl group, such protecting groups can be removed by a photo reaction (method by Amit et al., J. Org. Chem., vol. 39, p. 192–196 (1974)).

After completion of the reactions for removing the protecting groups, the compound of the formula (I) can be isolated by usual treatment such as column chromatography using silica gel or adsorptive resin, freeze-drying or crystallization.

Further, when the protecting group for the carboxyl group at the 3-position of the compound of the formula (IV) is a lower alkanoyloxyalkyl group such as an acetoxymethyl group or a pivaloyloxymethyl group, a methoxymethyl group, an indanyl group, or a phthalidyl group, such an ester will be physiologically hydrolyzed in vivo. Therefore, such a compound can directly be administered to a human being or to an animal without preliminarily removing the protecting group.

The compound of the formula (I) can be converted to a pharmaceutically acceptable salt or ester by a conventional method.

The starting material of the formula (II) can be prepared, for example, by a method by Salzmann et al. when $R^1$ is a hydrogen atom (J. Am. Chem. Soc., vol. 102, p.6161–6163 (1981)) or by a method by Shih et al. when $R^1$ is a methyl group (Heterocycles, vol. 21, p.29–40 (1984)).

The starting material of the formula (III) can be synthesized by the following method.

The hydroxyl group of the compound 1 is activated by a usual method, and a thioacetate such as potassium thioacetate is reacted thereto to convert it to an acetylthio derivative 3, followed by alkali or acid hydrolysis to obtain a thiol derivative of the formula (III).

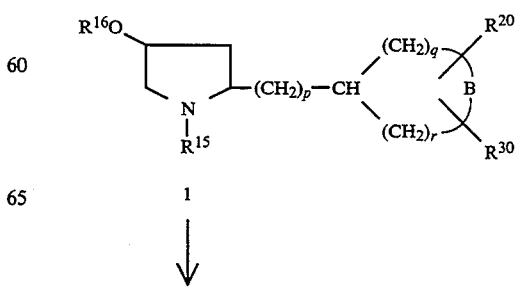

1

↓

-continued $$\text{X}\underset{\underset{R^{15}}{|}}{\overset{}{\text{N}}}\diagdown(CH_2)_p-CH\diagup_{(CH_2)_r}^{(CH_2)_q}\diagdown_{R^{30}}^{R^{20}}$$

2
↓

$$\text{AcS}\underset{\underset{R^{15}}{|}}{\overset{}{\text{N}}}\diagdown(CH_2)_p-CH\diagup_{(CH_2)_r}^{(CH_2)_q}\diagdown_{R^{30}}^{R^{20}}$$

3
↓

$$\text{HS}\underset{\underset{R^{15}}{|}}{\overset{}{\text{N}}}\diagdown(CH_2)_p-CH\diagup_{(CH_2)_r}^{(CH_2)_q}\diagdown_{R^{30}}^{R^{20}}$$

(III)

In the above formulas, $R^{16}$ is a hydrogen atom or a hydroxyl-protecting group, X is a leaving group selected from the group consisting of a chlorine atom, a bromine atom, an iodine atom, a trifluoroacetoxy group, a methanesulfonyloxy group, a trifluoromethanesulfonyloxy group and a p-toluenesulfonyloxy group, Ac is an acetyl group, and $R^{15}$, $R^{20}$, $R^{30}$, B, p, q and r are as defined above.

A group of compounds having the formula 1 can be prepared in accordance with the methods described in the Reference Examples.

The compounds of the present invention exhibit strong antibacterial activities against various gram positive bacteria and gram negative bacteria.

To demonstrate the usefulness of the compounds of the present invention, the in vitro antibacterial activities against bacteria were measured by the following agar plate dilution method (standard method by Japan Chemotherapy Society, Chemotherapy, vol. 29, p. 76–79 (1981)). One platinum loopful of each test microorganism incubated overnight in Mueller Hinton broth, was inoculated to Mueller Hinton agar (inoculum size: 106 CFU/ml). Such culture media contained antibacterial agents in various concentrations. After incubation at 37° C. for 16 hours, the minimum inhibitory concentrations (MIC: μg/ml) were measured.

The results of the antibacterial activities of the compounds of the present invention are shown in Table 1.

TABLE 1

| | Minimum Inhibitory Concentration(MIC: μg/ml) | | | | | | | |
|---|---|---|---|---|---|---|---|---|
| | Example 11 | | | Example 13 | | | | |
| Test microorganism | Diastereomer A | Diastereomer B | Example 12 Diastereomer A | Diastereomer A | Diastereomer B | Example 43 | Meropenem | Imipenem |
| P. aeruginosa MB5000 | 0.1 | 0.2 | — | 0.2 | 0.2 | 0.1 | 0.39 | 1.56 |
| P. aeruginosa MB5002 | 0.78 | 1.56 | 1.56 | 0.78 | 1.56 | 0.39 | 6.25 | 3.13 |
| P. aeruginosa AKR17* | 0.78 | 1.56 | 1.56 | 1.56 | — | 1.56 | 3.13 | 6.25 |

*β-lactamase producing microorganism

The antibacterial activities of the compounds of the present invention described in the Examples, as representative examples of the compound of the present invention, were measured by a disc diffusion test by the method of Bauer et al. (Amer. J. Clin. Pathol., vol. 45, p. 493 (1966)). Thienamycin or imipenem was used as the internal standard.

MIC of each test compound was calculated from the diameter of the inhibition ring formed by the disc containing the test compound by using the calculation formula reported by Humphrey and Lightbown (J. Gen. Microbiol., vol. 7, p. 129 (1952)). For each microorganism, a geometrical average of MIC was obtained, and the activity ratio to thienamycin was calculated.

The antibacterial activities are represented by the ratio to thienamycin (=1.0), whereby the larger the numerical value, the higher the activities.

The DHP-I susceptibility was quantitatively analyzed by the method by Kropp et al., Antimicrob. Agents Chemother., vol. 22, p. 62–70 (1982), whereby the smaller the numerical value representing the ratio to imipenem (=1.0), the higher the stability. The antibacterial potency and the DHP-I susceptibility of the compounds of the present invention were compared with imipenem and meropenem. The results are shown in Table 2.

TABLE 2

| | Relative antibacterial potency to thienamycin and DHP-I susceptibility | | | | | | |
|---|---|---|---|---|---|---|---|
| | Example 11 | | | | | | |
| | Diastereomer A | Diastereomer B | Example 13 | Example 32 | Example 43 | Meropenem | Imipenem |
| Meth-R S. aureus | 15.2 | 12.3 | — | — | 22.7 | 3.22 | 2.57 |
| THM-R P. aeruginosa | 12.7 | 11.5 | 11.5 | 19.5 | 21.6 | 6.9 | 2.0 |

TABLE 2-continued

Relative antibacterial potency to thienamycin and DHP-I susceptibility

| | Example 11 | | | | | | |
|---|---|---|---|---|---|---|---|
| | Diastereomer A | Diastereomer B | Example 13 | Example 32 | Example 43 | Meropenem | Imipenem |
| DHP-I susceptibility | <0.05 | <0.05 | <0.05 | <0.05 | 0.07 | 0.12 | 1.0 |

The compounds of the present invention have excellent antibacterial activities against various gram positive bacteria and gram negative bacteria and are useful as antibacterial agents for the treatment and prevention of the human infectious diseases caused by such bacteria. Typical pathogens sensitive to the antibacterial agents of the present invention include, for example, species of genus Staphylococcus, genus Enterococcus, genus Escherichia, genus Enterobacter, genus Klebsiella, genus Serratia, genus Proteus and genus Pseudomonas. The compounds of the present invention exhibit excellent antibacterial activities particularly against Methicillin resistant Staphylococcus aureus and against thienamycin resistant Pseudomonas aeruginosa.

The compounds of the present invention are very stable against DHP-I although the stability varies depending upon the individual compounds, and they are excellent also in the physicochemical stability and in the solubility in water.

The compounds of the present invention may be used in the form of drug formulations suitable for non-oral administration, oral administration or external administration, by mixing them with carriers of solid or liquid excipients known in this field. The main administration route is non-oral (intravenous or intramuscular injection) administration by injection or local administration. Drug formulations include liquid formulations such as injection solutions, syrups or emulsions, solid formulations such as tablets, capsules or granules, and external application formulations such as ointments or suppositories. These formulations may contain additives such as a base, an assisting agent, a stabilizer, a wetting agent, an emulsifier, an absorption-promoting agent, a surfactant, etc. which are commonly employed, as the case requires.

The additives include, for example, distilled water for injection, Ringer's solution, glucose, sucrose syrup, gelatin, edible oil, cacao butter, ethylene glycol, sucrose, corn starch, magnesium stearate and talc.

The dose varies depending upon the condition of the patient, the weight, the age, the sex, the type of formulation, the number of administration times, etc. Usually, however, a preferred daily dose of the active ingredient to an adult is from about 5 to 50 mg/kg, and a preferred daily dose to a child is within a range of from about 5 to 25 mg/kg, which is preferably administered once a day or in a few times a day.

The compound of the present invention may be administered in combination with a DHP-I inhibiting agent such as cilastatin [sodium (Z)-7-(L-amino-2-carboxyethylthio)-2-(2,2-dimethylcyclopropanecarboxamide)-2-heptenoate] (Japanese Unexamined Patent Publication No. 81518/1981; European Patent No. 28,778; J. Med. Chem., vol. 30, p. 1074 (1987)).

Now, the present invention will be described in further detail with reference to Examples and Reference Examples. However, it should be understood that the present invention is by no means restricted by such specific Examples.

In the thin layer chromatography in the Examples and Reference Examples, silica gel 60$F_{245}$ (Merck) was used as the plate, and an ultraviolet detector was used as a detecting device. As the silica gel for the column, Wakogel TM C-300 (Wako Junyaku) was used, and as the silica gel for reversed phase column, LC-SORB TM SP-B-ODS (Chemco) or YMC.GEL TM ODS-AQ 120-550 (Yamamura Chemical Laboratories) was used. As the high pressure liquid chromatograph, JASCO 800 series (Nippon Bunko) was used. When the NMR spectrum was measured using a dimethyl sulfoxide-$d_6$ or chloroform-d solution, tetramethylsilane (TMS) was used as the internal standard, and when measured using a deuterium oxide solution, 2,2-dimethyl-2-silapentane-5-sulfonate (DSS) was used as the internal standard, and the measurement was conducted by means of XL-200 (200 MHz;Varian) model spectrometer. All δ values are shown by ppm.

The meanings of the abbreviations used for the NMR measurement are as follows:
s: singlet
d: doublet
t: triplet
q: quartet
ABq: AB-type quartet
dd: double doublet
m: multiplet
br: broad
J: coupling constant
Hz: hertz
DMSO-$d_6$: dimethyl sulfoxide-$d_6$
CDCl$_3$: chloroform-d
CD$_3$OD: methanol-$d_4$
D$_2$O: deuterium oxide The meanings of the abbreviations used in the reaction formulas are as follows:
Ac: acetyl group
All: allyl group
Alloc: allyloxycarbonyl group
Boc: tert-butoxycarbonyl group
Bzl: benzyl group
Et: ethyl group
Me: methyl group
Ms: methanesulfonyl group
PNB: p-nitrobenzyl group
PNZ: p-nitrobenzyloxycarbonyl group
TBDMS: tert-butyldimethylsilyl group
Tr: trityl group

EXAMPLE 1

Sodium (5R,6S)-6-[(R)-1-hydroxyethyl]-2-[(2S,4S)-2-(2-pyrrolidon-4-yl )pyrrolidin-4-ylthio]-1-carbapen-2-em-3-carboxylate

1)

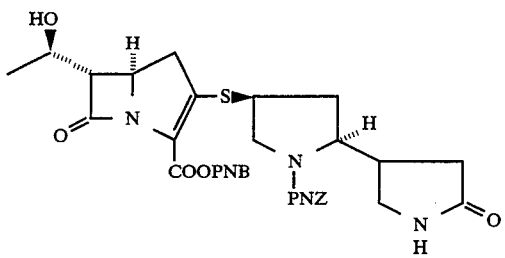

To a solution of p-nitrobenzyl (5R,6S)-2-diphenoxyphosphoryloxy-6-[(R)-1-hydroxyethyl]-1-carbapen-2-em-3-carboxylate (300 mg, 0.55 mmol) in acetonitrile (15 ml) were dropwise added in a nitrogen stream under cooling with ice a solution of (2S,4S)-4-mercapto-N-(p-nitrobenzyloxycarbonyl)-2-(2-pyrrolidon-4-yl)pyrrolidine (205 mg, 0.56 mmol, Compound of Reference Example 1-9) in acetonitrile (6 ml) and then N,N-diisopropylethylamine (0.10 ml, 0.57 mmol). The mixture was stirred at 0° C. for 7 hours. Then, ethyl acetate (70 ml) was added to the reaction solution. The organic layer was washed with water and a saturated sodium chloride aqueous solution, then dried over anhydrous magnesium sulfate and concentrated under reduced pressure. The residue was subjected to silica gel column chromatography (Wakogel TM C-300, ethyl acetate) to obtain p-nitrobenzyl (5R,6S)-6-[(R)-1-hydroxyethyl]-2-[(2S,4S)-N-(p-nitrobenzyloxycarbonyl)-2-(2-pyrrolidon-4-yl)pyrrolidin-4-ylthio]-1-carbapen-2-em-3-carboxylate (313 mg, yield: 86.2%). 1R(KBr)cm$^{-1}$: 1780, 1700, 1520, 1350.

NMR(CDCl$_3$) δ: 1.37(3H,d,J=6 Hz),5.24(3H,m),5.52(1H,d,J=14Hz),7.33(2H,d,J=9 Hz),7.46(2H,d,J=9 Hz),8.24(2H,d,J=9 Hz),8.26(2H,d,J=9 Hz).

2)

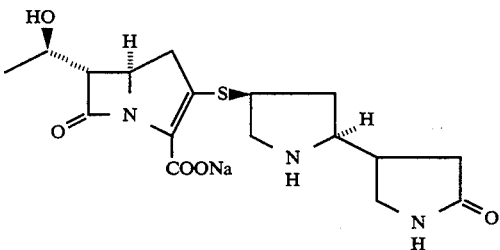

10% palladium-carbon catalyst (150 mg preliminarily stirred and activated with a 0.1M sodium 3-morpholinopropanesulfonate buffer solution in a hydrogen stream for one hour) was added to a solution of the compound obtained by the above reaction (300 mg, 0.45 mmol) in a mixture of tetrahydrofuran (10 ml) and a 0.1M sodium 3-morpholinopropanesulfonate buffer solution (10 ml). This mixture was stirred in a hydrogen stream at room temperature for two hours. The catalyst was filtered off from the reaction mixture, and the filtrate was washed with ethyl acetate (20 ml), and insoluble matters in the aqueous layer were filtered off. The obtained filtrate was concentrated to a volume of about 15 ml. The residue was subjected to reversed phase column chromatography (LC-SORB TM SP-B-ODS, 10% methanol aqueous solution). The desired fraction was concentrated and freeze-dried to obtain the above identified compound (70 mg, yield: 38.4%).

1R(KBr)cm$^{-1}$: 1760, 1680, 1590, 1390.

NMR(D$_2$O) δ: 1.26(3H,d,J=7 Hz),1.54(1H,m),2.28(1H,m),3.86(1H,m),4.21(2H,m).

HPLC: Column: YMC TM -Pack ODS-AQ, 5μ, 4.6φ×150 mm. Eluent: 0.01M Phosphatesbuffer (pH 6.5)-Methanol (80:20). Flow rate: 1.0 ml/min. Temperature: 40° C. Detector: 290 nm. Retention time: 2.23 min.

EXAMPLE 2

Sodium (5R,6S)-6-[(R)-1-hydroxyethyl]-2-[(2R,4S)-2-(2-pyrrolidon-4-yl)pyrrolidin-4-ylthio]-1-carbapen-2-em-3-carboxylate

1)

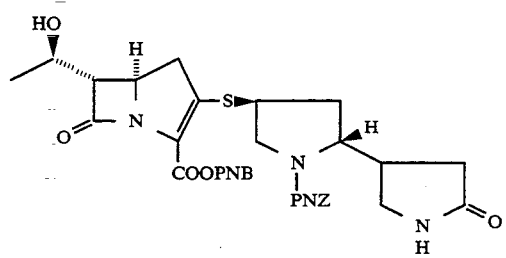

The same procedure as in Example 1-1 was carried out by using p-nitrobenzyl (5R,6S)-2-diphenoxyphosphoryloxy-6-[(R)-1-hydroxyethyl]-1-carbapen-2-em-3-carboxylate (300 mg, 0.55 mmol) and (2R,4S)-4-mercapto-N-(p-nitrobenzyloxycarbonyl)-2-(2-pyrrolidon-4-yl)pyrrolidine (200 mg, 0.55 mmol, compound of Reference Example 2) to obtain p-nitrobenzyl (5R,6S)-6-[(R)-1-hydroxyethyl]-2-[(2R,4S)-N-(p-nitrobenzyloxycarbonyl)-2-(2-pyrrolidon-4-yl)pyrrolidin-4-ylthio]-1-carbapen-2-em-3-carboxylate (127 mg, yield: 35%).

1R(KBr)cm$^{-1}$: 1790, 1710, 1520, 1350.

NMR(CDCl$_3$) δ: 1.36(3H,d,J=6 Hz),5.25(3H,m),5.52(1H,d,J=14 Hz),7.54(2H,d,J=9 Hz),7.66(2H,d,J=9 Hz),8.23(2H,d,J=9 Hz),8.26(2H,d,J=9 Hz).

2)

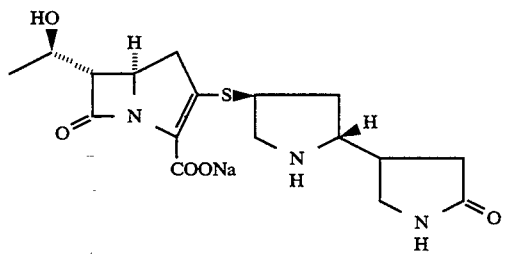

10% palladium-carbon catalyst (60 mg) was added to a solution of the compound obtained by the above reaction (127 mg, 0.19 mmol) in a mixture of tetrahydrofuran (10 ml) and a 0.1M sodium 3-morpholinopropanesulfonate buffer solution (10 ml). This mixture was stirred in a hydrogen stream of 2.9 atm at room temperature for 1.5 hours. The catalyst was filtered off from the reaction mixture, and the filtrate was washed with ethyl acetate (20 ml), and insoluble matters in the aqueous layer were filtered off. The obtained filtrate was subjected to reversed phase column chromatography (LC-SORB ™ SP-B-ODS, 10% methanol aqueous solution), then concentrated and freeze-dried to obtain the above identified compound (5.5 mg, yield: 7.1%).

IR(KBr)cm⁻¹: 1780, 1600, 1270.

NMR(D₂O) δ: 1.28(3H,d,J=8 Hz),2.54(3H,m).

HPLC (the same condition as in Example 1). Retention time: 5.54 min.

EXAMPLE 3

Sodium (1R,5S,6S)-6-[(R)-1-hydroxyethyl]-1-methyl-2-[(2S,4S)-2-(2-pyrrolidon-4-yl)pyrrolidin-4-ylthio]-1-carbapen-2-em-3-carboxylate

1)

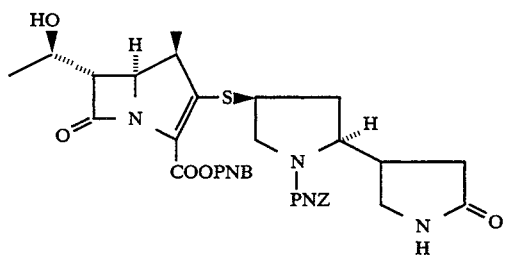

The same procedure as in Example 1-1 was conducted by using p-nitrobenzyl (1R,5S,6S)-2-diphenoxyphosphoryloxy-6-[(R)-1-hydroxyethyl]-1-methyl-1-carbapen-2-em-3-carboxylate (230 mg, 0.41 mmol) and (2S,4S)-4-mercapto-N-(p-nitrobenzyloxycarbonyl)-2-(2-pyrrolidon-4-yl)pyrrolidine (140 mg, 0.38 mmol, Compound of Reference Example 1-9) to obtain p-nitrobenzyl (1R,5S,6S)-6-[(R)-1-hydroxyethyl]-1-methyl-2-[(2S,4S)-N-(p-nitrobenzyloxycarbonyl)-2-(2-pyrrolidon-4-yl)pyrrolidin-4-ylthio]-1-carbapen-2-em-3-carboxylate (223 mg, yield: 80.6%).

IR(KBr)cm⁻¹: 1770, 1700, 1520, 1340.

NMR(CDCl₃) δ: 1.28(3H,d,J=8 Hz),1.33(3H,d,J=7 Hz),5.24(2H,m),5.31 and 5.52(2H,ABq,J=14 Hz),7.53(2H,d,J=8 Hz),7.66(2H,d,J=8 Hz),8.20(2H,d,J=8 Hz),8.22(2H,d,J=8 Hz).

2)

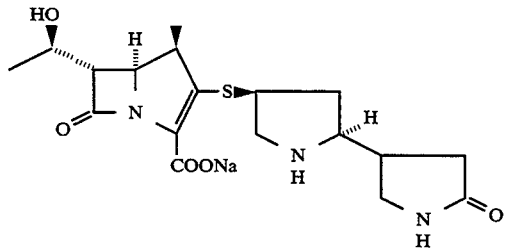

The same procedure as in Example 1-2 was carried out by using the compound obtained by the above reaction (223 mg, 0.33 mmol) to obtain the above identified compound (73 mg, yield: 53.2%, diastereomers A and B 44:56).

IR(KBr)cm⁻¹: 1760, 1680, 1590, 1390.

NMR(D₂O) δ: 1.23(3H,d,J=8 Hz),1.30(3H,d,J=7 Hz),1.77(1H,m),2.27–2.42(1H,m),4.06(1H,m),4.26(2H,m).

HPLC: Column: INERTSIL ™ ODS-2, 5μ, 4.6φ×250 mm. Eluent: 0.01M Phosphate buffer (pH7.0)-Methanol (90:10). Flow rate: 1.0 ml/min. Temperature: 40° C. Detector: 254 nm. Retention time: 13.2 min, 14.6 min (44:56).

EXAMPLE 4

Sodium (1R,5S,6S)-6-[(R)-1-hydroxyethyl]-1-methyl-2-[(2R,4S)-2-(2-pyrrolidon-4-yl)pyrrolidin-4-ylthiol-1-carbapen-2-em-3-carboxylate

1)

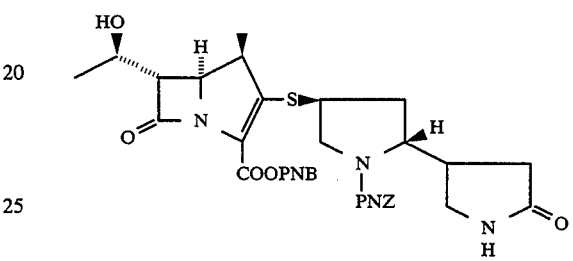

The same procedure as in Example 1-1 was carried out by using p-nitrobenzyl (1R,5S,6S)-2-diphenoxyphosphoryloxy-6-[(R)-1-hydroxyethyl]-1-methyl-1-carbapen-2-em-3-carboxylate (230 mg, 0.41 mmol) and (2R,4S)-4-mercapto-N-(p-nitrobenzyloxycarbonyl)-2-(2-pyrrolidon-4-yl)pyrrolidine (140 mg, 0.38 mmol, compound of Reference Example 2) to obtain p-nitrobenzyl (1R,5S,6S)-6-[(R)-1-hydroxyethyl]-1-methyl-2-[(2R,4S)-N-(p-nitrobenzyloxycarbonyl)-2-(2-pyrrolidon-4-yl)pyrrolidin-4-ylthio]-1-carbapen-2-em-3-carboxylate (174 mg, yield: 62.9%).

IR(KBr)cm⁻¹: 1780, 1700, 1520, 1340.

NMR(CDCl₃) δ: 1.27(3H,d,J=8 Hz),1.36(3H,d,J=6 Hz),5.25(3H,m),5.53(1H,d,J=14 Hz),7.54(2H,d,J=9 Hz),7.67(2H,d,J=9 Hz),8.24(2H,d,J=9 Hz),8.26(2H,d,J=9 Hz).

2)

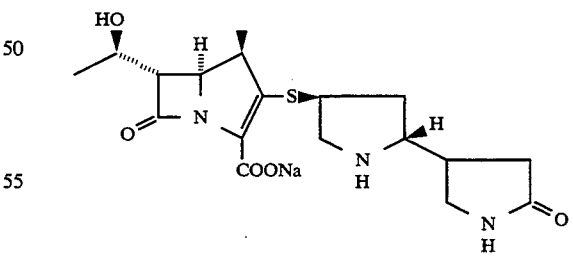

The same procedure as in Example 1-2 was carried out by using the compound obtained by the above reaction (174 mg, 0.26 mmol) to obtain the above identified compound (22 mg, yield: 20.6%).

IR(KBr)cm⁻¹: 1780, 1600, 1380, 1300.

NMR(D₂O) δ: 1.24(3H,d,J=8 Hz),1.31(3H,d,J=7 Hz),1.98–2.98(3H,m),3.44(3H,m),3.74(3H,m).

HPLC (the same condition as in Example 1). Retention time: 7.46 min.

EXAMPLE 5

Sodium (1R,5S,6S)-2-[(2S,4S)-2-azetidinon-4-yl)pyrrolidin-4-ylthio)-6-[(R)-1-hydroxyethyl]-1-methyl-1-carbapen-2-em-3-carboxylate diastereomer B

1)

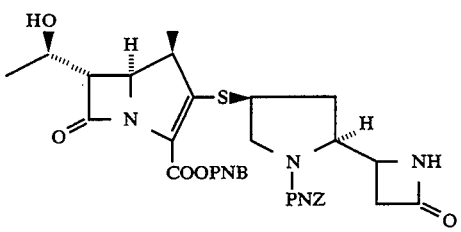

To a solution of p-nitrobenzyl (1R,5S,6S)-2-diphenoxyphosphoryloxy-6-[(R)-1-hydroxyethyl]-1-methyl-1-carbapen-2-em-3-carboxylate (110 mg, 0,195 mmol) in acetonitrile (5 ml) was added in a nitrogen stream at −10° C. a solution of (2S,4S)-2-(2-azetidinon-4-yl)-4-mercapto-N-(p-nitrobenzyloxycarbonyl)pyrrolidine diastereomer B (67 mg, 0.191 mmol, compound of Reference Example 3) in acetonitrile (5 ml), and then N,N-diisopropylamine (34 μl, 0.21 mmol) was dropwise added thereto. The mixture was stirred overnight at 4° C. Then, ethyl acetate (50 ml) was added to the reaction solution. This mixture was washed with water and a saturated sodium chloride aqueous solution. The organic layer was dried over anhydrous magnesium sulfate and concentrated under reduced pressure. The residue was subjected to silica gel column chromatography (Wakogel ™ C-300, 3% methanol-chloroform) to obtain p-nitrobenzyl (1R,5S,6S)-2-[(2S,4S)-2-(2-azetidinon-4-yl)-N-(p-nitrobenzyloxycarbonyl)pyrrolidin-4-ylthio]-6-[(R)-1-hydroxyethyl]-1-methyl-1-carbapen-2-em-3-carboxylate diastereomer B (88.5 mg, yield: 68.2%).

1R(KBr)cm$^{-1}$: 1760, 1700, 1520, 1340.

NMR(CDCl$_3$) δ: 1.28(3H,d,J=7 Hz),1.35(3H,d,J=6 Hz),1.67(1H,m),2.50–2.74(3H,m),3.08(1H,dd,J=15,5 Hz),3.24–3.45(3H,m),3.70(2H,m),3.-96–4.33(4H,m),5.23(3H,m),5.52(1H,d,J=13 Hz),7.52(2H,d,J=8 Hz),7.65(2H,d,J=8 Hz),8.22(2H,d,J=8 Hz),8.24(2H,d,J=8 Hz).

2)

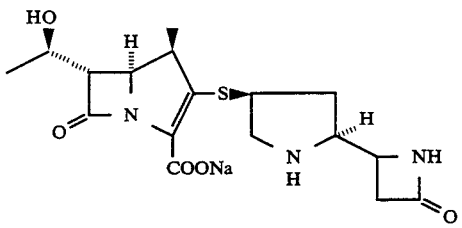

The same procedure as in Example 1-2 was carried out by using the compound obtained by the above reaction (88 mg, 0.13 mmol) to obtain the above identified compound (18 mg, yield: 33.7%).

1R(KBr)cm$^{-1}$: 1750, 1590, 1390.

NMR(D$_2$O) δ: 1.26(3H,d,J=7 Hz),1.31(3H,d,J=6 Hz),1.65(1H,m),2.69(1H,dd,J=16,8 Hz),2.73(1H,br d,J=16 Hz),3.20–3.53(4H,m),3.61(1H,dd,J=12,6 Hz),3.75(1H,q,J=8 Hz),3.85–4.40(4H,m).

HPLC (the same condition as in Example 1). Retention time: 3.8 min.

EXAMPLE 6

Sodium (1R,5S,6S)-2-[(2S,4S)-2-(2-azetidinon-4-yl)pyrrolidin-4-ylthio)-6-[(R)-1-hydroxyethyl]-1-methyl-1-carbapen-2-em-3-carboxylate diastereomer A

1)

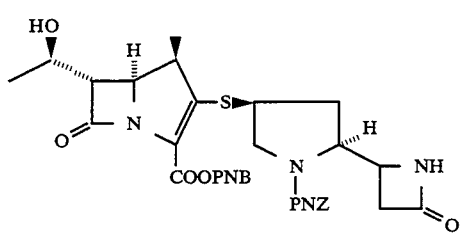

The same procedure as in Example 1-1 was carried out by using p-nitrobenzyl (1R,5S,6S)-2-diphenoxyphosphoryloxy-6-[(R)-1-hydroxyethyl]-1-methyl-1-carbapen-2-em-3-carboxylate (153 mg, 0.27 mmol) and (2S,4S)-2-(2-azetidinon-4-yl)-4-mercapto-N-(p-nitrobenzyloxycarbonyl)pyrrolidine diastereomer A (90 mg, 0.26 mmol, compound of Reference Example 4) to obtain p-nitrobenzyl (1R,5S,6S)-2-[(2S,4S)-2-(2-azetidinon-4-yl)-N-(p-nitrobenzyloxycarbonyl)pyrrolidin-4-ylthio]-6-[(R)-1-hydroxyethyl]-1-methyl-1-carbapen-2-em-3-carboxylate diastereomer A (128 mg, yield: 70.9%).

1R(KBr)cm$^{-1}$: 1760, 1700, 1520, 1340.

NMR(CDCl$_3$) δ: 1.28(3H,d,J=7 Hz),1.34(3H,d,J=6 Hz),1.91(2H,m),2.44–3.10(3H,m),3.-17–3.46(2H,m),3.66(1H,m),4.-00–4.36(5H,m),5.24(3H,m),5.50(1H,d,J=14 Hz),7.52(2H,d,J=8 Hz),7.65(2H,d,J=8 Hz),8.21(2H,d,J=8 Hz),8.23(2H,d,J=8 Hz).

2)

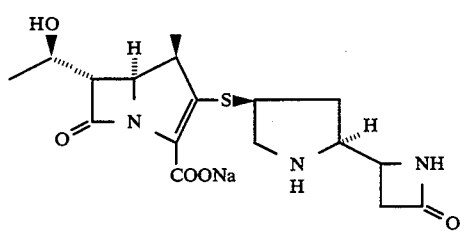

The same procedure as in Example 1-2 was carried out by using the compound obtained by the above reaction (128 mg, 0.19 mmol) to obtain the above identified compound 28.5 mg, yield: 36.7%).

1R(KBr)cm$^{-1}$: 1750, 1590, 1390.

NMR(D$_2$O) δ: 1.25(3H,d,J=7 Hz),1.32(3H,d,J=6 Hz),1.83(1H,m),2.75(1H,dd,J=15,8 Hz),2.88(1H,dd,J=15,2 Hz),3.18–3.55(4H,m),3.68(1H,dd,J=12,6 Hz),3.86–4.40(5H,m).

HPLC (the same condition as in Example 1). Retention time: 3.46 min.

EXAMPLE 7

(5R,6S)-6-[(R)-1-hydroxyethyl]-2-[(2R,4S)-2-(z-pyrolidon-3-ylmethyl)pyrrolidin-4-ylthio]-1-carbapen-2-em-3-carboxylic acid

1)

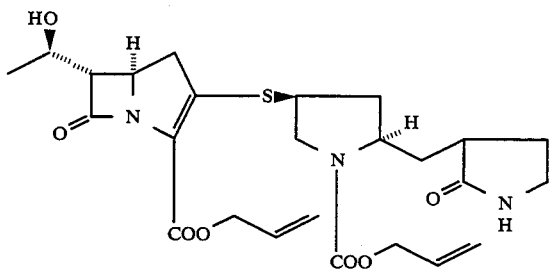

N,N-diisopropylethylamine (0.13 ml, 0.76 mmol) was dropwise added to a solution of allyl (5R,6S)-2-diphenoxyphosphoryloxy-6-[(R)-1-hydroxyethyl]-1-carbapen-2-em-3-carboxylate (369 mg, 0.76 mmol) and (2R,4S)-N-allyloxycarbonyl-4-mercapto-2-(2-pyrrolidon-3-ylmethyl)pyrrolidine (216 mg, 0.76 mmol) in acetonitrile (5.6 ml) under cooling with ice. The reaction mixture solution was stirred at the same temperature for one hour and further stirred at 5° C. for 16 hours. Ethyl acetate (60 ml) was added to the reaction solution. The mixture was washed sequentially with a saturated sodium hydrogen carbonate aqueous solution and a saturated sodium chloride aqueous solution, then dried over anhydrous sodium sulfate and concentrated. The residue was purified by silica gel flash column chromatography (Wakogel TM C-300, 40 ml, acetone-ethyl acetate 2:3). The fraction containing the desired product was concentrated to obtain allyl (5R,6S)-2-[(2R,4S)-N-allyloxycarbonyl-2-(2-pyrrolidon-3-ylmethyl)pyrrolidin-4-ylthio]-6-[(R)-1-hydroxyethyl]-1-carbapen-2-em-3-carboxylate (303 mg, yield: 76.7%) in the form of foam.

NMR(CDCl$_3$) δ: 1.35(3H,d,J=6 Hz),1.7–2.2(4H,m),2.34(2H,m),2.61(1H,m),3-.1–3.4(6H,m),3.55(1H,m),4.0–4.3(4H,m),4-.6–4.9(4H,m),5.2–5.5(4H,m),5.78(1H,br s),6.0(2H,m).

2)

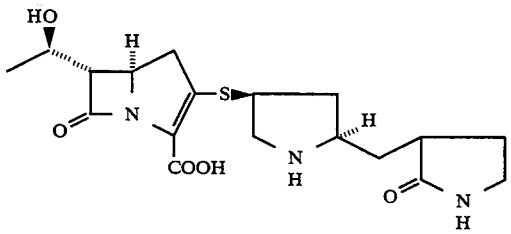

Water (52 μl) was added to a solution of the compound obtained by the above reaction (300 mg, 0.58 mmol) in methylene chloride (6 ml). This mixture was deaerated. Bis(triphenylphosphine)palladium(II) chloride (8 mg, 0.011 mmol) and tributyltin hydride (0.466 ml, 1.73 mmol) were added to this solution mixture under cooling with ice. This solution mixture was stirred at the same temperature for 5 minutes and further at room temperature for 30 minutes. Water (40 ml) was added to the reaction solution. The aqueous layer was washed with chloroform (20 ml, twice), and then the remaining organic solvent was removed under reduced pressure. Active carbon (50 mg) was added thereto. This mixture was stirred for 30 minutes and then filtered. The filtrate was concentrated to 700 mg, and ethanol (1.4 ml) was added thereto at room temperature. This solution mixture was left to stand at the same temperature for 30 minutes to form precipitate. To this suspension, ethanol (1.4 ml) was dropwise added under stirring over a period of one hour. Then, the suspension was stirred at room temperature for 30 minutes and further at 5° C. for 16 hours. The precipitate was collected by filtration and washed sequentially with a water-ethanol (1:4) mixture (1.3 ml, twice) and acetone (2 ml) and then dried under reduced pressure for two hours to obtain the above identified compound (159 mg, yield: 69.6%).

IR(KBr)cm$^{-1}$: 1740, 1690, 1600, 1380.
NMR(D$_2$O) δ: 1.26(3H,d,J=8 Hz),1.7–2.0(3H,m),1.18(1H,m),1.38(1H,m),2-.6–2.8(2H,m),3.2(2H,d,J=9 Hz),3.3–3.4(4H,m),3-.7–3.9(2H,m),4.0(1H,m),4.1–4.3(2H,m).

EXAMPLE 8

(1R,5S,6S)-6-[(R)-1-hydroxyethyl]-1-methyl-2-[(2R,4S)-2-(2-pyrrolidon-3-ylmethyl)pyrrolidin-4-ylthio]-1-carbapen-2-em-3-carboxylic acid

1)

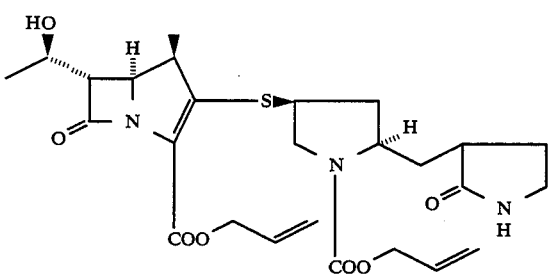

N,N-diisopropylethylamine (0.26 ml, 1.52 mmol) was dropwise added to a solution of allyl (1R,5S,6S)-2-diphenoxyphosphoryloxy-6-[(R)-1-hydroxyethyl]-1-methyl-1-carbapen-2-em-3-carboxylate (759 mg, 1.52 mmol) and (2R,4S)-N-allyloxycarbonyl-4-mercapto-2-(2-pyrrolidon-3-ylmethyl)pyrrolidine (432 mg, 1.52 mmol) in acetonitrile (11 ml) at −40° C. The reaction solution mixture was stirred at the same temperature for 3 hours and further at 5° C. for 16 hours. Ethyl acetate (60 ml) was added to the reaction solution. This solution mixture was washed sequentially with a saturated sodium hydrogen carbonate aqueous solution and a saturated sodium chloride aqueous solution, then dried over anhydrous sodium sulfate and concentrated. The residue was purified by silica gel flash column chromatography (Wakogel TM C-300, 40 ml, acetone-ethyl acetate 2:3), and the fraction containing the desired product was concentrated to obtain allyl (1R,5S,6S)-2-[(2R,4S)-N-allyloxycarbonyl-2-(2-pyrrolidon-3-ylmethyl)pyrrolidin-4-ylthio]-6-[(R)-1-hydroxyethyl]-1-methyl-1-carbapen-2-em-3-carboxylate (420 mg, yield: 51.8%) in the form of foam.

NMR(CDCl$_3$) δ: 1.26(3H,d,J=8 Hz),1.35(3H,d,J=6 Hz),1.7(1H,m),1.9–2.4(5H,m),2.60(1H,m),3-.2–3.4(5H,m),3.58(1H,m),3.9–4.3(4H,m),4-.5–4.9(4H,m),5.2–5.5(4H,m),5.8–6.1(3H,m).

2)

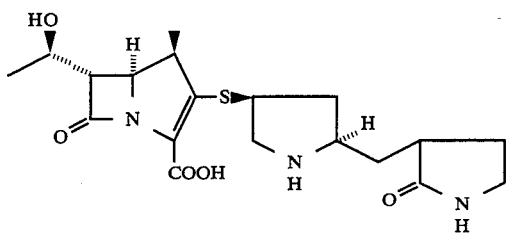

Water (71 μl) was added to a solution of the compound obtained by the above reaction (420 mg, 0.79 mmol) in methylene chloride (8.4 ml). This solution was deaerated. Bis(triphenylphosphine)palladium(II) chloride (11 mg, 0.016 mmol) and tributyltin hydride (0.635 ml, 2.36 mmol) were added to this solution mixture under cooling with ice. This solution mixture was stirred at the same temperature for 3 minutes and further at room temperature for 30 minutes. Water (40 ml) was added to the reaction solution, and the aqueous layer was washed with chloroform (20 ml, twice). Then, the remaining organic solvent was removed under reduced pressure. Active carbon (50 mg) was added thereto. This mixture was stirred for 30 minutes and then filtered. The filtrate was concentrated to 500 mg, and ethanol (1 ml) was added thereto at room temperature. This solution mixture was left to stand at the same temperature for one hour to form precipitate. To this suspension, ethanol (3.5 ml) was dropwise added under stirring over a period of one hour. This suspension was stirred at room temperature for 30 minutes and further at 5° C. for 16 hours. The precipitate was collected by filtration, then washed sequentially with a water-ethanol (1:9) mixture (1 ml, three times ) and acetone (3 ml) and dried for two hours under reduced pressure to obtain the above identified compound (232 mg, yield: 72.0%).

IR(KBr)cm$^{-1}$: 1760, 1700, 1640, 1590, 1390.

NMR(D$_2$O) δ: 1.21(3H,d,J=8 Hz),1.28(3H,d,J=6 Hz),1.7–2.0(3H,m),2.20(1H,m),2.40(1H,m),2-.6–2.9(2H,m),3-.3–3.5(5H,m),3.70(1H,m),3.86(1H,m),4.0(1H,m),4.24(2-H,m).

EXAMPLE 9

(1R,5S,6S)-2-[(2R,4S)-2-(2-azetidinon-3-ylmethyl)-pyrrolidin-4-ylthio]-6-[(R)-1-hydroxyethyl]-1-methyl-1-carbapen-2-em-3-carboxylic acid

1)

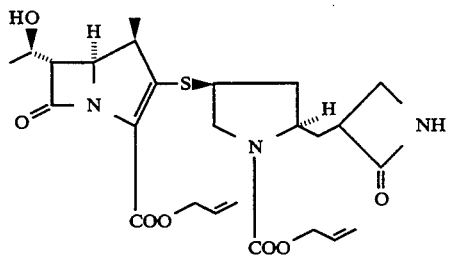

The same procedure as in Example 8-1 was carried out by using allyl (1R,5S,6S)-2-diphenoxyphosphoryloxy-6-[(R)-1-hydroxyethyl]-1-methyl-1-carbapen-2-em-3-carboxylate (331 mg, 0.66 mmol), (2R,4S)-N-allyloxycarbonyl-2-(2-azetidinon-3-ylmethyl)-4-mercaptopyrrolidine (180 mg, 0.66 mmol) and N,N-diisopropylethylamine (0.12 ml, 0.66 mmol) to obtain allyl (1R,5S,6S)-2-[(2R,4S)-N-allyloxycarbonyl-2-(2-azetidinon-3-ylmethyl)pyrrolidin-4-ylthio]-6-[(R)-1-hydroxyethyl]-1-methyl-1-carbapen-2-em-3-carboxylate (125 mg, yield: 36.3%) in the form of foam.

NMR(CDCl$_3$) δ: 1.29(3H,d,J=7 Hz),1.36(3H,d,J=6 Hz),1.8(1H,m),2.0(1H,m),2.65(2H,m),3.1(1H,m),3.3(3-H,m),3.48(1H,t,J=6 Hz),3.6(1H,m),4.0(2H,m),4.25(2H,m),4.62(2H,br d, J=6 Hz),4.8(2H,m),5.2–5.5(4H,m),5.66(1H,br s),5.98(2H,m).

2)

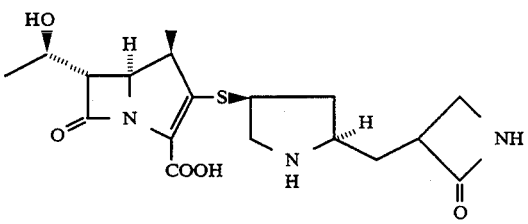

The same protecting group removal reaction and post treatment as in Example 8-2 were carried out by using the compound obtained by the above reaction (125 mg, 0.24 mmol), bis(triphenylphosphine)palladium(II) chloride (3.4 mg, 0.0048 mmol), tributyltin hydride (0.194 ml, 0.722 mmol) and water (22 μl). The obtained aqueous layer was purified by reversed phase column chromatography (YMC.GEL TM ODS-AQ 120-S50, 50 ml, methanol-water 15:85), and the fraction containing the desired product was concentrated and freeze-dried to obtain the above identified compound (20 mg, yield: 21.0%).

IR(KBr)cm$^{-1}$: 1740, 1600, 1390.

NMR(D$_2$O) δ: 1.18(3H,d,J=7 Hz),1.26(3H,d,J=6 Hz),1.3(1H,m),2.2(3H,m),2.7(1H,m),3.1–3.7(7H,m),3.9-2(1H,m),4.1–4.3(2H,m).

EXAMPLE 10

Potassium (1R,5S,6S)-6-[(R)-1-hydroxyethyl]-1-methyl-2-[(2S,4S)-2-(2-pyrrolidon-4-yl)pyrrolidin-4-ylthio]-1-carbapen-2-em-3-carboxylate diastereomers A and B

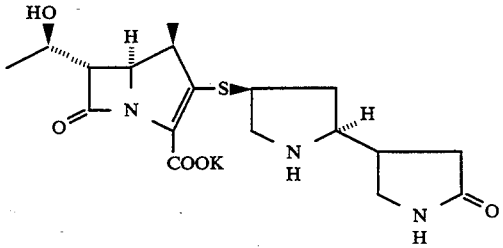

The compound of Example 3 (100 mg) was subjected to Waters 600E (column: YMC TM -Pack SH-365-5 S-5 120A ODS, eluent: 0.01M potassium phosphate buffer (pH 7.0)-methanol 85:15, flow rate: 14 ml/min, detector: 290 nm, temperature: 26° C.) to obtain fractions of diastereomer A (retention time: 25.5 min) and diastereomer B (retention time: 30.2 min), respectively. The fraction containing diastereomer A was concentrated to about 15 ml, and the concentrated solution was subjected to reversed phase column chromatography (YMC ™.GEL ODS-AQ 120-S50, distilled water was passed to remove salts and then the desired product was eluted by a 20% methanol aqueous solution). The desired fraction was concentrated and freeze-dried to obtain diastereomer A (16 mg) of the above identified compound. In the same manner as above, diastereomer B (14.8 mg) was obtained.

Diastereomer A

IR(KBr)cm$^{-1}$: 1760, 1680, 1590, 1390.

NMR(D$_2$O) δ: 1.22(3H,d,J=8 Hz),1.30(3H,d,J=7 Hz),1.67(1H,m),2.35(1H,dd,J=8,17 Hz),4.02(1H,m),4.25(2H,m).

Diastereomer B

IR(KBr)cm$^{-1}$: 1760, 1680, 1590, 1390.

NMR(D$_2$O) δ: 1.22(3H,d,J=8 Hz),1.30(3H,d,J=7 Hz),1.72(1H,m),2.28(1H,dd,J=8,17 Hz),4.02(1H,m),4.26(2H,m).

EXAMPLE 11

(1R,5S,6S)-6-[(R)-1-hydroxyethyl]-1-methyl-2-[(2S,4S)-2-(pyrrolidin-3-yl)pyrrolidin-4-ylthio]-1-carbapen-2-em-3-carboxylic acid diastereomers A and B

1)

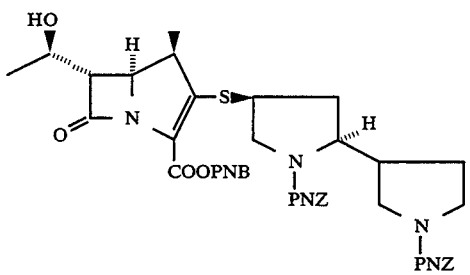

The same procedure as in Example 1-1 was carried out by using p-nitrobenzyl (1R,5S,6S)-2-diphenoxyphosphoryloxy-6-[(R)-1-hydroxyethyl]-1-methyl-1-carbapen-2-em-3-carboxylate (1.39 g, 2.34 mmol) and (2S,4S)-4-mercapto-N-(p-nitrobenzyloxycarbonyl)-2-[N-(p-nitrobenzyloxycarbonyl)pyrrolidin-3-yl]pyrrolidine (1.24 g, 2.34 mmol, compound of Reference Example 5-6) to obtain p-nitrobenzyl (1R,5S,6S)-6-[(R)-1-hydroxyethyl]-1-methyl-2-[(2S,4S)-N-(p-nitrobenzyloxycarbonyl)-2-[N-(p-nitrobenzyloxycarbonyl)pyrrolidin-3-yl]pyrrolidin-4-ylthio]-1-carbapen-2-em-3-carboxylate (1.59 g, yield: 77.7%).

IR(KBr)cm$^{-1}$: 1770, 1700, 1610, 1520, 1400, 1350.

NMR(CDCl$_3$) δ: 1.28(3H,d,J=7 Hz),1.34(3H,d,J=6 Hz),5.14–5.58(6H,m),7.52(4H,br d,J=8 Hz),7.65(2H,d,J=8Hz),8.20(6H,br d,J=8Hz).

2)

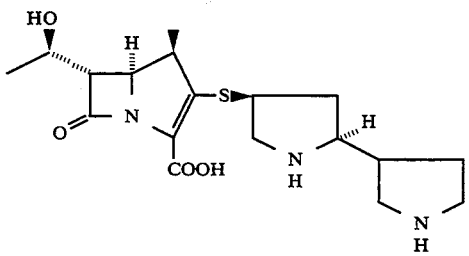

The compound obtained by the above reaction (1.52 g, 1.74 mmol) was dissolved in a solution mixture comprising tetrahydrofuran (40 ml), ethanol (2 ml) and a 0.25M sodium 3-morpholinopropanesulfonate buffer solution (pH 7.0, 18 ml). Then, 10% palladium-carbon catalyst (750 mg) was added thereto. This mixture was stirred in a hydrogen stream of 3 atm at room temperature for two hours. The catalyst was filtered off from the reaction mixture, and the filtrate was washed with ethyl acetate (50 ml). Then, insoluble matters in the aqueous solution were filtered off. The aqueous layer thus obtained was subjected to reversed phase column chromatography (LC-SORB ™ SP-B-ODS, 15% methanol aqueous solution→20% methanol aqueous solution), then concentrated and freeze-dried to obtain diastereomer A (97 mg, yield: 14.6%) and diastereomer B (110 mg, yield: 16.6%) of the above identified compound, respectively.

Diastereomer A

IR(KBr)cm$^{-1}$: 1760, 1580, 1540, 1380.

NMR(D$_2$O) δ: 1.16(3H,d,J=8 Hz),1.24(3H,d,J=7 Hz),1.74(1H,m),2.20(1H,m),2.44(2H,m),3.73(1H,m),4—17(2H,m).

HPLC (the same condition as in Example 1). Retention time: 2.6 min.

Diastereomer B

IR(KBr)cm$^{-1}$: 1750, 1590, 1390. NMR(D$_2$O) δ: 1.23(3H,d,J=8 Hz),1.30(3H,d,J=7 Hz),1.74(1H,m),2.23(1H,m),2.50(2H,m),3.78(1H,m),4.2-4(2H,m).

HPLC (the same condition as in Example 1). Retention time: 3.6 min.

EXAMPLE 12

(1R,5S,6S)-6-[(R)-1-hydroxyethyl]-1-methyl-2-[(2S,4S)-2-(N-methylpyrrolidin-3-yl)pyrrolidin-4-ylthio]-1-carbapen-2-em-3-carboxylic acid diastereomers A and B

1)

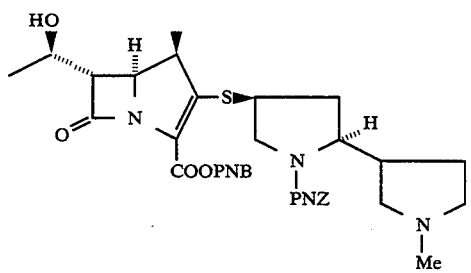

The same procedure as in Example 1-1 was carried out by using p-nitrobenzyl (1R,5S,6S)-2-diphenoxyphosphoryloxy-6-[(R)-1-hydroxyethyl]-1-methyl-1-carbapen-2-em-3-carboxylate (680 mg, 1.14 mmol) and (2S,4S)-4-mercapto-2-(N-methylpyrrolidin-3-yl)-N-(p-nitrobenzyloxycarbonyl)pyrrolidine trifluoromethane sulfonate (650 mg, 1.26 mmol, compound of Reference Examples 6–9) to obtain p-nitrobenzyl (1R,5S,6S)-6-[(R)-1-hydroxyethyl]-1-methyl-2-[(2S,4S)-N-(p-nitrobenzyloxycarbonyl)-2-(N-methylpyrrolidin-3-yl)pyrrolidin-4-ylthio]-1-carbapen-2-em-3-carboxylate (603 mg, yield: 74.3%).

1NMR(KBr)cm$^{-1}$: 1770, 1700, 1610, 1520.

NMR(CDCl$_3$) δ: 1.37(3H,d,J=6 Hz),1.42(3H,d,J=7 Hz),5.24(4H,m),7.54(2H,d,J=8 Hz),7.68(2H,d,J=8 Hz),8.25(2H,d,J=8 Hz),8.27(2H,d,J=8 Hz).

2)

-continued

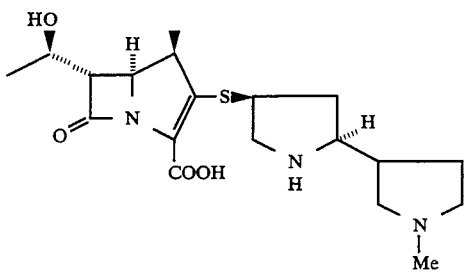

The same procedure as in Example 1-2 was carried out by using the compound obtained by the above reaction (290 mg, 0.41 mmol) to obtain diastereomer A (27 mg, yield: 16.7%) and diastereomer B (27 mg, yield: 16.7%) of the above identified compound, respectively.

Diastereomer A

1R(KBr)cm$^{-1}$: 1760, 1590, 1380.

NMR(D$_2$O) δ: 1.21(3H,d,J=8 Hz),1.30(3H,d,J=7 Hz),1.53(1H,m),1.92(1H,m),2.94(3H,s),3.91(1H,m),4.23-(2H,m).

HPLC (the same condition as in Example 1). Retention time: 3.5 min.

Diastereomer B

1R(KBr)cm$^{-1}$: 1750, 1590, 1380.

NMR(D$_2$O) δ: 1.18(3H,d,J=8 Hz),1.27(3H,d,J=7 Hz),1.80(1H,m),2.24(1H,m),2.88(3H,s),3.52(1H,m),3.74-(1H,m),4.20(2H,m).

HPLC (the same condition as in Example 1). Retention time: 4.3 min.

EXAMPLE 13

(1R,5S,6S)-6-[(R)-1-hydroxyethyl]-1-methyl-2-[(2S,4S)-2-(N,N-dimethyl-3-pyrrolidinio)pyrrolidin-4-ylthio]-1-carbapen-2-em-3-carboxylate diastereomers A and B

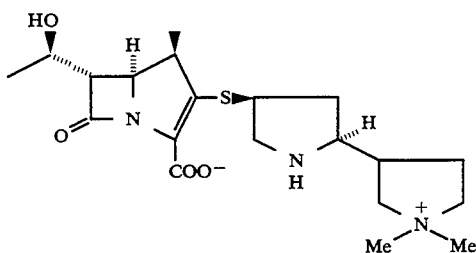

Methyl iodide (0.13 ml, 2.09 mmol) was added to a solution of the compound obtained in Example 12-1 (300 mg, 0.42 mmol) in acetone (5 ml), and the mixture was stirred overnight at room temperature. The reaction solution was concentrated under reduced pressure, and the obtained residue was treated in the same manner as in Example 1-2 to obtain diastereomer A (17 mg, yield: 9.8%) and diastereomer B (29 mg, yield: 16.7%) of the above identified compound, respectively.

Diastereomer A

1R(KBr)cm$^{-1}$: 1750, 1590, 1380.

NMR(D$_2$O) δ: 1.20(3H,d,J=8 Hz),1.29(3H,d,J=7 Hz),2.12(1H,m),2.44(2H,m),3.17(3H,s),3.24(3H,s),3.77(-2H,m),4.22(2H,m).

HPLC (the same condition as in Example 1). Retention time: 2.7 min.

Diastereomer B

1R(KBr) cm$^{-1}$: 1750, 1590, 1380.

NMR(D$_2$O) δ: 1.22(3H,d,J=8 Hz),1.30(3H,d,J=7 Hz),2.02(1H,m),2.52(2H,m),3.17(3H,s),3.25(3H,s),3.78(-2H,m),4.22(2H,m).

HPLC (the same condition as in Example 1). Retention time: 3.5 min.

EXAMPLE 14

Sodium (5R,6S)-6-[(R)-1-hydroxyethyl]-2-[(2S,4S)-2-(N-methyl-2-azetidinon-4-yl)pyrrolidin-4-ylthio]-1-carbapen-2-em-3-carboxylate

1)

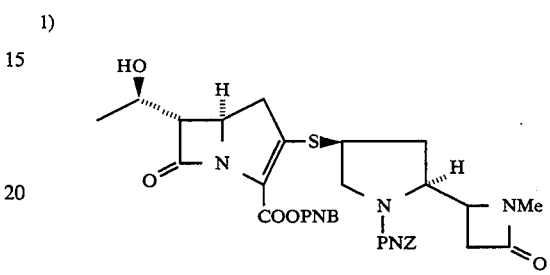

The same procedure as in Example 1-1 was carried out by using p-nitrobenzyl (5R,6S)-2-diphenoxyphosphoryloxy-6-8 (R)-1-hydroxyethyl]-1-carbapen-2-em-3-carboxylate (235 mg, 0.40 mmol) and (2S,4S)-4-mercapto-2-(N-methyl-2-azetidinon-4-yl)-N-(p-nitrobenzyloxycarbonyl)pyrrolidine (149 mg, 0.41 mmol, compound of Reference Example 7) to obtain p-nitrobenzyl (5R,6S)-6-[(R)-1-hydroxyethyl]-2-[(2S,4S)-2-(N-methyl-2-azetidinon-4-yl)-N-(p-nitrobenzyloxycarbonyl)pyrrolidin-4-ylthio]-1-carbapen-2-em-3-carboxylate (265 mg, yield: 94.5%).

IR(KBr)cm$^{-1}$: 1780, 1740, 1700, 1520, 1340.

NMR(CDCl$_3$) δ: 1.36(3H,d,J=6 Hz),2.78(3H,s),5.26(3H,m),5.52(1H,d,J=14 Hz),7.54(2H,d,j=8 Hz),7.66(2H,d,J=8 Hz),8.22(2H,d,J=8 Hz),8.24(2H,d,J=8 Hz).

2)

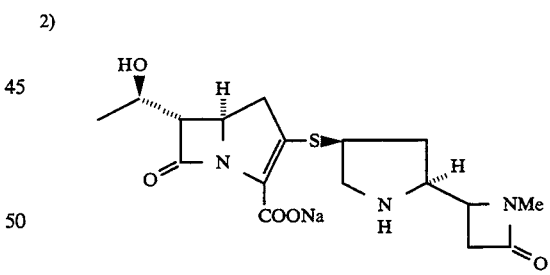

The same procedure as in Example 1-2 was carried out by using the compound obtained by the above reaction (265 mg, 0.37 mmol) to obtain diastereomer A (4 mg, yield: 2.7%), diastereomer B (25 mg, yield: 16.7%) and a mixture of diastereomers A and B (25 mg, yield: 16.7%) of the above identified compound.

Diastereomer A

IR(KBr)cm$^{-1}$: 1750, 1590, 1390.

NMR(D$_2$O) δ: 1.27(3H,d,J=6 Hz),1.66(1H,m),2.74(2H,m),2.90(3H,s),3.10-3.47(5H,m-),3.67(2H,m),4.22(2H,m).

HPLC (the same condition as in Example 1). Retention time: 2.68 min.

Diastereomer B

IR (KBr) cm$^{-1}$: 1750, 1590, 1390.

NMR(D₂O) δ: 1.28(3H,d,J=6 Hz),1.89(1H,m),2.88(3H,s),2.92(2H,m),3.16–3.48(5H,m-),3.75(1H,dd,J=12,6 Hz),4.24(2H,m).

HPLC (the same condition as in Example 1). Retention time: 2.85 min.

EXAMPLE 15

Sodium (1R,5S,6S)-6-[(R)-1-hydroxyethyl]-1-methyl-2-[(2S,4S)-2-(N-methyl-2-azetidinon-4-yl)pyrrolidin-4-ylthio]-1-carbapen-2-em-3-carboxylate

1)

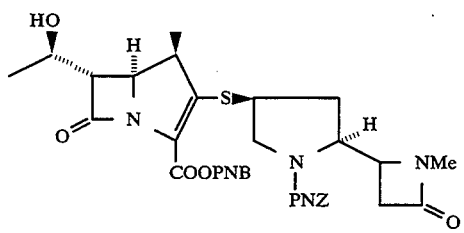

The same procedure as in Example 1-1 was carried out by using p-nitrobenzyl (1R,5S,6S)-2-diphenoxyphosphoryloxy-6-[(R)-1-hydroxyethyl]-1-methyl-1-carbapen-2-em-3-carboxylate (240 mg, 0.40 mmol) and (2S,4S)-4-mercapto-2-(N-methyl-2-azetidinon-4-yl)-N-(p-nitrobenzyloxycarbonyl)pyrrolidine (149 mg, 0.41 mmol) to obtain p-nitrobenzyl (1R,5S,6S)-6-[(R)-1-hydroxyethyl]-1-methyl-2-[(2S,4S)-2-(N-methyl-2-azetidinon-4-yl)-N-(p-nitrobenzyloxycarbonyl)pyrrolidin-4-ylthio]-1-carbapen-2-em-3-carboxylate (236 mg, yield: 82.7%).

IR(KBr)cm⁻¹: 1750, 1700, 1520, 1350.

NMR(CDCl₃) δ: 1.28(3H,d,J=7 Hz),1.36(1H,d,J=6 Hz),2.78(3H,s),5.26(3H,m),5.50(1H,d,J=14 Hz),7.54(2H,d,J=8 Hz),7.67(2H,d,J=8 Hz),8.22(2H,d,J=8 Hz),8.24(2H,d,J=8 Hz).

2)

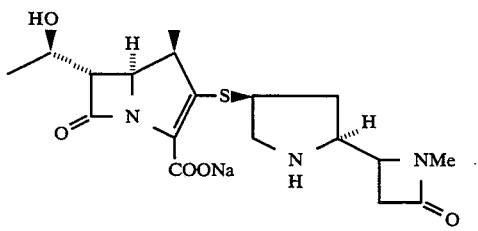

The same procedure as in Example 1-2 was carried out by using the compound obtained by the above reaction (236 mg, 0.33 mmol) to obtain diastereomer A (25 mg, yield: 18.1%) and diastereomer B (39 mg, yield: 28.2%) of the above identified compound.

Diastereomer A
IR(KBr)cm⁻¹: 1750, 1600, 1390.

NMR(D₂O) δ: 1.22(3H,d,J=7 Hz),1.30(3H,d,J=6 Hz),1.78(1H,m),2.81(2H,m),2.94(3H,s),3.20–3.55(5H,m-),3.74(1H,dd,J=12,6 Hz),4.26(2H,m)HPLC (the same condition as in Example 1). Retention time: 4.86 min.

Diastereomer B
IR(KBr)cm⁻¹: 1750, 1600, 1390.

NMR(D₂O) δ: 1.24(3H,d,J=7 Hz),1.30(3H,d,J=6 Hz),1.88(1H,m),2.90(3H,s),2.95(2H,m),3.18–3.34(5H,m-),3.70(1H,dd,J=12,6 Hz),4.26(2H,m).

HPLC (the same condition as in Example 1). Retention time: 5.43 min.

EXAMPLE 16

Sodium (1R,5S,6S)-6-[(R)-1-hydroxyethyl]-1-methyl-2-[(2S,4S)-2-(N-methyl-2,5-dioxopyrrolidin-3-yl)pyrrolidin-4-ylthio]-1-carbapen-2-em-3-carboxylate diastereomer A

1)

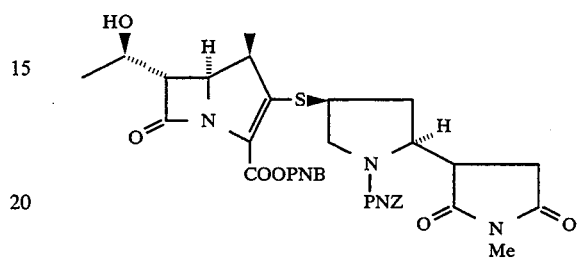

The same procedure as in Example 1-1 was carried out by using p-nitrobenzyl (1R,5S,6S)-2-diphenoxyphosphoryloxy-6-[(R)-1-hydroxyethyl]-1-methyl-1-carbapen-2-em-3-carboxylate-(500 mg, 0.84 mmol) and (2S,4S)-4-mercapto-2-(N-methyl-2,5-dioxopyrrolidin-3-yl)-N-(p-nitrobenzyloxycarbonyl)pyrrolidine diastereomer A (330 mg, 0.84 mmol, compound of Reference Example 8) to obtain p-nitrobenzyl (1R,5S,6S)-6-[(R)-1-hydroxyethyl]-1-methyl-2-[(2S,4S)-2-(N-methyl-2,5-dioxopyrrolidin-3-yl)-N-(p-nitrobenzyloxycarbonyl)pyrrolidin-4-ylthio]-1-carbapen-2-em-3-carboxylate diastereomer A (311 mg, yield: 50.1%).

IR(KBr)cm⁻¹: 1770, 1700, 1520, 1350.

NMR(CDCl₃) δ: 1.28(3H,d,J=8 Hz),1.34(3H,d,J=7 Hz),2.95(3H,br s),3.68(1H,m),4.57(1H,m),5.20(3H,m),5.52(1H,d,J=14 Hz),7.48(2H,d,J=8 Hz),7.66(2H,d,J=8 Hz),8.22(4H,d,J=8 Hz).

2)

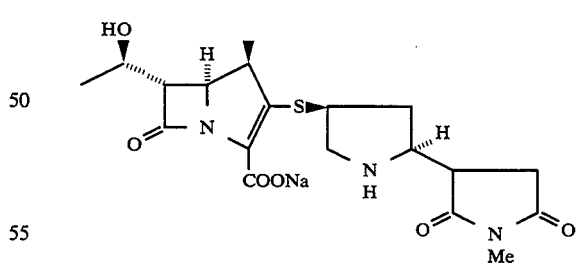

The same procedure as in Example 1-2 was carried out by using the compound obtained in the above reaction (311 mg, 0.42 mmol) to obtain the above identified compound (76.8 mg, yield: 40.9%).

IR(KBr)cm⁻¹: 1750, 1700, 1610, 1590.

NMR(D₂O) δ: 1.20(3H,d,J=7 Hz),1.26(3H,d,J=6 Hz),1.95(1H,m),2.96(3H,s),3.25–3.74(5H,m),4.00(2H,m-),4.20(2H,m).

HPLC (the same condition as in Example 1). Retention time: 4.60 min.

EXAMPLE 17

Sodium (1R,5S,6S)-6-[(R)-1-hydroxyethyl]-1-methyl-2-[(2S,4S)-2-(N-methyl-2,5-dioxopyrrolidin-3-yl)pyrrolidin-4-ylthio]-1-carbapen-2-em-3-carboxylate diastereomer B

1)

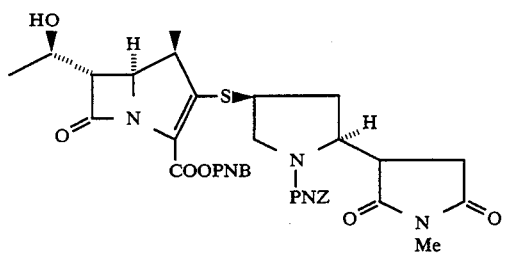

The same procedure as in Example 1-1 was carried out by using p-nitrobenzyl (1R,5S,6S)-2-diphenoxyphosphoryloxy-6-[(R)-1-hydroxyethyl]-1-methyl-1-carbapen-2-em-3-carboxylate (220 mg, 0.37 mmol) and (2S,4S)-4-mercapto-2-(N-methyl-2,5-dioxopyrrolidin-3-yl)-N-(p-nitrobenzyloxycarbonyl)pyrrolidine diastereomer B (140 mg, 0.36 mmol) to obtain p-nitrobenzyl (1R,5S,6S)-6-[(R)-1-hydroxyethyl]-1-methyl-2-[(2S,4S)-2-(N-methyl-2,5-dioxopyrrolidin-3-yl)-N-(p-nitrobenzyloxycarbonyl)pyrrolidin-4-ylthio]-1-carbapen-2-em-3-carboxylate diastereomer B (244 mg, yield: 89.4%).

IR(KBr)cm$^{-1}$: 1780, 1700, 1520, 1350.

NMR(CDCl$_3$) δ: 1.28(3H,d,J=7 Hz),1.34(3H,d,J=6 Hz),1.62(1H,m),2.96(3H,s),5.26(3H,m),5.50(1H,d,J=14 Hz),7.54(2H,d,J=8 Hz),7.67(2H,d,J=8 Hz),8.22(4H,d,J=8 Hz).

2)

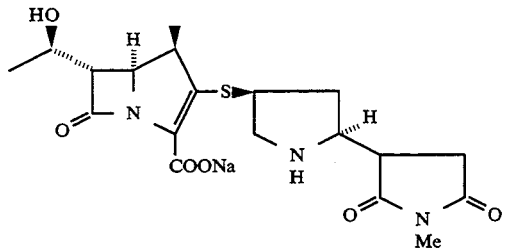

The same procedure as in Example 1-2 was carried out by using the compound obtained by the above reaction (244 mg, 0.322 mmol) to obtain the above identified compound (35 mg, yield: 23.7%).

IR(KBr)cm$^{-1}$: 1750, 1700, 1610, 1590.

NMR(D$_2$O) δ: 1.22(3H,d,J=7 Hz),1.30(3H,d,J=6 Hz),1.84(1H,m),2.66(1H,dd,J=18,6 Hz),2.84(1H,m),2.98(3H,s),3.12(1H,dd,J=18 Hz,9 Hz),3.30-3.58(4H,m),3.72(1H,dd,J=12,6 Hz),3.97(2H,m),4.25(2H,m).

HPLC (the same condition as in Example 1). Retention time: 6.99 min.

EXAMPLE 18

(1R,5S,6S)-2-[(2S,4S)-2-(2,5-dioxopyrrolidin-3-yl)pyrrolidin-4-ylthio]-6-[(R)-1-hydroxyethyl]-1-methyl-1-carbapen-2-em-3-carboxylic acid

1)

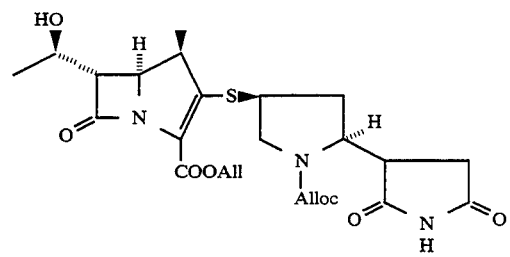

The same procedure as in Example 8-1 was carried out by using allyl (1R,5S,6S)-2-diphenoxyphosphoryloxy-6-[(R)-1-hydroxyethyl]-1-methyl-1-carbapen-2-em-3-carboxylate (230 mg, 0.46 mmol) and (2S,4S)-N-allyloxycarbonyl-2-(2,5-dioxopyrrolidin-3-yl)-4-mercaptopyrrolidine (130 mg, 0.46 mmol, compound of Reference Example 9) to obtain allyl (1R,5S,6S)-2-[(2S,4S)-N-allyloxycarbonyl-2-(2,5-dioxopyrrolidin-3-yl)pyrrolidin-4-ylthio]-6-[(R)-1-hydroxyethyl]-1-methyl-1-carbapen-2-em-3-carboxylate (125 mg, yield: 50.9%).

IR(KBr)cm$^{-1}$: 1780, 1720, 1410, 1330.

NMR(CDCl$_3$) δ: 1.24(3H,d,J=7 Hz),1.33(3H,d,J=6 Hz),1.63(1H,m),5.13-5.54(4H,m),5.78-6.08(2H,m).

2)

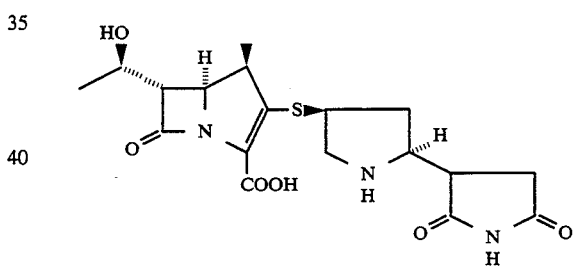

The same procedure as in Example 8-2 was carried out by using the compound obtained by the above reaction (120 mg, 0.23 mmol) to obtain the above identified compound (28.5 mg, yield: 30.9%).

IR(KBr)cm$^{-1}$: 1760, 1720, 1600, 1380.

NMR(D$_2$O) δ: 1.18(3H,d,J=7 Hz),1.25(3H,d,J=6 Hz),1.70(1H,m),2.53-2.80(2H,m),3.03(1H,m),3.25-3.50(4H,m),3.60(1H,m),3.80-4.00(2H,m),4.20(2H,m).

HPLC (the same condition as in Example 1). Retention time: 2.46 min.

EXAMPLE 19

(5R,6S)-6-[(R)-1-hydroxyethyl]-2-[(2S,4S)-2-(3-pyrazolidinon-5-yl)pyrrolidin-4-ylthio]-1-carbapen-2-em-3-carboxylic acid

1)

-continued

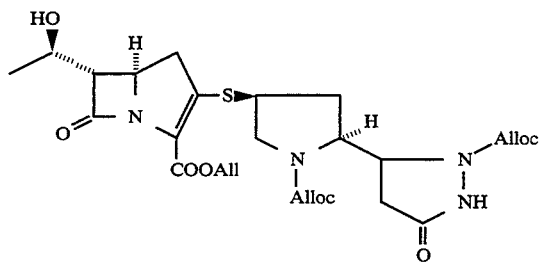

The same procedure as in Example 8-1 was carried out by using allyl (5R,6S)-2-diphenoxyphosphoryloxy-6-[(R)-1-hydroxyethyl]-1-carbapen-2-em-3-carboxylate (195 mg, 0.40 mmol) and (2S,4S)-N-allyloxycarbonyl-2-(1-allyloxycarbonyl-3-pyrazolidinon-5-yl)-4-mercaptopyrrolidine (162 mg, 0.40 mmol) to obtain allyl (5R,6S)-2-[(2S,4S)-N-allyloxycarbonyl-2-(1-allyloxycarbonyl-3-pyrazolidinon-5-yl)pyrrolidin-4-ylthio]-6-[(R)-1-hydroxyethyl]-1-carbapen-2-em-3-carboxylate (155 mg, yield: 65.4%).

IR(KBr)cm$^{-1}$: 1780, 1700, 1550, 1410, 1330.

NMR(CDCl$_3$) δ: 1.32(3H,d,J=6 Hz),4.52–4.90(6H,m),5.18–5.56(6H,m),5.78–6.10(3H,m).

2)

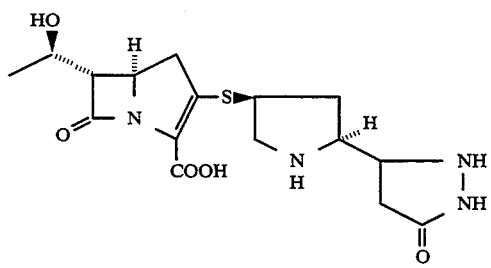

The same procedure as in Example 8-2 was carried out by using the compound obtained by the above reaction (155 mg, 0.26 mmol) to obtain the above identified compound (39 mg, yield: 38.8%).

IR(KBr)cm$^{-1}$: 1760, 1680, 1590, 1390.

NMR(CDCl$_3$) δ: 1.26(3H,d,J=6 Hz),1.88(1H,m),2.35(1H,m),2.70(1H,m),3.06–3.27(2H,-m),3.42(2H,m),3.70–3.90(2H,m).

HPLC (the same condition as in Example 1). Retention time: 1.53 min.

EXAMPLE 20

(1R,5S,6S)-6-[(R)-1-hydroxyethyl]-1-methyl-2-[(2S,4S)-2-(3-pyrazolidinon-5-yl)pyrrolidin-4-ylthio]-1-carbapen-2-em-3-carboxylic acid

1)

-continued

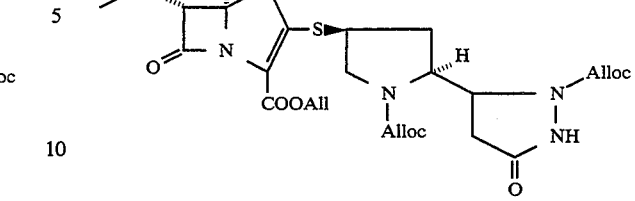

The same procedure as in Example 8-1 was carried out by using allyl (1R,5S,6S)-2-diphenoxyphosphoryloxy-6-[(R)-1-hydroxyethyl]-1-methyl-1-carbapen-2-em-3-carboxylate (330 mg, 0.66 mmol) and (2S,4S)-N-allyloxycarbonyl-2-(1-allyloxycarbonyl-3-pyrazolidinon-5-yl)-4-mercaptopyrrolidine (234 mg, 0.66 mmol) to obtain allyl (1R,5S,6S)-2-[(2S,4S)-N-allyloxycarbonyl-2-(1-allyloxycarbonyl-3-pyrazolidinon-5-yl)pyrrolidin-4-ylthio]-6-[(R)-1-hydroxyethyl]-1-methyl-1-carbapen-2-em-3-carboxylate (172 mg, yield: 43.1%).

IR(KBr)cm$^{-1}$: 1770, 1700, 1410, 1320.

NMR(CDCl$_3$) δ: 1.24(3H,d,J=7 Hz),1.35(3H,d,J=6 Hz),4.50–4.90(6H,m),5.20–5.56(6H,m),5.80–6.10(3H,m).

2)

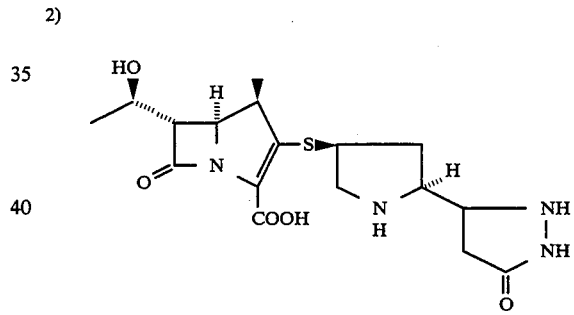

The same procedure as in Example 8-2 was carried out by using the compound obtained by the above reaction (172 mg, 0.285 mmol) to obtain the above identified compound (42 mg, yield: 37.2%).

IR(KBr)cm$^{-1}$: 1760, 1680, 1590, 1390.

NMR(D$_2$O) δ: 1.20(3H,d,J=7 Hz),1.26(3H,d,J=6 Hz),1.85(1H,m),2.35(1H,br d,J=18 Hz),2.70(1H,m),3.10(1H,dd,J=1S,9 Hz),3.15–3.52(3H,m),3.62–3.90(2H,m),3.93–4.32(4H,m).

HPLC (the same condition as in Example 1). Retention time: 2.23 min.

EXAMPLE 21

Sodium (5R,6S)-6-[(R)-1-hydroxyethyl]-2-[(2S,4S)-2-(2-pyrrolidon-3-yl)pyrrolidin-4-ylthio]-1-carbapen-2-em-3-carboxylate

1)

-continued

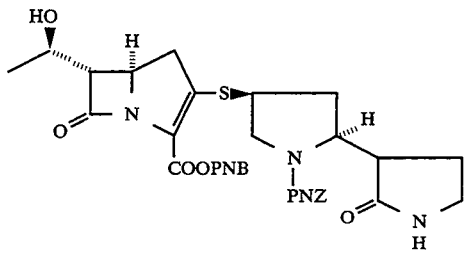

The same procedure as in Example 1-1 was carried out by using p-nitrobenzyl (5R,6S)-2-diphenoxyphosphoryloxy-6-[(R)-1-hydroxyethyl]-1-carbapen-2-em-3-carboxylate (180 mg, 0.31 mmol) and (2S,4S)-4-mercapto-N-(p-nitrobenzyloxycarbonyl)-2-(2-pyrrolidon-3-yl)pyrrolidine (110 mg, 0.30 mmol, compound of Reference Example 11) to obtain p-nitrobenzyl (5R,6S)-6-[(R)-1-hydroxyethyl]-2-[(2S,4S)-N-(p-nitrobenzyloxycarbonyl)-2-(2-pyrrolidon-3-yl)pyrrolidin-4-ylthio]-1-carbapen-2-em-3-carboxylate (151 mg, yield: 70%).

IR(KBr)cm$^{-1}$: 1780, 1700, 1520, 1350.

NMR(CDCl$_3$) δ: 1.38(3H,d,J=6 Hz),5.30(3H,m),5.56(1H,d,J=14 Hz),7.57(2H,d,J=8 Hz),7.70(2H,d,J=8 Hz),8.25(2H,d,J=8 Hz),8.28(2H,d,J=8 Hz).

2)

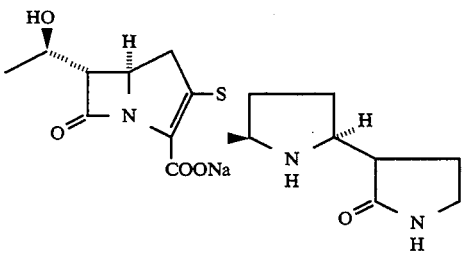

The same procedure as in Example 1-2 was carried out by using the compound obtained by the above reaction (150 mg, 0.22 mmol) to obtain the above identified compound (35 mg, yield: 38.1%).

IR(KBr)cm$^{-1}$: 1760, 1690, 1590, 1380.

NMR(D$_2$O) δ: 1.29(3H,d,J=6 Hz),1.72–2.07(3H,m),2.39(1H,m),2.80(1H,m),3.00(1H,m),3.20(2H,m),3.44(3H,m),3.78(2H,m),3.99(1H,m),4.24(2H,m).

HPLC (the same condition as in Example 1). Retention time: 1.93 min.

EXAMPLE 22

Sodium (1R,5S,6S)-6-[(R)-1-hydroxyethyl]-1-methyl-2-[(2S,4S)-2-(2-pyrrolidon-3-yl)pyrrolidin-4-ylthio]-1-carbapen-2-em-3-carboxylate

1)

-continued

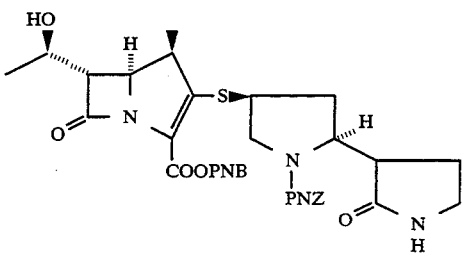

The same procedure as in Example 1-1 was carried out by using p-nitrobenzyl (1R,5S,6S)-2-diphenoxyphosphoryloxy-6-[(R)-1-hydroxyethyl]-1-methyl-1-carbapen-2-em-3-carboxylate (180 mg, 0.30 mmol) and (2S,4S)-4-mercapto-N-(p-nitrobenzyloxycarbonyl)-2-(2-pyrrolidon-3-yl)pyrrolidine (110 mg, 0.30 mmol) to obtain p-nitrobenzyl (1R,5S,6S)-6-[(R)-1-hydroxyethyl]-1-methyl-[(2S,4S)-N-(p-nitrobenzyloxycarbonyl)-2-(2-pyrrolidon-3-yl)pyrrolidin-4-ylthio]-1-carbapen-2-em-3-carboxylate (161 mg, yield: 74.9%).

IR(KBr)cm$^{-1}$: 1780, 1700, 1520, 1350.

NMR(CDCl$_3$) δ: 1.32(3H,d,J=7 Hz),1.40(3H,d,J=6 Hz),5.32(3H,m),5.56(1H,d,J=14 Hz),7.58(2H,d,J=8 Hz),7.70(2H,d,J=8 Hz),8.27(2H,d,J=8 Hz),8.29(2H,d,J=8 Hz).

2)

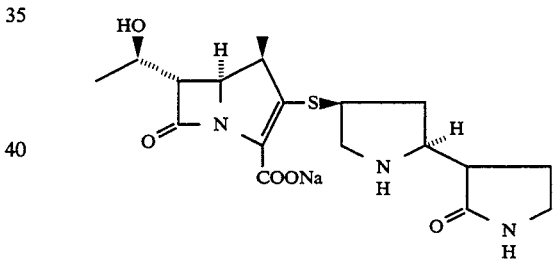

The same procedure as in Example 1-2 was carried out by using the compound obtained by the above reaction (160 mg, 0.23 mmol) to obtain the above identified compound (37 mg, yield: 37.5%).

IR(KBr)cm$^{-1}$: 1760, 1690, 1600, 1380.

NMR(D$_2$O) δ: 1.18(3H,d,J=7 Hz),1.25(3H,d,J=6 Hz),1.63–2.07(3H,m),2.36(1H,m),2.74(1H,m),2.98(1H,m),3.30–3.50(4H,m),3.72(2H,m),3.95(1H,m),4.22(2H,m).

HPLC (the same condition as in Example 1). Retention time: 3.23 min.

EXAMPLE 23

(1R,5S,6S)-2-[(2S,4S)-2-(2-carbamoylpyrrolidin-4-yl)pyrrolidin-4-ylthio]-6-[(R)-1-hydroxyethyl]-1-methyl-1-carbapen-2-em-3-carboxylic acid diastereomer I

1)

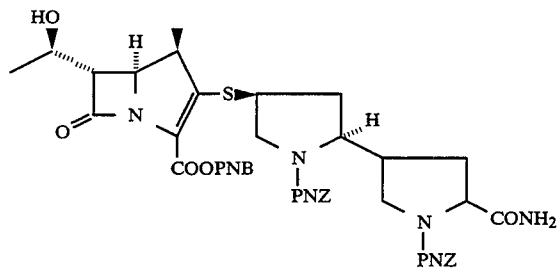

The same procedure as in Example 1-1 was carried out by using p-nitrobenzyl (1R,5S,6S)-2-diphenoxyphosphoryloxy-6-[(R)-1-hydroxyethyl]-1-methyl-1-carbapen-2-em-3-carboxylate (174 mg, 0.29 mmol) and (2S,4S)-2-[2-carbamoyl-N-(p-nitrobenzyloxycarbonyl)-pyrrolidin-4-yl]-4-mercapto-N-(p-nitrobenzyloxycarbonyl)pyrrolidine diastereomer I (160 mg, 0.28 mmol, compound of Reference Example 13) to obtain p-nitrobenzyl (1R,5S,6S)-2-[(2S,4S)-2-[2-carbamoyl-N-(p-nitrobenzyloxycarbonyl)pyrrolidin-4-yl]-N-(p-nitrobenzyloxycarbonyl)pyrrolidin-4-ylthio]-6-[(R)-1-hydroxyethyl]-1-methyl-1-carbapen-2-em-3-carboxylate diastereomer I (223 mg, yield: 82.9%).

IR(KBr)cm$^{-1}$: 1770, 1700, 1520, 1400, 1350.

NMR(CDCl$_3$) δ: 1.28(3H,d,J=7 Hz),1.37(3H,d,J=6 Hz),5.25(5H,m),5.52(1H,d,J=14 Hz),7.53(4H,d,J=8 Hz),7.67(2H,d,J=8 Hz),8.23(6H,d,J=8 Hz).

The same procedure as in Example 1-1 was carried out by using p-nitrobenzyl (1R,5S,6S)-2-diphenoxyphosphoryloxy-6-[(R)-1-hydroxyethyl]-1-methyl-1-carbapen-2-em-3-carboxylate (290 mg, 0.49 mmol) and (2S,4S)-2-[2-carbamoyl-N-(p-nitrobenzyloxycarbonyl)-pyrrolidin-4-yl]-4-mercapto-N-(p-nitrobenzyloxycarbonyl)pyrrolidine diastereomer II (280 mg, 0.49 mmol, compound of Reference Example 14) to obtain p-nitrobenzyl (1R,5S,6S)-2-[(2S,4S)-2-[2-carbamoyl-N-(p-nitrobenzyloxycarbonyl)pyrrolidin-4-yl]-N-(p-nitrobenzyloxycarbonyl)pyrrolidin-4-ylthio]-6-[(R)-1-hydroxyethyl]-1-methyl-1-carbapen-2-em-3-carboxylate diastereomer II (419 mg, yield: 93.4%).

IR(KBr)cm$^{-1}$: 1770, 1700, 1520, 1350.

NMR(CDCl$_3$) δ: 1.28(3H,d,J=7 Hz),1.37(3H,d,J=6 Hz),5.26(5H,m),5.52(1H,d,J=14 Hz),7.53(4H,d,J=8 Hz),7.68(2H,d,J=8 Hz),8.24(6H,d,J=8 Hz).

2)

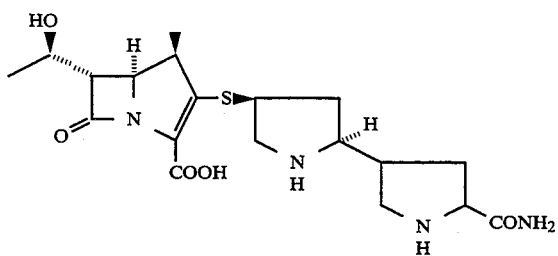

The same procedure as in Example 1-2 was carried out by using the compound obtained by the above reaction (223 mg, 0.24 mmol) to obtain the above identified compound (50.7 mg, yield: 49.8%).

IR(KBr)cm$^{-1}$: 1750, 1700, 1390.

NMR(D$_2$O) δ: 1.19(3H,d,J=7 Hz),1.27(3H,d,J=6 Hz),1.58(2H,m),2.00–2.32(2H,m),2.42–2.74(2H,m),2.82(1H,dd,J=12,8 Hz),3.22(1H,dd,J=12,4 Hz),3.30–3.54(4H,m),3.92(1H,m),4.10(1H,dd,J=9,4 Hz),4.20(2H,m).

EXAMPLE 24

(1R,5S,6S)-2-[(2S,4S)-2-(2-carbamoylpyrrolidin-4-yl)pyrrolidin-4-ylthio]-6-[(R)-1-hydroxyethyl]-1-methyl-1-carbapen-2-em-3-carboxylic acid diastereomer II

1)

2)

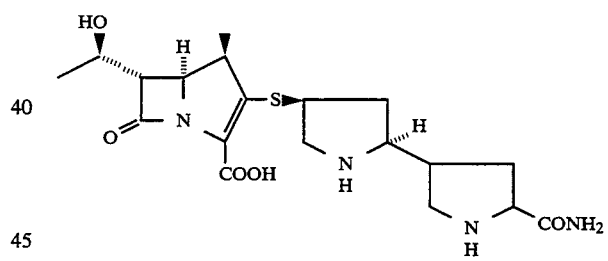

The same procedure as in Example 1-2 was carried out by using the compound obtained by the above reaction (419 mg, 0.46 mmol) to obtain the above identified compound (93 mg, yield: 48%).

IR(KBr)cm$^{-1}$: 1760, 1700, 1390.

NMR(D$_2$O) δ: 1.20(3H,d,J=7 Hz),1.28(3H,d,J=6 Hz),1.62(2H,m),2.44–2.75(3H,m),2.83(1H,dd,J=10,8 Hz),3.16–3.57(6H,m),3.94(1H,m),4.08(1H,m),4.23(2H,m).

HPLC (the same condition as in Example 1). Retention time: 2.84 min.

EXAMPLE 25

(5R,6S)-6-[(R)-1-hydroxyethyl]-2-[(2S,4S)-2-(pyrrolidin-3-yl)pyrrolidin-4-ylthio]-1-carbapen-2-em-3-carboxylic acid diastereomer A

1)

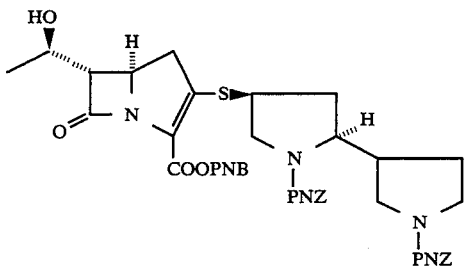

The same procedure as in Example 1-1 was carried out by using p-nitrobenzyl (5R,6S)-2-diphenoxyphosphoryloxy-6-[(R)-1-hydroxyethyl]-1-carbapen-2-em-3-carboxylate (255 mg, 0.45 mmol) and (2S,4S)-4-mercapto-N-(p-nitrobenzyloxycarbonyl)-2-[N-(p-nitrobenzyloxycarbonyl)pyrrolidin-3-yl]pyrrolidine (240 mg, 0.45 mmol, compound of Reference Example 5) to obtain p-nitrobenzyl (5R,6S)-6-[(R)-1-hydroxyethyl]-2-[(2S,4S)-N-(p-nitrobenzyloxycarbonyl)-2-[N-(p-nitrobenzyloxycarbonyl)pyrrolidin-3-yl]pyrrolidin-4-ylthio]-1-carbapen-2-em-3-carboxylate (297 mg, yield: 78.6%).

IR(KBr)cm$^{-1}$: 1780, 1700, 1520, 1350.
NMR(CDCl$_3$) δ: 1.25 (3H,d,J=6 Hz),4.00–4.40(4H,m),5.16–5.35(5H,m),5.52(1H,d,J=14 Hz),7.52(4H,d,J=8 Hz),7.65(2H,d,J=8 Hz),8.21(6H,m).

2)

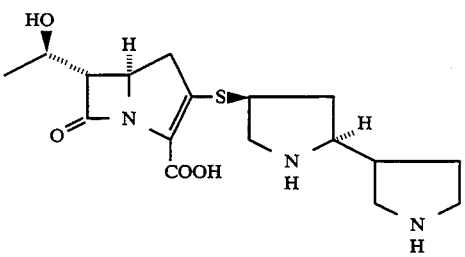

The same procedure as in Example 1-2 was carried out by using the compound obtained by the above reaction (297 mg, 0.345 mmol) to obtain diastereomer A (13.6 mg, yield: 10.7%) of the above identified compound.

IR(KBr)cm$^{-1}$: 1760, 1690, 1390.
NMR(D$_2$O) δ: 1.27(3H,d,J=6 Hz),1.46(1H,m),1.68–2.10(2H,m),2.-14–2.80(3H,m),3.80(2H,m),4.22(2H,m).

HPLC (the same condition as in Example 1). Retention time: 2.03 min.

EXAMPLE 26

(1R,5S,6S)-6-[(R)-1-hydroxyethyl]-1-methyl-2-[(2S,4S)-2-(pyrrolidin-3-yl)pyrrolidin-4-ylthio]-1-carbapen-2-em-3-carboxylic acid diastereomer A

1)

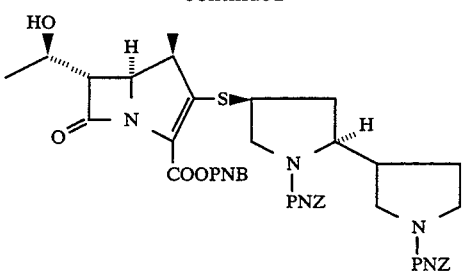

The same procedure as in Example 1-1 was carried out by using p-nitrobenzyl (1R,5S,6S)-2-diphenoxyphosphoryloxy-6-[(R)-1-hydroxyethyl]-1-methyl-1-carbapen-2-em-3-carboxylate (1.75 g, 2.94 mmol) and (2S,4S)-4-mercapto-N-(p-nitrobenzyloxycarbonyl)-2-[N-(p-nitrobenzyloxycarbonyl)pyrrolidin-3-yl]pyrrolidine diastereomer A (1.56 g, 2.94 mmol, compound of Reference Example 15-7) to obtain p-nitrobenzyl (1R,5S,6S)-6-[(R)-1-hydroxyethyl]-1-methyl-2-[(2S,4S)-N-(p-nitrobenzyloxycarbonyl)-2-[N-(p-nitrobenzyloxycarbonyl)pyrrolidin-3-yl]pyrrolidin-4-ylthio]-1-carbapen-2-em-3-carboxylate diastereomer A (2.37 g, yield: 92%).

IR(KBr)cm$^{-1}$: 1780, 1700, 1520, 1350.
NMR(CDCl$_3$) δ: 1.28(3H,t,J=7 Hz),1.37(3H,d,J=6 Hz),1.60–2.15(4H,m),2.55(1H,m),2.78(1H,m),4.-04–4.35(3H,m),5.24(5H,m),5.53(1H,br d,J=14 Hz),7.54(4H,br d,J=8 Hz),7.67(2H,d,J=8 Hz),8.24(6H,br d,J=8 Hz).

2)

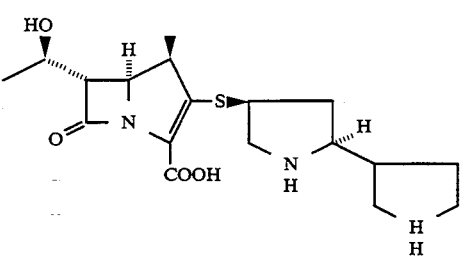

The same procedure as in Example 11-2 was carried out by using the compound obtained by the above reaction (2.37 g, 2.71 mmol) to obtain the above identified compound (298 mg, yield: 28.8%). Various spectra data of this compound agreed to the data of the diastereomer A obtained in Example 11-2.

EXAMPLE 27

(1R,5S,6S)-6-[(R)-1-hydroxyethyl]-1-methyl-2-[(2S,4S)-2-(pyrrolidin-3-yl)pyrrolidin-4-ylthio]-1-carbapen-2-em-3-carboxylic acid diastereomer B

1)

-continued

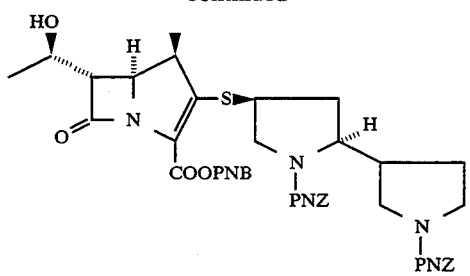

The same procedure as in Example 1-1 was carried out by using p-nitrobenzyl (1R,5S,6S)-2-diphenoxy-phosphoryloxy-6-[(R)-1-hydroxyethyl]-1-methyl-1-carbapen-2-em-3-carboxylate (1.27 g, 2.14 mmol) and (2S,4S)-4-mercapto-N-(p-nitrobenzyloxycarbonyl)-2-[N-(p-nitrobenzyloxycarbonyl)pyrrolidin-3-yl]pyrrolidine diastereomer B (1.14 g, 2.15 mmol, compound of Reference Example 16) to obtain p-nitrobenzyl (1R,5S,6S)-6-[(R)-1-hydroxyethyl]-1-methyl-2-[(2S,4S)-N-(p-nitrobenzyloxycarbonyl)-2-[N-(p-nitrobenzyloxycarbonyl)pyrrolidin-3-yl]pyrrolidin-4-ylthio]-1-carbapen-2-em-3-carboxylate diastereomer B (1.65 g, yield: 88.3%).

IR(KBr)cm$^{-1}$: 1780, 1700, 1520, 1350.

NMR(CDCl$_3$) δ: 1.28(3H,t,J=7 Hz),1.37(3H,t,J=6 Hz),1.50–2.08(4H,m),2.42–2.70(2H,m),3.-48–3.70(3H,m),4.-01–4.76(3H,m),5.24(5H,m),5.54(1H,d,J=14 Hz),7.54(4H,br d,J=8 Hz),7.67(2H,d,J=8 Hz),8.24(6H,br d,J=8 Hz).

2)

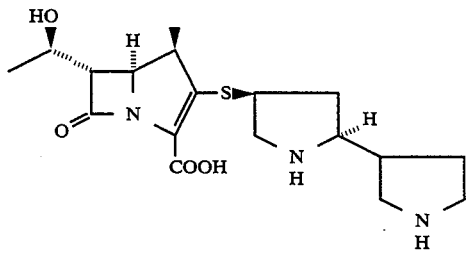

The same procedure as in Example 1-2 was carried out by using the compound obtained by the above reaction (1.65 g, 1.89 mmol) to obtain the above identified compound (220 mg, yield: 30.6%). Various spectra data of this compound agreed to those of the diastereomer B obtained in Example 11-2.

EXAMPLE 28

(1R,5S,6S)-6-[(R)-1-hydroxyethyl]-1-methyl-2-[(2S,4S)-2-(2-pyrrolidon-4-yl)pyrrolidin-4-ylthio]-1-carbapen-2-em-3-carboxylic acid diastereomer A

1)

-continued

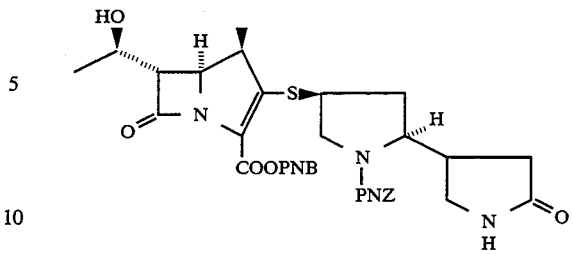

The same procedure as in Example 1-1 was carried out by using p-nitrobenzyl (1R,5S,6S)-2-diphenoxy-phosphoryloxy-6-[(R)-1-hydroxyethyl]-1-methyl-1-carbapen-2-em-3-carboxylate (6.67 g, 11.2 mmol) and (2S,4S)-4-mercapto-N-(p-nitrobenzyloxycarbonyl)-2-(2-pyrrolidon-4-yl)pyrrolidine diastereomer A (3.9 g, 10.7 mmol, compound of Reference Example 18-4) to obtain p-nitrobenzyl (1R,5S,6S)-6-[(R)-1-hydroxyethyl]-1-methyl-2-[(2S,4S)-N-(p-nitrobenzyloxycarbonyl)-2-(2-pyrrolidon-4-yl)pyrrolidin-4-ylthio]-1-carbapen-2-em-3-carboxylate diastereomer A (6.01 g, yield: 77.1%).

IR(KBr)cm$^{-1}$: 1770, 1700, 1520, 1340, 1250.

NMR(CDCl$_3$) δ: 1.28(3H,d,J=8 Hz),1.33(3H,d,J=7 Hz),1.72(2H,m),2.06–2.68(3H,m),2.96–3.7(5H,m),4.-04–4.36(2H,m),5.24(2H,m),5.31 and 5.52(2H,ABq,J=14 Hz),5.8(1H,br),7.53(2H,d,J=8 Hz),7.64(2H,d,J=8 Hz),8.20(2H,d,J=8 Hz),8.22(2H,d,J=8 Hz).

2)

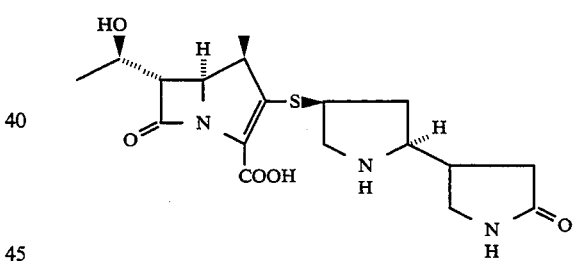

The same procedure as in Example 1-2 was carried out by using compound obtained by the above reaction (6 g, 8.62 mmol) to obtain the above identified compound (1.68 g, yield: 49.4%).

IR(KBr)cm$^{-1}$: 1755, 1680, 1595, 1385, 1280.

NMR(D$_2$O) δ: 1.15(3H,d,J=8 Hz),1.23(3H,d,J=7 Hz),1.7(1H,m),2.3(1H,m),2.54–3.1(3H,m),3-.1–3.5(3H,m),3.55–3.94(3H,m),4.0(1H,m),4.19(2H,m).

HPLC: Column: YMC AQ-304. Eluent: 0.01M Phosphate buffer (pH 7.0)-acetonitrile (96:4). Flow rate: 1.0 ml/min. Temperature: 40° C. Detector: 254 nm. Retention time: 14.83 min.

EXAMPLE 29

(1R,5S,6S)-6-[(R)-1-hydroxyethyl]-1-methyl-2-[(2S,4S)-2-(2-pyrrolidon-4-yl)pyrrolidin-4-ylthio]-1-carbapen-2-em-3-carboxylic acid diastereomer B

1)

173
-continued

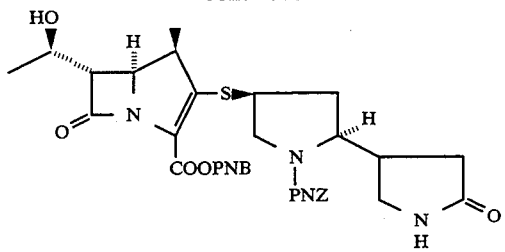

The same procedure as in Example 1-1 was carried out by using p-nitrobenzyl (1R,5S,6S)-2-diphenoxyphosphoryloxy-6-[(R)-1-hydroxyethyl]-1-methyl-1-carbapen-2-em-3-carboxylate (10.61 g, 17 mmol) and (2S,4S)-4-mercapto-N-(p-nitrobenzyloxycarbonyl)-2-(2-pyrrolidon-4-yl)pyrrolidine diastereomer B (5.92 g, 16.2 mmol, compound of Reference Example 19-4) to obtain p-nitrobenzyl (1R,5S,6S)-6-[(R)-1-hydroxyethyl]-1-methyl-2-[(2S,4S)-N-(p-nitrobenzyloxycarbonyl)-2-(2-pyrrolidon-4-yl)pyrrolidin-4-ylthio]-1-carbapen-2-em-3-carboxylate diastereomer B (9.9 g, yield: 83.7%).

IR(KBr)cm$^{-1}$: 1770, 1705, 1695, 1605, 1345, 1205.

NMR(D$_2$O) δ: 1.27(3H,d,J=8 Hz),1.36(3H,d,J=7 Hz),1.72–2.06(2H,m),2.1–2.68(3H,m),3.-02–3.7(5H,m),4.06–4.16(2H,m),5.31 and 5.52(2H,ABq,J=14 Hz),6.04(1H,br),7.53(2H,d,J=8 Hz),7.66(2H,d,J=8 Hz),8.20(2H,d,J=8 Hz),8.22(2H,d,J=8 Hz).

2)

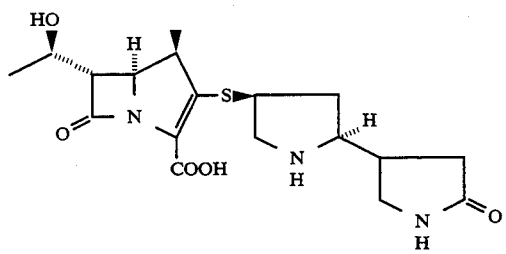

The same procedure as in Example 1-2 was carried out by using the compound obtained by the above reaction (9.8 g, 14.1 mmol) to obtain the above identified compound (1.42 g, yield: 25.5%).

IR(KBr) cm$^{-1}$: 1755, 1680, 1590, 1390, 1280.

NMR(D$_2$O) δ: 1.19(3H,d,J=8 Hz),1.26(3H,d,J=7 Hz),1.72(1H,m),2.28(1H,m),2.52–3.10(3H,m),3.-26–3.50(3H,m),3.-60–3.90(3H,m),4.02(1H,m),4.22(2H,m).

HPLC: Column: YMC AQ-304. Eluent: 0.01M Phosphate buffer (pH 7.0)-acetonitrile (96:4). Flow rate: 1.0 ml/min. Temperature: 40° C. Detector: 254 nm. Retention time: 15.18 min.

EXAMPLE 30

(1R,5S,6S)-2-[(2S,4S)-2-(3-amino-2-pyrrolidon-4-yl)pyrrolidin-4-ylthio]-6-[(R)-1-hydroxyethyl]-1-methyl-1-carbapen-2-em-3-carboxylic acid

1)

174
-continued

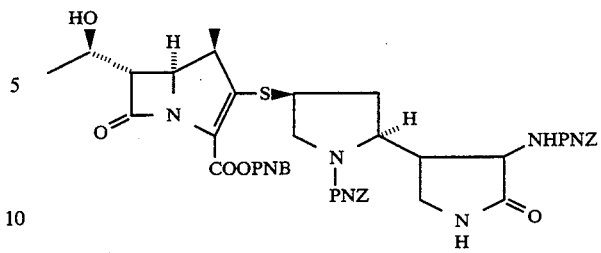

The same procedure as in Example 1-1 was carried out by using p-nitrobenzyl (1R,5S,6S)-2-diphenoxyphosphoryloxy-6-[(R)-1-hydroxyethyl]-1-methyl-1-carbapen-2-em-3-carboxylate (155.4 mg, 0.26 mmol) and (2S,4S)-4-mercapto-N-(p-nitrobenzyloxycarbonyl)-2-[3-[(p-nitrobenzyloxycarbonyl)amino]-2-pyrrolidon-4-yl]pyrrolidine (110 mg, 0.197 mmol, compound of Reference Example 20-6) to obtain p-nitrobenzyl (1R,5S,6S)-6-[(R)-1-hydroxyethyl]-1-methyl-2-[(2S,4S)-N-(p-nitrobenzyloxycarbonyl)-2-[3-[(p-nitrobenzyloxycarbonyl)amino]-2-pyrrolidon-4-yl]pyrrolidin-4-ylthio]-1-carbapen-2-em-3-carboxylate (87 mg, yield: 48.9%).

IR(KBr)cm$^{-1}$: 1775, 1710, 1605, 1525, 1350, 735.

NMR(CDCl$_3$) δ: 1.27(3H,d,J=8 Hz),1.35(3H,d,J=8 Hz),1.6–1.8(2H,m),2.78(1H,m),3-.1–3.5(6H,m),3.65(1H,m),4-.0–4.4(5H,m),5.2(4H,s),5.28(1H,d,J=16 Hz),5.5(1H,d,J=16 Hz),6.32(1H,br),7.52(4H,d,J=9 Hz),7.65(2H,d,J=8 Hz),8.2(6H,m).

2)

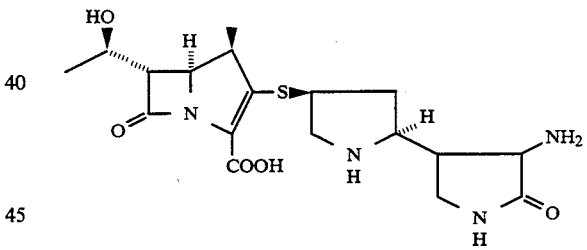

The same procedure as in Example 1-2 was carried out by using the compound obtained by the above reaction (87 mg, 0.096 mmol). The obtained reaction solution was subjected to column chromatography (HP-20 SS, 5–10% methanol aqueous solution), and the desired fraction was concentrated and freeze-dried to obtain the above identified compound (25.72 mg, yield: 65.1%).

IR(KBr)cm$^{-1}$: 1755, 1700, 1605, 1595, 1385.

NMR(D$_2$O) δ: 1.17(3H,d,J=8 Hz),1.24(3H,d,J=8 Hz),2.5–2.8(2H,m),2.6–2.8(2H,m),3.1–3.6(5H,m),3-.9–4.4(5H,m).

EXAMPLE 31

(1R,5S,6S)-6-[(R)-1-hydroxyethyl]-1-methyl-2-[(2R,4S)-2-(pyrrolidin-3-ylmethyl)pyrrolidin-4-ylthio]-1-carbapen-2-em-3-carboxylic acid

1)

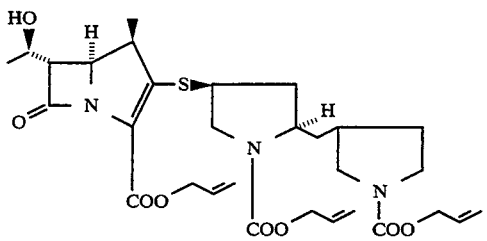

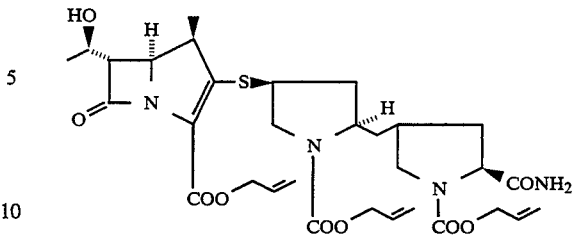

The same procedure as in Example 8-1 was carried out by using allyl (1R,5S,6S)-6-[(R)-1-hydroxyethyl]-1-methyl-2-diphenoxyphosphoryloxy-1-carbapen-2-em-3-carboxylate (790 mg, 1.6 mmol), (2R,4S)-N-allyloxycarbonyl-2-(N-allyloxycarbonylpyrrolidin-3-ylmethyl)-4-mercaptopyrrolidine (560 mg, 1.6 mmol) and N,N-diisopropylethylamine (0.28 ml, 1.6 mmol) to obtain allyl (1R,5S,6S)-2-[(2R,4S)-N-allyloxycarbonyl-2-(N-allyloxycarbonylpyrrolidin-3-ylmethyl)pyrrolidin-4-ylthio]-6-[(R)-1-hydroxyethyl]-1-methyl-1-carbapen-2-em-3-carboxylate (480 mg, yield: 50%).

NMR(CDCl$_3$) δ: 1.28(3H,d,J=6 Hz),1.36(3H,d,J=6 Hz),1.5–1.8(3H,m),1.9–2.2(4H,m),2.62(1H,m),3.02(1H,m),3.2–3.4(4H,m),3.5–3.7(3H,m),4.0–4.3(3H,m),4.6–4.9(6H,m),5.2–5.56(6H,m),5.9–6.1(3H,m).

The same procedure as in Example 8-1 was carried out by using allyl (1R,5S,6S)-6-[(R)-1-hydroxyethyl]-1-methyl-2-diphenoxyphosphoryloxy-1-carbapen-2-em-3-carboxylate (264 mg, 0.49 mmol), (2R,4S)-N-allyloxycarbonyl-2-[(2S)-N-allyloxycarbonyl-2-carbamoylpyrrolidin-4-ylmethyl]-4-mercaptopyrrolidine (210 mg, 0.49 mmol) and N,N-diisopropylethylamine (92 μl, 0.49 mmol) to obtain allyl (1R,5S,6S)-2-[(2R,4S)-N-allyloxycarbonyl-2-[(2S)-N-allyloxycarbonyl-2-carbamoylpyrrolidin-4-ylmethyl]pyrrolidin-4-ylthio]-6-[(R)-1-hydroxyethyl]-1-methyl-1-carbapen-2-em-3-carboxylate (250 mg, yield: 73%).

NMR(CDCl$_3$) δ: 1.25(3H,d,J=6 Hz),1.34(3H,d,J=7 Hz),1.5–1.8(3H,m),1.8–2.7(4H,m),3.0–3.4(4H,m),3.5–4.4(7H,m),4.5–4.9(6H,m),5.2–5.5(7H,m),5.8–6.1(3H,m),6.9 (0.5H,br s),7.3(0.5H,br s).

2)

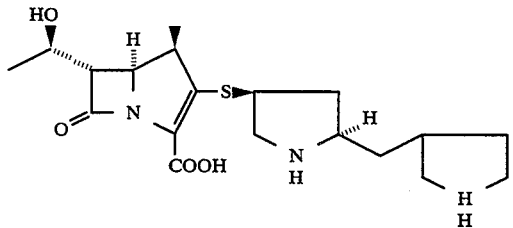

2)

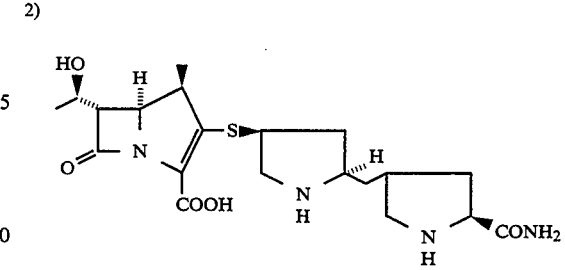

The same procedure as in Example 8-2 was carried out by using the compound obtained by the above reaction (480 mg, 0.8 mmol), bis(triphenylphosphine)palladium(II) chloride (11 mg, 0.016 mmol), tributyltin hydride (1.28 ml, 4.77 mmol) and water (107 μl, 5.96 mmol). The obtained aqueous layer was purified by reversed phase column chromatography (YMC-.GEL ™ ODS-AQ 120-S50, 50 ml, eluted with methanol-water (1:4)) and freeze-dried to obtain the above identified compound (128 mg, yield: 41%).

IR(KBr)cm$^{-1}$: 1760, 1600, 1390.

NMR(D$_2$O) δ: 1.2(3H,d,J=6 Hz),1.28(3H,d,J=7 Hz)1.6–1.9(3H,m),2.2–2.7(3H,m),2.9–3.6(10H,m),3.8(1H,m),4.2–4.4(2H,m).

EXAMPLE 32

(1R,5S,6S)-2-[(2R,4S)-2-[(2S)-2-carbamoylpyrrolidin-4-ylmethyl]pyrrolidin-4-ylthio]-6-[(R)-1-hydroxyethyl]-1-methyl-1-carbapen-2-em-3-carboxylic acid

1)

The same procedure as in Example 8-2 was carried out by using the compound obtained by the above reaction (250 mg, 0.387 mmol), bis(triphenylphosphine)palladium(II) chloride (5.4 mg, 0.008 mmol), tributyltin hydride (0.62 ml, 2.3 mmol) and water (52 μl, 2.9 mmol). The obtained aqueous layer was purified by reversed phase column chromatography (LC-SORB ™ SP-B-ODS, 14 ml, eluted with methanol-water (3:7)) and freeze-dried to obtain the above identified compound (107 mg, yield: 63%).

IR(KBr)cm$^{-1}$: 1750, 1680, 1590, 1390.

NMR(D$_2$O) δ: 1.22(3H,d,J=7 Hz),1.28(3H,d,J=6 Hz),1.58(1H,m),1.8–2.4(5H,m),2.6–2.84(2H,m),3.2–3.7(6H,m),3.95(1H,m),4.1(1H,dd,J=10,4 Hz),4.2–4.3(2H,m).

EXAMPLE 33

(1R,5S,6S)-6-[(R)-1-hydroxyethyl]-1-methyl-2-[(2R,4S)-2-[(2S)-2-(methylcarbamoyl)pyrrolidin-4-ylmethyl]pyrrolidin-4-ylthio]-1-carbapen-2-em-3-carboxylic acid

1)

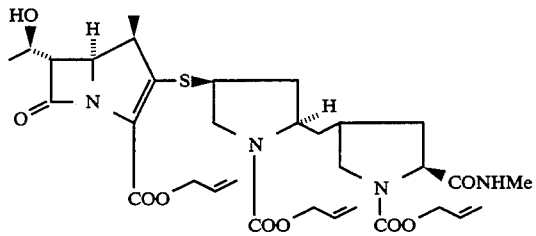

The same procedure as in Example 8-1 was carried out by using allyl (1R,5S,6S)-6-[(R)-1-hydroxyethyl]-1-methyl-2-diphenoxyphosphoryloxy-1-carbapen-2-em-3-carboxylate (204 mg, 0.41 mmol), (2R,4S)-N-allyloxycarbonyl-2-[(2S)-N-allyloxycarbonyl-2-(methylcarbamoyl)pyrrolidin-4-ylmethyl]-4-mercaptopyrrolidine (168 mg, 0.41 mmol) and N,N-diisopropylethylamine (71 μl, 0.41 mmol) to obtain allyl (1R,5S,6S)-2-[(2R,4S)-N-allyloxycarbonyl-2-[(2S)-N-allyloxycarbonyl-2-(methylcarbamoyl)pyrrolidin-4-ylmethyl]pyrrolidin-4-ylthio]-6-[(R)-1-hydroxyethyl]-1-methyl-1-carbapen-2-em-3-carboxylate (180 mg, yield: 67%).

NMR(CDCl₃) δ: 1.26(3H,d,J=6 Hz),1.36(3H,d,J=6 Hz),1.5–1.8(3H,m),1.8–2.6(4H,m),2.8(3H,d,J=4 Hz),3.0(1H,m),3.1–3.4(3H,m),3.8(2H,m),3-.9–4.4(5H,m),4.5–4.9(6H,m),5.1–5.5(6H,m),5-.8–6.0(3H,m),6.9(0.5H,br s),7.3(0.5H,br s).

2)

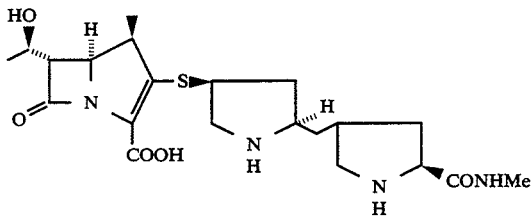

The same procedure as in-Example 8-2 was carried out by using the compound obtained by the above reaction (180 mg, 0.27 mmol), bis(triphenylphosphine)palladium(II) chloride (4 mg, 0.005 mmol), tributyltin hydride (0.44 ml, 1.6 mmol) and water (37 μl, 2 mmol). The obtained aqueous layer was purified by reversed phase column chromatography (LC-SORB ™ SP-B-ODS, 14 ml, eluted with methanol-water (3:7)) and feeze-dried to obtain the above identified compound (60 mg, yield: 49%).

IR(KBr)cm⁻¹: 1750, 1600, 1390.

NMR(D₂O) δ: 1.2(3H,d,J=6 Hz),1.28(3H,d,J=7 Hz),1.56(1H,m),1.8–2.3(5H,m),2-.6–2.8(2H,m),2.76(3H,s),3-.2–3.7(6H,m),3.95(1H,m),4.04(1H,dd,J=10,4 Hz),4.2–4.3(2H,m).

EXAMPLE 34

(1R,5S,6S)-6-[(R)-1-hydroxyethyl]-1-methyl-2-[(2R,4S)-2-[(2S)-2-(dimethylcarbamoyl)pyrrolidin-4-ylmethyl]pyrrolidin-4-ylthio]-1-carbapen-2-em-3-carboxylic acid

1)

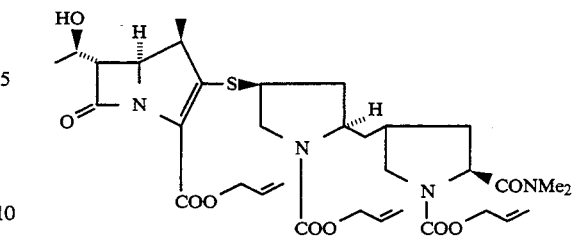

The same procedure as in Example 8-1 was carried out by using allyl (1R,5S,6S)-6-[(R)-1-hydroxyethyl]-1-methyl-2-diphenoxyphosphoryloxy-1-carbapen-2-em-3-carboxylate (129 mg, 0.26 mmol), (2R,4S)-N-allyloxycarbonyl-2-[(2S)-N-allyloxycarbonyl-2-(dimethylcarbamoyl)pyrrolidin-4-ylmethyl]-4-mercaptopyrrolidine (110 mg, 0.26 mmol) and N,N-diisopropylethylamine (45 μl, 0.26 mmol) to obtain allyl (1R,5S,6S)-2-[(2R,4S)-N-allyloxycarbonyl-2-[(2S)-N-allyloxycarbonyl-2-(dimethylcarbamoyl)pyrrolidin-4-ylmethyl]pyrrolidin-4-ylthio]-6-[(R)-1-hydroxyethyl]-1-methyl-1-carbapen-2-em-3-carboxylate (78 mg, yield: 45%).

NMR(CDCl₃) δ: 1.26(3H,d,J=6 Hz),1.37(3H,d,J=6 Hz),1.4–2.6(7H,m),2-.9–3.3(4H,m),2.98(3H,s),3.12(3H,s),3.5–4.3(7H,m),4-.5–4.9(6H,m),5.1–5.5(6H,m),5.9(3H,m).

2)

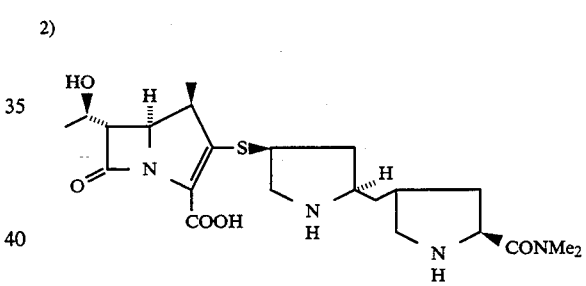

The same procedure as in Example 8-2 was carried out by using the compound obtained by the above reaction (78 mg, 0.12 mmol), bis(triphenylphosphine)palladium(II) chloride (2 mg, 0.002 mmol), tributyltin hydride (0.186 ml, 0.69 mmol) and water (16 μl, 0.87 mmol). The obtained aqueous layer was purified by reversed phase column chromatography (LC-SORB ™ SP-B-ODS, 14 ml, eluted with methanol-water (2:3)) and freeze-dried to obtain the above identified compound (11 mg, yield: 20%).

IR(KBr)cm⁻¹: 1750, 1640, 1600, 1390.

NMR(D₂O) δ: 1.2(3H,d,J=6 Hz),1.28(3H,d,J=7 Hz),1.5(1H,m),1.8–2.4(5H,m),2-.6–2.9(2H,m),2.96(3H,s),3.06(3H,s),3.1–3.6(6H,m),3-.8–4.0(2H,m),4.1–4.3(2H,m).

EXAMPLE 35

(1R,5S,6S)-2-[(2S,4S)-2-(2,4-dioxoimidazolidin-5-yl)pyrrolidin-4-ylthio]-6-[(R)-1-hydroxyethyl]-1-methyl-1-carbapen-2-em-3-carboxylic acid

1)

-continued

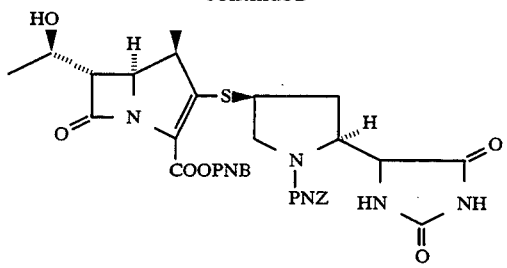

(2S,4S)-2-(2,4-dioxoimidazolidin-5-yl)-4-(p-methoxybenzylthio)-N-(p-nitrobenzyloxycarbonyl)pyrrolidine (250 mg, 0.499 mmol, compound of Reference Example 28) and anisole (0.27 ml, 2.48 mmol) were dissolved in trifluoroacetic acid (5 ml), and the solution was cooled with ice under a nitrogen stream. Then, trifluoromethanesulfonic acid (0.07 ml, 0.791 mmol) was dropwise added thereto, and the mixture was stirred for 50 minutes under cooling with ice. The solvent was distilled off, and the residue was washed with diethyl ether to obtain a crude thiol.

The same procedure as in Example 1-1 was carried out by using p-nitrobenzyl (1R,5S,6S)-2-diphenoxyphosphoryloxy-6-[(R)-1-hydroxyethyl]-1-methyl-1-carbapen-2-em-3-carboxylate (300 mg, 0.505 mmol) and the thiol obtained by the above reaction to obtain p-nitrobenzyl (1R,5S,6S)-2-[(2S,4S)-2-(2,4-dioxoimidazolidin-5-yl)-N-(p-nitrobenzyloxycarbonyl)pyrrolidin-4-ylthio]-6-[(R)-1-hydroxyethyl]-1-methyl-1-carbapen-2-em-3-carboxylate (100 mg, yield: 28%).

IR(KBr)cm$^{-1}$: 3430, 1775, 1725, 1610, 1520, 1350, 1285, 1250.

NMR(CDCl$_3$) δ: 1.27(3H,d,J=6 Hz),1.33(3H,d,J=6 Hz),4.4(1H,m),4.7 and 5.05(1H,s),5.25(2H,s),5.3 and 5.5(2H,ABq,J=14 Hz), 7.58 (2H,d,J=8 Hz), 7.69 (2H,d,J=8 Hz),8.2–8.3(4H,m).

2)

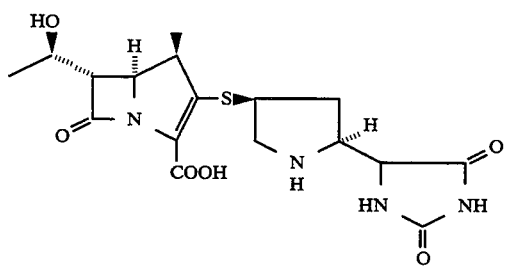

The same procedure as in Example 1-2 was carried out by using the compound obtained by the above reaction (100 mg, 0.138 mmol) to obtain the above identified compound (23 mg, yield: 41%).

IR(KBr)cm$^{-1}$: 3440, 1760, 1730, 1600, 1400.

NMR(D$_2$O) δ: 1.20(3H,d,J=7 Hz),1.27(3H,d,J=7 Hz),1.75(1H,m),2.6(1H,m),3.0–3.6(4H,m),3-.7–4.0(2H,m),4.1–4.3(2H,m),4.57(1H,d,J=8 Hz).

UV λ$_{max}$ (0.1M 3-morpholinopropanesulfonic acid buffer pH 7.0): 300 nm (ε=9400).

EXAMPLE 36

(5R,6S)-2-[(2S,4S)-2-(2,4-dioxoimidazolidin-5-yl)pyrrolidin-4-ylthio]-6-[(R)-1-hydroxyethyl]-1-carbapen-2-em-3-carboxylic acid

1)

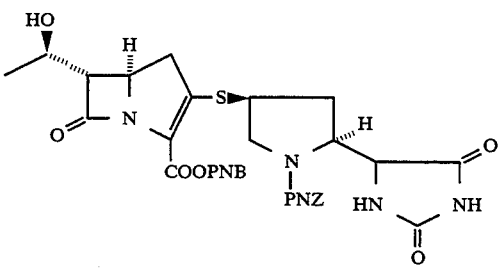

The same procedure as in Example 1-1 was carried out by using p-nitrobenzyl (5R,6S)-2-diphenoxyphosphoryloxy-6-[(R)-1-hydroxyethyl]-1-carbapen-2-em-3-carboxylate (150 mg, 0.258 mmol) and (2S,4S)-2-(2,4-dioxoimidazolidin-5-yl)-4-(p-methoxybenzylthio)-N-(p-nitrobenzyloxycarbonyl)pyrrolidine (120 mg, 0.240 mmol, compound of Reference Example 28) to obtain p-nitrobenzyl (5R,6S)-2-[(2S,4S)-2-(2,4-dioxoimidazolidin-5-yl)-N-(p-nitrobenzyloxycarbonyl)pyrrolidin-4-ylthio]-6-[(R)-1-hydroxyethyl]-1-carbapen-2-em-3-carboxylate (30 mg, yield: 18%).

IR(KBr)cm$^{-1}$: 3400, 1780, 1730, 1610, 1520, 1350.

NMR(CDCl$_3$+CD$_3$OD) δ: 1.32(3H,d,J=6 Hz),1.78(1H,m),2.40(1H,m),3.0–3.5(4H,m),4-.0–4.5(4H,m),4.73 and 5.04(1H,s),5.28(2H,s),5.28 and 5.49(2H,ABq,J=13 Hz),7.57(2H,d,J=9 Hz),7.67 (2H,d,J=9 Hz),8.1–8.3(4H,m).

2)

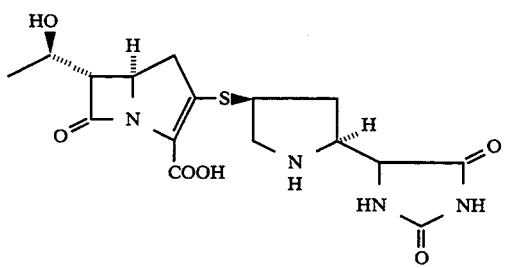

The same procedure as in Example 1-2 was carried out by using the compound obtained by the above reaction (30 mg, 0.042 mmol) to obtain the above identified compound (11 mg, yield: 66%).

IR(KBr)cm$^{-1}$: 3430, 1760, 1720, 1600, 1400.

NMR(D$_2$O) δ: 1.26(3H,d,J=7 Hz),1.55(1H,m),2.5(1H,m),3.1–3.6(4H,m),4-.1–4.3(2H,m),4.38(1H,d,J=5 Hz).

UV λ$_{max}$ (0.1M 3-morpholinopropanesulfonic acid buffer pH 7.0): 301 nm (ε=4600).

EXAMPLE 37

(1R,5S,6S)-2-[(2R,4S)-2-(2,4-dioxoimidazolidin-5-ylmethyl)pyrrolidin-4-ylthio]-6-[(R)-1-hydroxyethyl]-1-methyl-1-carbapen-2-em-3-carboxylic acid diastereomer A

1)

-continued

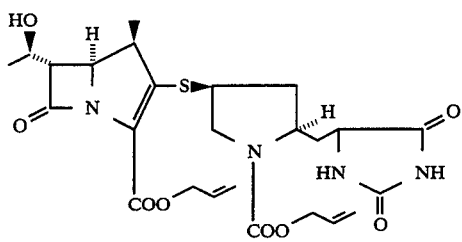

The same procedure as in Example 8-1 was carried out by using allyl (1R,5S,6S)-2-diphenoxyphosphoryloxy-6-[(R)-1-hydroxyethyl]-1-methyl-1-carbapen-2-em-3-carboxylate (220 mg, 0.440 mmol) and (2R,4S)-N-allyloxycarbonyl-2-(2,4-dioxoimidazolidin-5-ylmethyl)-4-tritylthiopyrrolidine diastereomer A (270 mg, 0.498 mmol, compound of Reference Example 29) to obtain allyl (1R,5S,6S)-2-[(2R,4S)-N-allyloxycarbonyl-2-(2,4-dioxoimidazolidin-5-ylmethyl)pyrrolidin-4-ylthio]-6-[(R)-1-hydroxyethyl]-1-methyl-1-carbapen-2-em-3-carboxylate diastereomer A (70 mg, yield: 26%).

IR(KBr)cm$^{-1}$: 3550, 3480, 3420, 3200, 1780, 1730, 1550, 1420.

NMR(CDCl$_3$) δ: 1.26(3H,d,J=7 Hz),1.36(3H,d,J=7 Hz),1.5–2.5(4H,m),2.7(2H,m),3.1–3.6(3H,m),3.7(1H,m),3.8–4.4(4H,m),4.4–4.9(4H,m),5.0–5.5(4H,m),5.6–6.05(2H,m),6.89(1H,s),8.78(1H,s).

2)

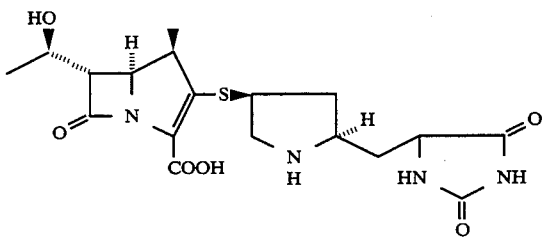

The same procedure as in Example 8-2 was carried out by using the compound obtained by the above reaction (70 mg, 0.128 mmol) to obtain the above identified compound 19 mg, yield: 35%).

IR(KBr)cm$^{-1}$: 3400, 3250, 1760, 1720, 1590, 1390.

NMR(D$_2$O) δ: 1.15(3H,d,J=6 Hz),1.22(3H,d,J=7 Hz),1.7(1H,m),2.3(2H,m),2.75(1H,m),3.2–3.5(3H,m),3.5–3.9(2H,m),3.95(1H,m),4.2(2H,m),4.34(1H,t,J=6 Hz).

UV λ$_{max}$ (0.1M 3-morpholinopropanesulfonic acid buffer pH 7.0): 298 nm (ε=9300).

EXAMPLE 38

(1R,5S,6S)-2-[(2R,4S)-2-(2,4-dioxoimidazolidin-5-ylmethyl)pyrrolidin-4-ylthio]-6-[(R)-1-hydroxyethyl]-1-methyl-1-carbapen-2-em-3-carboxylic acid diastereomer B

1)

-continued

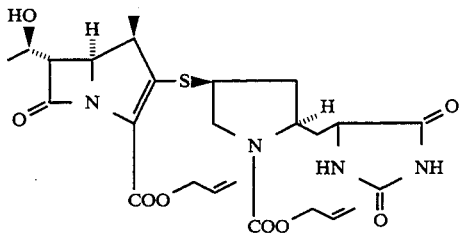

The same procedure as in Example 8-1 was carried out by using allyl (1R,5S,6S)-2-diphenoxyphosphoryloxy-6-(R)-1-hydroxyethyl]-1-methyl-1-carbapen-2-em-3-carboxylate (220 mg, 0.440 mmol) and (2R,4S)-N-allyloxycarbonyl-2-(2,4-dioxoimidazolidin-5-ylmethyl)-4-tritylthiopyrrolidine diastereomer B (220 mg, 0.406 mmol, compound of Reference Example 29) to obtain allyl (1R,5S,6S)-2-[(2R,4S)-N-allyloxycarbonyl-2-(2,4-dioxoimidazolidin-5-ylmethyl)pyrrolidin-4-ylthio]-6-[(R)-1-hydroxyethyl]-1-methyl-1-carbapen-2-em-3-carboxylate diastereomer B (70 mg, yield: 31%).

IR(KBr)cm$^{-1}$: 3420, 3270, 1775, 1730, 1550, 1415.

NMR(CDCl$_3$) δ: 1.27(3H,d,J=7 Hz),1.36(3H,d,J=7 Hz),1.5–2.1(4H,m),2.3(1H,m),2.7(1H,m),3.1–3.45(3H,m),3.65(1H,m),3.9–4.4(4H,m),4.4–4.9(4H,m),5.1–5.6(4H,m),5.7–6.1(2H,m),6.73(1H,s),8.34(1H,s).

2)

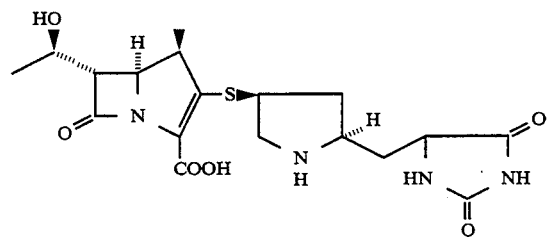

The same procedure as in Example 8-2 was carried out by using the compound obtained by the above reaction (70 mg, 0.128 mmol) to obtain the above identified compound (18 mg, yield: 33%).

IR(KBr)cm$^{-1}$: 3420, 3230, 1760, 1720, 1590, 1395.

NMR(D$_2$O) δ: 1.12(3H,d,J=7 Hz),1.19(3H,d,J=7 Hz),1.65(1H,m),2.3(2H,m),2.73(1H,m),3.2–3.5(3H,m),3.61(1H,m),3.8(1H,m),3.94(1H,m),4.15(2H,m),4.34(1H,t,J=6 Hz).

UV λ$_{max}$ (0.1M 3-morpholinopropanesulfonic acid buffer pH 7.0): 298 nm (ε=9400).

EXAMPLE 39

Sodium (1R,5S,6S)-2-[(2R,4S)-2-(2,5-dioxopyrrolidin-3-ylmethyl)pyrrolidin-4-ylthio]-6-[(R)-1-hydroxyethyl]-1-methyl-1-carbapen-2-em-3-carboxylate

1)

-continued

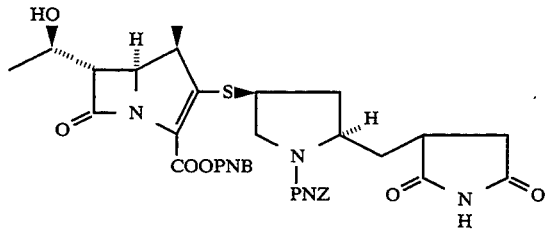

A 2N sodium hydroxide aqueous solution (0.34 ml, 0.68 mmol) was added to a solution of (2R,4S)-4-acetylthio-N-(p-nitrobenzyloxycarbonyl)-2-(2,5-dioxopyrrolidin-3-ylmethyl)pyrrolidine (250 mg, 0.57 mmol, compound of Reference Example 30) in methanol (5.0 ml) under cooling with ice, and the mixture was stirred for 30 minutes. Then, 6N hydrochloric acid (0.11 ml, 0.66 mmol) was added thereto, and the mixture was extracted with methylene chloride. The extract was dried over anhydrous magnesium sulfate and concentrated to obtain (2R,4S)-4-mercapto-N-(p-nitrobenzyloxycarbonyl)-2-(2,5-dioxopyrrolidin-3-ylmethyl)pyrrolidine.

The same procedure as in Example 1-1 was carried out by using the thiol obtained by the above reaction and p-nitrobenzyl (1R,5S,6S)-2-diphenoxyphosphoryloxy-6-[(R)-1-hydroxyethyl]-1-methyl-1-carbapen-2-em-3-carboxylate (273 mg, 0.46 mmol) to obtain p-nitrobenzyl (1R,5S,6S)-2-(2R,4S)-2-(2,5-dioxopyrrolidin-3-ylmethyl)-N-(p-nitrobenzyloxycarbonyl)pyrrolidin-4-ylthio]-6-[(R)-1-hydroxyethyl]-1-methyl-1-carbapen-2-em-3-carboxylate (229 mg, yield: 67%).

NMR(CDCl₃) δ: 1.28(3H,d,J=8 Hz),1.38(3H,d,J=8 Hz),5.24(4H,br s),7.54(4H,d,J=8 Hz),8.25(4H,d,J=8 Hz).

2)

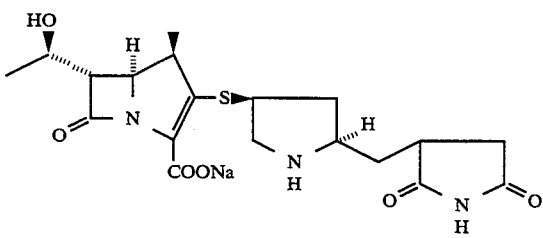

The same procedure as in Example 1-2 was conducted by using the compound obtained by the above reaction (210 mg, 0.28 mmol) to obtain the above identified compound (26 mg, yield: 21%).

IR(KBr)cm⁻¹: 3400, 2950, 1760, 1720, 1600, 1380, 1180.

NMR(D₂O) δ: 1.10(3H,d,J=6 Hz),1.16(3H,d,J=6 Hz),1.58(1H,m),2.00(1H,m),2.46(1H,m),2.66(1H,m),2.9-4(2H,m),3.28(2H,m),3.54(1H,m),3.74(1H,m),4.12(2H,m).

HPLC: Eluent: 0.01M Phosphate buffer (pH 6.5)-methanol (85:15). Flow rate: 0.8 ml/min. Other conditions are the same as in Example 1. Retention time: 4.28 min.

EXAMPLE 40

(1R,5S,6S)-2-[(2S,4S)-2-(5-oxopiperazin-2-yl)pyrrolidin-4-ylthio]-6-[(R)-1-hydroxyethyl]-1-methyl-1-carbapen-2-em-3-carboxylic acid diastereomer A

1)

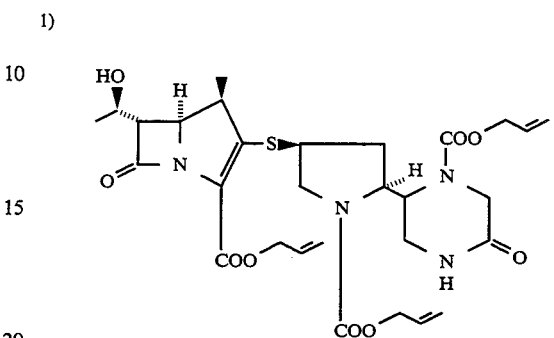

The same procedure as in Example 39-1 was carried out by using (2S,4S)-N-allyloxycarbonyl-4-acetylthio-2-(1-allyloxycarbonyl-5-oxopiperazin-2-yl)pyrrolidine diastereomer A (250 mg, 0.60 mmol, compound of Reference Example 31) to obtain (2S,4S)-N-allyloxycarbonyl-2-(1-allyloxycarbonyl-5-oxopiperazin-2-yl)-4-mercaptopyrrolidine diastereomer A.

The same procedure as in Example 1-1 was carried out by using the thiol obtained by the above reaction and allyl (1R,5S,6S)-2-diphenoxyphosphoryloxy-6-[(R)-1-hydroxyethyl]-1-methyl-1-carbapen-2-em-3-carboxylate (242 mg, 0.48 mmol) to obtain allyl (1R,5S,6S)-2-[(2S,4S)-N-allyloxycarbonyl-2-(1-allyloxycarbonyl-5-oxopiperazin-2-yl)pyrrolidin-4-ylthio]-6-[(R)-1-hydroxyethyl]-1-methyl-1-carbapen-2-em-3-carboxylate diastereomer A (222 mg, yield: 74%).

NMR(CDCl₃) δ: 1.26(3H,d,J=6 Hz),1.38(3H,d,J=6 Hz),1.80(1H,m),2.50(1H,m),3.0–5.0(19H,m),5.-20–5.60(6H,m),5.96(3H,m).

2)

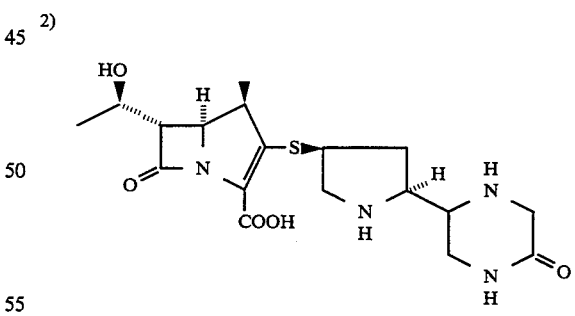

The same procedure as in Example 9-2 was conducted by using the compound obtained by the above reaction (diastereomer A, 220 mg, 0.35 mmol) to obtain the above identified compound (diastereomer A, 88 mg, yield: 60%).

IR(KBr)cm⁻¹: 3400, 2950, 1760, 1660, 1600, 1380.

NMR(D₂O) δ: 1.20(3H,d,J=6 Hz),1.26(3H,d,J=6 Hz),1.78(1H,m),2.64(1H,m),3.10–3.80(10H,m),4.00(1H,m),4.22(2H,m).

HPLC: Flow rate: 0.8 ml/min. Other conditions are the same as in Example 1. Retention time: 3.02 min.

EXAMPLE 41

(1R,5S,6S)-2-[(2S,4S)-2-(5-oxopiperazin-2-yl)pyrrolidin-4-ylthio]-6-[(R)-1-hydroxyethyl]-1-methyl-1-carbapen-2-em-3-carboxylic acid diastereomer B

1)

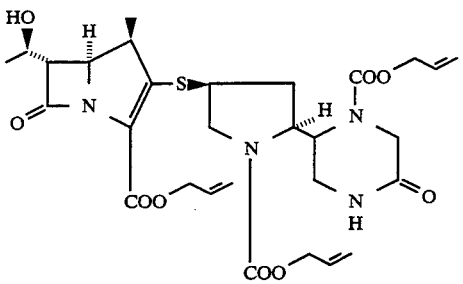

The same procedure as in Example 39-1 was carried out by using (2S,4S)-4-acetylthio-N-allyloxycarbonyl-2-(1-allyloxycarbonyl-5-oxopiperazin-2-yl)pyrrolidine diastereomer B (200 mg, 0.48 mmol, compound of Reference Example 31) to obtain (2S,4S)-N-allyloxycarbonyl-2-(1-allyloxycarbonyl-5-oxopiperazin-2-yl)-4-mercaptopyrrolidine diastereomer B.

The same procedure as in Example 1-1 was carried out by using the thiol obtained by the above reaction and allyl (1R,5S,6S)-2-diphenoxyphosphoryloxy-6-[(R)-1-hydroxyethyl]-1-methyl-1-carbapen-2-em-3-carboxylate (243 mg, 0.48 mmol) to obtain allyl (1R,5S,6S)-2-[(2S,4S)-N-allyloxycarbonyl-2-(1-allyloxycarbonyl-5-oxopiperazin-2-yl)pyrrolidin-4-ylthio]-6-[(R)-1-hydroxyethyl]-1-methyl-1-carbapen-2-em-3-carboxylate diastereomer B (246 mg, yield: 65%).

NMR(CDCl$_3$) δ: 1.24(3H,d,J=6 Hz),1.38(3H,d,J=6 Hz),1.80(1H,m),2.60(1H,m),3.10–3.80(10H,m),4-.0–5.0(9H,m),5.20–5.60(6H,m),5.96(3H,m).

2)

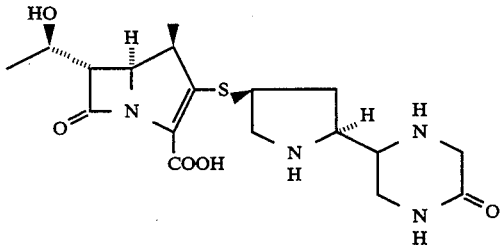

The same procedure as in Example 9-2 was carried out by using the compound obtained by the above reaction (diastereomer B, 240 mg, 0.39 mmol) to obtain the above identified compound (diastereomer B, 53 mg, yield: 33%).

IR(KBr)cm$^{-1}$: 3400, 1760, 1660, 1600, 1380.

NMR(D$_2$O) δ: 1.18(3H,d,J=6 Hz),1.20(3H,d,J=6 Hz),1.76(1H,m),2.64(1H,m),3.10–3.80(10H,m),3.94(1H,-m),4.18(2H,m).

HPLC: Eluent: 0.1M Phosphate buffer (pH 6.5)-methanol (85:15). Flow rate: 0.8 ml/min. Other conditions are the same as in Example 1. Retention time: 3.92 min.

EXAMPLE 42

(5R,6S)-6-[(R)-1-hydroxyethyl]-2-[(2S,4S)-2-(piperidin-4-yl)pyrrolidin-4-ylthio]-1-carbapen-2-em-3-carboxylic acid

1)

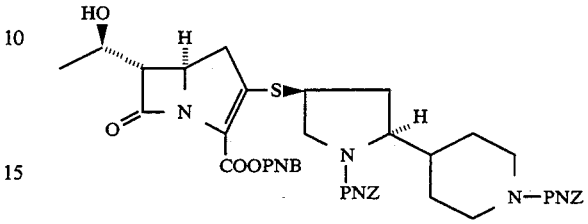

The same procedure as in Example 1-1 was carried out by using p-nitrobenzyl (5R,6S)-2-diphenoxyphosphoryloxy-6-[(R)-1-hydroxyethyl]-1-carbapen-2-em-3-carboxylate (270 mg, 0.46 mmol) and (2S,4S)-4-mercapto-N-(p-nitrobenzyloxycarbonyl)-2-[N-(p-nitrobenzyloxycarbonyl)piperidin-4-yl]pyrrolidine (216 mg, 0.40 mmol, compound of Reference Example 32) to obtain p-nitrobenzyl (5R,6S)-6-[(R)-1-hydroxyethyl]-2-[(2S,4S)-N-(p-nitrobenzyloxycarbonyl)-2-[N-(p-nitrobenzyloxycarbonyl)piperidin-4-yl]pyrrolidin-4ylthio]-1-carbapen-2-em-3-carboxylate (267 mg, yield: 65.6%).

IR(KBr)cm$^{-1}$: 1780, 1700, 1520, 1340.

NMR(CDCl$_3$) δ: 1.35(3H,d,J=6 Hz),2.76(2H,m),3.54(1H,m),4.00(1H,m),5.24(5H,m),5.5-2(1H,d,J=14 Hz),7.52(4H,d,J=8 Hz),7.66(2H,d,J=8 Hz),8.22(6H,m).

2)

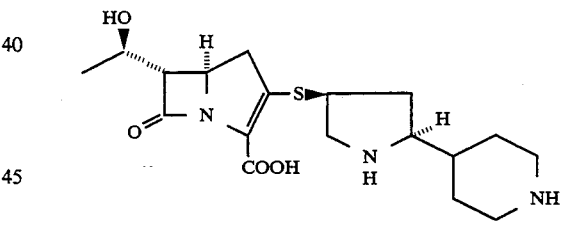

The same procedure as in Example 1-2 was carried out by using the compound obtained by the above reaction (265 mg, 0.30 mmol) to obtain the above identified compound (33 mg, yield: 28.5%).

IR(KBr)cm$^{-1}$: 1760, 1590, 1390.

NMR(D$_2$O) δ: 1.26(3H,d,J=6 Hz),1.31–1.56(3H,m),1.69(1H,m),1.-85–2.14(2H,m),2.50(1H,m),2.-81–3.06(4H,m),3.10(3H,m),3.40(3H,m),3.74(1H,m),4.20-(2H,m).

HPLC (the same condition as in Example 1). Retention time: 3.06 min.

EXAMPLE 43

(1R,5S,6S)-6-[(R)-1-hydroxyethyl]-1-methyl-2-[(2S,4S)-2-(piperidin-4-yl)pyrrolidin-4-ylthio]-1-carbapen-2-em-3-carboxylic acid

1)

187
-continued

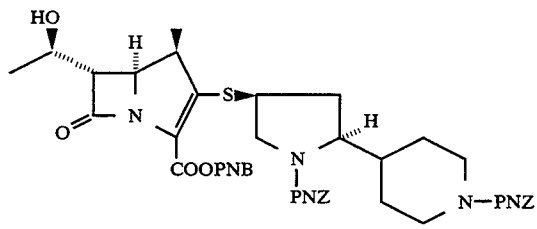

The same procedure as in Example 1-1 was carried out by using p-nitrobenzyl (1R,5S,6S)-2-diphenoxyphosphoryloxy-6-[(R)-1-hydroxyethyl]-1-methyl-1-carbapen-2-em-3-carboxylate (245 mg, 0.41 mmol) and (2S,4S)-4-mercapto-N-(p-nitrobenzyloxycarbonyl)-2-[N-(p-nitrobenzyloxycarbonyl)piperidin-4-yl]pyrrolidine (216 mg, 0.40 mmol, compound of Reference Example 32) to obtain p-nitrobenzyl (1R,5S,6S)-6-[(R)-1-hydroxyethyl]-1-methyl-2-[(2S,4S)-N-(p-nitrobenzyloxycarbonyl)-2-[N-(p-nitrobenzyloxycarbonyl)-piperidin-4-yl]pyrrolidin-4-ylthio]-1-carbapen-2-em-3-carboxylate (279 mg, yield: 76.2%).

IR(KBr)cm$^{-1}$: 1770, 1700, 1520, 1340.

NMR(CDCl$_3$) δ: 1.28(3H,t,J=7 Hz),1.36(3H,t,J=6 Hz),1.44–1.84(3H,m),5.15(5H,m),5.53(1H,d,J=14 Hz),7.56(4H,d,J=8 Hz),7.68(2H,d,J=8 Hz),8.24(6H,m).

2)

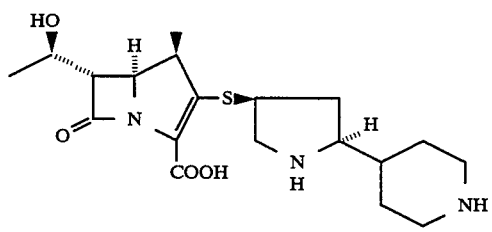

The same procedure as in Example 1-2 was carried out by using the compound obtained by the above reaction (275 mg, 0.31 mmol) to obtain the above identified compound (57 mg, yield: 46.6%).

IR(KBr) cm$^{-1}$: 1750, 1590, 1390.

NMR(D$_2$O) δ: 1.19(3H,d,J=7 Hz),1.27(3H,d,J=6 Hz),1.28–1.58(3H,m),1.70(1H,m),1.-85–2.15(2H,m),2.46(1H,m),2.-78–3.18(5H,m),3.40(4H,m),3.76(1H,m),4.22(2H,m).

HPLC (the same condition as in Example 1). Retention time: 3.28 min.

EXAMPLE 44

(1R,5S,6S)-2-[(2S,4S)-2-(2-carbamoylpyrrolidin-4-yl)pyrrolidin-4-ylthio]-6-[(R)-1-hydroxyethyl]-1-methyl-1-carbapen-2-em-3-carboxylic acid diastereomer III

1)

188
-continued

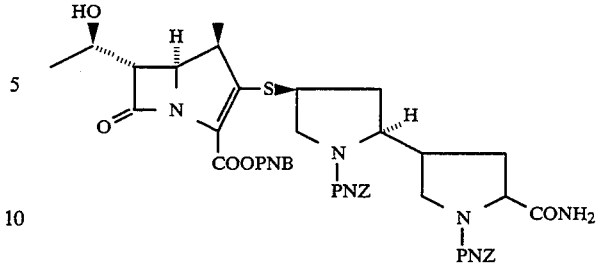

The same procedure as in Example 1-1 was carried out by using p-nitrobenzyl (1R,5S,6S)-2-diphenoxyphosphoryloxy-6-[(R)-1-hydroxyethyl]-1-methyl-1-carbapen-2-em-3-carboxylate (185 mg, 0.31 mmol) and (2S,4S)-2-[2-carbamoyl-N-(p-nitrobenzyloxycarbonyl)-pyrrolidin-4-yl]-4-mercapto-N-(p-nitrobenzyloxycarbonyl)pyrrolidine diastereomer III (175 mg, 0.31 mmol, compound of Reference Example 33) to obtain p-nitrobenzyl (1R,5S,6S)-2-[(2S,4S)-2-[2-carbamoyl-N-(p--nitrobenzyloxycarbonyl)pyrrolidin-4-yl]-N-(p-nitrobenzyloxycarbonyl)pyrrolidin-4-ylthio]-6-[(R)-1-hydroxyethyl]-1-methyl-1-carbapen-2-em-3-carboxylate (218 mg, yield: 76.3%).

IR(KBr)cm$^{-1}$: 1770, 1700, 1600, 1520, 1340.

NMR(CDCl$_3$) δ: 1.27(3H,d,J=7 Hz),1.36(3H,d,J=6 Hz),4.02–4.40(5H,m),5.22(5H,m),5.52(1H,d,J=14 Hz),7.50(4H,d,J=8 Hz),7.66(2H,d,J=8 Hz),8.22 (6H,m).

2)

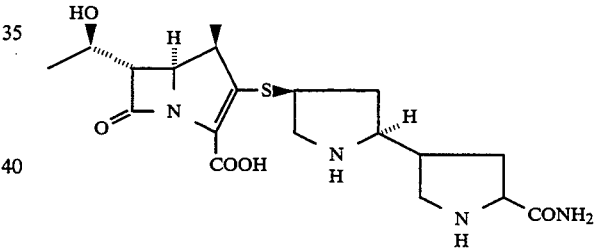

The same procedure as in Example 1-2 was carried out by using the compound obtained by the above reaction (218 mg, 0.24 mmol) to obtain the above identified compound (46 mg, yield: 45.6%).

IR(KBr)cm$^{-1}$: 1760, 1680, 1600, 1390.

NMR(D$_2$O) δ: 1.19(3H,d,J=7 Hz),1.27(3H,d,J=6 Hz),1.40–1.68(2H,m),2.45(2H,m),2.60(1H,m),2.82(1H,-m),3.04–3.47(6H,m),3.85(1H,m),3.98(1H,t,J=8 Hz),4.21(2H,m).

HPLC (the same condition as in Example 1). Retention time: 2.15 min.

REFERENCE EXAMPLE 1

(2S,4S)-4-mercapto-N-(p-nitrobenzyloxycarbonyl)-2-(2-pyrrolidon-4-yl)pyrrolidine

1)

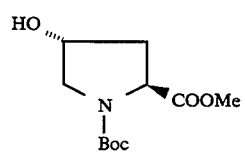

To an aqueous solution (40 ml) of L-hydroxyproline methyl ester hydrochloride (8.2 g, 45.2 mmol), triethylamine (7.54 ml, 54.2 mmol) was added at room temperature, and then a solution of 2-(tert-butoxycarbonylthio)-4,6-dimethylpyrimidine (10.8 g, 45 mmol) in dioxane (80 ml) was added thereto. The reaction solution was stirred at room temperature for 1.5 hours, and then dioxane was distilled off under reduced pressure. The residue was extracted with ethyl acetate (250 ml). The organic layer was washed sequentially with a 0.1N sodium hydroxide aqueous solution, dilute hydrochloric acid, water and a saturated sodium chloride aqueous solution and then dried over anhydrous magnesium sulfate and concentrated under reduced pressure. The residue was subjected to silica gel column chromatography (Wakogel TM C-300, 5% methanol-methylene chloride) to obtain N-tert-butoxycarbonyl-L-hydroxyproline methyl ester (9.3 g, yield: 84%).

NMR(CDCl₃) δ: 1.38–1.48(9H,m),1.98–2.38(2H,m),3.40–3.72(2H,m),3.86(3H,s),4.35–4.58(2H,m).

2)

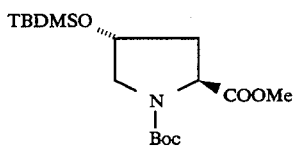

Imidazole (4.95 g, 72.7 mmol) and tert-butyldimethylsilyl chloride (10.7 g, 71.0 mmol) were added to a solution of the compound obtained by the above reaction (14.0 g, 57.1 mmol) in N,N-dimethylformamide (150 ml) in a nitrogen stream at room temperature. This solution was stirred overnight at room temperature. Ethyl acetate (500 ml) was added to the reaction solution, and the organic layer was washed twice with water and once with a saturated sodium chloride aqueous solution, then dried over anhydrous magnesium sulfate and concentrated under reduced pressure to obtain (2S,4R)-N-tert-butoxycarbonyl-4-tert-butyldimethylsiloxy-L-proline methyl ester (19 g, yield: 92.6%).

3)

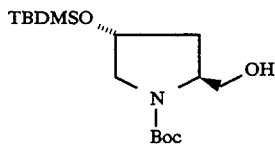

To a solution of the compound obtained by the above reaction (19.0 g, 52.9 mmol) in tetrahydrofuran (180 ml), lithium chloride (4.49 g, 106 mmol) and then sodium borohydride (4.0 g, 106 mmol) were added in a nitrogen stream. To this mixture, ethanol (180 ml) was dropwise added, and the reaction solution was stirred overnight at room temperature. A saturated ammonium chloride aqueous solution (100 ml) was added to this reaction mixture to decompose an excess reducing agent. Then, this mixture was concentrated under reduced pressure. The residue was extracted with ethyl acetate (500 ml), and the organic layer was washed sequentially with water and a saturated sodium chloride aqueous solution, then dried over anhydrous magnesium sulfate and concentrated under reduced pressure. The residue was subjected to silica gel column chroma-tography (Wakogel TM C-300, hexane-ethyl acetate 5:1) to obtain (2S,4R)-N-tert-butoxycarbonyl-4-tert-butyldimethylsiloxy-2-hydroxymethylpyrrolidine (14.88 g, yield: 84.9%).

4)

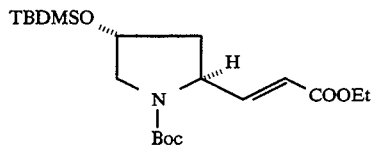

A solution of dimethyl sulfoxide (3.6 ml, 50.7 mmol) in methylene chloride (15 ml) was dropwise added to a solution of oxalyl chloride (2.89 ml, 33.9 mmol) in methylene chloride (100 ml) in a nitrogen stream at −78° C. The reaction solution was stirred at the same temperature for 30 minutes. To this mixture, a solution of (2S,4R)-N-tert-butoxycarbonyl-4-tert-butyldimethylsiloxy-2-hydroxymethylpyrrolidine (8.0 g, 24.2 mmol) in methylene chloride (50 ml) was dropwise added at −78° C. This mixture was stirred at the same temperature for 30 minutes, and then triethylamine (11.1 ml, 79.8 mmol) was added thereto. The mixture was stirred further for 30 minutes. The reaction mixture was poured into methylene chloride (200 ml), and the organic layer was washed sequentially with dilute hyrochloric acid, water and a saturated sodium chloride aqueous solution, then dried over anhydrous magnesium sulfate and concentrated under reduced pressure to obtain an oily residue of (2S,4R)-N-tert-butoxycarbonyl-4-tert-butyldimethylsiloxy-2-formylpyrrolidine.

Ethyl diethoxyphosphorylacetate (6.0 g, 26.8 mmol) was added to a suspension of 60% sodium hydride (1.0 g, 25.0 mmol) in tetrahydrofuran (100 ml) in a nitrogen stream under cooling with ice. This solution was stirred at the same temperature for 30 minutes. To this reaction solution, a tetrahydrofuran solution (20 ml) of (2S,4R)-N-tert-butoxycarbonyl-4-tert-butyldimethylsiloxy-2-formylpyrrolidine obtained by the above reaction, was dropwise added, and the mixture was stirred further at the same temperature for 30 minutes. The reaction solution was extracted with ethyl acetate (150 ml). The organic layer was washed sequentially with water and a saturated sodium chloride aqueous solution, then dried over anhydrous magnesium sulfate and concentrated under reduced pressure. The residue was subjected to silica gel column chromatography (Wakogel TM C-300, hexane-ethyl acetate 10:1) to obtain (E)-3-[(2S,4R)-N-tert-butoxycarbonyl-4-tert-butyldimethylsiloxypyrrolidin-2-yl]-acrylic acid ethyl ester (9.4 g, yield: 97.5%).

NMR(CDCl₃) δ: 0.06(6H,s),0.88(9H,s),1.30(3H,d,J=7 Hz),1.44(9H,br s),1.84(1H,m),2.10(1H,m),3.48(2H,m),4.12(2H,q,J=7 Hz),4.35(1H,m),5.88(1H,br d,J=16 Hz),6.86(1H,m).

5)

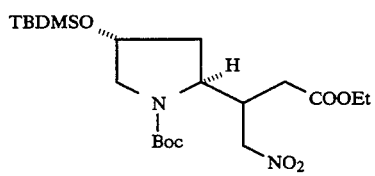

1,1,3,3-tetramethylguanidine (5.8 ml, 46.2 mmol) was dropwise added to a solution of the compound obtained by the above reaction (9.0 g, 22.6 mmol) in nitromethane (33 ml) in a nitrogen stream at room temperature. The mixture was stirred overnight at the same temperature. Ethyl acetate (200 ml) was added to the reaction solution, and the organic layer was washed sequentially with dilute hydrochloric acid, water and a saturated sodium chloride aqueous solution, then dried over anhydrous magnesium sulfate and concentrated under reduced pressure. The residue was subjected to silica gel column chromatography (Wakogel TM C-300, hexane-ethyl acetate 10:1) to obtain 3-[(2S,4R)-N-tert-butoxycarbonyl-4-tert-buthyldimethylsiloxypyrrolidin-2-yl]-4-nitrobutyric acid ethyl ester (10.1 g, yield: 97.3%).

NMR(CDCl3) δ: 0.06(6H,s),0.86(9H,s),1.27(3H,d,J=7 Hz),1.48(9H,br s),1.73(1H,m),2.00(1H,m),2.44(2H,m),3.16(1H,m),4.16(-4H,m),4.33(1H,m)4.53(1H,m).

6)

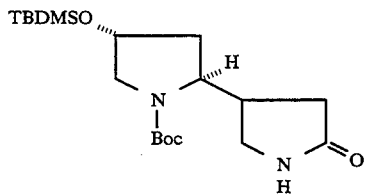

Raney nickel (W-2 type, 3.0 ml) was added to a solution of the compound obtained by the above reaction (3.6 g, 7.8 mmol) in ethanol (50 ml). The mixture was stirred overnight at room temperature in a hydrogen atmosphere. The catalyst was filtered off from the reaction solution. The filtrate was concentrated under reduced pressure. The residue was dissolved in benzene (50 ml) and the mixture was refluxed overnight. The reaction solution was concentrated under reduced pressure, and the residue was subjected to silica gel column chromatography (Wakogel TM C-300, 1% methanol-chloroform) to obtain (2S,4R)-N-tert-butoxycarbonyl-4-tert-butyldimethylsiloxy-2-(2-pyrrolidon-4-yl)pyrrolidine (1.87 g, yield: 62.2%).

NMR(CDCl3) δ: 0.06(6H,s),0.86(9H,s),1.47(9H,s),1.72(1H,m),1.88-2.48(-3H,m),2.95-3.75(5H,m),4.13(1H,m),4.30(1H,m).

7)

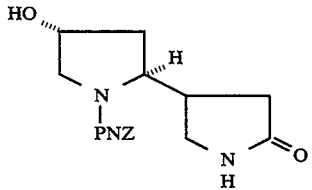

The compound obtained by the above reaction (1.87 g, 4.87 mmol) was dissolved in a 80% trifluoroacetic acid aqueous solution (20 ml), and the solution was stirred overnight at room temperature. The reaction solution was concentrated under reduced pressure, and the residue was dissolved in a mixture comprising dioxane (10 ml) and water (10 ml). The pH was adjusted to 8 with a 1N sodium hydroxide aqueous solution. Then, 4,6-dimethyl-2-(p-nitrobenzyloxycarbonylthio)pyrimidine (1.55 g, 4.86 mmol) was added thereto. This solution was stirred at room temperature for 3 hours. The reaction solution was concentrated under reduced pressure, and the residue was extracted with ethyl acetate (100 ml). The organic layer was washed with water and a saturated sodium chloride aqueous solution, then dried over anhydrous magnesium sulfate and concentrated under reduced pressure. The residue was subjected to silica gel column chromatography (Wakogel TM C-300, 3% methanol-chloroform) to obtain (2S,4R)-4-hydroxy-N-(p-nitrobenzyloxycarbonyl)-2-(2-pyrrolidon-4-yl)pyrrolidine (769 mg, yield: 45.2%).

NMR(CDCl3) δ: 1.72-2.52(5H,m),2.-98-3.58(3H,m),3.78(1H,m),4.24(1H,m),4.48(1H,m),5.25-(2H,br s),7.54(2H,d,J=9 Hz),8.24(2H,d,J=9 Hz).

8)

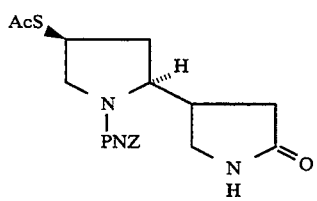

and

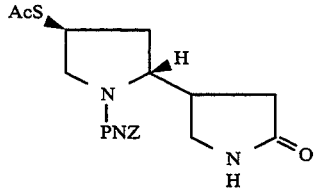

Triphenylphosphine (567 mg, 2.16 mmol) was added to a solution of the compound obtained by the above reaction (302 mg, 0.87 mmol) in tetrahydrofuran (10 ml) under a nitrogen stream, and then diethyl azodicarboxylate (0.341 ml, 2.17 mmol) was dropwise added thereto under cooling with ice. The reaction solution was stirred for 30 minutes under cooling with ice. Then, thioacetic acid (0.155 ml, 2.17 mmol) was dropwise added thereto. The mixture was stirred at room temperature for two hours. Then, the reaction solution was extracted with ethyl acetate (100 ml). The organic layer was washed with water and a saturated sodium chloride aqueous solution, then dried over anhydrous magnesium sulfate and concentrated under reduced pressure. The residue was subjected to silica gel column chromatography (Wakogel TM C-300) to obtain (2S,4S)-4-acetylthio-N-(p-nitrobenzyloxycarbonyl)-2-(2-pyrrolidon-4-yl)pyrrolidine (166 mg, yield: 47.1%) by the elution with hexane-ethyl acetate (1:1) and (2R,4S)-4-acetylthio-N-(p-nitrobenzyloxycarbonyl)-2-(2-pyrrolidon-4-yl)pyrrolidine (166 mg, yield: 47.1%) by the elution with 3% methanol-chloroform.

(2S,4S) isomer
IR(KBr)cm−1: 1700, 1520, 1340, 1110.
NMR(CDCl3) δ: 1.70(1H,m),1.98-2.62(4H,m),2.37(3H,s),3.17(2H,m),3.4-2(1H,m),3.87(1H,m),4.05-4.35(2H,m),5.24(2H,br s),7.55(2H,d,J=9 Hz),8.26(2H,d,J=9 Hz).

(2R,4S) isomer
IR(KBr)cm−1: 1700, 1520, 1350, 1120.
NMR(CDCl3) δ: 1.68(1H,m),2.30-2.95(4H,m),2.38(3H,s),3.20(1H,m),3.5-

5(1H,m),3.88(2H,m),4.06–4.30(2H,m),5.26(2H,br s),7.56(2H,d,J=9 Hz),8.26(2H,d,J=9 Hz).

9)

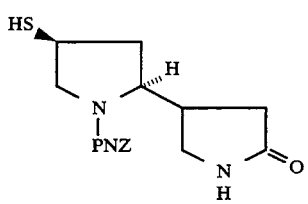

A 1N sodium hydroxide aqueous solution (0.42 ml) was dropwise added to a solution of the (2S,4S) isomer obtained by the above reaction (166 mg, 0.41 mmol) in methanol (10 ml) in a nitrogen stream under cooling with ice. This solution was stirred at the same temperature for 15 minutes. To the reaction solution, 1N hydrochloric acid (0.45 ml) was dropwise added. Then, the reaction solution was concentrated under reduced pressure. The residue was extracted with ethyl acetate (70 ml). The organic layer was washed with water and a saturated sodium chloride aqueous solution, then dried over anhydrous magnesium sulfate and concentrated under reduced pressure to obtain (2S,4S)-4-mercapto-N-(p-nitrobenzyloxycarbonyl)-2-(2-pyrrolidon-4-yl)pyrrolidine (140 mg, yield: 94%).

REFERENCE EXAMPLE 2

(2R,4S)-4-mercapto-N-(p-nitrobenzyloxycarbonyl)-2-(2-pyrrolidon-4-yl)pyrrolidine

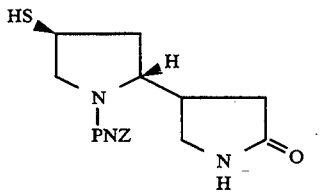

The same procedure as in Reference Example 1-9 was carried out by using (2R,4S)-4-acetylthio-N-(p-nitrobenzyloxycarbonyl)-2-(2-pyrrolidon-4-yl)pyrrolidine (166 mg, 0.41 mmol, compound of Reference Example 1-8) to obtain the above identified compound (140 mg, yield: 94%).

REFERENCE EXAMPLE 3

(2S,4S)-2-(2-azetidinon-4-yl)-4-mercapto-N-(p-nitrobenzyloxycarbonyl)pyrrolidine diastereomer B

1)

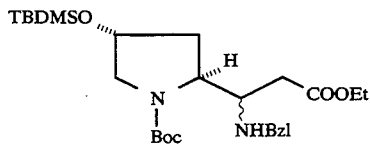

Benzylamine (1.2 ml, 11 mmol) was added to [(2S,4R)-N-tert-butoxycarbonyl-4-tert-butyldimethylsiloxypyrrolidin-2-yl]acrylic acid ethyl ester (2.18 g, 5.46 mmol, compound of Reference Example 1-4). The mixture was stirred at room temperature for five days. Then, this mixture was subjected to silica gel column chromatography (Wakogel TM C-300, hexane-ethyl acetate 3:1) to obtain 3-benzylamino-3-[(2S,4R)-N-tert-butoxycarbonyl-4-tert-butyldimethylsiloxypyrrolidin-2-yl]propionic acid ethyl ester (1.95 g, yield: 70.5%).

NMR(CDCl₃) δ: 0.05(6H,s),0.86(9H,s),1.24(3H,t,J=8 Hz),1.44(9H,s),1.90(1H,m),2.35(2H,m),3.26(1H,m),3.89 and 3.96(2H,ABq,J=8 Hz),4.14(2H,q,J=8 Hz),4.39(1H,m),7.31(5H,m).

2)

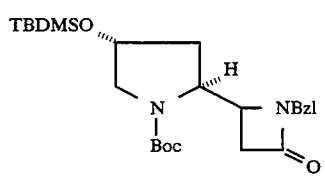

A 1N sodium hydroxide aqueous solution (4.3 ml) was dropwise added to a solution of the compound obtained by the above reaction (1.98 g, 3.9 mmol) in ethanol (30 ml) at room temperature. This solution was stirred overnight at the same temperature. 1N hydrochloric acid (4.3 ml) was added to this reaction solution. This solution was concentrated under reduced pressure. Tetrahydrofuran (50 ml) was added to the residue, and insoluble matters were filtered off. The organic layer was dried over anhydrous magnesium sulfate and concentrated under reduced pressure. The obtained oily substance (1.83 g) was dissolved in acetonitrile (380 ml). Triphenylphosphine (1.2 g, 4.58 mmol) and 2,2'-dipyridyl disulfide (1.01 g, 4.58 mmol) were added thereto in a nitrogen stream. This solution was stirred at 80° C. for 4.5 hours. The reaction solution was concentrated under reduced pressure and extracted with ethyl acetate (150 ml). The organic layer was washed sequentially with a 0.1N sodium hydroxide aqueous solution, water and a saturated sodium chloride aqueous solution, then dried over anhydrous magnesium sulfate and concentrated under reduced pressure. The residue was subjected to silica gel column chromatography (Wakogel TM C-300, hexane-ethyl acetate 10:1→3:1) to obtain (2S,4R)-2-(N-benzyl-2-azetidinon-4-yl)-N-tert-butoxycarbonyl-4-tert-butyldimethylsiloxypyrrolidine diastereomer B (1.07 g, yield: 60.7%, highly polar compound) and diastereomer A (0.47 g, yield: 26.8%).

Diastereomer B

1R(KBr)cm⁻¹: 1730, 1690, 1390, 1170.

NMR(CDCl₃) δ: 0.06(6H,s),0.88(9H,s),1.50(9H,br s),2.54(1H,br d,J=14 Hz),2.93(1H,dd,J=14,4 Hz),3.16(1H,dd,J=12,4 Hz),7.35(5H,m).

Diastereomer A

1R(KBr)cm⁻¹: 1760, 1700, 1400, 1260.

NMR(CDCl₃) δ: 0.04(6H,s),0.85(9H,s),1.45(9H,br s),1.84(2H,m),2.58(1H,br d,J=16 Hz),2.92(2H,m),3.44(1H,m),3.95–4.30(4H,m), 4.60 (1H,m), 7.30 (5H,m).

3)

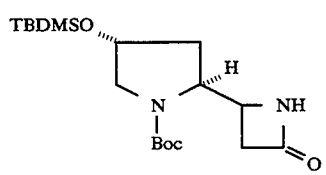

Liquid ammonia (about 30 ml) was added to a solution of the diastereomer B obtained in the above reaction (470 mg, 0.98 mmol) in tetrahydrofuran (10 ml) and tert-butyl alcohol (1 ml) at −78° C. Sodium metal (100 mg, 4.35 mmol) was added to the reaction solution at the same temperature. The mixture was stirred for 15 minutes, and ammonium chloride (465 mg, 8.69mmol) was added thereto. The reaction mixture was returned to room temperature, and ammonia was distilled off. The residue was extracted with ethyl acetate (100 ml). The organic layer was washed sequentially with water and a saturated sodium chloride solution, then dried over anhydrous magnesium sulfate and concentrated under reduced pressure. The residue was subjected to silica gel column chromatography (Wakogel TM C-300, hexane-ethyl acetate 1:1) to obtain (2S,4R)-2-(2-azetidinon-4-yl)-N-tert-butoxycarbonyl-4-tert-butyldimethylsiloxypyrrolidine diastereomer B (340 mg, yield: 89.1%).

IR(KBr)cm⁻¹: 1750, 1700, 1380, 1260.

NMR(CDCl₃) δ: 0.06(6H,s),0.87(9H,s),1.47(9H,s),1.61(1H,m),2.02(1H,m-),2.62(1H,br d,J=16 Hz),3.02(1H,dd,J=16,6 Hz),3.33(1H,m),3.50(2H,m),4.05(1H,m),4.30(1H,m).

4)

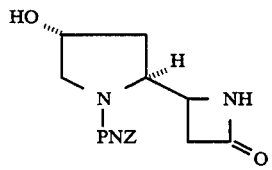

Anisole (one drop) and trifluoroacetic acid (3 ml) were dropwise added to a solution of the compound obtained by the above reaction (340 mg, 0.88 mmol) in methylene chloride (3 ml) in a nitrogen stream under cooling with ice. The reaction solution was stirred for one hour under cooling with ice and concentrated under reduced pressure. The residue was dissolved in tetrahydrofuran (5 ml). Triethylamine (1.2 ml, 8.6 mmol) and 4,5-dimethyl-2-(p-nitrobenzyloxycarbonylthio)pyrimidine (280 mg, 0.88 mmol) were added thereto under cooling with ice, and the mixture was stirred at room temperature for 1.5 hours. The reaction solution was extracted with ethyl acetate (70 ml). The organic layer was washed sequentially with a 0.1N sodium hydroxide aqueous solution, water and a saturated sodium chloride aqueous solution, then dried over anhydrous magnesium sulfate and concentrated under reduced pressure. The residue was dissolved in acetonitrile (5 ml), and 46% hydrofluoric acid (0.5 ml) was dropwise added thereto at room temperature. The mixture was stirred at room temperature for 1.5 hours. Then, the reaction solution was extracted with ethyl acetate (70 ml). The organic layer was washed sequentially with a 5% sodium hydrogen carbonate solution, water and a saturated sodium chloride aqueous solution, then dried over anhydrous magnesium sulfate and concentrated under reduced pressure. The residue was subjected to silica gel column chromatography (Wakogel TM C-300, 3% methanol-chloroform) to obtain (2S,4R)-2-(2-azetidinon-4-yl)-4-hydroxy-N-(p-nitrobenzyloxycarbonyl)pyrrolidine diastereomer B (177 mg, yield: 60.3%).

IR(KBr)cm⁻¹: 1750, 1700, 1520, 1340.

NMR(CDCl₃) δ: 1.72(1H,m),2.14(1H,m),2.64(1H,d,J=14 Hz),3.06(2H,m),3.57(1H,m),3.74(1H,m),4.12(1H,m),4.4-4(1H,m),5.22(2H,br s),7.52(2H,d,J=8 Hz),8.22(2H,d,J=8 Hz).

5)

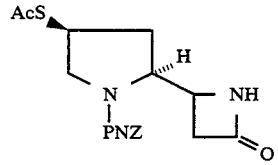

Triphenylphosphine (347 mg, 1.32 mmol) was added to a solution of the compound obtained by the above reaction (177 mg, 0.53 mmol) in tetrahydrofuran (10 ml) in a nitrogen stream under cooling with ice, and then diethyl azodicarboxylate (0.208 ml, 0.132 mmol) was dropwise added thereto. The reaction solution was stirred for 30 minutes under cooling with ice, and then thioacetic acid (95 µl, 0.132 mmol) was dropwise added thereto. This reaction mixture was stirred at the same temperature for 3 hours. Then, the reaction solution was extracted with ethyl acetate (50 ml). The organic layer was washed sequentially with water and a saturated sodium chloride aqueous solution, then dried over anhydrous magnesium sulfate and concentrated under reduced pressure. The residue was subjected to silica gel column chromatography (Wakogel TM C-300, ethyl acetate) to obtain (2S,4S)-4-acetylthio-2-(2-azetidinon-4-yl)-N-(p-nitrobenzyloxycarbonyl)pyrrolidine diastereomer B (77 mg, yield: 37.1%).

NMR(CDCl₃) δ: 1.65(1H,m),2.38(3H,s),3.08(1H,dd,J=16,4 Hz),3.30(1H,t,J=9 Hz),3.64–4.28(4H,m),5.25(2H,br s),7.55(2H,d,J=8 Hz),8.26(2H,d,J=8 Hz).

6)

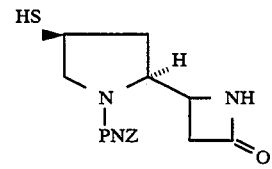

A 0.1N sodium hydroxide aqueous solution (0.196 ml) was dropwise added to a solution of the compound obtained by the above reaction (77 mg, 0.22 mmol) in methanol (10 ml) in a nitrogen stream under cooling with ice. The reaction solution was stirred for 15 minutes under cooling with ice, and then 1N hydrochloric acid (0.21 ml) was added thereto. This reaction mixture was concentrated under reduced pressure. The residue was extracted with ethyl acetate (50 ml). The organic layer was washed with water and a saturated sodium chloride aqueous solution, then dried over anhydrous magnesium sulfate and concentrated under reduced pressure to obtain (2S,4S)-2-(2-azetidinon-4-yl)-4-mercapto-N-(p-nitrobenzyloxycarbonyl)pyrrolidine diastereomer B (67 mg, yield: 97%).

REFERENCE EXAMPLE 4

(2S,4S)-2-(2-azetidinon-4-yl)-4-mercapto-N-(p-nitrobenzyloxycarbonyl)pyrrolidine diastereomer A

1)

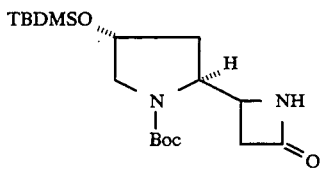

The same procedure as in Reference Example 3-3 was carried out by using (2S,4R)-2-(N-benzyl-2-azetidinon-4-yl)-N-tert-butoxycarbonyl-4-tert-butyldimethylsiloxypyrrolidine diastereomer A (500 mg, 1.05 mmol) and sodium metal (75 mg, 3.26 mmol) to obtain (2S,4R)-2-(2-azetidinon-4-yl)-N-tert-butoxycarbonyl-4-tert-butyldimethylsiloxypyrrolidine diastereomer A (360 mg, yield: 88.4%).

IR(KBr)cm$^{-1}$: 1760, 1740, 1690, 1390, 1260.
NMR(CDCl$_3$) δ: 0.06(6H,s),0.86(9H,s),1.47(9H,s),1.93(2H,m),2.66(1H,d,J=16 Hz),2.97(1H,ddd,J=16,5,2 Hz),3.26(1H,dd,J=12,5 Hz),3.55(1H,m),4.00–4.44(3H,m).

2)

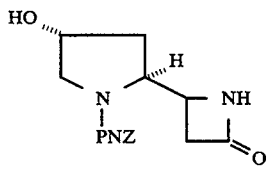

The same procedure as in Reference Example 3-4 was carried out by using the compound obtained by the above reaction (350 mg, 0.90 mmol) to obtain (2S,4R)-2-(2-azetidinon-4-yl)-4-hydroxy-N-(p-nitrobenzyloxycarbonyl)pyrrolidine diastereomer A (185 mg, yield: 61%).

IR(KBr)cm$^{-1}$: 1740, 1670, 1520, 1440, 1340.
NMR(CDCl$_3$) δ: 2.06(2H,m),2.70(1H,d,J=16 Hz),3.02(1H,br d,J=16 Hz),3.47(1H,m),3.76(1H,m),4.16(1H,m),4.34(1H,m),4.-50 (1H,m),5.26(2H,br s),7.54(2H,d,J=8 Hz),8.24(2H,d,J=8 Hz).

3)

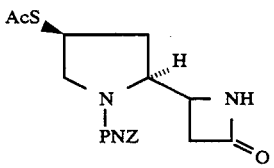

The same procedure as in Reference Example 3-5 was carried out by using the compound obtained by the above reaction (185 mg, 0.55 mmol), diethyl azodicarboxylate (0.218 ml, 0.138 mmol), triphenylphosphine (365 mg, 0.138 mmol) and thioacetic acid (99 μl, 0.138 mmol) to obtain (2S,4S)-4-acetylthio-2-(2-azetidinon-4-yl)-N-(p-nitrobenzyloxycarbonyl)pyrrolidine diastereomer A (107 mg, yield: 49.3%).

NMR(CDCl$_3$) δ: 1.87(1H,m),2.36(3H,s),2.52(1H,m),2.78(1H,m),3.04(1H,br d,J=12 Hz),3.18(1H,t,J=10 Hz),3.80–4.32(4H,m),5.24(2H,br s),7.54(2H,d,J=8 Hz),8.23(2H,d,J=8 Hz).

4)

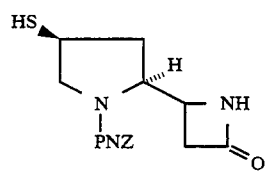

The same procedure as in Reference Example 3-6 was carried out by using the compound obtained by the above reaction (107 mg, 0.27 mmol) and a 1N sodium hydroxide aqueous solution (0.27 ml) to obtain (2S,4S)-2-(2-azetidinon-4-yl)-4-mercapto-N-(p-nitrobenzyloxycarbonyl)pyrrolidine diastereomer A (90.8 mg, yield: 95%).

REFERENCE EXAMPLE 5

(2S,4S)-4-mercapto-N-(p-nitrobenzyloxycarbonyl)-2-[N-(p-nitrobenzyloxycarbonyl)pyrrolidin-3-yl]pyrrolidine

1)

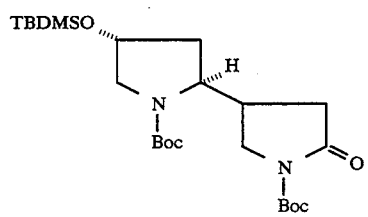

Triethylamine (0.53 ml, 3.81 mmol), 4-dimethylaminopyridine (465 mg, 3.81 mmol) and di-tert-butyl dicarbonate (1.66 g, 760 mmol) were added to a solution of the compound obtained in Reference Example 1-6 (1.46 g, 3.80 mmol) in methylene chloride (15 ml) in a nitrogen stream at room temperature. The mixture was stirred at the same temperature for 4.5 hours. The reaction solution was concentrated under reduced pressure, and the residue was extracted with ethyl acetate (50 ml). The organic layer was washed with dilute hydrochloric acid, water and a saturated sodium chloride aqueous solution, then dried over anhydrous magnesium sulfate and concentrated under reduced pressure. The residue was subjected to silica gel column chromatography (Wakogel ™ C-300, hexane-ethyl acetate 5:1) to obtain (2S,4R)-N-tert-butoxycarbonyl-4-tert-butyldimethylsiloxy-2-(N-tert-butoxycarbonyl-2-pyrrolidon-4-yl)pyrrolidine (1.76 g, yield 96%).

NMR(CDCl$_3$) δ: 0.06(6H,s),0.86(9H,s),1.48(9H,s),1.54(9H,s),1.68(1H,m),2.00(1H,m),3.25(1H,m),4.10(1H,m),4.34(1H,m).

2)

199

-continued

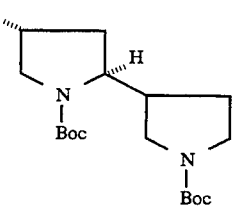

A borane-dimethyl sulfide complex (1.09 ml, 10.9 mmol) was dropwise added to a solution of the comound obtained by the above reaction (1.76 g, 3.64 mmol) in tetrahydrofuran (18 ml) in a nitrogen stream at room temperature, and the mixture was then refluxed for 1.5 hours. Methanol (5 ml) was added to the reaction solution under cooling with ice and concentrated under reduced pressure. The residue was subjected to silica gel column chromatography (Wakogel TM C-300, hexane-ethyl acetate 10:1) to obtain (2S,4R)-N-tert-butoxycarbonyl-4-tert-butyldimethylsiloxy-2-(N-tert-butoxycarbonylpyrrolidin-3-yl)pyrrolidine (1.62 g, yield: 94.8%).

NMR(CDCl₃) δ: 0.05(6H,s),0.86(9H,s),1.46(18H,s),1.60–2.04(4H,m),4.07-(1H,m),4.34(1H,m).

3)

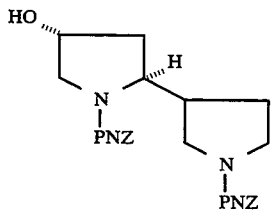

A solution of 1.6N hydrogen chloride in methanol (15 ml) was added to the compound obtained by the above reaction (1.60 g, 3.40 mmol), and the mixture was stirred at room temperature for 2 hours. The reaction solution was concentrated under reduced pressure. The residue was dissolved in a mixture of dioxane (20 ml) and water (10 ml), and the solution was adjusted to pH 8.5 with triethylamine. Then, 4,6-dimethyl-2-(p-nitrobenzyloxycarbonylthio)pyrimidine (2.17 g, 6.80 mmol) was added thereto. This reaction solution was stirred at room temperature for 1.5 hours. The reaction solution was concentrated under reduced pressure, and the residue was extracted with ethyl acetate (50 ml). The organic layer was washed with a 1N sodium hydroxide aqueous solution, water and a saturated sodium chloride aqueous solution, then dried over anhydrous magnesium sulfate and concentrated under reduced pressure. The residue was subjected to silica gel column chromatography (Wakogel TM C-300, 2% methanol-chloroform) to obtain (2S,4R)-4-hydroxy-N-(p-nitrobenzyloxycarbonyl)-2-[N-(p-nitrobenzyloxycarbonyl)pyrrolidin-3-yl]pyrrolidine (1.55 g, yield: 88.6%).

NMR(CDCl₃) δ: 1.52–2.20(4H,m),3.76(1H,m),4.23(1H,m),4.48(1H,m),5.-22(4H,s),7.52(4H,d,J=8 Hz),8.20(4H,d,J=8 Hz).

4)

200

-continued

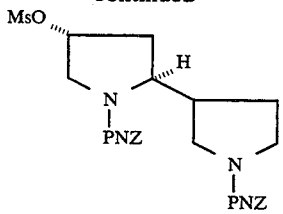

Triethylamine (0.52 ml, 3.74 mmol) and methanesulfonyl chloride (0.28 ml, 3.62 mmol) were added to a solution of the compound obtained by the above reaction (1.55 g, 3.02 mmol) in tetrahydrofuran (15 ml) in a nitrogen stream under cooling with ice, and the mixture was stirred at the same temperature for 30 minutes. The reaction solution was extracted with ethyl acetate (50 ml). The organic layer was washed with water and a saturated sodium chloride aqueous solution, then dried over anhydrous magnesium sulfate and concentrated under reduced pressure. The residue was subjected to silica gel column chromatography (Wakogel TM C-300, ethyl acetate) to obtain (2S,4R)-4-methanesulfonyloxy-N-(p-nitrobenzyloxycarbonyl)-2-[N-(p-nitrobenzyloxycarbonyl)pyrrolidin-3-yl]pyrrolidine (1.76 g, yield 98.6%).

NMR(CDCl₃) δ: 3.04(3H,s),4.18(2H,m),5.24(4H,br s),7.53(4H,d,J=8 Hz),8.24(4H,d,J=8 Hz).

5)

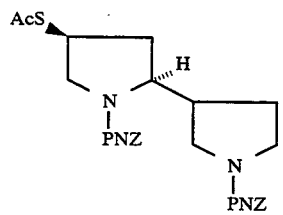

Thioacetic acid (0.31 ml, 4.50 mmol) was dropwise added to a solution of anhydrous potassium carbonate (616 mg, 4.46 mmol) in N,N-dimethylformamide (30 ml) in a nitrogen stream at 0° C., and the mixture was stirred at the same temperature for 20 minutes. To this mixture, a solution of the compound obtained by the above reaction (1.76 g, 2.97mmol) in N,N-dimethylformamide (5 ml) and sodium iodide (450 mg, 30 mmol) were added at 0° C. This reaction mixture was stirred overnight at a temperature of from 60° to 70°. The reaction mixture was extracted with ethyl acetate (100 ml). The organic layer was washed with water and a saturated sodium chloride aqueous solution, then dried over anhydrous magnesium sulfate and concentrated under reduced pressure. The residue was subjected to silica gel column chromatography (Wakogel TM C-300, hexane-ethyl acetate 1:1) to obtain (2S,4S)-4-acetylthio-N-(p-nitrobenzyloxycarbonyl)-2-[N-(p-nitrobenzyloxycarbonyl)pyrrolidin-3-yl]pyrrolidine (1.34 g, yield: 78.8%).

NMR(CDCl₃) δ: 1.54–2.10(4H,m),2.36(3H,s),3.90(1H,m),4.12(1H,m),4.2-6(1H,m),5.24(4H,s),7.52(4H,d,J=8 Hz),8.24(4H,d,J=8 Hz).

6)

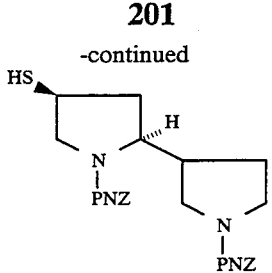

The compound obtained by the above reaction (1.34 g, 2.34 mmol) was dissolved in a mixture of methanol (25 ml) and tetrahydrofuran (10 ml). A 1N sodium hydroxide aqueous solution (2.46 ml) was dropwise added thereto in a nitrogen stream under cooling with ice, and the mixture was stirred at the same temperature for 15 minutes. 1N hydrochloric acid (2.53 ml) was dropwise added to the reaction solution, and the mixture was concentrated under reduced pressure. The residue was extracted with ethyl acetate (50 ml). The organic layer was washed with water and a saturated sodium chloride aqueous solution, then dried over anhydrous magnesium sulfate and concentrated under reduced pressure to obtain the above identified compound (1.24 g, yield: 100%).

REFERENCE EXAMPLE 6

(2S,4S)-4-mercapto-2-(N-methylpyrrolidin-3-yl)-N-(p-nitrobenzyloxycarbonyl)pyrrolidine trifluoromethanesulfonate

1)

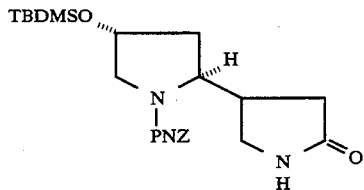

2,6-lutidine (1.04 ml, 8.93 mmol) and trimethylsilyl trifluoromethanesulfonate (1.34 ml, 6.70 mmol) were added to a solution of the compound obtained in Reference Example 1-6 (1.72 g, 4.48 mmol) in methylene chloride (17 ml) in a nitrogen stream at room temperature, and the mixture was stirred at the same temperature for 30 minutes. Methanol (5 ml) was dropwise added to the reaction solution, and then the solution was concentrated. Dioxane (15 ml) was added to the residue. Triethylamine (0.94 ml, 6.72 mmol) and 4,6-dimethyl-2-(p-nitrobenzyloxycarbonylthio)pyrimidine (1.43 g, 4.48 mmol) were added to this reaction solution, and the mixture was stirred at room temperature for 2 hours. The reaction solution was concentrated under reduced pressure, and the residue was extracted with ethyl acetate (50 ml). The organic layer was washed with dilute hydrochloric acid, water and a saturated sodium chloride aqueous solution, then dried over anhydrous magnesium sulfate and concentrated under reduced pressure. The residue was subjected to silica gel column chromatography (Wakogel ™ C-300, ethyl acetate) to obtain (2S,4R)-4-tert-butyldimethylsiloxy-N-(p-nitrobenzyloxycarbonyl)-2-(2-pyrrolidon-4-yl)pyrrolidine (813 mg, yield: 39.2%).

NMR(CDCl₃) δ: 0.03 (3H,s),0.06(3H,s),0.84(9H,s),1.78(1H,m),1.92–2.50(3H,m),2.93–3.54(4H,m),3.66(1H,m),4.10(1H,m),4.38(1H,m-),5.23(2H,ABq,J=14 Hz),7.52(2H,d,J=8 Hz),8.23(2H,d,J=8 Hz).

2)

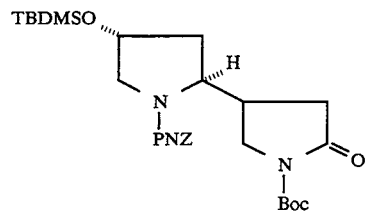

The same procedure as in Reference Example 5-1 was carried out by using the compound obtained by the above reaction (813 mg, 1.76 mmol) and di-tert-butyl dicarbonate (766 mg, 3.51 mmol) to obtain (2S,4R)-4-tert-butyldimethylsiloxy-2-(N-tert-butoxycarbonyl-2-pyrrolidon-4-yl)-N-(p-nitrobenzyloxycarbonyl)pyrrolidine (944 mg, yield: 95.5%).

NMR(CDCl₃) δ: 0.04(3H,s),0.06(3H,s),0.84(9H,s),1.52(9H,s),1.74(1H,m)-,2.00(1H,m),2.20–2.96(3H,m),4.19(1H,m),4.39(1H,br s),5.24(2H,ABq,J=14 Hz),7.53(2H,d,J=8 Hz),8.24(2H,d,J=8 Hz).

3)

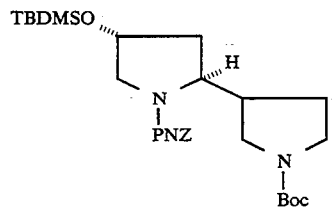

The same procedure as in Reference Example 5-2 was carried out by using the compound obtained by the above reaction (944 mg, 1.68 mmol) and a borane-dimethyl sulfide complex (0.50 ml, 5.0 mmol) to obtain (2S,4R)-4-tert-butyldimethylsiloxy-2-(N-tert-butoxycarbonylpyrrolidin-3-yl)-N-(p-nitrobenzyloxycarbonyl)pyrrolidine (730 mg, yield: 79.3%).

NMR(CDCl₃) δ: 0.05(3H,s),0.07(3H,s),0.85(9H,s),1.45(9H,s),1.52–2.08(4-H,m),2.82(1H,m),2.90–3.80(6H,m),4.15(1H,m),4.40(1H,br s),5.24(2H,m),7.54(2H,d,J=8 Hz),8.23(2H,d,J=8 Hz).

4)

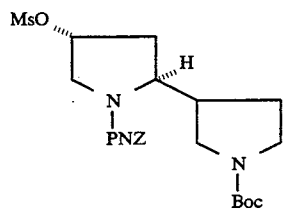

A solution of 1M tetrabutylammonium fluoride in tetrahydrofuran (13.7 ml) was added to a solution of the compound obtained by the above reaction (6.98 g, 12.7 mmol) in tetrahydrofuran (100 ml) in a nitrogen stream under cooling with ice, and the mixture was stirred at the same temperature for 40 minutes. A saturated ammonium chloride aqueous solution (20 ml) was added to the reaction solution, and the mixture was extracted with ethyl acetate (150 ml). The organic layer was washed with water and a saturated sodium chloride aqueous solution, then dried over anhydrous magnesium sulfate and concentrated under reduced pressure. The residue was dissolved in tetrahydrofuran (100 ml). Then, triethylamine (1.77 ml, 12.7 mmol) and methanesulfonyl chloride (0.99 ml, 12.8 mmol) were added thereto under cooling with ice, and the mixture was stirred at the same temperature for 1 hour. The reaction solution was extracted with ethyl acetate (150 ml). The organic layer was washed with water and a saturated sodium chloride aqueous solution, then dried over anhydrous magnesium sulfate and concentrated under reduced pressure. The residue was subjected to silica gel column chromatography (Wakogel TM C-300, hexane-ethyl acetate 1:1) to obtain (2S,4R)-2-(N-tert-butoxycarbonylpyrrolidin-3-yl)-4-methanesulfonyloxy-N-(p-nitrobenzyloxycarbonyl)pyrrolidine (6.64 g, yield: 100%).

NMR(CDCl₃) δ: 1.36(9H,s),2.96(3H,s),3.98–4.24(2H,m),5.18(2H,m),7.46-(2H,d,J=8 Hz),8.16(2H,d,J=8 Hz).

5)

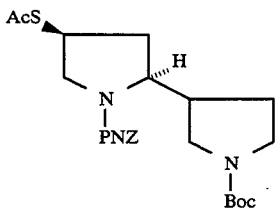

The same procedure as in Reference Example 5-5 was carried out by using the compound obtained by the above reaction (6.6 g, 12.9 mmol) and thioacetic acid (1.33 ml, 19.3 mmol) to obtain (2S,4S)-4-acetylthio-2-(N-tert-butoxycarbonylpyrrolidin-3-yl)-N-(p-nitrobenzyloxycarbonyl)pyrrolidine (4.57 g, yield: 72.1%).

NMR(CDCl₃) δ: 1.44(9H,s),2.35(3H,s),3.86(1H,m),4.08(1H,m),4.24(1H,m),5.23(2H,br s),7.53(2H,d,J=8 Hz),8.24(2H,d,J=8 Hz).

6)

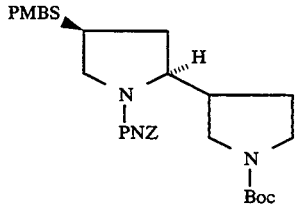

A 1N sodium hydroxide aqueous solution (9.7 ml) was added to a solution of the compound obtained by the above reaction (4.56 g, 9.25 mmol) in methanol (100 ml) in a nitrogen stream under cooling with ice. The mixture was stirred at the same temperature for 15 minutes. Triethylamine (2.0 ml, 14.4 mmol) and p-methoxybenzyl chloride (1.82 ml, 13.4 mmol) were added to this reaction solution, and the mixture was stirred at the same temperature for 2 hours. The reaction solution was concentrated under reduced pressure, and the residue was extracted with ethyl acetate (300 ml). The organic layer was washed with water and a saturated sodium chloride aqueous solution, then dried over anhydrous magnesium sulfate and concentrated under reduced pressure. The residue was subjected to silica gel column chromatography (Wakogel TM C-300, hexane-ethyl acetate 3:1) to obtain (2S,4S)-2-(N-tert-butoxycarbonylpyrrolidin-3-yl)-4-(p-methoxybenzylthio)-N-(p-nitrobenzyloxycarbonyl)pyrrolidine (4.97 g, yield: 94.1%).

NMR(CDCl₃) δ: 1.44(9H,s),1.50–1.98(3H,m),2.33(1H,m),2.70(1H,m),3.7-4(2H,s),3.80(3H,s),3.96(1H,m),5.20(2H,br s),6.86(2H,d,J=8 Hz),7.24(2H,d,J=8 Hz),7.50(2H,d,J=8 Hz),8.24(2H,d,J=8 Hz).

7)

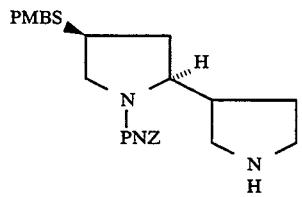

Trifluoroacetic acid (6.7 ml, 10.0 mmol) was added to a solution of the compound obtained by the above reaction (4.97 g, 8.70 mmol) in methylene chloride (50 ml) under cooling with ice, and the mixture was stirred at room temperature for 2 hours. The reaction solution was concentrated under reduced pressure, and the residue was extracted with ethyl acetate (150 ml). The organic layer was washed with a saturated sodium hydrogen carbonate aqueous solution and a saturated sodium chloride aqueous solution, then dried over anhydrous magnesium sulfate and concentrated under reduced pressure to obtain (2S,4S)-4-(p-methoxybenzylthio)-N-(p-nitrobenzyloxycarbonyl)-2-(3-pyrrolidinyl)-pyrrolidine (4.0 g, yield: 97.6%).

NMR(CDCl₃) δ: 1.62(1H,m),1.75–2.18(2H,m),2.42(1H,m),2.82(1H,m),3.-75(2H,s),3.82(3H,s),4.09(1H,m),5.20(2H,br s),6.86(2H,d,J=8 Hz),7.24(2H,d,J=8 Hz),7.50(2H,d,J=8 Hz),8.27(2H,d,J=8 Hz).

8)

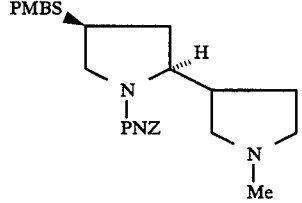

A 37% formaldehyde aqueous solution (0.6 ml, 7.5 mmol) and sodium cyanoborohydride (300 mg, 4.77 mmol) were added to a solution of the compound obtained by the above reaction (1.4 g, 2.97 mmol) in acetonitrile (15 ml) at room temperature, and the mixture was stirred at the same temperature for 15 minutes. This reaction mixture was neutralized with acetic acid and then further stirred at room temperature for 1 hour. The reaction mixture was extracted with ethyl acetate (50 ml). The organic layer was washed with a 1N sodium hydroxide aqueous solution, water and a saturated sodium chloride aqueous solution, then dried over anhydrous magnesium sulfate and concentrated under reduced pressure. The residue was subjected to silica gel column chromatography (Wakogel ™ C-300, ethyl acetate-methanol 1:1) to obtain (2S,4S)-4-(p-methoxybenzylthio)-2-(N-methylpyrrolidin-3-yl)-N-(p-nitrobenzyloxycarbonyl)pyrrolidine (617 mg, yield: 42.8%).

NMR(CDCl3) δ: 1.42–2.04(3H,m),3.74(2H,s),3.82(3H,s),3.98(1H,m),5.20-(2H,br s),6.86(2H,d,J=8 Hz),7.24(2H,d,J=8 Hz),7.47(2H,br d,J=8 Hz),8.25(2H,d,J=8 Hz).

9)

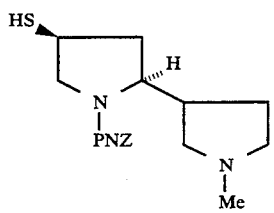

Anisole (0.34 ml, 3.13 mmol) and trifluoromethanesulfonic acid (0.27 ml, 3.05 mmol) were added to a solution of the compound obtained by the above reaction (617 mg, 1.27 mmol) in trifluoroacetic acid (2.26 ml) at 0° C., and the mixture was stirred at the same temperature for 1 hour. The reaction solution was concentrated under reduced pressure, and the residue was repeatedly subjected to decantation with dry diethyl ether to obtain the above identified compound (650 mg, yield: 99%).

REFERENCE EXAMPLE 7

(2S,4S)-4-mercapto-2-(N-methyl-2-azetidinon-4-yl)-N-(p-nitrobenzyloxycarbonyl)pyrrolidine

1)

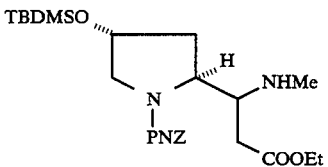

A 5.3M methylamine-ethanol solution (5 ml, 26.6 mmol) was added to 3-[(2S,4R)-4-tert-butyldimethylsiloxy-N-(p-nitrobenzyloxycarbonyl)pyrrolidin-2-yl]acrylic acid ethyl ester (2.94 g, 6.15 mmol, compound of Reference Example 1-6 of Japanese Patent Application No. 342,948/1989) at room temperature, and the mixture was left to stand at the same temperature for 2 days. The reaction mixture was concentrated under reduced pressure, and the residue was subjected to silica gel column chromatography (Wakogel ™ C-300, ethyl acetate) to obtain 3-methylamino-3-[(2S,4R)-4-tert-butyldimethylsiloxy-N-(p-nitrobenzyloxycarbonyl)pyrrolidin-2-yl]propionic acid ethyl ester (1.67 g, yield: 53.3%).

NMR(CDCl3) δ: 0.04(3H,s),0.06(3H,s),0.84(9H,s),1.26(3H,t,J=7 Hz),1.80–2.16(2H,m),2.-24–2.50(6H,m),3.40(2H,m),3.65(1H,m),4.16(2H,m),4.40-(1H,m),5.30(2H,m), 7.56(2H,m),8.24(2H,d,J=8 Hz).

2)

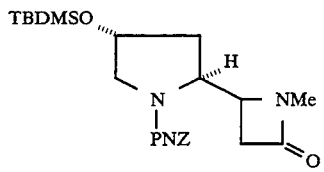

The same procedure as in Reference Example 3-2 was carried out by using the compound obtained by the above reaction (1.67 g, 3.28 mmol) to obtain (2S,4R)-4-tert-butyldimethylsiloxy-2-(N-methyl-2-azetidinon-4-yl)-N-(p-nitrobenzyloxycarbonyl)pyrrolidine (700 mg, yield: 46.1%).

NMR(CDCl3) δ: 0.04(3H,s),0.06(3H,s),0.84(9H,s),1.72–2.00(2H,m),2.55(-1H,m),2.80(3H,s),2.94(1H,m),3.36(1H,m),3.70(1H,m),4-.10(1H,m),4.40(2H,m),5.16–5.22(2H,m),7.67(2H,d,J=8 Hz),8.24(2H,d,J=8 Hz).

3)

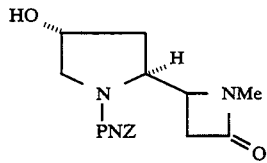

46% hydrofluoric acid (1 ml) was added to a solution of the compound obtained by the above reaction (700 mg, 1.51 mmol) in acetonitrile (10 ml) at room temperature, and the mixture was stirred at the same temperature for 1 hour. Then, the reaction solution was extracted with ethyl acetate (70 ml). The organic layer was washed sequentially with a 5% sodium hydrogen carbonate aqueous solution, water and a saturated sodium chloride aqueous solution, then dried over anhydrous magnesium sulfate and concentrated under reduced pressure. The residue was subjected to silica gel column chromatography (Wakogel ™ C-300, 2% methanol-chloroform) to obtain (2S,4R)-4-hydroxy-2-(N-methyl-2-azetidinon-4-yl)-N-(p-nitrobenzyloxycarbonyl)pyrrolidine (316 mg, yield: 59.9%).

NMR(CDCl3) δ: 1.70–2.18(2H,m),2.52(1H,m),2.74(3H,s),2.88(1H,m),3.-60–3.88(2H,m),4.08(1H,m),4.40(2H,m),5.22(2H, br s),7.50(2H,d,J=8 Hz),8.16(2H,d,J=8 Hz).

4)

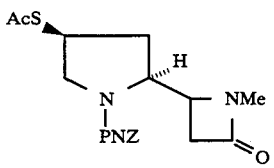

The same procedure as in Reference Example 3-5 was carried out by using the compound obtained by the above reaction (315 mg, 0.90 mmol) to obtain (2S,4S)-4-acetylthio-2-(N-methyl-2-azetidinon-4-yl)-N-(p-nitrobenzyloxycarbonyl)pyrrolidine (348 mg, yield: 94.7%).

IR(KBr)cm$^{-1}$: 1760, 1700, 1520, 1340.

NMR(CDCl₃) δ:
1.75(1H,m),2.37(3H,s),2.79(3H,s),3.88(1H,m),3.98–4.20-(3H,m),5.28(2H,br s),7.55(2H,d,J=8 Hz),8.25(2H,d,J=8 Hz).

5)

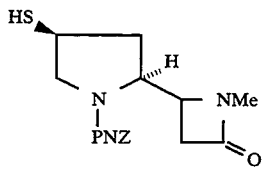

The same procedure as in Reference Example 1-9 was carried out by using the compound obtained by the above reaction (348 mg, 0.86 mmol) to obtain the above identified compound (298 mg, yield: 95.5%).

REFERENCE EXAMPLE 8

(2S,4S)-4-mercapto-2-(N-methyl-2,5-dioxopyrrolidin-3-yl)-N-(p-nitrobenzyloxycarbonyl)pyrrolidine diastereomers A and B

1)

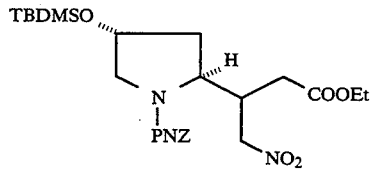

The same procedure as in Reference Example 1-5 was carried out by using 3-[(2S,4R)-4-tert-buthyldimethyl-siloxy-N-(p-nitrobenzyloxycarbonyl)pyrrolidin-2-yl]a-crylic acid ethyl ester (3.8 g, 7.95 mmol, compound of Reference Example 1-6 of Japanese Patent Application No. 342,948/1989) to obtain 3-[(2S,4R)-4-tert-butyl-dimethylsiloxy-N-(p-nitrobenzyloxycarbonyl)pyrroli-din-2-yl]-4-nitrobutyric acid ethyl ester (4.0 g, yield: 93.3%).

NMR(CDCl₃) δ:
0.04(3H,s),0.06(3H,s),0.82(9H,s),1.26(3H,m),1.80(1H,m-),2.03(1H,m),2.22–2.54(3H,m),3.27(2H,m),4.15(3H,m),-4.32–4.70(2H,m),5.24(2H,br s),7.54(2H,m),8.25(2H,d,J=8 Hz).

2)

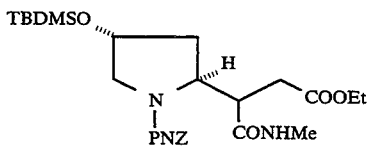

Sodium nitrite (2.56 g, 37.1 mmol) was added to a solution of the compound obtained by the above reaction (4.0 g, 7.42 mmol) in dimethyl sulfoxide (40 ml) in a nitrogen stream at room temperature. Then, butyl nitrite (1.74 ml, 14.9 mmol) was dropwise added thereto, and the mixture was stirred overnight at the same temperature. The reaction solution was extracted with ethyl acetate (150 ml). The organic layer was washed three times with water and once with a saturated sodium chloride aqueous solution, then dried over anhydrous magnesium sulfate and concentrated under reduced pressure. The residue was dissolved in tetrahydrofuran (50 ml). Then, triethylamine (0.97 ml, 6.95 mmol) and isobutyl chloroformate (0.90 ml, 6.94 mmol) were dropwise added thereto in a nitrogen stream at −20° C. and the mixture was stirred at the same temperature for 30 minutes. Then, 40% methylamine (1 ml) was added thereto. The reaction mixture was stirred for 30 minutes under cooling with ice and then extracted with ethyl acetate (100 ml). The organic layer was washed seqnentially with water and a saturated sodium chloride aqueous solution, then dried over anhydrous magnesium sulfate and concentrated under reduced pressure. The residue was subjected to silica gel column chromatography (Wakogel ™ C-300, ethyl acetate) to obtain (2S,4R)-4-tert-butyldimethylsiloxy-2-(2-ethoxycarbonyl-1-methylcarbamoylethyl)-N-(p-nitrobenzyloxycarbonyl)pyrrolidine (1.8 g, yield: 45.6%).

NMR(CDCl₃) δ:
0.04(3H,s),0.05(3H,s),0.83(9H,s),1.24(3H,t,J=7 Hz),3.34(1H,m),3.56(1H,m),4.12(2H,m),4.32(1H,m),5.2-8(2H,m),7.52(2H,m),8.25(2H,m).

3)

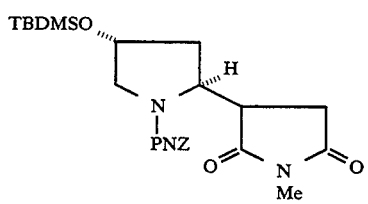

A 1N sodium hydroxide aqueous solution (3.7 ml) was dropwise added to a solution of the compound obtained by the above reaction (1.8 g, 3.35 mmol) in ethanol (30 ml) at room temperature, and the mixture was stirred overnight at the same temperature. 1N hydrochloric acid (3.7 ml ) was added to the reaction solution, and the mixture was concentrated under reduced pressure. Then, the residue was extracted with ethyl acetate (70 ml). The organic layer was washed with water and a saturated sodium chloride aqueous solution, then dried over anhydrous magnesium sulfate and concentrated under reduced pressure. The residue was dissolved in acetic anhydride (15 ml), and sodium acetate (1.38 g, 16.8 mmol) was added thereto. The mixture was stirred at 100° C. for 1.5 hours. The reaction mixture was concentrated under reduced pressure, and then the residue was extracted with ethyl acetate (70 ml). The organic layer was washed with water and a saturated sodium chloride aqueous solution, then dried over anhydrous magnesium sulfate and concentrated under reduced pressure. The residue was subjected to silica gel column chromatography (Wakogel ™ C-300, hexane-ethyl acetate 3:1) to obtain (2S,4R)-4-tert-butyldimethylsiloxy-2-(N-methyl-2,5-dioxopyrrolidin-3-yl)-N-(p-nitrobenzyloxycarbonyl)-pyrrolidine (1.28 g, yield: 77.8%).

NMR(CDCl₃) δ:
0.04(3H,s),0.06(3H,s),0.84(9H,s),1.71(1H,m),2.96(3H,s)-,3.16–3.87(3H,m),4.37(1H,m),4.54(1H,m),5.22(2H,m),7.-50(2H,m),8.20(2H,m).

4)

-continued

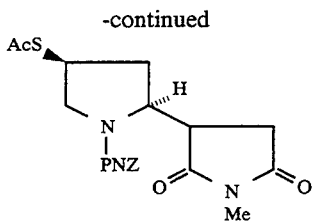

The same procedures as in Reference Example 7-3 and 7-4 were carried out by using the compound obtained by the above reaction (1.28 g, 2.61 mmol) to obtain (2S,4S)-4-acetylthio-2-(N-methyl-2,5-dioxopyrrolidin-3-yl)-N-(p-nitrobenzyloxycarbonyl)pyrrolidine diastereomer A (406 mg, yield: 35.8%) and diastereomer B (170 mg, yield: 15%), respectively.

Diastereomer A
NMR(CDCl₃) δ: 1.60(1H,m),2.34(3H,s),2.97(3H,s),3.60–3.98(2H,m),4.22-(1H,m),4.47(1H,m),5.24(2H,br s),7.56(2H,d,J=8 Hz),8.24(2H,d,J=8 Hz).

Diastereomer B
IR(KBr)cm⁻¹: 1700, 1520, 1440, 1350.
NMR(CDCl₃) δ: 1.72(1H,m),2.36(3H,s),2.97(3H,br s),3.25(2H,m),3.88(1H,m),4.18(1H,m),4.42(1H,m),5.07–5.30(2H,m),7.51(2H,d,J=8 Hz),8.24(2H,d,J=8 Hz).

5)

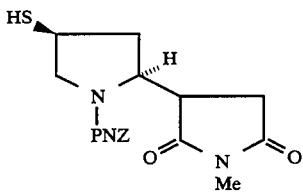

The same procedure as in Reference Example 1-9 was carried out by using the diastereomer A obtained by the above reaction (406 mg, 0.93 mmol) to obtain diastereomer A of the above identified compound (330 mg, yield: 90%).

6)

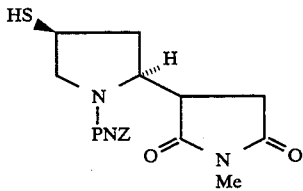

The same procedure as in Reference Example 1-9 was carried out by using the diastereomer B obtained in Reference Example 8-4 (170 mg, 0.39 mmol) to obtain diastereomer B of the above identified compound (145 mg, yield: 94.6%).

REFERENCE EXAMPLE 9

(2S,4S)-N-allyloxycarbonyl-2-(2,5-dioxopyrrolidin-3-yl)-4-mercaptopyrrolidine

1)

-continued

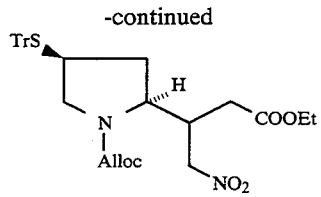

The same procedure as in Reference Example 1-5 was carried out by using 3-[(2S,4S)-N-allyloxycarbonyl-4-tritylthiopyrrolidin-2-yl]acrylic acid ethyl ester (5.23 g, 9.9 mmol) which was obtained by a reaction similar to Reference Example 1-4, to obtain 3-[(2S,4S)-N-allyloxycarbonyl-4-tritylthiopyrrolidin-2-yl]-4nitrobutyric acid ethyl ester (4.74 g, yield: 81.2%).

NMR(CDCl₃) δ: 1.24(3H,t,J=8 Hz),3.92(1H,m),4.12(2H,q,J=8 Hz),4.47(3H,m),5.26(2H,m),5.86(1H,m),7.16–7.74(15H,m).

2)

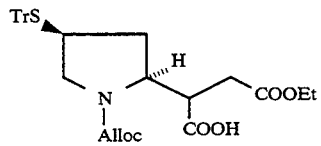

Sodium nitrite (2.76 g, 40 mmol) was added to a solution of the compound obtained by the above reaction (4.7 g, 8.0 mmol) in dimethyl sulfoxide (35 ml) in a nitrogen stream at room temperature. Then, butyl nitrite (1.87 ml, 16 mmol) was dropwise added thereto, and the mixture was stirred overnight at the same temperature. The reaction solution was extracted with ethyl acetate (150 ml). The organic layer was washed three times with water and once with a saturated sodium chloride aqueous solution, then dried over anhydrous magnesium sulfate and concentrated under reduced pressure. The residue was subjected to silica gel column chromatography (Wakogel TM C-300, 1% methanol-chloroform) to obtain (2S,4S)-N-allyloxycarbonyl-2-(1-carboxy-2-ethoxycarbonylethyl)-4-tritylthiopyrrolidine (1.9 g, yield: 41.5%).

NMR(CDCl₃): δ: 1.23(3H,m),3.90–4.24(3H,m),4.48(2H,m),5.-18–5.32(2H,m),5.86(1H,m),7.16–7.60(15H,m).

3)

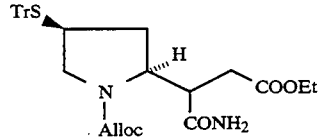

Triethylamine(0.56 ml, 4.0 mmol) and isobutyl chloroformate (0.52 ml, 4.0 mmol) were dropwise added to a solution of the compound obtained by the above reaction (1.9 g, 3.3 mmol) in tetrahydrofuran (30 ml) in a nitrogen stream at −20° C., and the mixture was stirred at the same temperature for 30 minutes. Then, concentrated aqueous ammonia (0.7 ml, 10.5 mmol) was added thereto, and the mixture was stirred further for 30 minutes under cooling with ice. The reaction solution was extracted with ethyl acetate (100 ml). The organic layer was washed sequentially with water and a saturated sodium chloride aqueous solution, then dried over anhydrous magnesium sulfate and concentrated under reduced pressure. The residue was subjected to silica gel column chromatography (Wakogel TM C-300, hexane-ethyl acetate 5:1) to obtain a polar compound (744 mg, yield: 39.2%) and a less polar compound (711 mg, yield: 37.5%) of (2S,4S)-N-allyloxycarbonyl-2-(1-carbamoyl-2-ethoxycarbonylethyl)-4-tritylthiopyrrolidine.

Polar Compound

NMR(CDCl$_3$) δ: 1.23(3H,t,J=7 Hz),1.98(2H,m),3.85(1H,m),4.15(2H,q,J=7 Hz),4.50(2H,m),5.24(2H,m),5.85(1H,m),7.15–7.60(15H,m).

Less Polar Compound

NMR(CDCl$_3$) δ: 1.23(3H,t,J=7 Hz),1.95(2H,m),2.26(1H,m),3.76(1H,m),4.12(2H,q,J=7 Hz),4.50(2H,m),5.24(2H,m),5.84(1H,m),7.14–7.57(15H,m).

4)

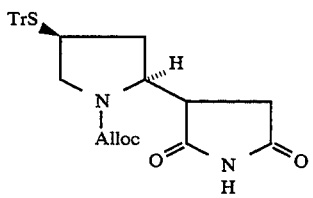

Sodium hydride (57 mg, 1.43 mmol) was added to a solution of the polar compound obtained by the above reaction (744 mg, 1.3 mmol) in tetrahydrofuran (37 ml) under cooling with ice, and the mixture was stirred at the same temperature for 15 minutes. To the reaction solution, water (1 ml) and then 1N hydrochloric acid (1.43 ml) were added, and the mixture was extracted with ethyl acetate (70 ml). The organic layer was washed with water and a saturated sodium chloride aqueous solution, then dried over anhydrous magnesium sulfate and concentrated under reduced pressure. The residue was subjected to silica gel column chromatography (Wakogel TM C-300, hexane-ethyl acetate 3:1) to obtain (2S,4S)-N-allyloxycarbonyl-2-(2,5-dioxopyrrolidin-3-yl)-4-tritylthiopyrrolidine (630 mg, yield: 92.1%).

NMR(CDCl$_3$) δ: 1.40(1H,m),2.14(1H,m),2.15–2.95(4H,m),3.88(1H,m),4.-10(1H,m),4.47(2H,m),5.13–5.36(2H,m),5.84(1H,m),7.-10–7.60(15H,m).

5)

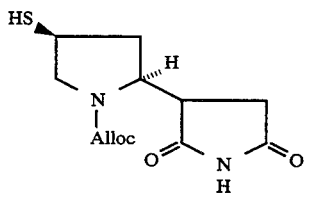

The same procedure as in Reference Example 22-2 was carried out by using the compound obtained by the above reaction (630 mg, 1.2 mmol) to obtain the above identified compound (219 mg, yield: 64.4%).

NMR(CDCl$_3$—CD$_3$OD) δ: 2.38–2.78(4H,m),2.-95–3.26(2H,m),3.-80–4.22(1H,m),4.34(1H,m),4.56(2H,m),5.-16–5.38(2H,m),5.90(1H,m).

REFERENCE EXAMPLE 10

(2S,4S)-N-allyloxycarbonyl-4-mercapto-2-(1-allyloxycarbonyl-3-pyrazolidinon-5-yl)pyrrolidine

1)

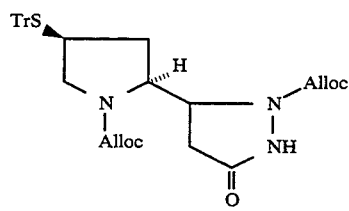

Hydrazine monohydrate (0.61 ml, 12.6 mmol) was dropwise added to a solution of 3-[(2S,4S)-N-allyloxycarbonyl-4-tritylthiopyrrolidin-2-yl]acrylic acid ethyl ester (1.53 g, 2.9 mmol) in ethanol (7.5 ml) under cooling with ice, and the mixture was stirred at the same temperature for 1.5 hours. The reaction solution was concentrated under reduced pressure. The residue was subjected to silica gel column chromatography (Wakogel TM C-300, 2% methanol-chloroform) to obtain (2S,4S)-N-allyloxycarbonyl-2-(3-pyrazolidinon-5-yl)-4-tritylthiopyrrolidine (830 mg, yield: 51.1%). This compound was immediately dissolved in methylene chloride (10 ml). Then, triethylamine (0.24 ml, 1.7 mmol) and allyl chloroformate (0.18 ml, 1.7 mmol) were dropwise added thereto under cooling with ice, and the mixture was stirred at the same temperature for 1 hour. The reaction solution was concentrated under reduced pressure, and the residue was extracted with ethyl acetate (50 ml). The organic layer was washed with water and a saturated sodium chloride aqueous solution, then dried over anhydrous magnesium sulfate and concentrated under reduced pressure. The residue was subjected to silica gel column chromatography (Wakogel TM C-300, 1% methanol-chloroform) to obtain (2S,4S)-N-allyloxycarbonyl-2-(1-allyloxycarbonyl-3-pyrazolidinon-5-yl)-4-tritylthiopyrrolidine (592 mg, yield: 62%).

NMR(CDCl$_3$) δ: 1.46–1.88(2H,m),1.-94–2.24(2H,m),2.56–3.00(4H,m),3.70(1H,m),4.-34–4.50(4H,m),5.12–5.40(4H,m),5.75–6.00(2H,m),7.-15–8.60(15H,m).

2)

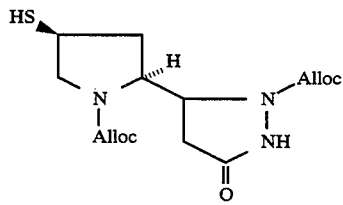

The same procedure as in Reference Example 22-2 was carried out by using the compound obtained by the above reaction (592 mg, 0.92 mmol) to obtain (2S,4S)-N-allyloxycarbonyl-4-mercapto-2-(1-allyloxycarbonyl-3-pyrazolidinon-5-yl)pyrrolidine (324 mg, yield: 87.8%).

NMR(CDCl₃) δ:
1.60–1.95(2H,m),2.30(1H,dd,J=17,3 Hz),2.56(1H,m),2.88–3.30(3H,m),3.88–4.24(2H,m),4.-52–4.98(4H,m),5.00–5.45(4H,m),5.82–6.08(2H,m).

REFERENCE EXAMPLE 11

(2S,4S)-4-mercapto-N-(p-nitrobenzyloxycarbonyl)-2-(2-pyrrolidon-3-yl)pyrrolidine

1)

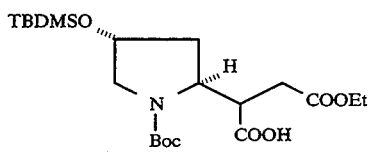

The same procedure as in Reference Example 9-2 was carried out by using 3-[(2S,4R)-N-tert-butoxycarbonyl-4-tert-butyldimethylsiloxypyrrolidin-2-yl]-4-nitrobutyric acid ethyl ester obtained in Reference Example 1-5 (5.9 g, 12.8 mmol) to obtain (2S,4R)-2-(2-ethoxycarbonyl-1-carboxyethyl)-4-tert-butyldimethylsiloxy-N-tert-butoxycarbonylpyrrolidine (3.57 g, yield: 62.5%).
NMR(CDCl₃) δ:
0.05(6H,s),0.86(9H,s),1.26(3H,t,J=8 Hz),1.48(9H,s),2.01(1H,m),2.34(1H,m),2.38(1H,m),3.25-(1H,dd,J=12,4 Hz),3.38–3.90(3H,m),4.16(2H,q,J=8 Hz),4.25–4.55(2H,m).

2)

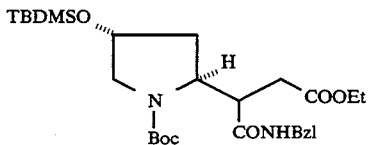

The same procedure as in Reference Example 9-3 was carried out by using the compound obtained by the above reaction (3.57 g, 8.0 mmol) and benzylamine (1.55 ml, 14.2 mmol) to obtain (2S,4R)-2-(1-benzylcarbamoyl-2-ethoxycarbonylethyl)-4-tert-butyldimethylsiloxy-N-tert-butoxycarbonylpyrrolidine (3.7 g, yield: 86.3%).
NMR(CDCl₃) δ:
0.04(6H,s),0.85(9H,s),1.24(3H,t,J=8 Hz),1.33–1.55(9H,m),1.90(1H,m),2.30(1H,m),2.82(1H,-m),3.22(1H,m),3.35–3.82(2H,m),4.-00–4.65(5H,m),7.30(5H,m).

3)

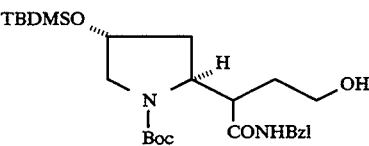

A 1N sodium hydroxide aqueous solution (3.9 ml) was added to a solution of the compound obtained by the above reaction (1.89 g, 3.5 mmol) in ethanol (30 ml) at room temperature, and the mixture was stirred overnight at the same temperature. 1N hydrochloric acid (3.9 ml) was added to the reaction solution, and the mixture was concentrated under reduced pressure to obtain (2S,4R)-2-(1-benzylcarbamoyl-2-carboxyethyl)-N-tert-butoxycarbonyl-4-tert-butyldimethylsiloxypyr-rolidine (1.79 g, yield: 100%). A borane-dimethyl sulfide complex (0.72 ml, 7.2 mmol) was dropwise added to a solution of this compound in tetrahydrofuran (35 ml) in a nitrogen stream at room temperature, and the mixture was stirred at the same temperature for 1 hour. Methanol (5 ml) was added to the reaction solution, and the mixture was concentrated under reduced pressure. The residue was subjected to silica gel column chromatography (Wakogel ™ C-300, hexane-ethyl acetate 1:1) to obtain 3-benzylcarbamoyl-3-[(2S,4R)-N-tert-butoxycarbonyl-4-tert-butyldimethylsiloxypyrrolidin-2-yl]-1-propanol (1.27 g, yield: 72.9%).
NMR(CDCl₃) δ:
0.04(6H,s),0.86(9H,s),1.24–1.60(11H,m),1.-73–2.32(2H,m),3.32–3.73(3H,m),4.-12–4.34(2H,m),4.40(1H,m),7.30(5H,m).

4)

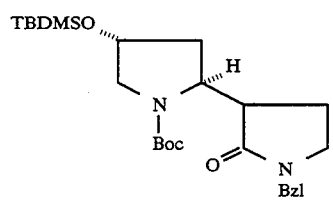

A solution of the compound obtained by the above reaction (1.27 g, 2.6 mmol) in hexamethylphosphoric triamide (17 ml) was dropwise added to a solution of potassium tert-butoxide (640 mg, 5.7 mmol) in tetrahydrofuran (17 ml) in a nitrogen stream at 0° C., and the mixture was stirred at the same temperature for 1 hour. A solution of p-toluenesulfonyl chloride (520 mg, 2.7 mmol) in tetrahydrofuran (3 ml) was dropwise added to the reaction solution, and the mixture was stirred at 0° C. for 1 hour and at 50° C. for 2 hours. The reaction mixture was cooled with ice, and a saturated ammonium chloride aqueous solution (5 ml) was added thereto. The mixture was extracted with ethyl acetate (100 ml). The organic layer was washed three times with water and once with a saturated sodium chloride aqueous solution, then dried over anhydrous magnesium sulfate and concentrated under reduced pressure. The residue was subjected to silica gel column chromatography (Wakogel ™ C-300, hexane-ethyl acetate 10:1) to obtain (2S,4R)-2-(N-benzyl-2-pyrrolidon-3-yl)-N-tert-butoxycarbonyl-4-tert-butyldimethylsiloxypyrrolidine (343 mg, yield: 39.8%).
NMR(CDCl₃) δ:
0.06(6H,s),0.87(9H,s),1.46(9H,s),1.90–2.30(3H,m),3.-00–3.60(5H,m),4.18–4.64(5H,m),7.18–7.42(5H,m).

5)

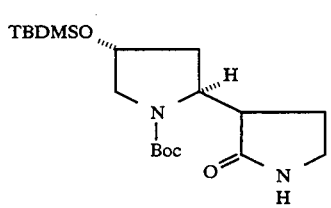

The same procedure as in Reference Example 3-3 was carried out by using the compound obtained by the above reaction (760 mg, 1.6 mmol) to obtain (2S,4R)-N- tert-butoxycarbonyl-4-tert-butyldimethylsiloxy-2-(2-pyrrolidon-3-yl)pyrrolidine (476 mg, yield: 77.2%).

NMR(CDCl₃) δ: 0.05(6H,s),0.86(9H,s),1.46(9H,s),1.82(1H,m),2.04(2H,m-),3.20–3.70(5H,m),4.32(1H,m),4.42(1H,m).

6)

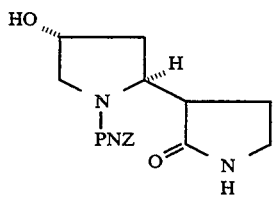

The same procedure as in Reference Example 3-4 was carried out by using the compound obtained by the above reaction (476 mg, 1.24 mmol) to obtain (2S,4R)-4-hydroxy-N-(p-nitrobenzyloxycarbonyl)-2-(2-pyrrolidon-3-yl)pyrrolidine (342 mg, yield: 79.1%).

IR(KBr)cm⁻¹: 1700, 1520, 1350.

NMR(CDCl₃) δ: 1.70–2.28(4H,m),3.18–3.50(3H,m),3.52–3.88 (2H,m),4.28–4.68(2H,m),5.22(2H,m),7.53(2H,d,J=8 Hz),8.20(2H,d,J=8 Hz).

7)

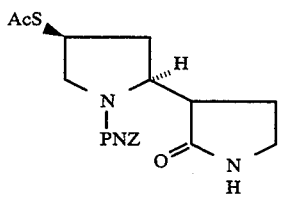

The same procedure as in Reference Example 3-5 was carried out by using the compound obtained by the above reaction (342 mg, 0.98 mmol) to obtain (2S,4S)-4-acetylthio-N-(p-nitrobenzyloxycarbonyl)-2-(2-pyrrolidon-3-yl)pyrrolidine (271 mg, yield: 68.2%).

IR(KBr)cm⁻¹: 1700, 1530, 1520.

NMR(CDCl₃) δ: 1.62–2.18(3H,m),2.35(3H,s),3.02–3.70(5H,m),3.83(1H,m),4.25(1H,m),4.44(1H,m),5.28-(2H,br s),7.56(2H,d,J=8 Hz),8.25(2H,d,J=8 Hz).

8)

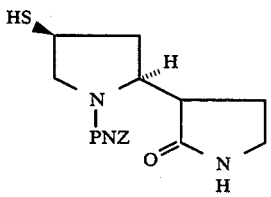

The same procedure as in Reference Example 1-9 was carried out by using the compound obtained by the above reaction (271 mg, 0.67 mmol) to obtain the above identified compound (220 mg, yield: 90.5%).

REFERENCE EXAMPLE 12

(2S,4R)-N-tert-butoxycarbonyl-4-tert-butyldimethylsiloxy-2-(2-pyrrolidon-4-yl)pyrrolidine diastereomers A and B

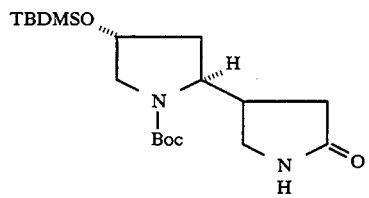

To the compound of Reference Example 1-6 (10.82 g, 22.32 mmol), n-hexane (75 ml) was added, and the mixture was heated to 40° C. for dissolution and then filtered. The filtrate was left to stand overnight at room temperature. The precipitate was collected by filtration and dried to obtain a polar compound (diastereomer A; 3.74 g, yield: 34.6%) of the above identified compound. The filtrate was concentrated, and n-hexane (70 ml) was added to the residue. Then, the above operation was repeated to obtain a low polar compound (diastereomer B; 1.87 g, yield: 17.3%) of the above identified compound.

Diastereomer A (Polar compound) mp: 92°–95° C. [α]$_D^{20}$: −50.8° (C=1.031, MeOH).

IR(KBr)cm⁻¹: 1685, 1395, 1250, 1175.

NMR(CDCl₃) δ: 0.06(6H,s), 0.86(9H,s),1.46(9H,s),1.72–1.97(2H,m),2.2(1H,dd,J=1-8,8 Hz),2.41(1H,dd,J=18,8 Hz),2.9–3.8(5H,m),4.15(1H,br),4.32(1H,br),6.06(1H,br).

Diastereomer B (Less polar compound) mp: 97°–100° C. [α]$_D^{20}$: −53.9° (C=0.978, MeOH).

IR(KBr)cm⁻¹: 1685, 1665, 1385, 1255, 1160.

NMR(CDCl₃) δ: 0.06(6H,s),0.86(9H,s),1.46(9H,s),1.7–1.95(2H,m),2.04(1H,dd,J=16,8 Hz),2.32(1H,dd,J=16,8 Hz),2.9–3.6(5H,m),4.1(1H,br),4.32(1H,br),6.0(1H,br).

HPLC: Column: Daicel CHIRALCEL OD. Eluent: Hexane:isopropanol=9:1. Flow rate: 0.5 ml/min. Temperature: 38° C. Detector: 210 nm. Retention time: Diastereomer A: 19.8 min. Diastereomer B: 16.3 min.

REFERENCE EXAMPLE 13

(2S,4S)-2-[2-carbamoyl-N-(p-nitrobenzyloxycarbonyl)-pyrrolidin-4-yl]-4-mercapto-N-(p-nitrobenzyloxycarbonyl)pyrrolidine diastereomer I

1)

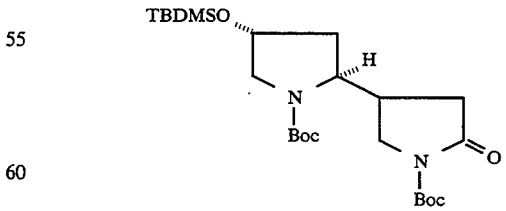

The same procedure as in Reference Example 6-2 was carried out by using the (2S,4R)-N-tert-butoxycarbonyl-4-tert-butyldimethylsiloxy-2-(2-pyrrolidon-4-yl)pyrrolidine diastereomer A (polar compound; 8.0 g, 20.8 mmol) obtained in Reference Example 12 to obtain (2S,4R)-N-tert-butoxycarbonyl-4-tert-butyldimethylsiloxy-2-(N-tert-butoxycarbonyl-2-pyrrolidon-4-yl)pyrrolidine diastereomer A (9.5 g, yield: 94.2%).

NMR(CDCl₃) δ: 0.05(6H,s),0.86(9H,s),1.46(9H,s),1.53(9H,s),1.70(1H,m)-,1.97(1H,m),2.16–2.90(3H,m),3.24(1H,dd,J=12,4 Hz),3.36–3.70(2H,m),3.76(1H,dd,J=10,8 Hz),4.12(1H,m),4.33(1H,m).

2)

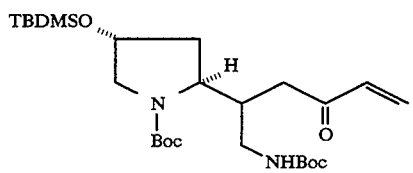

A 1M vinyl magnesium bromide-tetrahydrofuran solution (23 ml) was dropwise added to a solution of the compound obtained by the above reaction (9.3 g, 19.2 mmol) in tetrahydrofuran (120 ml) in a nitrogen stream at −40° C., and the mixture was stirred at the same temperature for 2 hours. A 50% acetic acid-methanol solution (10 ml) was dropwise added to the reaction solution, and the mixture was extracted with ethyl acetate (200 ml). The organic layer was washed sequantially with a saturated sodium hydrogen carbonate aqueous solution, water and a saturated sodium chloride aqueous solution, then dried over anhydrous magnesium sulfate and concentrated under reduced pressure. The residue was subjected to silica gel column chromatography (Wakogel ™ C-300, hexane-ethyl acetate 10:1) to obtain 5-[(2S,4R)-N-tert-butoxycarbonyl-4-tert-butyldimethylsiloxypyrrolidin-2-yl]-6-tert-butoxycarbonylamino-1-hexen-3-one diastereomer A (4.1 g, yield: 41.7%).

NMR(CDCl₃) δ: 0.05(6H,s),0.86(9H,s),1.42(9H,s),1.46(9H,s),4.04(1H,m)-,4.24(1H,m),5.80(1H,br d,J=10 Hz),6.22(1H,d,J=17 Hz),6.38(1H,dd,J=17,10 Hz).

3)

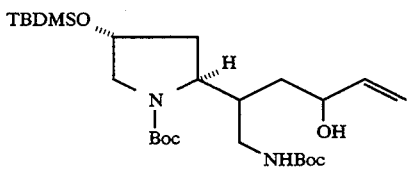

A solution of cerium chloride hexahydrate (2.84 g, 8.0 mmol) in methanol (30 ml) was added to the compound obtained by the above reaction (4.1 g, 8.0 mmol). Then, sodium borohydride (310 mg, 8.2 mmol) was added thereto at −15° C., and the mixture was stirred at the same temperature for 15 minutes. Water (10 ml) was added to the reaction mixture, and the mixture was concentrated under reduced pressure. The residue was extracted with ethyl acetate (100 ml). The organic layer was washed sequentially with water and a saturated sodium chloride aqueous solution, then dried over anhydrous magnesium sulfate and concentrated under reduced pressure. The residue was subjected to silica gel column chromatography (Wakogel ™ C-300, hexane-ethyl acetate 8:1) to obtain 5-[(2S,4R)-N-tert-butoxycarbonyl-4-tert-butyldimethylsiloxypyrrolidin-2-yl]-6-tert-butoxycarbonylamino-1-hexen-3-ol (3.53 g, yield: 85.8%).

NMR(CDCl₃) δ: 0.04(6H,s),0.86(9H,s),1.43(9H,s),1.46(9H,s),4.30(2H,m)-,5.12(1H,br d,J=10 Hz),5.28(1H,br d,J=16 Hz),5.90(1H,m).

4)

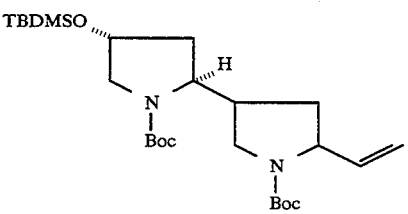

A solution of the compound obtained by the above reaction (3.53 g, 6.9 mmol) in tetrahydrofuran (15 ml) was dropwise added to a solution of potassium tert-butoxide (1.7 g, 15.1 mmol) in tetrahydrofuran (50 ml) in a nitrogen stream at −10° C., and the mixture was stirred at the same temperature for 30 minutes. Then, a solution of p-toluenesulfonyl chloride (1.44 g, 7.5 mmol) in tetrahydrofuran (10 ml) was dropwise added thereto. The reaction solution was stirred at the same temperature for 1 hours. Then, a saturated ammonium chloride aqueous solution (10 ml) was added thereto, and the mixture was extracted with ethyl acetate (100 ml). The organic layer was washed with water and a saturated sodium chloride aqueous solution, then dried over anhydrous magnesium sulfate and concentrated under reduced pressure. The residue was subjected to silica gel column chromatography (Wakogel ™ C-300, hexane-ethyl acetate 10:1) to obtain (2S,4R)-N-tert-butoxycarbonyl-4-tert-butyldimethylsiloxy-2-(N-tert-butoxycarbonyl-2-vinylpyrrolidin-4-yl)pyrrolidine (2.09 g, yield: 61.5%).

NMR(CDCl₃) δ: 0.04(6H,s),0.86(9H,s),1.42(9H,s),1.45(9H,s),2.98(1H,m)-,3.14(1H,dd,J=12,4 Hz),3.32–3.72(2H,m),3.-92–4.20(2H,m),4.34(1H,m),4.-96–5.20(2H,m),5.74(1H,m).

5)

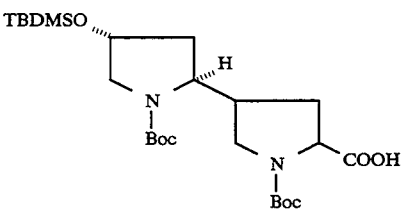

Water (13 ml) and sodium periodate (3.70 g, 17.3 mmol) were added to a solution of the compound obtained by the above reaction (2.09 g, 4.2 mmol) in a mixture of carbon tetrachloride (10 ml) and acetonitrile (10 ml), and the mixture was vigorously stirred. Ruthenium chloride hydrate (20 mg, 0.096 mmol) was added to this reaction mixture, and the mixture was vigorously stirred at room temperature for 2 hours. The reaction mixture was concentrated under reduced pressure, and the residue was extracted with ethyl acetate (100 ml). The organic layer was washed sequentially with water and a saturated sodium chloride aqueous solution, then dried over anhydrous magnesium sulfate and concentrated under reduced pressure. The residue was subjected to silica gel column chromatography (Wakogel ™ C-300, 1% methanol-chloroform) to obtain (2S,4R)-N-tert-butoxycarbonyl-4-tert-butyldimethylsiloxy-2-(N-tert-butoxycarbonyl-2-carboxypyrrolidin-4-yl)pyrrolidine (1.07 g, yield: 50.7%).

NMR(CDCl₃) δ: 0.05(6H,s),0.86(9H,s),1.46(18H,br s),3.10(1H,m),3.24(1H,m),3.40–3.74(2H,m),3.96–4.40(3H,m).

6)

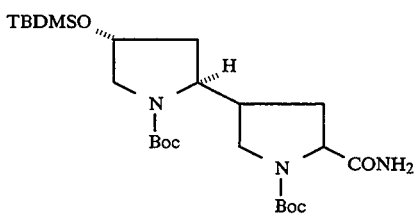

The same procedure as in Reference Example 9-3 was conducted by using the compound obtained by the above reaction (1.07 g, 2.1 mmol) to obtain (2S,4R)-N-tert-butoxycarbonyl-4-tert-butyldimethylsiloxy-2-(N-tert-butoxycarbonyl-2-carbamoylpyrrolidin-4-yl)pyrrolidine (867 mg, yield: 81.2%).

NMR(CDCl₃) δ: 0.05(6H,s),0.86(9H,s),1.46(18H,s),3.06(1H,br t,J=12 Hz),3.23(1H,dd,J=12,4 Hz),3.36–3.82(2H,m),3.98–4.40(3H,m).

7)

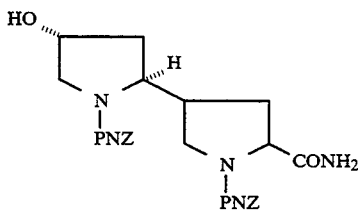

The same procedure as in Reference Example 5-3 was carried out by using the compound obtained by the above reaction (861 mg, 1.68 mmol) to obtain (2S,4R)-2-[2-carbamoyl-N-(p-nitrobenzyloxycarbonyl)pyrrolidin-4-yl]-4-hydroxy-N-(p-nitrobenzyloxycarbonyl)pyrrolidine diastereomer I (polar compound, 621 mg, yield: 66.4%) and diastereomer II (less polar compound, 216 mg, yield: 23.1%).

Polar compound
NMR(CDCl₃) δ: 3.78(2H,m),4.26(2H,m),4.50(1H,m),5.26(4H,br S),7.54(4H,d,J=8 Hz),8.25(4H,d,J=8 Hz).

Less polar compound
NMR(CDCl₃) δ: 3.70(2H,m),4.00–4.53(3H,m),5.24(4H,br s),7.51(4H,d,J=8 Hz),8.20(4H,d,J=8 Hz).

8)

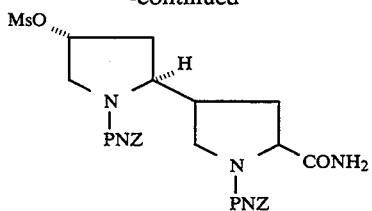

The same procedure as in Reference Example 5-4 was carried out by using the polar compound obtained by the above reaction (621 mg, 1.1 mmol) to obtain (2S,4R)-2-[2-carbamoyl-N-(p-nitrobenzyloxycarbonyl)-pyrrolidin-4-yl]-4-methanesulfonyloxy-N-(p-nitrobenzyloxycarbonyl)pyrrolidine diastereomer I (670 mg, yield: 94.6%).

NMR(DMSO-d₆) δ: 3.25(3H,s),3.48–3.70(2H,m),3.92–4.22(3H,m),5.04–5.34(5H,m),7.64(4H,d,J=8 Hz),8.24(4H,m).

9)

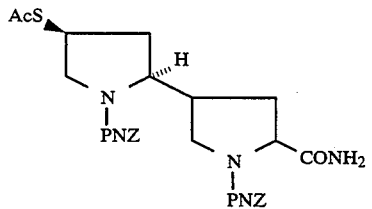

Sodium iodide (174 mg, 1.16 mmol) and potassium thioacetate (240 mg, 2.1 mmol) were added to a solution of the compound obtained by the above reaction (670 mg, 1.06 mmol) in N,N-dimethylformamide (10 ml) in a nitrogen stream, and the mixture was stirred overnight at a temperature of from 60° to 70° C. The reaction solution was extracted with ethyl acetate (70 ml). The organic layer was washed three times with water and once with a saturated sodium chloride aqueous solution, then dried over anhydrous magnesium sulfate and concentrated under reduced pressure. The residue was subjected to silica gel column chromatography (Wakogel ™ C-300, 1% methanol-chloroform) to obtain (2S,4S)-4-acetylthio-2-[2-carbamoyl-N-(p-nitrobenzyloxycarbonyl)pyrrolidin-4-yl]-N-(p-nitrobenzyloxycarbonyl)pyrrolidine diastereomer I (479 mg, yield: 73.8%).

NMR(CDCl₃) δ: 1.74(1H,m),2.00(1H,m),2.35(3H,s),2.40–2.90(3H,m),5.2–4(4H,br s),7.54(4H,br d,J=8 Hz),8.22(4H,br d,J=8 Hz).

10)

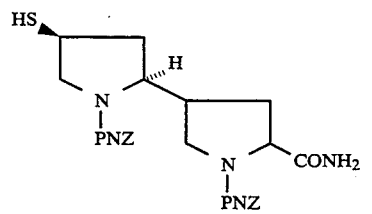

The same procedure as in Reference Example 1-9 was carried out by using the compound obtained by the above reaction (479 mg, 0.78 mmol) to obtain (2S,4S)-2-

[2-carbamoyl-N-(p-nitrobenzyloxycarbonyl)pyrrolidin-4-yl]-4-mercapto-N-(p-nitrobenzyloxycarbonyl)pyrrolidine diastereomer I (280 mg, yield: 62.7%).

REFERENCE EXAMPLE 14

(2S,4S)-2-[2-carbamoyl-N-(p-nitrobenzyloxycarbonyl)-pyrrolidin-4-yl]-4-mercapto-N-(p-nitrobenzyloxycarbonyl)pyrrolidine diastereomer II

1)

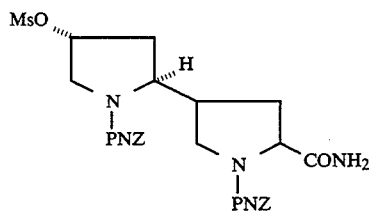

The same procedure as in Reference Example 5-4 was carried out by using the (2S,4R)-2-[2-carbamoyl-N-(p-nitrobenzyloxycarbonyl)pyrrolidin-4-yl]-4-hydroxy-N-(p-nitrobenzyloxycarbonyl)pyrrolidin (less polar compound, 216 mg, 0.39 mmol) obtained in Reference Example 13-7, to obtain (2S,4R)-2-[2-carbamoyl-N-(p-nitrobenzyloxycarbonyl)pyrrolidin-4-yl]-4-methanesulfonyloxy-N-(p-nitrobenzyloxycarbonyl)pyrrolidine diastereomer II (221 mg, yield: 89.7%).

NMR(CDCl₃) δ: 3.04(3H,s),3.58(2H,m),4.08–4.32(2H,m),4.42(1H,m),5.-10–5.38(5H,m),5.50–5.68(1H,m).

2)

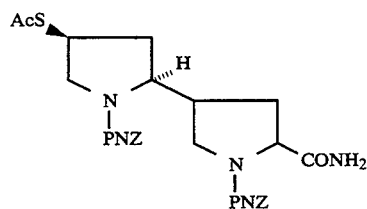

The same procedure as in Reference Example 13-9 was carried out by using the compound obtained by the above reaction (221 mg, 0.35 mmol) to obtain (2S,4S)-4-acetylthio-2-[2-carbamoyl-N-(p-nitrobenzyloxycarbonyl)pyrrolidin-4-yl]-N-(p-nitrobenzyloxycarbonyl)-pyrrolidine diastereomer II (180 mg, yield: 84.0%).

NMR(CDCl₃) δ: 1.66(1H,m),1.88–2.28(2H,m),2.36(3H,s),2.54(1H,m),2.8-2(1H,m),3.06–3.35(2H,m),3.63(1H,m),3.86(1H,m),4.08(-1H,m),4.27 (1H,m),4.47 (1H,m),5.62(4H,m),7.54(4H,d,J=8 Hz),8.24(4H,d,J=8 Hz).

3)

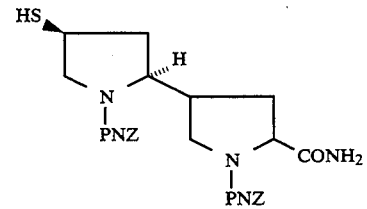

The same procedure as in Reference Example 1-9 was carried out by using the compound obtained by the above reaction (180 mg, 0.29 mmol) to obtain (2S,4S)-2-[2-carbamoyl-N-(p-nitrobenzyloxycarbonyl)pyrrolidin-4-yl]-4-mercapto-N-(p-nitrobenzyloxycarbonyl)pyrrolidine diastereomer II (160 mg, yield: 95%).

REFERENCE EXAMPLE 15

(2S,4S)-4-mercapto-N-(p-nitrobenzyloxycarbonyl)-2-[N-(p-nitrobenzyloxycarbonyl)pyrrolidin-4-yl]pyrrolidine diastereomer A

1)

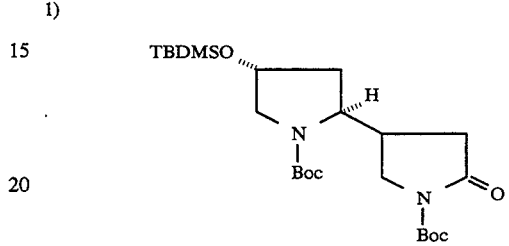

The same procedure as in Reference Example 5-1 was carried out by using the (2S,4R)-4-tert-butyldimethylsiloxy-N-tert-butoxycarbonyl-2-(2-pyrrolidon-4-yl)pyrrolidine diastereomer A (4.8 g, 12.0 mmol) obtained in Reference Example 12 to obtain crude (2S,4R)-4-tert-butyldimethylsilyloxycarbonyl-2-(N-tert-butoxycarbonyl-2-pyrrolidon-4-yl)pyrrolidine diastereomer A (6.8 g).

NMR(CDCl₃) δ: 0.06(6H,s),0.86(9H,s),1.48(9H,s),1.52(9H,s),1.60(1H,m)-,1.90(1H,m),2.10–2.58(2H,m),3.22(1H,m),3.-42–3.88(3H,m),4.08(1H,m),4.30(1H,m).

2)

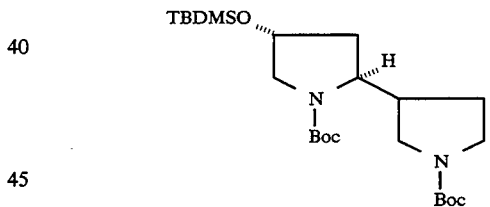

The same procedure as in Reference Example 5-2 was carried out by using the compound obtained by the above reaction (6.8 g) to obtain a yellow oily substance (5.7 g) of (2S,4R)-4-tert-butyldimethylsiloxy-N-tert-butoxycarbonyl-2-(N-tert-butoxycarbonylpyrrolidin-4-yl)pyrrolidine diastereomer A, which was used for the subsequent reaction without purification.

NMR(CDCl₃) δ: 0.05(6H,s),0.86(9H,s),1.44(18H,s),1.56–2.04(4H,m),3.-02–3.70(6H,m),4.00(1H,m),4.34(1H,m).

3)

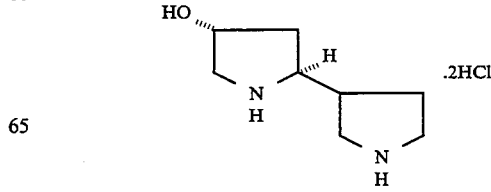

The compound obtained by the above reaction (5.7 g) was added to an about 3N hydrogen chloride-methanol solution, and the mixture was stirred overnight at room temperature. The reaction mixture was concentrated under reduced pressure to obtain crystals of (2S,4R)-4-hydroxy-2-(3-pyrrolidinyl)pyrrolidine diastereomer A dihydrochloride (2.4 g).

IR(KBr)cm⁻¹: 3300, 2900, 2700, 1430, 1410, 1060.

NMR(D₂O) δ: 1.92(2H,m),2.16-2.46(2H,m),2.68(1H,m),3.06(1H,dd,J=12,10 Hz),3.34(2H,br d,J=12 Hz),3.42-3.66(3H,m),3.82(1H,m),4.67(1H,m).

4)

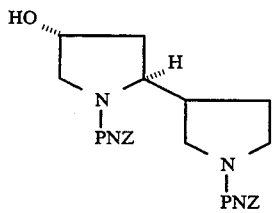

The same procedure as in Reference Example 5-3 was carried out by using the compound obtained by the above reaction (1.1 g) to obtain an oily substance (2.2 g, yield: 88%) of (2S,4R)-4-hydroxy-N-(p-nitrobenzyloxycarbonyl)-2-[N-(p-nitrobenzyloxycarbonyl)pyrrolidin-4-yl]pyrrolidine diastereomer A.

5)

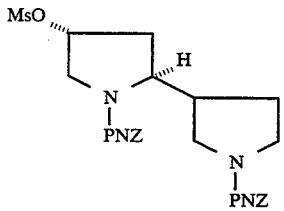

The same procedure as in Reference Example 5-4 was carried out by using the compound obtained by the above reaction (2.2 g) to obtain a foamy substance (2.6 g) of (2S,4R)-4-methanesulfonyloxy-N-(p-nitrobenzyloxycarbonyl)-2-[N-(p-nitrobenzyloxycarbonyl)pyrrolidin-4-yl]pyrrolidine diastereomer A.

NMR(CDCl₃) δ: 2.02(2H,m),2.50(2H,m),3.04(3H,s),3.14-3.82(6H,m),4.20(2H,m),5.24(4H,br s),7.53(4H,d,J=8 Hz),8.24(4H,d,J=8 Hz).

6)

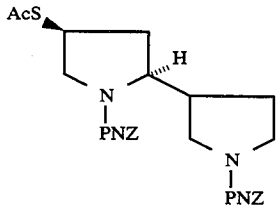

The same procedure as in Reference Example 5-5 was carried out by using the compound obtained by the above reaction (2.6 g) to obtain (2S,4S)-4-acetylthio-N-(p-nitrobenzyloxycarbonyl)-2-[N-(p-nitrobenzyloxycarbonyl)pyrrolidin-4-yl]pyrrolidine (1.7 g, yield from the first step: 73%).

NMR(CDCl₃) δ: 1.54-2.10(4H,m),2.36(3H,s),2.40-2.82(2H,m),3.02-3.70(6H,m),3.88(1H,m),4.00-4.32(2H,m),5.24(4H,br s),7.52(4H,d,J=8 Hz),8.24(4H,d,J=8 Hz).

7)

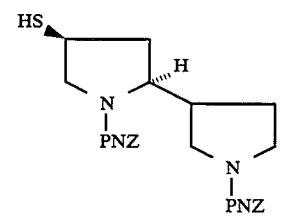

The same procedure as in Reference Example 1-9 was carried out by using the compound obtained by the above reaction (1.7 g) to obtain the above identified compound (1.59 g).

REFERENCE EXAMPLE 16

(2S,4S)-4-mercapto-N-(p-nitrobenzyloxycarbonyl)-2-[N-(p-nitrobenzyloxycarbonyl)pyrrolidin-4-yl]pyrrolidine diastereomer B

1)

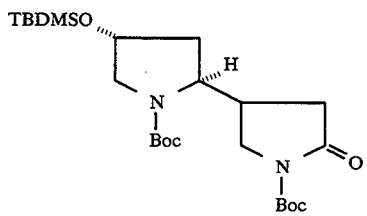

The same procedure as in Reference Example 5-1 was carried out by using the (2S,4R)-4-tert-butyldimethylsiloxy-N-tert-butoxycarbonyl-2-(2-pyrrolidon-4-yl)pyrrolidine diastereomer B (5.1 g, 13.3 mmol) obtained in Reference Example 12, to obtain crude (2S,4R)-4-tert-butyldimethylsiloxycarbonyl-2-(N-tert-butoxycarbonyl-2-pyrrolidon-4-yl)pyrrolidine diastereomer B (7.5 g).

2)

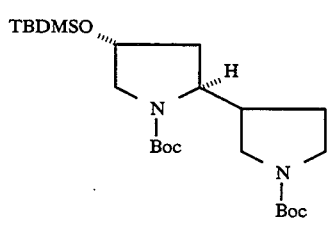

The same procedure as in Reference Example 5-2 was carried out by using the compound obtained by the above reaction (7.5 g) to obtain a yellow oily substance (6.9 g) of (2S,4R)-4-tert-butyldimethylsiloxy-N-tert-butoxycarbonyl-2-(N-tert-butyloxycarbonylpyrrolidin-4-yl)pyrrolidine diastereomer B, which was used for the subsequent reaction without purification.

3)

-continued

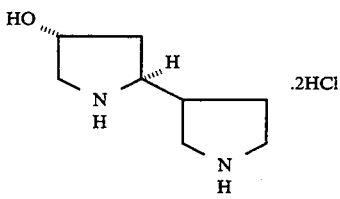

The compound obtained by the above reaction (6.9 g) was added to an about 3N hydrogen chloride-methanol solution, and the mixture was stirred overnight at room temperature. The reaction mixture was concentrated under reduced pressure to obtain crystals of (2S,4R)-4-hydroxy-2-(3-pyrrolidinyl)pyrrolidine diastereomer B dihydrochloride (3.0 g).

4)

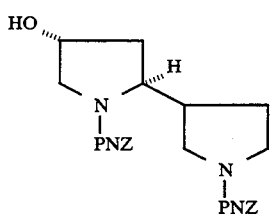

The same procedure as in Reference Example 5-3 was carried out by using the compound obtained by the above reaction (3.0 g) to obtain an oily substnace (6.8 g, yield: 99%) of (2S,4R)-4-hydroxy-N-(p-nitrobenzyloxycarbonyl)-2-[N-(p-nitrobenzyloxycarbonyl)pyrrolidin-4-yl]pyrrolidine diastereomer B.

5)

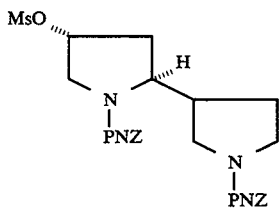

The same procedure as in Reference Example 5-4 was carried out by using the compound obtained by the above reaction (6.8 g) to obtain a foamy substance (7.8 g) of (2S,4R)-4-methanesulfonyloxy-N-(p-nitrobenzyloxycarbonyl)-2-[N-(p-nitrobenzyloxycarbonyl)pyrrolidin-4-yl]pyrrolidine diastereomer B.

6)

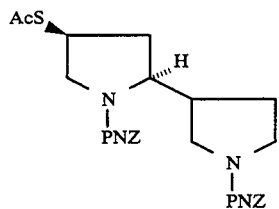

The same procedure as in Reference Example 5-5 was carried out by using the compound obtained by the above reaction (3.6 g, 5.8 mmol) to obtain (2S,4S)-4-acetylthio-N-(p-nitrobenzyloxycarbonyl)-2-[N-(p-nitrobenzyloxycarbonyl)pyrrolidin-4-yl]pyrrolidine diastereomer B (1.3 g, yield: 39%).

NMR(CDCl$_3$) δ: 1.54–2.10(4H,m),2.36(3H,s),2.-40–2.82(2H,m),3.02–3.70(6H,m),3.88(1H,m),4.-00–4.32(2H,m),5.24(4H,br s),7.52(4H,d,J=8 Hz),8.24(4H,d,J=8 Hz).

7)

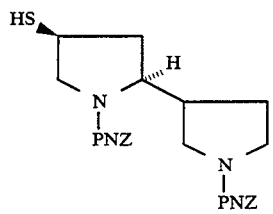

The same procedure as in Reference Example 1-9 was carried out by using the compound obtained by the above reaction (1.7 g) to obtain the above identified compound (1.6 g).

REFERENCE EXAMPLE 17

(2S,4R)-4-hydroxy-2-(3-pyrrolidinyl)pyrrolidine dihydrochloride

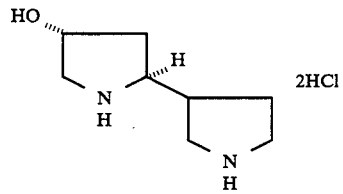

The same procedure as in Reference Example 15-3 was carried out by using (2S,4R)-N-tert-butoxycarbonyl-4-tert-butyldimethylsiloxy-2-(N-tert-butoxycarbonylpyrrolidin-3-yl)pyrrolidine (308 g, 0.654 mol, compound of Reference Example 5-2) to obtain the above identified compound (133 g, yield: 88%).

IR(KBr)cm$^{-1}$: 3390, 3000–2400, 1600, 1420, 1270, 1065, 980.

NMR(D$_2$O) δ: 1.76–2.18(2H,m),2.20–2.48(2H,m),2.-58–2.98(2H,m),3.10–3.28(1H,m),3.30–3.50(2H,m),3.-50–3.82(3H,m),3.82–4.04(1H,m),4.70(1H,m).

REFERENCE EXAMPLE 18

(2S,4S)-4-mercapto-N-(p-nitrobenzyloxycarbonyl)-2-(2-pyrrolidon-4-yl)pyrrolidine diastereomer A

1)

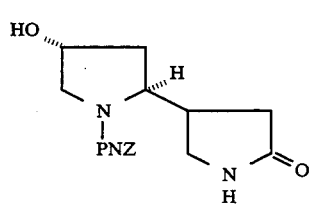

The same procedure as in Reference Example 1-7 was carried out by using (2S,4R)-N-tert-butoxycarbonyl-4-tert-butyldimethylsiloxy-2-(2-pyrrolidon-4-yl)pyrrolidine diastereomer A (61.38 g, 160 mmol, compound of Reference Example 12) to obtain (2S,4R)-4-hydroxy-N-

(p-nitrobenzyloxycarbonyl)-2-(2-pyrrolidon-4-yl)pyrrolidine diastereomer A (41.68 g, yield: 74.6%).

IR(KBr)cm$^{-1}$: 1695, 1605, 1520, 1430, 1345, 1110.

NMR(CDCl$_3$) δ: 1.6-2.0(2H,m),2.0-2.54(2H,m),3.0-3.56(4H,m),3.8(1H,m),4.26(1H,m),4.5(1H,m),5.25(2H,s),5.83(1H,br),7.54(2H,d,J=9 Hz),8.22(2H,d,J=9 Hz).

2)

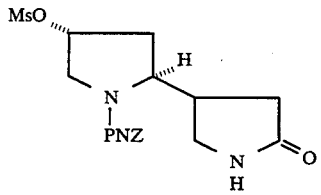

The same procedure as in Reference Example 5-4 was carried out by using the compound obtained by the above reaction (41.6 g, 120 mmol) to obtain (2S,4R)-4-methanesulfonyloxy-N-(p-nitrobenzyloxycarbonyl)-2-(2-pyrrolidon-4-yl)pyrrolidine diastereomer A (47.28 g, yield: 92.3%).

IR(KBr)cm$^{-1}$: 1710, 1695, 1605, 1525, 1345, 1170.

NMR(CDCl$_3$) δ: 1.5-2.1(4H,m),2.4-2.8(2H,m),3.04(3H,s),3.1-3.64(3H,m),4.0-4.5(2H,m),5.2(2H,s),6.32(1H,br),7.52(2H,d,J=9 Hz),8.22(2H,d,J=9 Hz).

3)

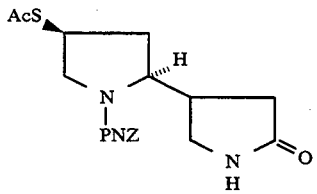

The same procedure as in Reference Example 5-5 was carried out by using the compound obtained by the above reaction (13 g, 30 mmol) to obtain (2S,4S)-4-acetylthio-N-(p-nitrobenzyloxycarbonyl)-2-(2-pyrrolidon-4-yl)pyrrolidine diastereomer A (4.61 g, yield: 37.7%).

IR(KBr)cm$^{-1}$: 1705, 1695, 1515, 1405, 1345, 1110.

NMR(CDCl$_3$) δ: 1.68(2H,m),2.04-2.64(4H,m),2.35(3H,s),3.18(2H,m),3.42(1H,m),3.84(1H,m),4.04-4.34(2H,m),5.23(2H,s),5.97(1H,br),7.53(2H,d,J=9 Hz),8.25(2H,d,J=9 Hz).

4)

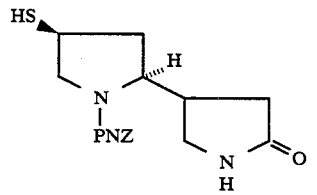

The same procedure as in Reference Example 5-6 was carried out by using the compound obtained by the above reaction (4.61 g, 11 mmol) to obtain the above identified compound (3.92 g, yield: 97.5%).

IR(KBr)cm$^{-1}$: 1695, 1525, 1400, 1345, 1110.

NMR(CDCl$_3$) δ: 1.42-1.8(2H,m),1.73(1H,d,J=8 Hz),2.04-2.6(3H,m),2.98-3.48(5H,m),4.10(2H,m),5.24(2H,s),6.0(1H,br),7.52(2H,d,J=9 Hz),8.24(2H,d,J=9 Hz).

REFERENCE EXAMPLE 19

(2S,4S)-4-mercapto-N-(p-nitrobenzyloxycarbonyl)-2-(2-pyrrolidon-4-yl)pyrrolidine diastereomer B

1)

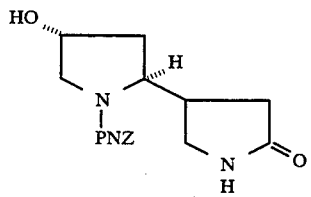

(2S,4R)-N-tert-butoxycarbonyl-4-tert-butyldimethylsiloxy-2-(2-pyrrolidon-4-yl)pyrrolidine diastereomer B (62.48 g, 163 mmol, compound of Reference Example 12) was dissolved in methanol (600 ml), and the solution was cooled to 0° C. Then, a 2.5N hydrochloric acid/methanol solution (230 ml, 570 mmol) was added thereto, and the mixture was stirred at room temperature for 3 hours. The precipitate was collected by filtration and dried to obtain white powder (30.01 g, yield: 89.1%) of (2S,4R)-4-hydroxy-2-(2-pyrrolidon-4-yl)pyrrolidine hydrochloride. This white powder (10.53 g, 50 mmol) was dissolved in a solvent mixture of dioxane (50 ml) and water (50 ml), and the pH was adjusted to 8 with triethyl amine. Then, 4,6-dimethyl-2-(p-nitrobenzyloxycarbonylthio)pyrimidine (17.55 g, 55 mmol) was added thereto, and the mixture was reacted for 6 hours while maintaining the pH at a level of 8. The reaction solution was concentrated, and tetrahydrofuran (100 ml) was added thereto. Insoluble matters were filtered off, and the filtrate was concentrated. The residue was subjected to column chromatography (Wakogel TM C-300, chloroform-methanol 40:1) to obtain (2S,4R)-4-hydroxy-N-(p-nitrobenzyloxycarbonyl)-2-(2-pyrrolidon-4-yl)pyrrolidine diastereomer B (17.48 g, yield: 98.2%).

IR(KBr)cm$^{-1}$: 1690, 1680, 1525, 1345, 1110, 1095.

NMR(CDCl$_3$) δ: 1.5-1.96(2H,m),1.98-2.46(2H,m),3.0-3.56(4H,m),3.7-3.9(1H,m),4.25(1H,m),4.5(1H,br),5.26(2H,s),6.02(1H,br),7.54(2H,d,J=9 Hz),8.25(2H,d,J=9 Hz).

2)

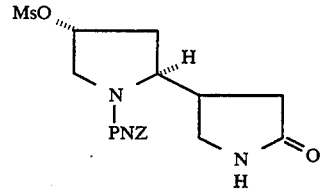

The same procedure as in Reference Example 5-4 was carried out by using the compound obtained by the above reaction (17.46 g, 50 mmol) to obtain (2S,4R)-4-methanesulfonyloxy-N-(p-nitrobenzyloxycarbonyl)-2-(2-pyrrolidon-4-yl)pyrrolidine diastereomer B (17.46 g, yield: 81.8%).

IR(KBr)cm$^{-1}$: 1705, 1690, 1520, 1345, 1170, 905.

NMR(CDCl$_3$) δ: 1.74(2H,br),1.9-2.6(4H,m),3.04(3H,s),3.2-3.64(3H,m),4-

.1–4.36(2H,m),5.28(2H,s),5.92(1H,br),7.54(2H,d,J=9 Hz),8.24(2H,d,J=9 Hz).

3)

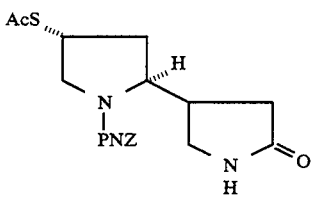

The same procedure as in Reference Example 5-5 was carried out by using the compound obtained by the above reaction (17.4 g, 41 mmol) to obtain (2S,4S)-4-acetylthio-N-(p-nitrobenzyloxycarbonyl)-2-(2-pyrrolidon-4-yl)pyrrolidine diastereomer B (14.29 g, yield: 85.6%).

IR(KBr)cm$^{-1}$: 1705, 1695, 1520, 1400, 1345, 1110.
NMR(CDCl$_3$) δ: 1.74(2H,m),2.0–2.60(4H,m),2.34(3H,s),3-.0–3.5(3H,m),3.84(1H,m),4-.0–4.3(2H,m),5.22(2H,s),6.02(1H,br), 7.52(2H,d,J=9 Hz),8.24(2H,d,J=9 Hz).

4)

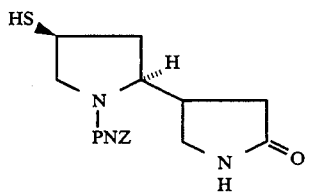

The same procedure as in Reference Example 5-6 was carried out by using the compound obtained by the above reaction (7 g, 17 mmol) to obtain the above identified compound (5.94 g, yield: 95.6%).

IR(KBr)cm$^{-1}$: 1695, 1520, 1400, 1345, 1105.
NMR(CDCl$_3$) δ: 1.5–1.88(2H,m),1.75(1H,d,J=8 Hz),2.12(1H,dd,J=18,8 Hz),2.37(1H,dd,J=18,8 Hz),2.44(1H,m),3.0–3.56(5H,m),4-.0–4.22(2H,m),5.22(2H,s),6.14(1H,br),7.52(2H,d,J=9 Hz),8.23(2H,d,J=9 Hz).

REFERENCE EXAMPLE 20

(2S,4S)-4-mercapto-N-(p-nitrobenzyloxycarbonyl)-2-[3-[(p-nitrobenzyloxycarbonyl)amino]-2-pyrrolidon-4-yl]pyrrolidine

1)

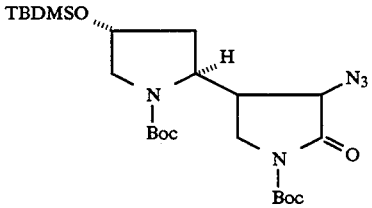

1.6M n-butyllithium (2.5 ml, 4 mmol) was dropwise added to a solution of diisopropylamine (0.64 ml, 4.6 mmol) in tetrahydrofuran (40 ml) under a nitrogen stream at −78° C., and the reaction solution was stirred for 45 minutes. A solution of (2S,4R)-N-tert-butoxycarbonyl-4-tert-butyldimethylsiloxy-2-(N-tert-butoxycarbonyl-2-pyrrolidon-4-yl)pyrrolidine (986 mg, 2 mmol, compound of Reference Example 5-1) in tetrahydrofuran (10 ml) was dropwise added to this solution, and the mixture was stirred at the same temperature for 2 hours. Then, p-toluenesulfonyl azide (945 mg, 4.8 mmol) was added thereto, and the mixture was stirred further for 1 hour. Then, trimethylsilyl chloride (1.29 ml, 10 mmol) was added to this reaction solution, and the mixture was stirred at room temperature for 1 hour. The reaction solution was concentrated under reduced pressure. A saturated sodium hydrogen carbonate aqueous solution was added to the residue, and then the mixture was extracted with methylene chloride (50 ml). The organic layer was washed with a saturated sodium chloride aqueous solution, then dried over anhydrous magnesium sulfate and concentrated under reduced pressure. The residue was subjected to silica gel column chromatography (Wakogel ™ C-300, chloroform) to obtain (2S,4R)-2-(3-azido-N-tert-butoxycarbonyl-2-pyrrolidon-4-yl)-N-tert-butoxycarbonyl-4-(tert-butyldimethylsiloxy)pyrrolidine (720 mg, yield: 68.5%).

IR(KBr)cm$^{-1}$: 2110, 1790, 1760, 1695, 1315, 1155.
NMR(CDCl$_3$) δ: 0.06(6H,s),0.86(9H,s),1.48(9H,s),1.6–2.2(2H,m),3-.1–3.85(5H,m),4.10(1H,br),4.26(1H,br),4.5(1H,br).

2)

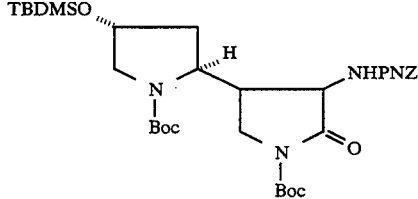

The compound obtained by the above reaction (720 mg, 1.37 mmol) was dissolved in methanol (50 ml), and a 10% palladium-carbon catalyst (200 mg) was added thereto. The mixture was vigorously stirred under a hydrogen stream for 2 hours. The mixture was filtered, and the obtained filtrate was concentrated to obtain crude oil (730 mg). This oil was dissolved in a mixture of dioxane (20 ml) and water (20 ml). The pH was adjusted to 8 with triethylamine, and then 4,6-dimethyl-2-(p-nitrobenzyloxycarbonylthio)pyrimidine (504 mg, 1.6 mmol) was added thereto. This solution was stirred for 6 hours, while maintaining the pH at a level of 8. The reaction solution was concentrated under reduced pressure. The residue was extracted with ethyl acetate (50 ml). The extract was washed sequentially with a saturated sodium hydrogen carbonate aqueous solution and a saturated sodium chloride aqueous solution. The organic layer was dried over anhydrous magnesium sulfate and concentrated under reduced pressure. The residue was subjected to silica gel column chromatography (Wakogel ™ C-300, chloroform-methanol 100:1) to obtain (2S,4R)-N-tert-butoxycarbonyl-4-tert-butyldimethylsiloxy-2-[N-tert-butoxycarbonyl-3-[(p-nitrobenzyloxycarbonyl)amino]-2-pyrrolidon-4-yl]pyrrolidine (840 mg, yield: 90.6%).

IR(KBr)cm$^{-1}$: 1795, 1695, 1525, 1350, 1255, 1155.
NMR(CDCl$_3$) δ: 0.06(6H,s),0.86(9H,s),1.48(9H,s),1.54(9H,s),1.72–2.1(2-H,m),3.08–3.78(5H,m),4-

.1–4.3(3H,m),5.2(2H,br),7.5(2H,d,J=9 Hz),8.24(2H,d,J=9 Hz).

3)

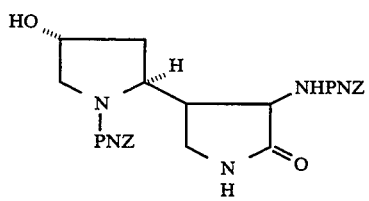

The compound obtained by the above reaction (840 mg, 1.2 mmol) was dissolved in dry methylene chloride (20 ml), and the solution was cooled to 0° C. Then, trifluoroacetic acid (1 ml, 13 mmol) was added thereto, and the mixture was stirred at room temperature for 16 hours. The reaction solution was concentrated, and trifluoroacetic acid was removed. Then, the residue was dissolved in methanol (30 ml), and a 2.5N hydrochloric acid-methanol solution (0.63 ml, 1.6 mmol) was added thereto, and the mixture was stirred at room temperature for 16 hours. The reaction solution was concentrated. Then, the obtained residue was dissolved in a mixture of dioxane (20 ml) and water (20 ml). While adjusting the pH to a level of 8 with triethylamine, 4,6-dimethyl-2-(p-nitrobenzyloxycarbonylthio)pyrimidine (850 mg, 2.6 mmol) was added thereto, and the mixture was stirred at room temperature for 16 hours. The reaction solution was concentrated, and the residue was extracted with ethyl acetate (100 ml). The organic layer was washed with a saturated sodium chloride aqueous solution. The organic layer was dried over anhydrous magnesium sulfate and concentrated under reduced pressure. The residue was subjected to silica gel column chromatography (Wakogel TM C-300, chloroform-methanol 50:1) to obtain (2S,4R)-4-hydroxy-N-(p-nitrobenzyloxycarbonyl)-2-[3-[(p-nitrobenzyloxycarbonyl)amino]-2-pyrrolidon-4-yl]pyrrolidine (450 mg, yield: 69%).

IR(KBr)cm⁻¹: 1700, 1520, 1345.
NMR(CDCl₃+CD₃OD) δ: 1.96–2.24(2H,m),3.06–3.84(5H,m),4.08–4.5(3H,m),5.22(2H,s),5.24(2H,s),7.54(4H,d,J=9 Hz),8.22(4H,d,J=9 Hz).

4)

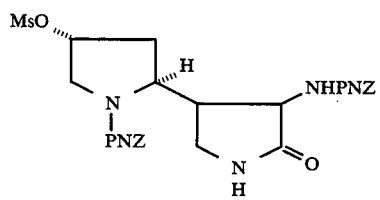

The same procedure as in Reference Example 5-4 was carried out by using the compound obtained by the above reaction (450 mg, 0.83 mmol) to obtain crude (2S,4R)-4-methanesulfonyloxy-N-(p-nitrobenzyloxycarbonyl)-2-[3-[(p-nitrobenzyloxycarbonyl)amino]-2-pyrrolidon-4-yl]pyrrolidine (620 mg).

IR(KBr)cm⁻¹: 1710, 1610, 1525, 1350, 1175.

5)

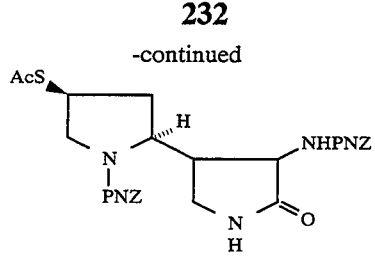

The same procedure as in Reference Example 5-5 was carried out by using the compound obtained by the above reaction (620 mg) to obtain (2S,4S)-4-acetylthio-N-(p-nitrobenzyloxycarbonyl)-2-[3-[(p-nitrobenzyloxycarbonyl)amino]-2-pyrrolidon-4-yl]pyrrolidine (130 mg, yield: 26%).

IR(KBr)cm⁻¹: 1710, 1700, 1610, 1525, 1350, 1110.
NMR(CDCl₃) δ: 1.86–1.96(2H,m),2.34(3H,s),2.68(1H,br),3.0–3.4(4H,m),-4.84(1H,m),4.1–4.4(2H,m),5.2(4H,br),5.92(1H,br),6.84(-1H,br),7.54(4H,d,J=9 Hz),8.22(4H,d,J=9 Hz).

6)

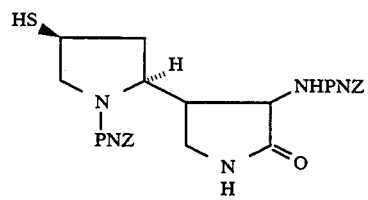

The same procedure as in Reference Example 5-6 was carried out by using the compound obtained by the above reaction (130 mg, 0.21 mmol) to obtain the above identified compound i.e. (2S,4S)-4-mercapto-N-(p-nitrobenzyloxycarbonyl)-2-[3-[(p-nitrobenzyloxycarbonyl)amino]-2-pyrrolidon-4-yl]pyrrolidine (110 mg, yield: 91%).

IR(KBr)cm⁻¹: 1710, 1610, 1515, 1350.
NMR(CDCl₃) δ: 1.6–1.9(2H,br),1.77(1H,d,J=8 Hz),2.77(1H,br),3.95–4.42(4H,m),4.-05–4.2(3H,br),5.19(2H,s),5.21(2H,s),5.9(1H,br),6.92(1H-,br),7.54(4H,d,J=9 Hz),8.2(4H,d,J=9 Hz).

REFERENCE EXAMPLE 21

(2S,4S)-N-allyloxycarbonyl-2-iodomethyl-4-tritylthiopyrrolidine

1)

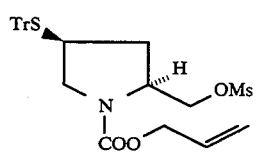

A solution of methanesulfonyl chloride (20.5 ml, 265 mmol) in methylene chloride (20 ml) was dropwise added to a solution of (2S,4S)-N-allyloxycarbonyl-2-hydroxymethyl-4-tritylthiopyrrolidine (119 g, 259 mmol, compound of Reference Example 3-1 of Japanese Patent Application No. 192,093/1990) and triethylamine (40.3 ml, 289 mmol) in methylene chloride (1 l) under cooling with ice, and the mixture was stirred at the same temperature for 30 minutes. The reaction solution was washed sequentially with water (500 ml), a saturated sodium hydrogen carbonate aqueous solution (250 ml) and a saturated sodium chloride aqueous solution (250 ml), then dried over anhydrous sodium sulfate and concentrated. To the residue, ethyl acetate (30 ml) and diisopropyl ether (270 ml) were added, and the precipitated crystals were collected by filtration to obtain (2S,4S)-N-allyloxycarbonyl-2-methanesulfonyloxymethyl-4-tritylthiopyrrolidine (130.8 g, yield: 94%).

NMR(CDCl₃) δ: 1.8(1H,m),2.1(1H,m),1.7–2.4(3H,m),3.0(3H,s), 3.9(1H,m),4.1–4.6(4H,m),5.2–5.4(2H,m),5.9(1H,m),7.2–7.6(15H,m).

2)

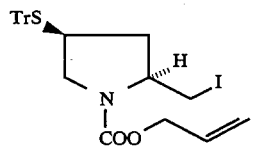

A solution comprising the compound obtained by the above reaction (130.8 g, 243 mmol), sodium iodide (180 g, 1.2 mol) and 2-butanone (1.3 l), was heated and stirred for 3 hours. The reaction solution was washed sequentially with water (300 ml), a 10% sodium thiosulfate aqueous solution (200 ml) and a saturated sodium chloride aqueous solution (500 ml), then dried over anhydrous sodium sulfate and concentrated. To the residue, diisopropyl ether (120 ml) and n-hexane (300 ml) were added, and the precipitated crystals were collected by filtration to obtain the above identified compound (123.7 g, yield: 89%).

NMR(CDCl₃) δ: 1.6(1H,m),2.1(1H,m),2.7–3.1(3H,m),3-.3–3.6(3H,m),4.5(2H,br s),5.25(2H,m),5.9(1H,m),7.2–7.6(15H,m).

REFERENCE EXAMPLE 22

(2R,4S)-N-allyloxycarbonyl-4-mercapto-2-(2-oxopyrrolidin-3-ylmethyl)pyrrolidine

1)

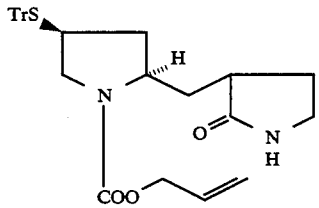

Lithium diisopropylamide (2.1M tetrahydrofuran solution, 6.45 ml, 13.5 mmol) was dropwise added to a solution of N-tert-butyldimethylsilyl-2-oxopyrrolidine (1.80 g, 9.03 mmol) in tetrahydrofuran (150 ml) at −78° C. and the mixture was stirred at the same temperature for 15 minutes. Then, a solution of (2S,4S)-N-allyloxycarbonyl-2-iodomethyl-4-tritylthiopyrrolidine (2.57 g, 4.5 mmol) in tetrahydrofuran (18 ml) was dropwise added thereto, and the mixture was stirred at the same temperature for 1 hour. The reaction solution was poured into a mixture of ethyl acetate (150 ml) and a 10% ammonium chloride aqueous solution (50 ml) for liquid separation. The organic layer was washed sequentially with a 10% sodium dihydrogen phosphate aqueous solution (100 ml) and a saturated sodium chloride aqueous solution (100 ml), then dried over anhydrous sodium sulfate and concentrated. The residue was dissolved in tetrahydrofuran (12 ml) and methanol (3 ml), and 6N hydrochloric acid (3 ml) was added thereto under cooling with ice. The mixture was stirred for 1 hour. Ethyl acetate (50 ml) was added to the reaction solution, and the organic layer was washed sequentially with a saturated sodium hydrogen carbonate aqueous solution (30 ml) and a saturated sodium chloride aqueous solution (30 ml), then dried over anhydrous sodium sulfate and concentrated. The residue was subjected to silica gel flash column chromatography (Wakogel ™ C-300, 40 ml, ethyl acetate-n-hexane 3:1) to obtain (2R,4S)-N-allyloxycarbonyl-2-(2-oxopyrrolidin-3-ylmethyl)-4-tritylthiopyrrolidine (880 mg, yield: 37%).

NMR(CDCl₃) δ: 1.5(1H,m),1.7–2.3(6H,m),2-.6–3.0(3H,m),3.34(2H,m),3.66(1H,m),4.5(2H,br s),5.3(2H,m),5.9(2H,m),7.2–7.6(15H,m).

2)

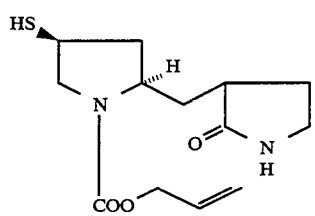

Trifluoroacetic acid (1.3 ml) and triethylsilane (0.42 ml, 2.63 mmol) were added to a solution of the compound obtained by the above reaction (1.32 g, 2.51 mmol) in methylene chloride (1.3 ml) under cooling with ice, and the mixture was stirred at room temperature for 30 minutes. The organic solvent was removed under reduced pressure, and ethyl acetate (50 ml) was added to the residue. The mixture was washed sequentially with a 1M phosphate buffer solution (pH 5.5, 30 ml×2) and a saturated sodium chloride aqueous solution (30 ml), then dried over anhydrous sodium sulfate and concentrated. The residue was purified by silica gel flash column chromatography (Wakogel ™ C-300, 40 ml, acetone-ethyl acetate 3:7) to obtain the above identified compound (650 mg, yield: 91%).

NMR(CDCl₃) δ: 1.5–1.7(2H,m),1-.9–2.4(5H,m),2.65(1H,m),3-.1–3.4(4H,m),3.92(1H,m),4.1(1H,m),4.6(2H,br d,J=6Hz),5.2–5.4(2H,m),5.95(2H,m).

REFERENCE EXAMPLE 23

(2R,4S)-N-allyloxycarbonyl-4-mercapto-2-(2-oxoazetidin-3-ylmethyl)pyrrolidine

1)

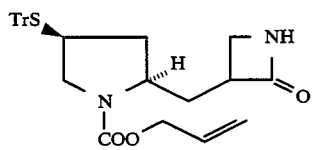

The same procedure as in Reference Example 22-1 was carried out by using N-tert-butyldimethylsilyl-2-oxoazetidine (650 mg, 3.5 mmol), lithium diisopropylamide (2.1M tetrahydrofuran solution, 3.34 ml, 7.0 mmol), and (2S,4S)-N-allyloxycarbonyl-2-iodomethyl-4-tritylthiopyrrolidine (1 g, 1.75 mmol) to obtain (2R,4S)-N-allyloxycarbonyl-2-(2-oxoazetidin-3-ylmethyl)-4-tritylthiopyrrolidine (220 mg, yield: 24%).

NMR(CDCl₃) δ: 1.5(1H,m),1.9–2.3(2H,m),2.7–3.1(4H,m),3.2(1H,m),3.4(1H,t,J=5 Hz),3.7(1H,m),4.5(2H,br s),5.3(2H,m),5.62(1H,br s),5.9(1H,m),7.2–7.6(15H,m).

2)

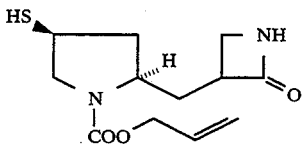

The same procedure as in Reference Example 22-2 was carried out by using the compound obtained by the above reaction (510 mg, 0.99 mmol) and triethylsilane (0.17 ml, 1.05 mmol) to obtain the above identified compound, which was used for the subsequent reaction without purification.

REFERENCE EXAMPLE 24

(2R,4S)-N-allyloxycarbonyl-2-(N-allyloxycarbonyl-pyrrolidin-3-ylmethyl)-4-mercaptopyrrolidine

1)

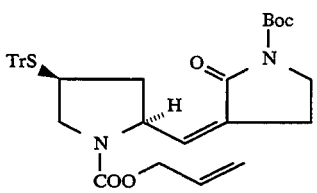

Di-tert-butyl dicarbonate (1.97 ml, 8.6 mmol) was added to a solution comprising (2S,4S)-N-allyloxycarbonyl-2-[(Z)-2-oxopyrrolidin-3-ylidenemethyl]-4-tritylthiopyrrolidine (3 g, 5.7 mmol, compound of Reference Example 7-1 of Japanese Patent Application No. 192,093/1990), triethylamine (0.8 ml, 5.7 mmol), 4-(dimethylamino)pyridine (699 mg, 5.7 mmol) and tetrahydrofuran (30 ml). The mixture was stirred at room temperature for 5 hours, and then the solvent was removed under reduced pressure. Ethyl acetate (50 ml) was added to the residue, and the mixture was washed sequentially with a 10% sodium dihydrogen phosphate aqueous solution (20 ml) and a saturated sodium chloride aqueous solution (20 ml), then dried over anhydrous sodium sulfate and concentrated. The residue was purified by silica gel flash column chromatography (Wakogel TM C-300, 40 ml, ethyl acetate-n-hexane 1:2) to obtain (2S,4S)-N-allyloxycarbonyl-2-[(Z)-N-tert-butoxycarbonyl-2-oxopyrrolidin-3-ylidenemethyl]-4-tritylthiopyrrolidine (3.24 g, yield: 91%).

NMR(CDCl₃) δ: 1.5(1H,m),1.56(9H,s),2.4–3.2(6H,m),3.7(2H,m),4.3–4.6(2H,m),5.1–5.5(3H,m),5.7–6.0(2H,m),7.2–7.6(15H,m).

2)

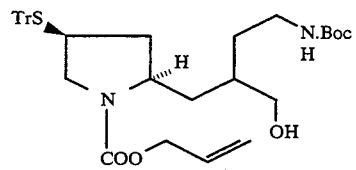

Lithium chloride (68 mg, 1.6 mmol), sodium borohydride (61 mg, 1.6 mmol) and ethanol (5 ml) were sequentially added to a solution comprising the compound obtained by the above reaction (500 mg, 0.8 mmol) and tetrahydrofuran (2.5 ml), and the mixture was stirred at room temperature for 16 hours. Ethyl acetate (30 ml) was added to the reaction solution, and the mixture was washed sequentially with water (15 ml×2) and a saturated sodium chloride aqueous solution (15 ml), then dried over anhydrous sodium sulfate and concentrated. The residue was purified by silica gel flash column chromatography (Wakogel TM C-300, 40 ml, ethyl acetate-n-hexane 1:1) to obtain (2R,4S)-N-allyloxycarbonyl-2-[4-tert-butoxycarbonylamino-2-(hydroxymethyl)-butyl]-4-tritylthiopyrrolidine (270 mg, yield: 54%).

NMR(CDCl₃) δ: 1.2–1.5(4H,m),1.44(9H,s),1.7–2.1(2H,m),2.22(1H,m),2.6–3.0(3H,m),3.16(2H,m),3.4–3.8(3H,m),4.5(2H,br s),4.7(0.5H,br s),4.9(0.5H,br s),5.2–5.4(2H,m),5.9(1H,m),7.2–7.6(15H,m).

3)

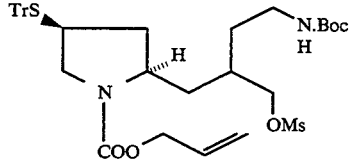

Methanesulfonyl chloride (35 μl, 0.45 mmol) was dropwise added to a solution comprising the compound obtained by the above reaction (270 mg, 0.43 mmol), triethylamine (66 μl, 0.47 mmol) and methylene chloride (3 ml) under cooling with ice, and the mixture was stirred at the same temperature for 30 minutes. Methylene chloride (30 ml) was added to the reaction solution, and the mixture was washed sequantially with water (15 ml), a saturated sodium hydrogen carbonate aqueous solution (15 ml) and a saturated sodium chloride aqueous solution (15 ml), then dried over anhydrous sodium sulfate and concentrated. The residue was purified by silica gel flash column chromatography (Wakogel TM C-300, 40 ml, ethyl acetate-n-hexane 1:1) to obtain (2R,4S)-N-allyloxycarbonyl-2-[4-tert-butoxycarbonylamino-2-(methanesulfonyloxymethyl)butyl]-4-tritylthiopyrrolidine (270 mg, yield: 89%).

NMR(CDCl₃) δ: 1.3–2.0(6H,m),1.44(9H,s),2.2(1H,m),2.6–3.3(5H,m),3.0(1.5H,s),3.02(1.5H,s),3.8(1H,m),4.14(2H,m),4.4–4.7(2.5H,m),5.02(0.5H,br s),5.2–5.4(2H,m),5.9(1H,m),7.2–7.6(15H,m).

4)

-continued

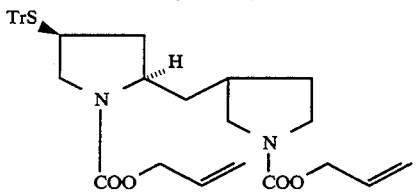

The compound obtained by the above reaction (260 mg, 0.367 mmol) was dissolved in a 1.55N hydrogen chloride-methanol solution (0.7 ml), and the mixture was stirred at room temperature for 4 hours. The solvent was removed under reduced pressure, and then tetrahydrofuran (5 ml) and triethylamine (0.11 ml, 0.81 mmol) were added thereto, and the mixture was stirred at room temperature for 1 hour. Triethylamine (0.11 ml, 0.81 mmol) was added to the reaction solution, and then allyl chloroformate (43 μl, 0.4 mmol) was dropwise added thereto under cooling with ice. The mixture was stirred at the same temperature for 30 minutes. Ethyl acetate (30 ml) was added to the reaction solution, and the mixture was washed sequentially with water (15 ml), a saturated sodium hydrogen carbonate aqueous solution (15 ml) and a saturated sodium chloride aqueous solution (15 ml), then dried over anhydrous sodium sulfate and concentrated. The residue was purified by silica gel flash column chromatography (Wakogel TM C-300, 40 ml, ethyl acetate-n-hexane 1:1) to obtain (2R,4S)-N-allyloxycarbonyl-2-(N-allyloxycarbonylpyrrolidin-3-ylmethyl)-4-tritylthiopyrrolidine (180 mg, yield: 82%).

NMR(CDCl$_3$) δ: 1.3–1.5(3H,m),1.8–2.2(4H,m),2-.6–3.0(4H,m),3.3(1H,m),3.4–3.7(3H,m),4.5(2H,br s),4.6(2H,br d,J=5Hz),5.2–5.4(4H,m),5.8–6.1(2H,m),7-.2–7.6(15H,m).

5)

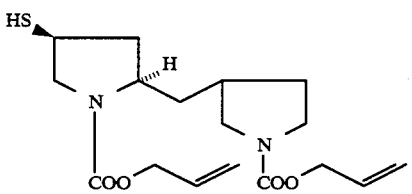

The same procedure as in Reference Example 22-2 was carried out by using the compound obtained by the above reaction (1.03 g, 1.73 mmol) and triethylsilane (0.29 ml, 1.81 mmol) to obtain the above identified compound (560 mg, yield: 92%).

NMR(CDCl$_3$) δ: 1.5–1.8(4H,m),1-.9–2.3(4H,m),2.62(1H,m),2.9–4.2(7H,m),4.6(4H,m),5-.2–5.4(4H,m),5.9–6.1(2H,m).

REFERENCE EXAMPLE 25

(2R,4S)-N-allyloxycarbonyl-2-[(2S)-N-allyloxycarbonyl-2-carbamoylpyrrolidin-4-ylmethyl]-4-mercaptopyrrolidine

1)

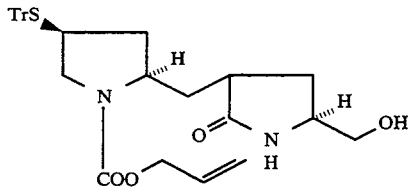

The same procedure as in Reference Example 22-1 was carried out by using N-tert-butyldimethylsilyl-5-tert-butyldimethylsiloxymethyl-2-oxopyrrolidine (10.67 g, 31.6 mmol), lithium diisopropylamide (2.1M tetrahydrofuran solution, 15.1 ml, 31.6 mmol) and (2S,4S)-N-allyloxycarbonyl-2-iodomethyl-4-tritylthiopyrrolidine (10 g, 17.6 mmol) to obtain (2R,4S)-N-allyloxycarbonyl-2-(5S)-5-hydroxymethyl-2-oxopyrrolidin-3-ylmethyl]-4-tritylthiopyrrolidine (2 g, yield: 21%).

NMR(CDCl$_3$) δ: 1.3–2.4(8H,m),2-.7–3.0(2H,m),3.5(1H,m),3.6–3.8(3H,m),4.5(2H,br s),5.2–5.4(2H,m),5.9(1H,m),6.3(1H,br s),7.2–7.6(15H,m).

2)

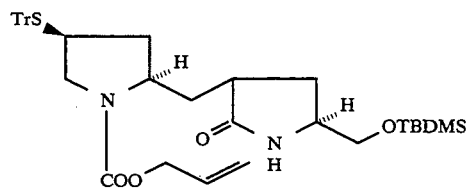

4-(dimethylamino)pyridine (88 mg, 0.72 mmol) and triethylamine (1.2 ml, 8.6 mmol) were sequentially added to a solution comprising the compound obtained by the above reaction (4 g, 7.18 mmol), tert-butyldimethylsilyl chloride (1.19 g, 7.9 mmol) and N,N-dimethylformamide (20 ml) under cooling with ice, and the mixture was stirred at room temperature for 3 hours. Ethyl acetate (80 ml) was added to the reaction solution, and the mixture was washed sequentially with water (40 ml×2), a saturated sodium hydrogen carbonate aqueous solution (40 ml) and a saturated sodium chloride aqueous solution (40 ml), then dried over anhydrous sodium sulfate and concentrated. The residue was purified by silica gel flash column chromatography (Wakogel TM C-300, 40 ml, ethyl acetate-n-hexane 2:1) to obtain (2R,4S)-N-allyloxycarbonyl-2-[(5S)-5-tert-butyldimethylsiloxymethyl-2-oxopyrrolidin-3-ylmethyl]-4-tritylthiopyrrolidine (4.1 g, yield: 85%).

NMR(CDCl$_3$) δ: 0.05(6H,s),0.9(9H,s),1.3–2.4(8H,m),2.8–3.0(2H,m),3-.3–3.7(4H,m),4.5(2H,br s),5.2–5.4(2H,m),5.9(2H,m),7-.2–7.6(15H,m).

3)

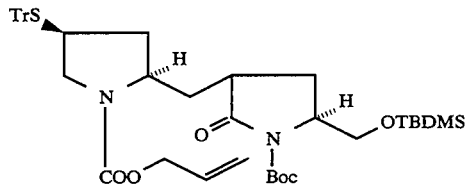

The same procedure as in Reference Example 24-1 was carried out by using the compound obtained by the above reaction (4.1 g, 6.1 mmol), di-tert-butyl dicarbonate (2.53 ml, 11 mmol), 4-(dimethylamino)pyridine (746 mg, 6.1 mmol) and triethylamine (0.94 ml, 6.7 mmol) to obtain (2R,4S)-N-allyloxycarbonyl-2-[(5S)-N-tert-butoxycarbonyl-5-tert-butyldimethylsiloxymethyl-2-oxopyrrolidin-3-ylmethyl]-4-tritylthiopyrrolidine (4.7 g, yield: 100%).

NMR(CDCl₃) δ: 0.04(3H,s),0.06(3H,s),0.9(9H,s),1.5(2H,m),1.52(9H,s),1.-9(2H,m),2.15(2H,m),2.8–3.0(4H,m),3.62(1H,m),3.7(1H,-dd,J=10,2Hz),3.9(1H,dd,J=10,4Hz),4.1(1H,m),4.5(2H,br s),5.1–5.3(2H,m),5.9(1H,m),7.2–7.6(15H,m).

4)

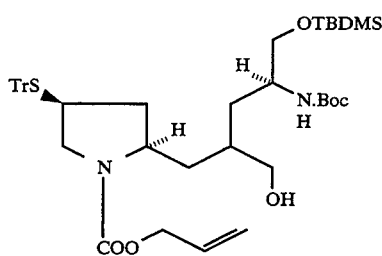

The same procedure as in Reference Example 24-2 was carried out by using the compound obtained by the above reaction (4.7 g, 6.1 mmol), lithium chloride (518 mg, 12.2 mmol) and sodium borohydride (463 mg, 12.2 mmol) to obtain (2R,4S)-N-allyloxycarbonyl-2-[(4S)-4-tert-butoxycarbonylamino-5-tert-butyldimethylsiloxy-2-hydroxymethylpentyl]-4-tritylthiopyrrolidine (2.18 g, yield: 46%).

NMR(CDCl₃) δ: 0.04(6H,s),0.9(9H,s),1.4–1.8(6H,m),1.48(9H,s),2.2(1H,-m),2.6–3.0(3H,m),3.5–3.9(6H,m),4.5(2H,br s),4.7(1H,br s),5.2–5.4(2H,m),5.9(1H,m),7.2–7.6(15H,m).

5)

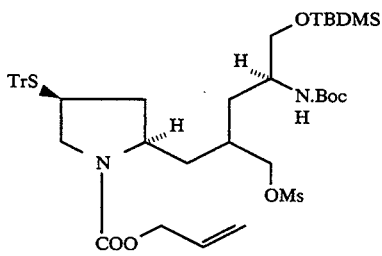

The same procedure as in Reference Example 24-3 was carried out by using the compound obtained by the above reaction (2.18 g, 2.8 mmol), methanesulfonyl chloride (0.24 ml, 3 mmol) and triethylamine (0.47 ml, 3.4 mmol) to obtain (2R,4S)-N-allyloxycarbonyl-2-[(4S)-4-tert-butoxycarbonylamino-5-tert-butyldimethylsiloxy-2-methanesulfonyloxymethylpentyl]-4-tritylthiopyrrolidine (2.15 g, yield: 90%).

NMR(CDCl₃) δ: 0.04(6H,s),0.9(9H,s),1.3–1.9(6H,m),1.45(9H,s),2.2(1H,-m),2.6–3.0(3H,m),3.0(3H,s),3.4–3.8(4H,m),4-.1–4.7(5H,m),5.1–5.3(2H,m),5.9(1H,m),7.2–7.6(15H,m).

6)

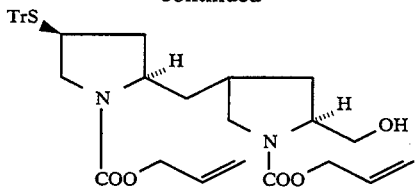

The same procedure as in Reference Example 24-4 was carried out by using the compound obtained by the above reaction (2.15 g, 2.52 mmol), a 1N hydrogen chloride-methanol solution (25 ml), allyl chloroformate (0.35 ml, 3.28 mmol) and triethylamine (1.76 ml, 12.6 ml) to obtain (2R,4S)-N-allyloxycarbonyl-2-[(2S)-N-allyloxycarbonyl-2-hydroxymethylpyrrolidin-4-ylmethyl]-4-tritylthiopyrrolidine (1.21 g, yield: 77%).

NMR(CDCl₃) δ: 1.3–2.2(7H,m),2.6–3.05(4H,m),3-.5–3.7(4H,m),4.05(1H,m),4.45(2H,br d,J=4 Hz),4.6(2H,m),5.1–5.3(4H,m),5.8–6.0(2H,m),7-.2–7.6(15H,m).

7)

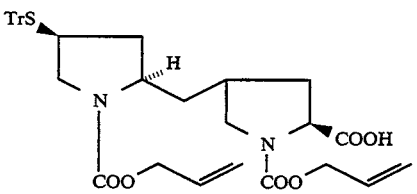

A solution comprising the compound obtained by the above reaction (1.21 g, 1.93 mmol), pyridinium dichromate (3.63 g, 9.65 mmol) and N,N-dimethylformamide (7.2 ml), was stirred at room temperature for 16 hours. Ethyl acetate (50 ml) was added to the reaction solution, and the mixture was washed with water (20 ml×2). To the organic layer, water (30 ml) containing potassium carbonate (270 mg, 1.93 mmol) was added for liquid separation. The aqueous layer was acidified with 6N hydrochloric acid, and ethyl acetate (50 ml) was added for liquid separation. The organic layer was washed with a saturated sodium chloride aqueous solution (20 ml), then dried over anhydrous sodium sulfate and concentrated to obtain (2R,4S)-N-allyloxycarbonyl-2-[(2S)-N-allyloxycarbonyl-2-carboxypyrrolidin-4-ylmethyl]-4-tritylthiopyrrolidine (1 g, yield: 81%).

NMR(CDCl₃) δ: 1.3–1.5(2H,m),1.8–2.4(5H,m),2-.7–3.1(4H,m),3.5–3.9(2H,m),4.3–4.8(5H,m), 5.1–5.5(4H,m),5.8–6.0(2H,m),7.2–7.6(15H,m).

8)

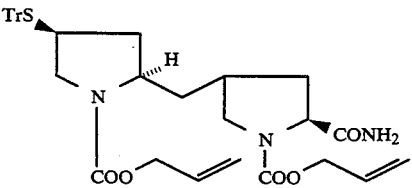

Isobutyl chloroformate (90 μl, 0.69 mmol) was dropwise added to a solution comprising the compound obtained by the above reaction (400 mg, 0.62 mmol), triethylamine (96 μl, 0.69 mmol) and tetrahydrofuran (6 ml) at −15° C. and the mixture was stirred at the same temperature for 20 minutes. Then, concentrated aqueous ammonia (0.18 ml) was added thereto, and the mixture was stirred at 0° C. for 1 hour. Ethyl acetate (30 ml) was added to the reaction solution, and the mixture was washed sequentially with a saturated sodium hydrogen carbonate aqueous solution (15 ml) and a saturated sodium chloride aqueous solution (15 ml), then dried over anhydrous sodium sulfate and concentrated to obtain (2R,4S)-N-allyloxycarbonyl-2-[(2S)-N-allyloxycarbonyl-2-carbamoylpyrrolidin-4-ylmethyl]-4-tritylthiopyrrolidine (310 mg, yield: 78%).

NMR(CDCl₃) δ: 1.3–2.5(7H,m),2-.7–3.1(4H,m),3.72(2H,m),4.3–4.7(5H,m),5-.1–5.5(5H,m),5.9–6.1(2.5H,m)6.8(0.5H,br s),7.2–7.6(15H,m).

9)

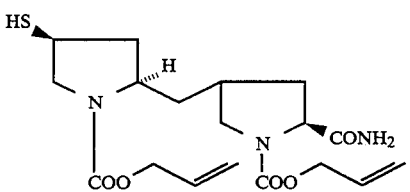

The same procedure as in Reference Example 22-2 was carried out by using the compound obtained by the above reaction (310 mg, 0.48 mmol) and triethylsilane (81 μl, 0.51 mmol) to obtain the above identified compound (190 mg, yield: 100%).

NMR(CDCl₃) δ: 1.5–2.7(8H,m),3-.0–3.3(3H,m),3.7(1H,m),3.86(1H,m),4.06(1H,m),4.4(1H,d,J=8 Hz),4.6(4H,m),5.2–5.5(5H,m),5-.8–6.0(2.5H,m),6.8(0.5H,br s).

REFERENCE EXAMPLE 26

(2R,4S)-N-allyloxycarbonyl-2-[(2S)-N-allyloxycarbonyl-2-(methylcarbamoyl)pyrrolidin-4-ylmethyl]-4-mercaptopyrrolidine

1)

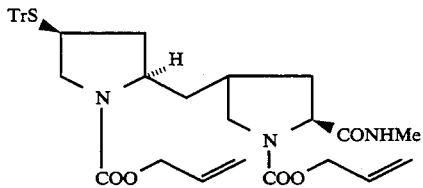

The same procedure as in Reference Example 25-8 was carried out by using (2R,4S)-N-allyloxycarbonyl-2-[(2S)-N-allyloxycarbonyl-2-carboxypyrrolidin-4-ylmethyl]-4-tritylthiopyrrolidine (300 mg, 0.47 mmol), isobutyl chloroformate (74 μl, 0.56 mmol), triethylamine (78 μl, 0.56 mmol) and a 40% methylamine aqueous solution (0.19 ml) to obtain (2R,4S)-N-allyloxycarbonyl-2-[(2S)-N-allyloxycarbonyl-2-(methylcarbamoyl)pyrrolidin-4-ylmethyl]-4-tritylthiopyrrolidine (300 mg, yield: 98%).

NMR(CDCl₃) δ: 1.3–2.5(7H,m),2-.6–3.0(3H,m),2.8(3H,d,J=5 Hz),3.6(2H,m),4.3(1H,d,J=8 Hz),4.4–4.6(4H,m),5-.1–5.4(4H,m),5.8–6.0(2.5H,m),6.7(0.5H,br s),7.2–7.6(15H,m).

2)

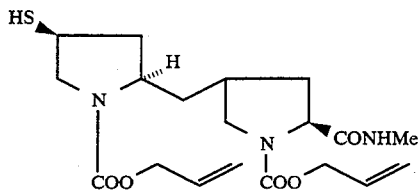

The same procedure as in Reference Example 22-2 was carried out by using the compound obtained by the above reaction (300 mg, 0.46 mmol) and triethylsilane (83 μl, 0.5 mmol) to obtain the above identified compound (168 mg, yield: 89%).

NMR(CDCl₃) δ: 1.5–2.7(8H,m),2,82(3H,d,J=5 Hz),3.0–3.3(3H,m), 3.7(1H,m),3–9(1H,m),4.1(1H,m),4.4(1H,d,J=8 Hz),4.6(4H,m),5.2–5.4(4H,m),5-.8–6.1(2.5H,m),6.9(0.5H,br s).

REFERENCE EXAMPLE 27

(2R,4S)-N-allyloxycarbonyl-2-[(2S)-N-allyloxycarbonyl-2-(dimethylcarbamoyl)pyrrolidin-4-ylmethyl]-4-mercaptopyrrolidine

1)

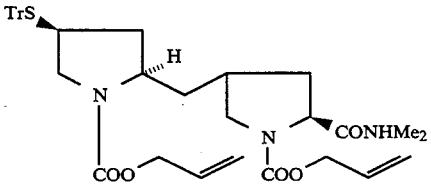

The same procedure as in Reference Example 25-8 was carried out by using (2R,4S)-N-allyloxycarbonyl-2-[(2S)-N-allyloxycarbonyl-2-carboxypyrrolidin-4-ylmethyl]-4-tritylthiopyrrolidine (300 mg, 0.47 mmol), isobutyl chloroformate (74 μl, 0.56 mmol), triethylamine (78 μl, 0.56 mmol) and a 50% dimethylamine aqueous solution (0.27 ml) to obtain (2R,4S)-N-allyloxycarbonyl-2-[(2S)-N-allyloxycarbonyl-2-(dimethylcarbamoyl)pyrrolidin-4-ylmethyl]-4-tritylthiopyrrolidine (290 mg, yield: 93%).

NMR(CDCl₃) δ: 1.3–2.3(7H,m),2-.6–3.0(4H,m),2.9(6H,s),3.5(2H,m), 4.1–4.7(5H,m),5-.1–5.3(4H,m),5.7–5.9(2H,m),7.2–7.6(15H,m).

2)

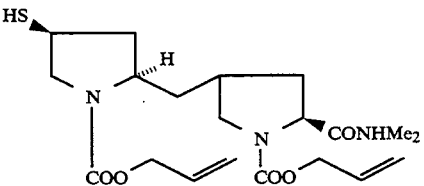

The same procedure as in Reference Example 22-2 was carried out by using the compound obtained by the above reaction (290 mg, 0.43 mmol) and triethylsilane (76 μl, 0.48 mmol) to obtain the above identified compound (110 mg, yield: 60%).

NMR (CDCl₃) δ: 1.5–2.7 (8H,m),2.9–3.3(3H,m),2.98(3H,s

),3.1(3H,s),3.7-4.2(3H,m),4.4-4.8(5H,m),5-.2-5.4(4H,m),5.9(2H,m).

REFERENCE EXAMPLE 28

(2S,4S)-2-(2,4-dioxoimidazolidin-5-yl)-4-(p-methoxybenzylthio)-N-(p-nitrobenzyloxycarbonyl)pyrrolidine

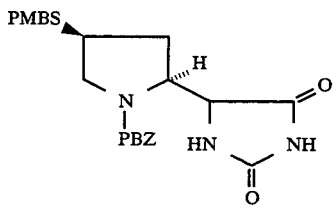

Oxalyl chloride (1.3 ml, 14.9 mmol) was dropwise added to a solution of dimethyl sulfoxide (2.2 ml, 3.10 mmol) in methylene chloride (30 ml) under a nitrogen stream at −78° C. and the reaction solution was stirred at the same temperature for 30 minutes. A solution of (2S,4S)-2-hydroxymethyl-4-(p-methoxybenzylthio)-N-(p-nitrobenzyloxycarbonyl)pyrrolidine (4.32 g, 9.99 mmol) in methylene chloride (20 ml) cooled to −78° C., was dropwise added to this mixture. This mixture was stirred at the same temperature for 30 minutes, and then triethylamine (7.0 ml, 50.2 mmol) was dropwise added thereto. This mixture was stirred at the same temperature for 10 minutes and further at room temperature for 1 hour. Then, methylene chloride (400 ml) was added thereto, and the mixture was washed with a 1N potassium hydrogen sulfate aqueous solution and water. The organic layer was dried over anhydrous sodium sulfate. Then, solvent was distilled off to obtain a crude aldehyde.

The crude aldehyde obtained by the above reaction was dissolved in a solvent mixture comprising ethanol (15 ml), water (15 ml) and N,N-dimethylformamide (6 ml). Then, ammonium carbonate (4.50 g, 46.8 mmol) and then sodium cyanide (0.98 g, 20.0 mmol) were added thereto, and the mixture was stirred at 60° C. for 6 hours. The mixture was cooled to room temperature. Then, the organic solvent was distilled off, and water (100 ml) and chloroform (100 ml) were added to the residue. The organic layer was separated, and then the aqueous layer was extracted with chloroform (100 ml×2). The organic layers were put together, then washed sequentially with water and a saturated sodium chloride aqueous solution and dried over anhydrous sodium sulfate. The solvent was distilled off under reduced pressure, and the residue was subjected to silica gel column chromatography (Wakogel TM C-300, methanol-chloroform) to obtain the above identified compound (1.82 g, yield: 36%).

IR(KBr)cm⁻¹: 3250, 1770, 1730, 1710, 1610, 1510, 1350.

NMR(CDCl₃+CD₃OD) δ: 1.9-2.3(2H,m),3-.7-4.1(1H,m),4.26(1H,m),4.72 and 5.04(1H,s),5.22(2H,s),6.86(2H,d,J=8 Hz),7.24(2H,d,J=8 Hz),7.51(2H,d,J=8 Hz),8.26(2H,d,J=8 Hz).

REFERENCE EXAMPLE 29

(2R,4S)-N-allyloxycarbonyl-2-(2,4-dioxoimidazolidin-5-ylmethyl)-4-tritylthiopyrrolidine diastereomers A and B

1)

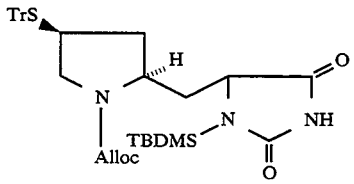

A 1.6M n-butyllithium-hexane solution (4.1 ml, 6.56 mmol) was dropwise added to a solution of diisopropylamine (1 ml, 7.14 mmol) in tetrahydrofuran (5 ml) under a nitrogen stream at −78° C., and the reaction solution was stirred at the same temperature for 10 minutes and under cooling with ice for 30 minutes. A solution of N,N′-bis(tert-butyldimethylsilyl)hydantoin (1.65 g, 5.02 mmol) in tetrahydrofuran (2 ml) was dropwise added to this reaction solution at −78° C. This solution was stirred at the same temperature for 1 hour. Then, hexamethylphosphoric triamide (1.75 ml, 10 mmol) was added to this reaction solution, and the mixture was stirred for 10 minutes. Then, a solution of (2S,4S)-N-allyloxycarbonyl-2-iodomethyl-4-tritylthiopyrrolidine (2.28 g, 4.00 mmol, compound of Reference Example 21-2) in tetrahydrofuran (3 ml) was dropwise added thereto. The reaction solution was stirred at the same temperature for 2 hours. To the reaction solution, a saturated ammonium chloride aqueous solution (10 ml) and ethyl acetate (300 ml) were added. The organic layer was washed sequentially with a 1N potassium hydrogen sulfate aqueous solution, water and a saturated sodium chloride aqueous solution and then dried over anhydrous sodium sulfate. The solvent was distilled off under reduced pressure, and the residue was subjected to silica gel column chromatography (Wakogel TM C-300, hexane-ethyl acetate) to obtain (2R,4S)-N-allyloxycarbonyl-2-(1-tert-butyldimethylsilyl-2,4-dioxoimidazolidin-5-ylmethyl)-4-tritylthiopyrrolidine (1.19 g, yield: 45%).

IR(KBr)cm⁻¹: 3420, 3250, 1765, 1700, 1400, 1200.

NMR(CDCl₃) δ: 0.27 and 0.35(6H,s),0.94 and 0.97(9H,s),1.5(1H,m),1.7(1H,m),2.25(1H,m),2.6-3.0(3H,m),4.2(1H,m),4.3-4.6(3H,m),5.25(2H,m),6.85(1H,m),7-.1-7.7(15H,m),8.06 and 8.11(1H,s).

2)

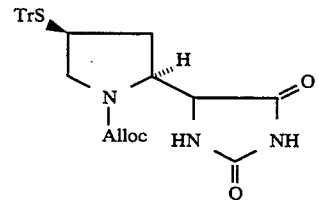

A mixture of a 49% hydrofluoric acid (1.5 ml) and acetonitrile (13.5 ml) was added to a solution of the compound obtained by the above reaction (1.10 g, 1.68 mmol) in acetonitrile (15 ml). This solution was stirred overnight at room temperature. Ethyl acetate (300 ml)

was added to this reaction solution. This solution was washed sequentially with water, a saturated sodium hydrogen carbonate aqueous solution, water and a saturated sodium chloride aqueous solution and then dried over anhydrous sodium sulfate. The solvent was distilled off under reduced pressure, and the residue was subjected to silica gel column chromatography (Wakogel TM C-300, methanol-chloroform) to obtain diastereomer A (550 mg, yield: 61%, polar compound) and diastereomer B (220 mg, yield: 24%, low polar compound) of the above identified compound.

Diastereomer A
IR(KBr)cm$^{-1}$: 3550, 3480, 3420, 1770, 1730, 1680, 1445, 1410.
NMR(CDCl$_3$) δ: 1.2–2.4(4H,m),2.75(2H,m),3.05(1H,m),3.8(1H,m),4.10(-1H,d,J=8 Hz),4.49(2H,d,J=6 Hz),5.26(2H,m),5.9(1H,m),6.54(1H,s),7.0–7.7(15H,m),8-.41(1H,s).

Diastereomer B
IR(KBr)cm$^{-1}$: 3420, 3230, 1775, 1730, 1700, 1445, 1410.
NMR(CDCl$_3$) δ: 1.2–1.9(2H,m),1.-95–2.45(2H,m),2.7(2H,m),3.05(1H,m),3-.8–4.05(2H,m),4.46(2H,d,J=5 Hz),5.26(2H,m),5.85(1H,m),6.59(1H,s),7.1–7.6(15H,m),-8.12(1H,s).

REFERENCE EXAMPLE 30

(2R,4S)-4-acetylthio-N-(p-nitrobenzyloxycarbonyl)-2-(2,5-dioxopyrrolidin-3-ylmethyl)pyrrolidine

1)

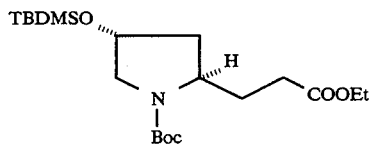

Ethyl 3-[(2S,4R)-4-tert-butyldimethylsiloxy-N-tert-butoxycarbonylpyrrolidin-2-yl]acrylate (10 g, 26.8 mmol) was subjected to catalytic hydrogenation in ethanol (200 ml) by means of 10% palladium carbon (500 mg) at 60° C. for 3 hours. The reaction solution was left to cool, and the catalyst was filtered off. The filtrate was concentrated under reduced pressure, and the residue was subjected to silica gel column chromatography (Wakogel TM C-300, 300 ml, ethyl acetate-hexane 1:10) to obtain ethyl 3-[(2R,4R)-4-tert-butyldimethylsiloxy-N-tert-butoxycarbonylpyrrolidin-2-yl]propionate (9.91 g, yield: 98%).
NMR(CDCl$_3$) δ: 0.04(6H,s),0.90(9H,s),1.28(3H,t,J=8 Hz),1.48(9H,s),1.78(2H,m),2.00(2H,m),2.30(2H,m),3.38-(2H,m),3.96(1H,m),4.14(2H,q,J=8 Hz),4.32(1H,m).

2)

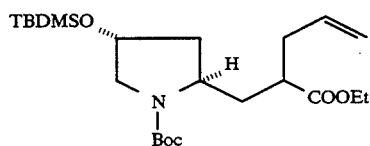

2.1M lithium diisopropylamide (7.6 ml, 16.0 mmol) was dropwise added to a solution of the compound obtained by the above reaction (5.0 g, 13.3 mmol) in tetrahydrofuran (250 ml) in a nitrogen stream at −78° C., and the mixture was stirred for 10 minutes. Then, allyl bromide (3.46 ml, 40 mmol) was dropwise added thereto, and the mixture was stirred at the same temperature for 30 minutes. After removing the cooling medium, the mixture was stirred for 30 minutes. Then, a saturated ammonium chloride aqueous solution was added thereto, and the mixture was extracted with ethyl acetate. The organic layer was dried over anhydrous magnesium sulfate and then concentrated. The residue was subjected to silica gel column chromatography (Wakogel TM C-300, ethyl acetate-hexane 1:6) to obtain 2-ethoxycarbonyl-1-[(2R,4R)-4-tert-butyldimethylsiloxy-N-tert-butoxycarbonylpyrrolidin-2-yl]-4-pentene (6.09 g, yields: 110%).
NMR(CDCl$_3$) δ: 0.08(6H,s),0.86(9H,s),1.26(3H,t,J=8 Hz),1.48(9H,s),1.50–2.20(3H,m),2.-16–2.74(2H,m),3.34(2H,m), 3.90(1H,m),4.14(2H,m),4.32(1H,m),5.04(2H,m),5.70(1-H,m).

3)

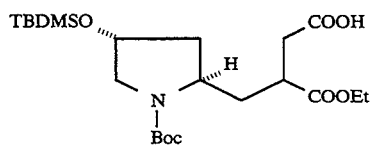

Ruthenium trichloride (6.25 mg, 30 μmol) was added to a mixture comprising the compound obtained by the above reaction (507 mg, 1.22 mmol), carbon tetrachloride (2.5 ml), acetonitrile (2.5 ml), sodium periodate (1.1 g, 5.14 mmol) and water (3.75 ml). The reaction solution was stirred for 2 hours and then extracted with methylene chloride. The organic layer was dried over anhydrous magnesium sulfate and concentrated. The residue was subjected to silica gel column chromatography (Wakogel TM C-300, ethyl acetate-hexane 1:1) to obtain 3-ethoxycarbonyl-4-[(2R,4R)-4-tert-butyldimethylsiloxy-N-tert-butoxycarbonylpyrrolidin-2-yl]butyric acid (480 mg, yield: 90%).
NMR(CDCl$_3$) δ: 0.08(6H,s),0.88(9H,s),1.28(3H,t,J=8 Hz),1.48(9H,s),1.78(2H,m),2.04(2H,m),2.80(3H,m),3.38-(2H,m),3.90(1H,m),4.20(2H,m),4.36(1H,m).

4)

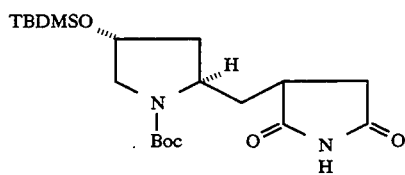

Carbonyldiimidazole (475 mg, 2.93 mmol) was added to a solution of the compound obtained by the above reaction (847 mg, 1.95 mmol) in tetrahydrofuran (17 ml) at room temperature, and the reaction solution was stirred for 1 hour. Then, concentrated aqueous ammonia (3.4 ml) was added thereto. The reaction solution was stirred further for 30 minutes and then diluted with ethyl acetate. The organic layer was washed with a saturated ammonium chloride aqueous solution, then dried over anhydrous magnesium sulfate and concentrated. The residue was dissolved in tetrahydrofuran (15 ml). Then, 60% sodium hydride (94 mg, 2.3 mmol) was added thereto under cooling with ice, and the mixture was stirred for 20 minutes. Then, the mixture was subjected to liquid separation treatment as described above, and the organic layer was dried and concentrated. The residue was subjected to silica gel column chromatography (Wakogel TM C-300, ethyl acetate-hexane 1:1) to obtain (2R,4R)-4-tert-butyldimethylsiloxy-N-tert-butoxycarbonyl-2-(2,5-dioxopyrrolidin-3-ylmethyl)pyrrolidine (576 mg, yield: 76%).

NMR(CDCl$_3$) δ: 0.08(6H,s),0.90(9H,s),1.48(6H,s),1.70(2H,m),2.00(2H,m),2.58(1H,m),2.90(3H,m),3.38(2H,m),4.12(1H,m),4.40(1H,m).

5)

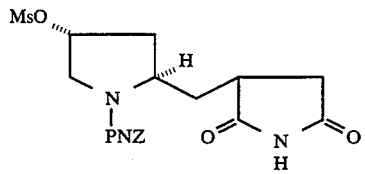

The compound obtained by the above reaction (570 mg, 1.47 mmol) was dissolved in a mixture of methanol (11 ml) and thionyl chloride (0.32 ml, 4.4 mmol) under cooling with ice. The reaction solution was returned to room temperature and stirred for 30 minutes, and it was then concentrated under reduced pressure. The residue was dissolved in chloroform (10 ml). Then, triethylamine (0.61 ml, 5.86 mmol) and 4,6-dimethyl-2-(p-nitrobenzyloxycarbonylthio)pyrimidine (470 mg, 1.47 mmol) were added thereto, and the mixture was stirred overnight. The reaction solution was washed with 1N hydrochloric acid, then dried over anhydrous magnesium sulfate and concentrated. The residue was dissolved in methylene chloride (10 ml). Then, methanesulfonyl chloride (0.14 ml, 1.77 mmol) and triethylamine (0.31 ml, 2.2 mmol) were added thereto, and the mixture was stirred at room temperature for 30 minutes. The reaction solution was poured into a saturated sodium hydrogen carbonate aqueous solution and extracted with methylene chloride. The organic layer was dried over anhydrous magnesium sulfate and concentrated. The residue was subjected to silica gel column chromatography (Wakogel TM C-300, ethyl acetate) to obtain (2R,4R)-4-methanesulfonyloxy-N-(p-nitrobenzyloxycarbonyl)-2-(2,5-dioxopyrrolidin-3-ylmethyl)pyrrolidine (420 mg, yield: 62%).

NMR(CDCl$_3$) δ: 1.80-2.40(4H,m),2.45-3.30(5H,m),3.06(3H,s),4.00-4.40(2H,m),5.26(2H,m),7.54(2H,d,J=8 Hz),8.28(2H,d,J=8 Hz).

6)

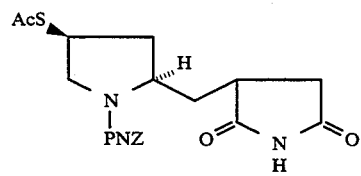

A mixture comprising the compound obtained by the above reaction (410 mg, 0.90 mmol), N,N-dimethylformamide (4.1 ml) and potassium thioacetate (308 mg, 2.70 mmol) was stirred at 70° C. for 1 hour. The reaction solution was poured into water and extracted with ethyl acetate. The organic layer was dried and concentrated. The residue was subjected to silica gel column chromatography (Wakogel TM C-300, ethyl acetate-hexane 1:1) to obtain (2R,4S)-4-acetylthio-N-(p-nitrobenzyloxycarbonyl)-2-(2,5-dioxopyrrolidin-3-ylmethyl)pyrrolidine (251 mg, yield: 64%).

NMR(CDCl$_3$) δ: 1.70(2H,m),2.16(2H,m),2.38(3H,s),2.40-3.40(5H,m),3.80-4.30(2H,m),5.22(2H,m),7.56(2H,d,J=8 Hz),8.24(2H,d,J=8 Hz).

REFERENCE EXAMPLE 31

(2S,4S)-4-acetylthio-N-allyloxycarbonyl-2-(1-allyloxycarbonyl-5-oxopiperazin-2-yl)pyrrolidine

1)

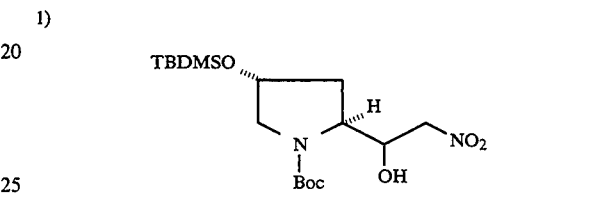

Triethylamine (1.27 ml, 9.55 mmol) was added to a solution of (2S,4R)-4-tert-butyldimethylsiloxy-N-tert-butoxycarbonylprolinal (19.1 g, 57.87 mmol) in nitromethane (95 ml) under stirring and cooling with ice. This solution was left to stand at room temperature for 15 hours. The solvent was distilled off under reduced pressure, and the residue was subjected to silica gel column chromatography (Wakogel TM C-300, 350 g, hexane-ethyl acetate 9:1) to obtain oily (2S,4R)-4-tert-butyldimethylsiloxy-N-tert-butoxycarbonyl-2-(1-hydroxy-2nitroethyl)pyrrolidine (14.81 g, yield: 65.5%).

IR(KBr)cm$^{-1}$: 3420, 1675–1700, 1560, 1415, 1255, 1165, 840, 780.

NMR(CDCl$_3$) δ: 0.07(6H,s),0.87(9H,s),1.49(9H,s),1.7-2.1(2H,m),3.2-3.6(2H,m),4.12-4.56(5H,m).

2)

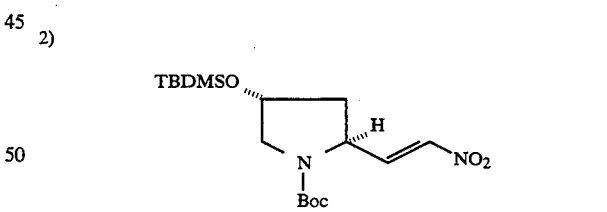

Thionyl chloride (3.58 ml, 49.33 mmol) was dropwise added to a solution of the compound obtained by the above reaction (14.8 g, 37.89 mmol) in methylene chloride (150 ml) at −50° C. The reaction solution was stirred at −50° C. for 5 minutes, and then triethylamine (16.5 ml, 118.39 mmol) was dropwise added thereto. The cooling bath was removed, and the reaction solution was stirred at room temperature for 3 hours, then poured into ice water (100 ml) and extracted with methylene chloride. The organic layer was washed with water and a 10% sodium hydrogen carbonate aqueous solution, then dried over anhydrous sodium sulfate and concentrated. The residue was subjected to silica gel column chromatography (Wakogel TM C-300, hexane-ethyl acetate 95:5) to obtain (2S,4R)-4-tert-butyldimethylsiloxy-N-tert-butoxycarbonyl-2-(2-nitrovinyl)pyrrolidine (11.48 g, yield: 81.3%) as solid.

IR(KBr)cm$^{-1}$: 1685, 1520, 1400, 1350, 1250, 1160, 835, 770.

NMR(CDCl$_3$) δ: 0.09(6H,s),0.80(9H,s),1.46(9H,br s),1.80–2.28(2H,m),3.40–3.71(2H,m),4.-36–4.76(2H,m),7.02–7.24(2H,m).

3)

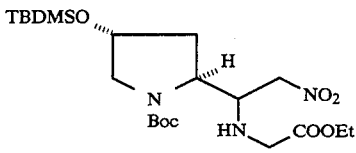

Triethylamine (0.74 ml, 5.58 mmol) was added to a mixture comprising the compound obtained by the above reaction (2.0 g, 5.37 mmol), methylene chloride (40 ml), tetrahydrofuran (10 ml) and glycine ethyl ester hydrochloride (750 mg, 5.37 mmol) at room temperature, and the mixture was stirred for 30 minutes, then poured into a saturated sodium hydrogen carbonate aqueous solution and extracted with methylene chloride. The organic layer was dried over anhydrous magnesium sulfate and concentrated. The residue was subjected to silica gel column chromatography (Wakogel ™ C-300, ethyl acetate-hexane 1:3) to obtain (2S,4R)-N-tert-butoxycarbonyl-4-tert-butyldimethylsiloxy-2-[1-(ethoxycarbonylmethyl)amino-2-nitroethyl]pyrrolidine (2.32 g, yield: 91%).

NMR(CDCl$_3$) δ: 0.08(6H,s),0.88(9H,s),1.28(3H,t,J=6 Hz),1.50(9H,br s),1.98(2H,m),3.24(1H,m),3.50(2H,m),3.80(1H,m),4.08(-1H,m),4.18(1H,m),4.20(2H,q,J=6 Hz),4.40(3H,m).

4)

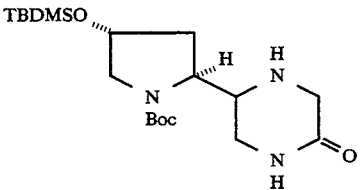

A mixture of the compound obtained by the above reaction (1.26 g, 2.65 mmol), ammonium formate (1.67 g, 26.6 mmol) and methanol (25 ml) was treated with 10% palladium carbon (300 mg) at room temperature for 1 hour, then at 60° C. for 1 hour. The reaction mixture was filtrated to remove palladium carbon and concentrated. The residue was dissolved in methylene chloride and washed with water. The organic layer was dried over anhydrous magnesium sulfate and concentrated to obtain an oily substance containing (2S,4R)-N-tert-butoxycarbonyl-4-tert-butyldimethylsiloxy-2-(5-oxopiperazin-2-yl)pyrrolidine.

NMR(CDCl$_3$) δ: 0.06(6H,s),0.86(9H,s),1.48(9H,br s),1.96(2H,m),3.22(3H,m),3.52(3H,m),4.10(1H,m),4.32(-1H,m),4.38(1H,m).

5)

-continued

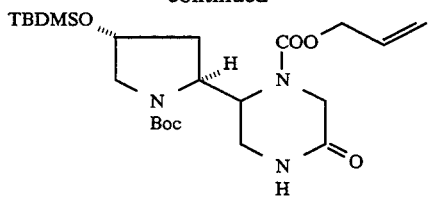

Allyl chlorocarbonate (0.33ml, 3.18 mmol) and triethylamine (0.55 ml, 3.98 mmol) were added to a solution of the compound obtained by the above reaction in methylene chloride (25 ml) under cooling with ice, and the mixture was stirred for 1 hour. The reaction solution was poured into a saturated sodium hydrogen carbonate aqueous solution, then extracted with methylene chloride, dried over anhydrous magnesium sulfate and concentrated. The residue was subjected to silica gel column chromatography (Wakogel ™ C-300, ethyl acetate-hexane 3:1) to obtain (2S,4R)-N-tert-butoxycarbonyl-4-tert-butyldimethylsiloxy-2-(1-allyloxycarbonyl-5-oxopiperazin-2-yl)pyrrolidine-diastereomer A (low polar compound, 710 mg, yield (2 steps): 59%) and diastereomer B (highly polar compound, 290 mg, yield (2 steps): 24%).

Diastereomer A

NMR(CDCl$_3$) δ: 0.06(6H,s),0.86(9H,s),1.46(9H,br s),1.86(2H,m),3.20–3.90(5H,m),4.10(1H,m),4.38(1H,m),-4.48(2H,m),4.64(2H,m),5.30(2H,m),5.90(1H,m).

Diastereomer B

NMR(CDCl$_3$) δ: 0.06(6H,s),0.86(9H,s),1.44(9H,br s),1.82(1H,m),2.00(1H,m),3.10–3.80(4H,m),4.-00–4.50(5H,m),4.60(2H,m),5.30(2H,m),5.90(1H,m).

6)

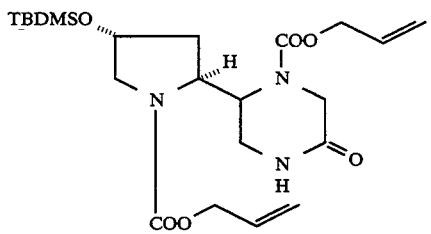

Methylene chloride (4.5 ml) and trifluoroacetic acid (4.5 ml) were added to the compound obtained by the above reaction (diastereomer A, 993 mg, 2.05 mmol) under cooling with ice, and the mixture was returned to room temperature, then stirred for 10 minutes and concentrated under reduced pressure. Then, methylene chloride (18 ml) and triethylamine (1.51 ml, 10.3 mmol) were added thereto, and a solution of allyl chlorocarbonate (0.69 ml, 6.16 mmol) in methylene chloride (2.8 ml) was dropwise added thereto under cooling with ice. The mixture was stirred for 1 hour, then poured into a saturated sodium hydrogen carbonate aqueous solution and extracted with methylene chloride. The organic layer was dried over anhydrous magnesium sulfate and concentrated. The residue was subjected to silica gel column chromatography (Wakogel ™ C-300, ethyl acetate) to obtain (2S,4R)-N-allyloxycarbonyl-4-tert-butyldimethylsiloxy-2-(1-allyloxycarbonyl-5-oxopiperazin-2-yl)pyrrolidine diastereomer A (698 mg, yield: 73%).

The same operation was carried out by using the diastereomer B obtained by the above reaction (726 mg, 1.50 mmol) to obtain (2S,4R)-N-allyloxycarbonyl-4-tert-butyldimethylsiloxy-2-(1-allyloxycarbonyl-5-oxopiperazin-2-yl)pyrrolidine diastereomer B (451 mg, yield: 64%).

Diastereomer A
NMR(CDCl₃) δ:
0.04(6H,s),0.86(9H,s),1.86(2H,m),3.50(4H,m),3.80(1H,m),4.16(1H,m),4.44(3H,m),4.58(2H,m),4.66(2H,m),5.32-(4H,m),5.96(2H,m).

Diastereomer B
NMR(CDCl₃) δ:
0.04(6H,s),0.86(9H,s),1.86(1H,m),2.02(1H,m),3.20-3.80-(4H,m),4.20(3H,m),4.44(2H,m),4.60(4H,m),5.30(4H,m),5.92(2H,m).

7)

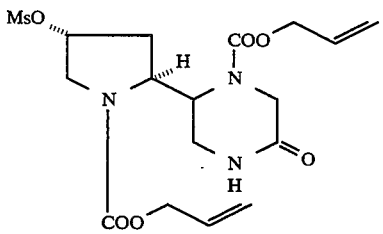

A 1M tetrabutylammonium fluoride solution (2.28 ml, 2.28 mmol) was added to a solution of the compound obtained by the above reaction (diastereomer A, 698 mg, 1.49 mmol) in tetrahydrofuran (7.0 ml) under cooling with ice, and the mixture was stirred at room temperature for 2 hours. The reaction solution was diluted with ethyl acetate, then washed with a saturated sodium hydrogen carbonate aqueous solution, dried over anhydrous magnesium sulfate and concentrated. The residue was dissolved in methylene chloride (14 ml), and triethylamine (0.88 ml, 5.98 mmol) and methanesulfonyl chloride.(0.24 ml, 2.99 mmol) were added thereto under cooling with ice. The mixture was stirred for 40 minutes. The reaction solution was poured into a sodium hydrogen carbonate aqueous solution, then extracted with methylene chloride, dried over anhydrous magnesium sulfate and concentrated. The residue was subjected to silica gel column chromatography (Wakogel ™ C-300, ethyl acetate) to obtain (2S,4R)-N-allyloxycarbonyl-4-methanesulfonyloxy-2-(1-allyloxycarbonyl-5-oxopiperazin-2-yl)pyrrolidine diastereomer A (487 mg, yield: 75%).

The same operation was carried out by using the diastereomer B obtained by the above reaction (451 mg, 0.96 mmol) to obtain (2S,4R)-N-allyloxycarbonyl-4-methanesulfonyloxy-2-(1-allyloxycarbonyl-5-oxopiperazin-2-yl)pyrrolidine diastereomer B (285 mg, yield: 68%).

Diastereomer A
NMR(CDCl₃) δ:
2.24(2H,m),3.08(3H,s),3.56(2H,m),3.58(1H,m),3.72(2H,m),4.18(2H,m),4.50(2H,m),4.64(4H,m),5.36(4H,m),5.86-(2H,m).

Diastereomer B
NMR(CDCl₃) δ:
2.18(1H,m),2,48(1H,m),3.04(3H,s),3.20-3.80(4H,m),3.-90-4.30(4H,m),4.62(5H,m),5.30(4H,m),5.92(2H,m).

8)

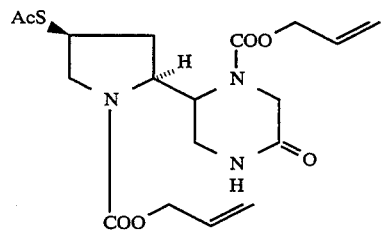

A mixture comprising the compound obtained by the above reaction (diastereomer A, 487 mg, 1.12 mmol), potassium thioacetate (386 mg, 3.38 mmol) and N,N-dimethylformamide (9.7 ml), was stirred at 70° C. for 1.5 hours. The mixture was left to cool, then diluted with ethyl acetate, washed with a saturated sodium chloride aqueous solution, dried over anhydrous magnesium sulfate and concentrated. The residue was subjected to silica gel column chromatography (Wakogel ™ C-300, ethyl acetate) to obtain (2S,4S)-N-allyloxycarbonyl-4-acetylthio-2-(1-allyloxycarbonyl-5-oxopiperazin-2-yl)pyrrolidine diastereomer A (508 mg, yield: 109%).

The operation was conducted in the same manner as above by using the diastereomer B obtained by the above reaction, to obtain (2S,4S)-N-allyloxycarbonyl-4-acetylthio-2-(1-allyloxycarbonyl-5-oxopiperazin-2-yl)pyrrolidine diastereomer B (200 mg, yield: 73 %).

Diastereomer A
NMR(CDCl₃) δ:
1.78(1H,m),2.36(3H,s),2.44(1H,m),3.10(1H,m),3.52(2H,m),3.82(2H,m),4.36(4H,m),4.66(4H,m),5.34(4H,m),5.98-(2H,m).

Diastereomer B
NMR(CDCl₃) δ:
1.80(1H,m),2.64(1H,m),2.38(3H,s),3.30(1H,m),3.68(2H,m),3.96(1H,m),4.10-4.60(5H,m),4.62(4H,m),5.28(4H,m),5.98(2H,m).

REFERENCE EXAMPLE 32

(2S,4S)-4-mercapto-N-(p-nitrobenzyloxycarbonyl)-2-[N-(p-nitrobenzyloxycarbonyl)piperidin-4-yl]pyrrolidine

1)

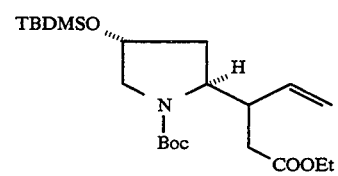

To a mixture of cuprous iodide (50 mg, 0.26 mmol) and a 1M vinylmagnesium bromide tetrahydrofuran solution (15 ml) in tetrahydrofuran (100 ml), a mixture of trimethylsilyl chloride (3.18 ml, 25.0 mmol) and (E)-3-[(2S,4R)-N-tert-butoxycarbonyl-4-tert-butyldimethylsiloxypyrrolidin-2-yl]acrylic acid ethyl ester (2.0 g, 5.0 mmol) in tetrahydrofuran (30 ml) was dropwise added over 30 minutes in a nitrogen stream at −78° C. The reaction mixture was stirred for 2 hours at the same temperature, then quenched with a saturated ammonium chloride aqueous solution (15 ml) and extracted with ethyl acetate (100 ml). The organic layer was washed sequentially with water and a saturated sodium chloride aqueous solution, then dried over anhydrous sodium sulfate and concentrated under reduced pressure. The residue was subjected to silica gel column chromatography (Wakogel ™ C-300, hexane-ethyl acetate 15:1) to obtain 3-[(2S,4R)-N-tert-butoxycarbonyl-4-tert-butyldimethylsiloxypyrrolidin-2-yl]-5-pentenoic acid ethyl ester (1.7 g, yield: 79.4%).

NMR(CDCl₃) δ: 0.05(6H,s),0.86(9H,s),1.24(3H,t,J=8 Hz),1.48(9H,s),1.66–1.97(2H,m),2.12–2.59(2H,m),3.-10–3.30(2H,m),3.33–3.70(1H,m),3.-93–4.24(3H,m),4.30(1H,m),5.08(1H,d,J=10 Hz),5.11(1H,d,J=18 Hz),5.64(1H,m).

2)

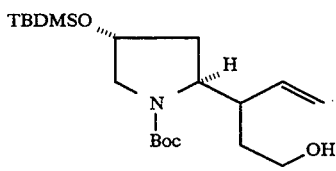

To a solution of lithium aluminum hydride (113 mg, 2.98 mmol) in tetrahydrofuran (30 ml), the compound obtained by the above reaction (1.7 g, 3.98 mmol) in tetrahydrofuran (10 ml) was added in a nitrogen stream at 0° C., and the reaction mixture stirred for 1 hour at the same temperature. The reaction mixture was quenched with a saturated ammonium chloride aqueous solution (5 ml) and extracted with ethyl acetate (100 ml). The organic layer was successively washed with a 1N sodium hydroxide aqueous solution, water and a saturated sodium chloride aqueous solution, dried over sodium sulfate and concentrated under reduced pressure. The residue was subjected to silica gel column chromatography (Wakogel ™ C-300, hexane-ethyl acetate 5:1) to obtain 3-[(2S,4R)-N-tert-butoxycarbonyl-4-tert-butyldimethylsiloxypyrrolidin-2-yl]pent-4-en-1-ol (1.09 g, yield: 59.9%).

NMR(CDCl₃) δ: 0.04(6H,s),0.86(3H,s),1.46(9H,s),1.50–1.95(4H,m),2.73(-1H,m),3.12(1H,dd,J=12,4 Hz),3.32–3.77(3H,m),3.-88–4.20(1H,m),4.32(1H,m),5.12(2H,m),5.64(1H,m).

3)

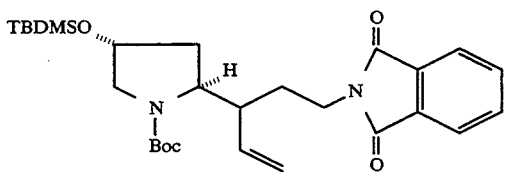

Triphenylphosphine (1.0 g, 3.81 mmol) and phthalimide (0.63 g, 4.28 mmol) were added to a stirred solution of the compound obtained by the above reaction (1.09 g, 2.83 mmol) in tetrahydrofuran (30 ml) under a nitrogen stream, and then diethyl azodicarboxylate (0.58 ml, 3.68 mmol) added thereto under cooling with ice. The reaction mixture was stirred for 2 hours at the same temperature, then extracted with ethyl acetate (70 ml). The organic layer was washed with water and a saturated sodium chloride aqueous solution, then dried over anhydrous sodium sulfate and concentrated under reduced pressure. The residue was subjected to silica gel column chromatography (Wakogel ™ C-300, hexane-ethyl acetate 6:1) to obtain 3-[(2S,4R)-N-tert-butoxycarbonyl-4-tert-butyldimethylsiloxypyrrolidin-2-yl]-5-phthalimido-1-pentene (1.31 g, yield: 90.0%).

NMR(CDCl₃) δ: 0.03(6H,s),0.84(9H,s),1.42(9H,s),1.50–1.93(4H,m),2.73(-1H,m),3.20(1H,dd,J=12,4 Hz),3.28–3.80(3H,m),3.-84–4.17(1H,m),4.28(1H,m),5.-04–5.30(2H,m),5.62(1H,m),7.71(2H,m),7.84(2H,m).

4)

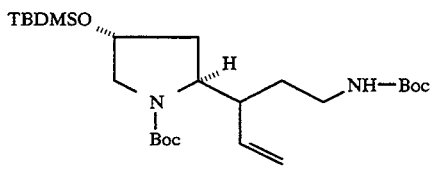

To a solution of the compound obtained by the above reaction (1.31 g, 2.55 mmol) in ethanol (15 ml) was added hydrazine monohydrate (0.37 ml, 7.63 mmol) at room temperature. The reaction mixture was stirred overnight at the same temperature, then concentrated under reduced pressure. The residue was taken up in water and ethyl acetate. The organic layer was successively washed with a 2N ammonium hydroxide aqueous solution, water and a saturated sodium chloride aqueous solution, then dried over anhydrous sodium sulfate and concentrated under reduced pressure. The residue was dissolved in tetrahydrofuran (30 ml) and then di-tert-butyl dicarbonate (640 mg, 2.93 mmol) added thereto at room temperature. After being stirred for 1 hour, the reaction mixture was concentrated under reduced pressure and the residue subjected to silica gel column chromatography (Wakogel ™ C-300, hexane-ethyl acetate 1) to obtain 3-[(2S,4R)-N-tert-butoxycarbonyl-4-tert-butyldimethylsiloxypyrrolidin-2-yl]-5-tert-butoxycarbonylamino-1-pentene (983 mg, yield: 79.3%).

NMR(CDCl₃) δ: 0.04(6H,s),0.86(9H,s),1.42(9H,s),1.46(9H,s),1.82(2H,m-),2.48–2.82(1H,m),3.00(1H,m),3.22(2H,m),3.-37–3.73(1H,m),4.01(1H,m),4.30(1H,m),4.-42–4.75(1H,m),5.02–5.22(2H,m),5.58(1H,m).

5)

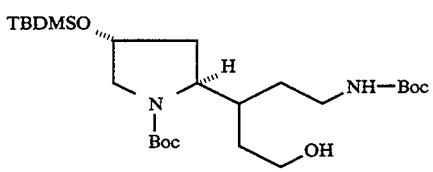

To a solution of 9-borabicyclo[3.3.1]nonane (545 mg, 2.23 mmol) in tetrahydrofurane (10 ml) was added a solution of the compound obtained by the above reaction (980 mg, 2.02 mmol) in tetrahydrofuran (5 ml) in a nitrogen stream at room temperature and the reaction mixture stirred for 2.5 hours at the same temperature. Water (6 ml) and sodium perborate tetrahydrate (1.23 g, 7.99 mmol) were added thereto. The resulting mixture was stirred vigorously overnight at room temperature, and then extracted with ethyl acetate (50 ml). The organic layer was washed with water and a saturated sodium chloride aqueous solution, then dried over anhydrous sodium sulfate, and concentrated under reduced pressure. The residue was subjected to silica gel column chromatography (Wakogel ™ C-300, hexane-ethyl acetate 2:1) to obtain 3-[(2S,4R)-N-tert-butoxycarbonyl-4-tert-butyldimethylsiloxypyrrolidin-2-yl]-5-tert-butoxycarbonylamino-1-propanol (753 mg, yield: 71.5%).

NMR(CDCl₃)  δ: 0.06(6H,s),0.87(9H,s),1.44(9H,s),1.48(9H,s),2.30(1H,m),3.00–3.40(4H,m),3.54(1H,m),3.74(2H,m),4.08(1H,m),4.30(1H,m).

6)

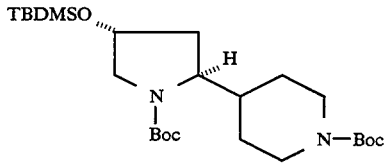

The same procedure as in Reference Example 13-4 was carried out by using the compound obtained by the above reaction (753 mg, 1.50 mmol), potassium tert-butoxide (370 mg, 3.30 mmol) and p-toluenesulfonyl chloride (315 mg, 1.65 mmol) to obtain (2S,4R)-N-tert-butoxycarbonyl-4-tert-butyldimethylsiloxy-2-(N-tert-butoxycarbonylpiperidin-4-yl)pyrrolidine (494 mg, yield: 68.0%).

NMR(CDCl₃)  δ: 0.05(6H,s),0.87(9H,s),1.00–1.28(2H,m),1.45(18H,s),1.78(2H,m),2.64(2H,m),3.22(1H,dd,J=12,4 Hz),3.38–3.66(1H,m),3.96(1H,m),4.14(2H,m),4.29(1H,m).

7)

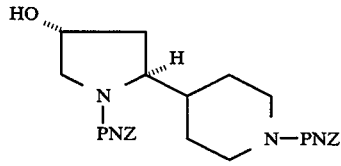

The same procedure as in Reference Example 5-3 was carried out by using the compound obtained by the above reaction (494 mg, 1.02 mmol) and 4,6-dimethyl-2-(p-nitrobenzyloxycarbonylthio)pyrimidine (684 mg, 2.14 mmol) to obtain (2S,4R)-4-hydroxy-N-(p-nitrobenzyloxycarbonyl)-2-[N-(p-nitrobenzyloxycarbonyl)-piperidin-4-yl]pyrrolidine (485 mg, yield: 89.8%).

NMR(CDCl₃)  δ: 1.05–1.34(2H,m),1.42–1.70(2H,m),1.94(2H,m),2.13–2.46(2H,m),2.58–2.94(2H,m),3.38(1H,m),3.76(1H,m),4.03–4.36(3H,m),4.45(1H,m),5.12–5.37(4H,m),7.54(4H,d,J=8 Hz),8.23(2H,d,J=8 Hz),8.24(2H,d,J=8 Hz).

8)

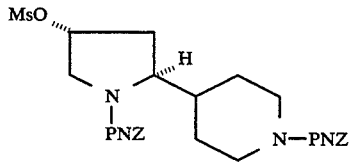

The same procedure as in Reference Example 5-4 was carried out by using the compound obtained by the above reaction (485 mg, 0.92 mmol) and methanesulfonyl chloride (82 μl, 1.06 mmol) to obtain (2S,4R)-4-methanesulfonyloxy-N-(p-nitrobenzyloxycarbonyl)-2-[N-(p-nitrobenzyloxycarbonyl)piperidin-4-yl]pyrrolidine (556 mg, yield: 99.9%).

NMR(CDCl₃)  δ: 1.04–1.32(2H,m),1.44–1.75(2H,m),1.93–2.38(3H,m),2.78(2H,m),3.05(3H,s),3.48(1H,m),4.04–4.35(4H,m),5.12–5.38(5H,m),7.53(2H,d,J=8 Hz),7.55(2H,d,J=8 Hz),8.25(2H,d,J=8 Hz),8.26(2H,d,J=8 Hz).

9)

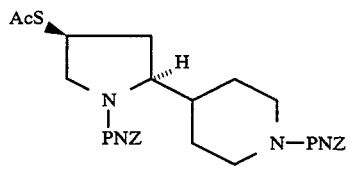

The same procedure as in Reference Example 13-9 was carried out by using the compound obtained by the above reaction (556 mg, 0.92 mmol), potassium thioacetate (210 mg, 1.84 mmol) and sodium iodide (155 mg, 1.03 mmol) to obtain (2S,4S)-4-acetylthio-N-(p-nitrobenzyloxycarbonyl)-2-[N-(p-nitrobenzyloxycarbonyl)piperidin-4-yl]pyrrolidine (476 mg, yield: 88.5%).

NMR(CDCl₃)  δ: 1.07–1.35(2H,m),1.45–1.84(3H,m),2.10–2.46(5H,m),2.76(2H,m),3.00(1H,t,J=10 Hz),3.80(1H,m),3.98(1H,m),4.26(3H,m),5.23(4H,s),7.52(2H,d,J=8 Hz),7.54(2H,d,J=8 Hz),8.23(2H,d,J=8 Hz),8.24(2H,d,J=8 Hz).

10)

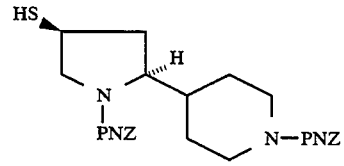

The same procedure as in Reference Example 1-9 was carried out by using the compound obtained by the above reaction to obtain the above identified compound (433 mg, yield: 98%).

REFERENCE EXAMPLE 33

(2S,4S)-2-[2-carbamoyl-N-(p-nitrobenzyloxycarbonyl)-pyrrolidin-4-yl]-4-mercapto-N-(p-nitrobenzyloxycarbonyl)pyrrolidine diastereomer III

1)

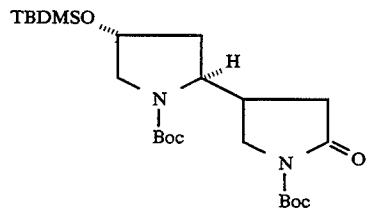

The same procedure as in Reference Example 6-2 was carried out by using (2S,4R)-N-tert-butoxycarbonyl-4-tert-butyldimethylsiloxy-2-(2-pyrrolidon-4-yl)pyrrolidine diastereomer B (10.0 g, 26.0 mmol, compound of Reference Example 12) to obtain (2S,4R)-N-tert-butoxycarbonyl-4-tert-butyldimethylsiloxy-2-(N-tert-butoxycarbonyl-2-pyrrolidon-4-yl)pyrrolidine diastereomer B (12.37 g, yield: 98.1%).

NMR(CDCl₃) δ: 0.06(6H,s),0.86(9H,s),1.46(9H,s),1.52(9H,s),1.66(1H,m)-,1.96(1H,m),2.27(1H,dd,J=18,10 Hz),2.50(1H,dd,J=18,8 Hz),3.24(1H,dd,J=13,4 Hz),3.62(1H,dd,J=13,8 Hz),3.82(1H,dd,J=10,8 Hz),4.09(1H,m),4.32(1H,m).

2)

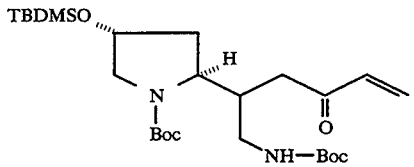

The same procedure as in Reference Example 13-2 was carried out by using the compound obtained by the above reaction (12.3 g, 25.4 mmol) to obtain 5-[(2S,4R)-N-tert-butoxycarbonyl-4-tert-butyldimethylsiloxypyrrolidin-2-yl]-6-tert-butoxycarbonylamino-1-hexen-3-one diastereomer B (10.39 g, yield: 79.8%).

NMR(CDCl₃) δ: 0.04(6H,s),0.85(9H,s),1.42(9H,s),1.47(9H,s),1.68(1H,m)-,1.92(1H,m),2.24-2.57(2H,m),3.16(1H,dd,J=12,4 Hz),3.23-3.68(2H,m),4.03(1H,m),4.33(1H,m),5.82(1H,br d,J=10 Hz),6.20(1H,br d,J=18 Hz),6.38(1H,dd,J=18,10 Hz).

3)

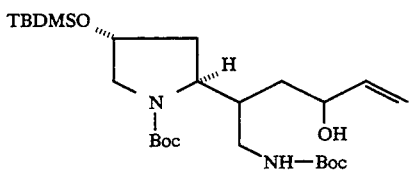

The same procedure as in Reference Example 13-3 was carried out by using the compound obtained by the above reaction (10.3 g, 20.1 mmol) to obtain 5-[(2S,4R)-N-tert-butoxycarbonyl-4-tert-butyldimethylsiloxypyrrolidin-2-yl]-6-tert-butoxycarbonylamino-1-hexen-3-ol (2.84 g, yield: 27.5%).

NMR(CDCl₃) δ: 0.04(6H,s),0.86(9H,s),1.44(9H,s),1.46(9H,s),1.73(1H,m)-,1.95(1H,m),2.95(1H,m),3.18(1H,dd,J=12,4 Hz),3.56(2H,m),3.94(1H,m),4.30(1H,m),5.10(1H,d,J=-10 Hz),5.30(1H,d,J=18 Hz),5.86(1H,m).

4)

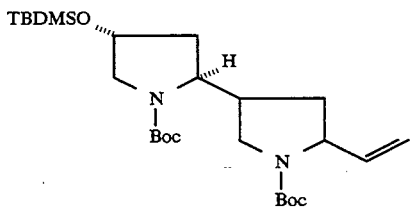

The same procedure as in Reference Example 13-4 was carried out by using the compound obtained by the above reaction (2.84 g, 5.52 mmol) to obtain (2S,4R)-N-tert-butoxycarbonyl-4-tert-butyldimethylsiloxy-2-(N-tert-butoxycarbonyl-2-vinylpyrrolidin-4-yl)pyrrolidine (1.04 g, yield: 37.9%).

NMR(CDCl₃) δ: 0.05(6H,s),0.86(9H,s),1.42(9H,s),1.46(9H,s),1.66-2.34(4-H,m),3.02-3.34(2H,m),3.30-3.84(2H,m),3.-86-4.28(2H,m),4.34(1H,m),5.08(2H,m),5.76(1H,m).

5)

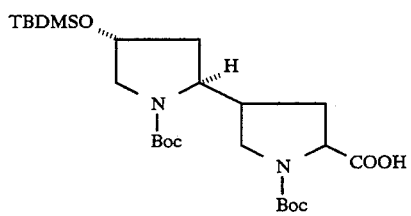

The same procedure as in-Reference Example 13-5 was carried out by using the compound obtained by the above reaction (1.04 g, 2.1 mmol) to obtain (2S,4R)-N-tert-butoxycarbonyl-4-tert-butyldimethylsiloxy-2-(N-tert-butoxycarbonyl-2-carboxypyrrolidin-4-yl)pyrrolidine (500 mg, yield: 46.4%).

NMR(CDCl₃) δ: 0.06(6H,s),0.86(9H,s),1.46(18H,s),1.68-2.50(5H,m),3.26-(2H,m),3.38-3.80(2H,m),3.90-4.40(3H,m).

6)

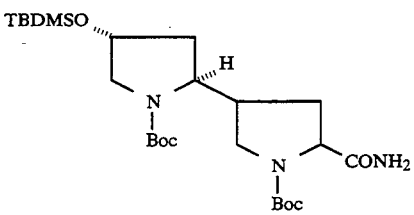

The same procedure as in Reference Example 9-3 was carried out by using the compound obtained by the above reaction (500 mg, 0.97 mmol)-to obtain (2S,4R)-N-tert-butoxycarbonyl-4-tert-butyldimethylsiloxy-2-(N-tert-butoxycarbonyl-2-carbamoylpyrrolidin-4-yl)pyrrolidine (388 mg, yield: 77.7%).

NMR(CDCl₃) δ: 0.02(6H,s),0.84(9H,s),1.42(18H,s),1.64-2.42(5H,m),3.25-(2H,m),3.36-3.80(2H,m),3.88-4.35(3H,m).

7)

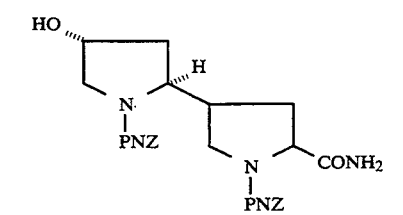

The same procedure as in Reference Example 5-3 was carried out by using the compound obtained by the above reaction (388 mg, 0.76 mmol) to obtain (2S,4R)-2-[2-carbamoyl-N-(p-nitrobenzyloxycarbonyl)pyrrolidin-4-yl]-4-hydroxy-N-(p-nitrobenzyloxycarbonyl)pyrrolidine (360 mg, yield: 85.4%).

NMR(CDCl₃) δ: 1.72–2.50(5H,m),3.-22–3.55(2H,m),3.62–3.92(2H,m),4.-04–4.35(2H,m),4.46(1H,m),5.24(4H,m),7.52(4H,m),8.20-(4H,m).

8)

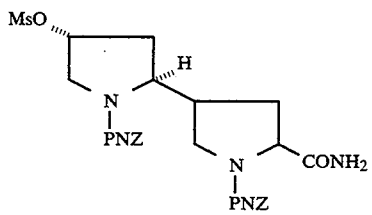

The same procedure as in Reference Example 5-4 was carried out by using the compound obtained by the above reaction (360 mg, 0.65 mmol) to obtain (2S,4R)-2-[2-carbamoyl-N-(p-nitrobenzyloxycarbonyl)pyrrolidin-4-yl]-4-methanesulfonyloxy-N-(p-nitrobenzyloxycarbonyl)pyrrolidine (229 mg, yield: 55.8%).

NMR(CDCl₃) δ: 1.72–2.64(5H,m),3.07(3H,.s),3.-26–3.65(2H,m),3.84(1H,m),4.-08–4.36(3H,m),5.26(5H,m),7.52(4H,m),8.18(4H,m).

9)

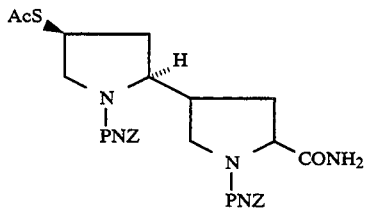

The same procedure as in Reference Example 13-9 was carried out by using the compound obtained by the above reaction (229 mg, 0.36 mmol) to obtain (2S,4S)-4-acetylthio-2-[2-carbamoyl-N-(p-nitrobenzyloxycarbonyl)pyrrolidin-4-yl]-N-(p-nitrobenzyloxycarbonyl)-pyrrolidine (191 mg, yield: 86.5%).

NMR(CDCl₃−CD₃OD) δ: 1.58–1.88(2H,m),2.28(3H,s),2.48(3H,m),3.10(1H,m),3.3-8(1H,m),3.78(2H,m),4.00(1H,m),4.09(2H,m),5.15(4H,br s),7.46(4H,m),8.10(4H,br d,J=8 Hz).

10)

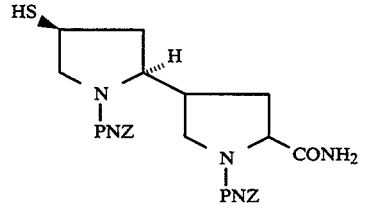

The same procedure as in Reference Example 1-9 was carried out by using the compound obtained by the above reaction (191 mg, 0.31 mmol) to obtain the above identified compound (175 mg, 98.3%).

We claim:

1. A compound of the formula:

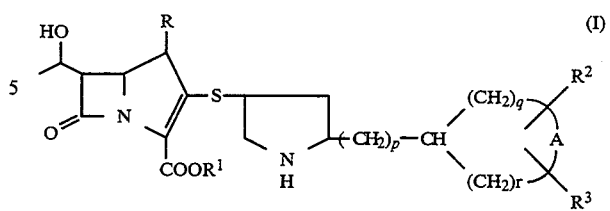

wherein R is a hydrogen atom or a methyl group, $R^1$ is a hydrogen atom or a negative charge each of $R^2$ and $R^3$, which may be the same or different, is a hydrogen atom, a lower alkyl group, a hydroxy lower alkyl group, a formimidoyl group, an acetoimidoyl group, —$COOR^4$, —$CON(R^5)R^6$, —$N(R^5)R^6$, —$CH_2COOR^4$, —$CH_2N(R^5)R^6$ or —$CH_2CON(R^5)R^6$ (wherein $R^4$ is a hydrogen atom or a lower alkyl group, each of $R^5$ and $R^6$, which may be the same or different, is a hydrogen atom or a lower alkyl group, or $R^5$ and $R^6$ form together with the adjacent nitrogen atom a heterocyclic group selected from the group consisting of an aziridinyl group, an azetidinyl group, a pyrrolidinyl group and a piperidyl group), A is =$NR^7$, =$N^+(R^7)R^8$, —$CON(R^7)$—, —$CON(R^7)CO$—, —$CON(R^7)CON(R^8)$—, —$N(R^7)CO(CH_2)_sN(R^8)$—, —$N(R^7)CO(CH_2)_sCON(R^8)$—, —$CON(R^7)N(R^8)$— or —$N(R^7)(CH_2)_sN(R^8)$— (wherein each of $R^7$ and $R^8$, which may be the same or different is a hydrogen atom, a lower alkyl group, a hydroxy lower alkyl group, a formimidoyl group, an acetoimidoyl group, —$COOR^4$, —$CON(R^5)R^6$, —$N(R^5)R^6$, —$CH_2COOR^4$, —$CH_2N(R^5)R^6$ or —$CH_2CON(R^5)R^6$ (wherein $R^4$, $R^5$ and $R^6$ are as defined above), s is an integer of from 1 to 3), p is an integer of from 0 to 3, and each of q and r, which may be the same or different, is an integer of from 0 to 5, provided that q and r are not simultaneously 0 and q+r≦6; or a pharmaceutically acceptable salt or ester thereof;

with the proviso that when A is =$N^+(R^7)R^8$, $R^1$ is a negative charge.

2. The compound according to claim 1, which is represented by the formula:

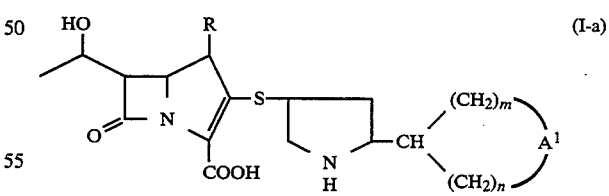

wherein R is a hydrogen atom or a methyl group, $A^1$ is =$NR^9$, —$CON(R^{10})$— or —$CON(R^{10})CO$— (wherein $R^9$ is a hydrogen atom, a lower alkyl group, a formimidoyl group or an acetoimidoyl group, and $R^{10}$ is a hydrogen atom or a lower alkyl group), and each of m and n, which may be the same or different, is an integer of from 0 to 3, provided that m and n are not simultaneously 0.

3. The compound according to claim 1 which is represented by the formula:

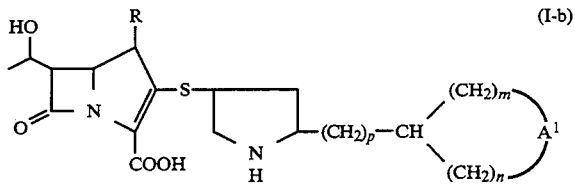

wherein R is a hydrogen atom or a methyl group, A is =NR$^9$, —CON(R$^{10}$)— or —CON(R$^{10}$)CO— (wherein R$^9$ is a hydrogen atom, a lower alkyl group, a formimidoyl group or an acetoimidoyl group, R$^{10}$ is a hydrogen atom or a lower alkyl group), and each of m, n and p, which may be the same or different, is an integer of from 0 to 3, provided that m and n are not simultaneously 0.

4. The compound according to claim 1, which is represented by the formula:

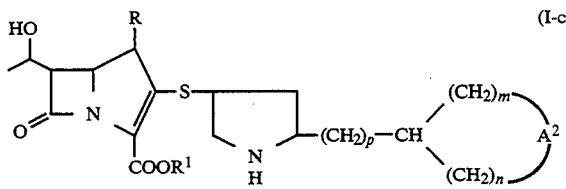

wherein R is a hydrogen atom or a methyl group, R$^1$ is a hydrogen atom or a negative charge, A$^2$ is =NR$^9$, =N$^+$(R$^{11}$)R$^{12}$, —CON(R$^{10}$)— or —CON(R$^{10}$)CO— (wherein R$^9$ is a hydrogen atom, a lower alkyl group, a formimidoyl group or an acetoimidoyl group, R$^{10}$ is a hydrogen atom or a lower alkyl group, and each of R$^{11}$ and R$^{12}$, which may be the same or different, is a lower alkyl group), and each of m, n and p, which may be the same or different, is an integer of from 0 to 3, provided that m, n and p are not simultaneously 0, and with the proviso that when A$^2$ is =N$^+$(R$^{11}$)R$^{12}$, R$^1$ is a negative charge.

5. The compound according to claim 1, wherein A is =NR$^7$, =N$^+$(R$^7$)R$^8$, —CON(R$^7$)—, —CON(R$^7$)CO—, —CON(R$^7$)CON(R$^8$)—, —N(R$^7$)COCH$_2$N(R$^8$)—, —CON(R$^7$)N(R$^8$)— or —N(R$^7$)(CH$_2$)$_2$N(R$^8$)— (wherein each of R$^7$ and R$^8$, which may be the same or different, is a hydrogen atom, a lower alkyl group, a hydroxy lower alkyl group, a formimidoyl group, an acetoimidoyl group, —COOR$^4$, —CON(R$^5$)R$^6$, —N(R$^5$)R$^6$, —CH$_2$COOR$^4$, —CH$_2$N(R$^5$)R$^6$ or —CH$_2$CON(R$^5$)R$^6$ (wherein R$^4$ is a hydrogen atom or a lower alkyl group, each of R$^5$ and R$^6$, which may be the same or different, is a hydrogen atom or a lower alkyl group, or R$^5$ and R$^6$ form together with the adjacent nitrogen atom a heterocyclic group selected from the group consisting of an aziridinyl group, an azetidinyl group, a pyrrolidinyl group and a piperidyl group)).

6. The compound according to claim 1, wherein A is =NR$^7$, =N$^+$(R$^7$)R$^8$, or —CON(R$^7$)— (wherein each of R$^7$ and R$^8$, which may be the same or different, is a hydrogen atom, a lower alkyl group, a hydroxy lower alkyl group, a formimidoyl group, an acetoimidoyl group, —COOR$^4$, —CON(R$^5$)R$^6$, —N(R$^5$)R$^6$, —CH$_2$COOR$^4$, —CH$_2$N(R$^5$)R$^6$ or —CH$_2$CON(R$^5$)R$^6$ (wherein R$^4$ is a hydrogen atom or a lower alkyl group, each of R$^5$ and R$^6$, which may be the same or different, is a hydrogen atom or a lower alkyl group, or R$^5$ and R$^6$ form together with the adjacent nitrogen atom a heterocyclic group selected from the group consisting of an aziridinyl group, an azetidinyl group, a pyrrolidinyl group and a piperidyl group)).

7. The compound according to claim 2 or 3, wherein A$^1$ is =NR$^9$ or —CON(R$^{10}$)—.

8. The compound according to claim 4, wherein A$^2$ is =NR$^9$, =N$^+$(R$^{11}$)R$^{12}$, or —CON(R$^{10}$)—.

9. The compound according to claim 1, wherein each of R$^2$ and R$^3$, which may be the same or different, is a hydrogen atom, a carbamoyl group, a lower alkyl carbamoyl group, a di-lower alkyl carbamoyl group or an amino group.

10. The compound according to claim 1, wherein p is 0.

11. The compound according to claim 1, wherein p is 1 or 2.

12. The compound according to claim 1, wherein the group of the formula:

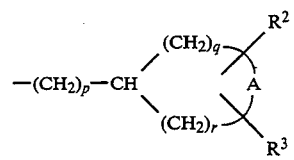

is a substituent selected from the group consisting of an aziridinyl group, an azetidinyl group, a 2-carbamoylazetidinyl group, a 2-oxoazetidinyl group, an N-methyl-2-oxoazetidinyl group, a pyrrolidinyl group, an N-methylpyrrolidinyl group, an N,N-dimethylpyrrolidinio group, a 2-oxopyrrolidinyl group, a 2,5-dioxopyrrolidinyl group, an N-(2-hydroxyethyl)pyrrolidinyl group, a 2,5-dioxo-N-methylpyrrolidinyl group, a 2-carbamoylpyrrolidinyl group, a 2-(N-methylcarbamoyl)pyrrolidinyl group, a 2-(N,N-dimethylcarbamoyl)pyrrolidinyl group, a 3-amino-2-oxopyrrolidinyl group, a pyrazolidinyl group, a 3-oxopyrazolidinyl group, an imidazolidinyl group, a 2,4-dioxoimidazolidinyl group, a piperazinyl group, a 2-oxopiperazinyl group, a piperidyl group, an N-methylpiperidyl group, an N,N-dimethylpiperidinio group, a 2-oxopiperidyl group, a 2,6-dioxopiperidyl group, a 2-carbamoylpiperidyl group, a hexahydroazepinyl group, an N-methylhexahydroazepinyl group, an N,N-dimethylhexahydroazepinio group, a hexahydro-2-oxoazepinyl group, a 2,7-dioxohexahydroazepinyl group, a 2-carbamoylhexahydroazepinyl group, a hexahydro-1H-1,4-diazepinyl group, a hexahydro-2-oxo-1H-1,4-diazepinyl group, an octahydroazocinyl group, an N-methyloctahydroazocinyl group and an N,N-dimethyloctahydroazocinio group and p=0.

13. The compound according to claim 1, wherein the group of the formula:

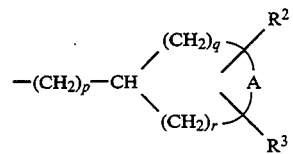

is a substituent selected from the group consisting of a 2-oxoazetidinyl group, a pyrrolidinyl group, an N,N-dimethylpyrrolidinio group, a 2-carbamoylpyrrolidinyl group, a 3-amino-2-oxopyrrolidinyl group, a 2-oxopyrrolidinyl group, a piperidyl group and a 2-oxopiperidyl group and p=0.

14. The compound according to claim 1, wherein the group of the formula:

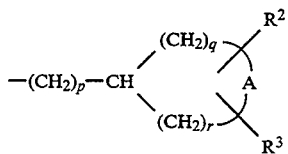

is a substituent selected from the group consisting of an aziridinylmethyl group, an azetidinylmethyl group, a 2-carbamoylazetidinylmethyl group, a 2-oxoazetidinylmethyl group, an N-methyl-2-oxoazetidinylmethyl group, a pyrrolidinylmethyl group, an N-methylpyrrolidinylmethyl group, an N,N-dimethylpyrrolidiniomethyl group, a 2-oxopyrrolidinylmethyl group, a 2,5-dioxopyrrolidinylmethyl group, an N-(2-hydroxyethyl)pyrrolidinylmethyl group, a 2,5-dioxo-N-methylpyrrolidinylmethyl group, a 2-carbamoylpyrrolidinylmethyl group, a 2-(N-methylcarbamoyl)pyrrolidinylmethyl group, a 2-(N,N-dimethylcarbamoyl)pyrrolidinylmethyl group, a 3-amino-2-oxopyrrolidinylmethyl group, a pyrazolidinylmethyl group, a 3-oxopyrazolidinylmethyl group, an imidazolidinylmethyl group, a 2,4-dioxoimidazolidinylmethyl group, a piperazinylmethyl group, a 2-oxopiperazinylmethyl group, a piperidylmethyl group, an N-methylpiperidylmethyl group, an N,N-dimethylpiperidiniomethyl group, a 2-oxopiperidylmethyl group, a 2,6-dioxopiperidylmethyl group, a 2-carbamoylpiperidylmethyl group, a hexahydroazepinylmethyl group, an N-methylhexahydroazepinylmethyl group, an N,N-dimethylhexahydroazepiniomethyl group, a hexahydro-2-oxoazepinylmethyl group, a 2,7-dioxohexahydroazepinylmethyl group, a 2-carbamoylhexahydroazepinylmethyl group, a hexahydro-1H-1,4-diazepinylmethyl group, a hexahydro-2-oxo-1H-1,4-diazepinylmethyl group, an octahydroazocinylmethyl group, an N-methyloctahydroazocinylmethyl group and an N,N-dimethyloctahydroazociniomethyl group and p=1.

15. The compound according to claim 1, wherein the group of the formula:

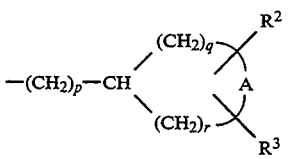

is a substituent selected from the group consisting of a 2-oxoazetidinylmethyl group, a pyrrolidinylmethyl group, an N,N-dimethylpyrrolidiniomethyl group, a 2-carbamoylpyrrolidinylmethyl group, a 3-amino-2-oxopyrrolidinylmethyl group, a 2-oxopyrrolidinylmethyl group, a piperidylmethyl group and a 2-oxopiperidylmethyl group and p=1.

16. The compound according to claim 1, which is:
(5R,6S)-6-[(R)-1-hydroxyethyl]-2-[(2S,4S)-2-(2-pyrrolidon-4-yl)pyrrolidin-4-ylthio]-1-carbapen-2-em-3-carboxylic acid,
(1R,5S,6S)-6-[(R)-1-hydroxyethyl]-1-methyl-2-[(2S,4S)-2-(2-pyrrolidon-4-yl)pyrrolidin-4-ylthio]-1-carbapen-2-em-3-carboxylic acid,
(5R,6S)-6-[(R)-1-hydroxyethyl]-2-[(2R,4S)-2-(2-pyrrolidon-4-yl)pyrrolidin-4-ylthio]-1-carbapen-2-em-3-carboxylic acid,
(1R,5S,6S)-6-[(R)-1-hydroxyethyl]-1-methyl-2-[(2R,4S)-2-(2-pyrrolidon-4-yl)pyrrolidin-4-ylthio]-1-carbapen-2-em-3-carboxylic acid,
(5R,6S)-2-[(2S,4S)-2-(2-azetidinon-4-yl)pyrrolidin-4-ylthio]-6-[(R)-1-hydroxyethyl]-1-carbapen-2-em-3-carboxylic acid,
(1R,5S,6S)-2-[(2S,4S)-2-(2-azetidinon-4-yl)pyrrolidin-4-ylthio]-6-[(R)-1-hydroxyethyl]-1-methyl-1-carbapen-2-em-3-carboxylic acid,
(5R,6S)-6-[(R)-1-hydroxyethyl]-2-[(2R,4S)-2-(2-pyrrolidon-3-ylmethyl)pyrrolidin-4-ylthio]-1-carbapen-2-em-3-carboxylic acid,
(1R,5S,6S)-6-[(R)-1-hydroxyethyl]-1-methyl-2-[(2R,4S)-2-(2-pyrrolidon-3-ylmethyl)pyrrolidin-4-ylthio]-1-carbapen-2-em-3-carboxylic acid,
(5R,6S)-2-[(2R,4S)-2-(2-azetidinon-3-ylmethyl)pyrrolidin-4-ylthio]-6-[(R)-1-hydroxyethyl]-1-carbapen-2-em-3-carboxylic acid,
(1R,5S,6S)-2-[(2R,4S)-2-(2-azetidinon-3-ylmethyl)pyrrolidin-4-ylthio]-6-[(R)-1-hydroxyethyl]-1-methyl-1-carbapen-2-em-3-carboxylic acid,
(5R,6S)-6-[(R)-1-hydroxyethyl]-2-[(2S,4S)-2-(pyrrolidin-3-yl)pyrrolidin-4-ylthio]-1-carbapen-2-em-3-carboxylic acid,
(1R,5S,6S)-6-[(R)-1-hydroxyethyl]-1-methyl-2-[(2S,4S)-2-(pyrrolidin-3-yl)pyrrolidin-4-ylthio]-1-carbapen-2-em-3-carboxylic acid,
(5R,6S)-6-[(R)-1-hydroxyethyl]-2-[(2S,4S)-2-(N-methylpyrrolidin-3-yl)pyrrolidin-4-ylthio]-1-carbapen-2-em-3-carboxylic acid,
(1R,5S,6S)-6-[(R)-1-hydroxyethyl]-1-methyl-2-[(2S,4S)-2-(N-methylpyrrolidin-3-yl)pyrrolidin-4-ylthio]-1-carbapen-2-em-3-carboxylic acid,
(5R,6S)-2-[(2S,4S)-2-(N,N-dimethyl-3-pyrrolidinio)pyrrolidin-4-ylthio]-6-[(R)-1-hydroxyethyl]-1-carbapen-2-em-3-carboxylate,
(1R,5S,6S)-2-[(2S,4S)-2-(N,N-dimethyl-3-pyrrolidinio)pyrrolidin-4-ylthio]-6-[(R)-1-hydroxyethyl]-1-methyl-1-carbapen-2-em-3-carboxylate,
(5R,6S)-6-[(R)-1-hydroxyethyl]-2-[(2S,4S)-2-(N-methyl-2-azetidinon-4-yl)pyrrolidin-4-ylthio]-1-carbapen-2-em-3-carboxylic acid,
(1R,5S,6S)-6-[(R)-1-hydroxyethyl]-1-methyl-2-[(2S,4S)-2-(N-methyl-2-azetidinon-4-yl)pyrrolidin-4-ylthio]-1-carbapen-2-em-3-carboxylic acid,
(5R,6S)-6-[(R)-1-hydroxyethyl]-2-[(2S,4S)-2-(N-methyl-2,5-dioxopyrrolidin-3-yl)pyrrolidin-4-ylthio]-1-carbapen-em-3-carboxylic acid,
(1R,5S,6S)-6-[(R)-1-hydroxyethyl]-1-methyl-2-[(2S,4S)-2-(N-methyl-2,5-dioxopyrrolidin-3-yl)pyrrolidin-4-ylthio]-1-carbapen-2-em-3-carboxylic acid,
(5R,6S)-2-[(2S,4S)-2-(2,5-dioxopyrrolidin-3-yl)pyrrolidin-4-ylthio]-6-[(R)-1-hydroxyethyl]-1-carbapen-2-em-3-carboxylic acid,
(1R,5S,6S)-2-[(2S,4S)-2-(2,5-dioxopyrrolidin-3-yl)pyrrolidin-4-ylthio]-6-[(R)-1-hydroxyethyl]-1-methyl-1-carbapen-2-em-3-carboxylic acid,
(5R,6S)-6-[(R)-1-hydroxyethyl]-2-[(2S,4S)-2-(3-pyrazolidinon-5-yl)pyrrolidin-4-ylthio]-1-carbapen-2-em-3-carboxylic acid,
(1R,5S,6S)-6-[(R)-1-hydroxyethyl]-1-methyl-2-[(2S,4S)-2-(3-pyrazolidinon-5-yl)pyrrolidin-4-ylthio]-1-carbapen-2-em-3-carboxylic acid, (5R,6S)-6-[(R)-1-hydroxyethyl]-2-[(2S,4S)-2-(2-pyr-rolidon-3-yl)pyrrolidin-4-ylthio]-1-carbapen-2-em-3-carboxylic acid, (1R,5S,6S)-6-[(R)-1-hydroxyethyl]-1-methyl-2-[(2S,4S)-2-(2-pyrrolidon-3-yl)pyrrolidin-4-ylthio]-1-carbapen-2-em-3-carboxylic acid, (5R,6S)-2-[(2S,4S)-2-(2-carbamoylpyrrolidin-4-yl)pyrrolidin-4-ylthio]-6-[(R)-1-hydroxyethyl]-1-carbapen-2-em-3-carboxylic acid, (1R,5S,6S)-2-[(2S,4S)-2-(2-carbamoylpyrrolidin-4-yl)pyrrolidin-4-ylthio]-6-[(R)-1-hydroxyethyl]-1-methyl-1-carbapen-2-em-3-carboxylic acid, (5R,6S)-2-[(2S,4S)-2-(3-amino-2-pyrrolidon-4-yl)pyrrolidin-4-ylthio]-6-[(R)-1-hydroxyethyl]-1-carbapen-2-em-3-carboxylic acid, (1R,5S,6S)-2-[(2S,4S)-2-(3-amino-2-pyrrolidon-4-yl)pyrrolidin-4-ylthio]-6-[(R)-1-hydroxyethyl]-1-methyl-1-carbapen-2-em-3-carboxylic acid, (5R,6S)-6-[(R)-1-hydroxyethyl]-2-[(2R,4S)-2-(pyr-rolidin-3-ylmethyl)pyrrolidin-4-ylthio]-1-carbapen-2-em-3-carboxylic acid, (1R,5S,6S)-6-[(R)-1-hydroxyethyl]-1-methyl-2-[(2R,4S)-2-(pyrrolidin-3-ylmethyl)pyrrolidin-4-ylthio]-1-carbapen-2-em-3-carboxylic acid, (5R,6S)-2-[(2R,4S)-2-[(2S)-2-carbamoylpyrrolidin-4-ylmethyl]pyrrolidin-4-ylthio]-6-[(R)-1-hydroxyethyl]-1-carbapen-2-em-3-carboxylic acid, (1R,5S,6S)-2-[(2R,4S)-2-[(2S)-2-carbamoylpyrrolidin-4-ylmethyl]pyrrolidin-4-ylthio]-6-[(R)-1-hydroxyethyl]-1-methyl-1-carbapen-2-em-3-carboxylic acid, (5R,6S)-6-[(R)-1-hydroxyethyl]-2-[(2R,4S)-2-[(2S)-2-(N-methylcarbamoyl)pyrrolidin-4-ylmethyl]pyr-rolidin-4-ylthio]-1-carbapen-2-em-3-carboxylic acid, (1R,5S,6S)-6-[(R)-1-hydroxyethyl]-1-methyl-2-[(2R,4S)-2-[(2S)-2-(N-methylcarbamoyl)pyrrolidin-4-ylmethyl]pyrrolidin-4-ylthio]-1-carbapen-2-em-3-carboxylic acid, (5R,6S)-6-[(R)-1-hydroxyethyl]-2-[(2R,4S)-2-[(2S)-2-(N,N-dimethylcarbamoyl)pyrrolidin-4-ylmethyl]-pyrrolidin-4-ylthio]-1-carbapen-2-em-3-carboxylic acid, (1R,5S,6S)-6-[(R)-1-hydroxyethyl]-1-methyl-2-[(2R,4S)-2-[(2S)-2-(N,N-dimethylcarbamoyl)pyr-rolidin-4-ylmethyl]pyrrolidin-4-ylthio]-1-carbapen-2-em-3-carboxylic acid, (5R,6S)-2-[(2S,4S)-2-(2,4-dioxoimidazolidin-5-yl)pyr-rolidin-4-ylthio]-6-[(R)-1-hydroxyethyl]-1-carbap-en-2-em-3-carboxylic acid, (1R,5S,6S)-2-[(2S,4S)-2-(2,4-dioxoimidazolidin-5-yl)pyrrolidin-4-ylthio]-6-[(R)-1-hydroxyethyl]-1-methyl-1-carbapen-2-em-3-carboxylic acid, (5R,6S)-2-[(2R,4S)-2-(2,4-dioxoimidazolidin-5-ylme-thyl)pyrrolidin-4-ylthio]-6-[(R)-1-hydroxyethyl]-1-carbapen-2-em-3-carboxylic acid, (1R,5S,6S)-2-[(2R,4S)-2-(2,4-dioxoimidazolidin-5-ylmethyl)pyrrolidin-4-ylthio]-6-[(R)-1-hydroxye-thyl]-1-methyl-1-carbapen-2-em-3-carboxylic acid, (5R,6S)-2-[(2R,4S)-2-(2,5-dioxopyrrolidin-3-ylme-thyl)pyrrolidin-4-ylthio]-6-[(R)-1-hydroxyethyl]-1-carbapen-2-em-3-carboxylic acid, (1R,5S,6S)-2-[(2R,4S)-2-(2,5-dioxopyrrolidin-3-ylme-thyl)pyrrolidin-4-ylthio]-6-[(R)-1-hydroxyethyl]-1-methyl-1-carbapen-2-em-3-carboxylic acid, (5R,6S)-2-[(2S,4S)-2-(2-oxopiperazin-5-yl)pyrrolidin-4-ylthio]-6-[(R)-1-hydroxyethyl]-1-carbapen-2-em-3-carboxylic acid, (1R,5S,6S)-2-[(2S,4S)-2-(2-oxopiperazin-5-yl)pyrroli-din-4-ylthio]-6-[(R)-1-hydroxyethyl]-1-methyl-1-carbapen-2-em-3-carboxylic acid, (5R,6S)-6-[(R)-1-hydroxyethyl]-2-[(2S,4S)-2-(piperi-din-4-yl)pyrrolidin-4-ylthio]-1-carbapen-2-em-3-carboxylic acid, or (1R,5S,6S)-6-[(R)-1-hydroxyethyl]-1-methyl-2-[(2S,4S)-2-(piperidin-4-yl)pyrrolidin-4-ylthio]-1-carbapen-2-em-3-carboxylic acid.

17. The compound according to claim 1, which is (1R,5S,6S)-6-[(R)-1-hydroxyethyl]-1-methyl-2-[(2S,4S)-2-(pyrrolidin-3-yl)pyrrolidin-4-ylthio]-1-carbapen-2-em-3-carboxylic acid.

18. The compound according to claim 1, which is (1R,5S,6S)-6-[(R)-1-hydroxyethyl]-1-methyl-2-[(2S,4S)-2-piperidin-4-yl)pyrrolidin-4-ylthio]-1-carbapen-2-em-3-carboxylic acid.

19. An antibacterial agent comprising an antibacterially effective amount of a compound of the formula:

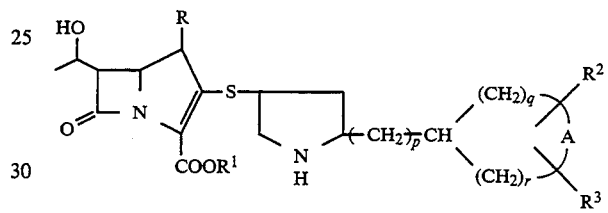

wherein R is a hydrogen atom or a methyl group, $R^1$ is a hydrogen atom or a negative charge, each of $R^2$ and $R^3$, which may be the same or different, is a hydrogen atom, a lower alkyl group, a hydroxy lower alkyl group, a formimidoyl group, an acetoimidoyl group, —COOR$^4$, —CON(R$^5$)R$^6$, —N(R$^5$)R$^6$, —CH$_2$COOR$^4$, —CH$_2$N(R$^5$)R$^6$ or —CH$_2$CON(R$^5$)R$^6$ (wherein R$^4$ is a hydrogen atom or a lower alkyl group, each of R$^5$ and R$^6$, which may be the same or different, is a hydrogen atom or a lower alkyl group, or R$^5$ and R$^6$ form together with the adjacent nitrogen atom a heterocyclic group selected from the group consisting of an aziridinyl group, an azetidinyl group, a pyrrolidyl group and a piperidyl group), A is =N$^7$, =N$^+$(R$^7$)R$^8$, —CON(R$^7$)—, —CON(R$^7$)CO—, —CON(R$^7$)CON(R$^8$)—, —N(R$^7$)CO(CH$_2$)$_s$N(R$^8$)—, —N(R$^7$)CO(CH$_2$)$_s$CON(R$^8$)—, —CON(R$^7$)N(R$^8$)— or —N(R$^7$)(CH$_2$)$_s$N(R$^8$)— (wherein each of R$^7$ and R$^8$, which may be the same or different, is a hydrogen atom, a lower alkyl group, a hydroxy lower alkyl group, a formimidoyl group, an acetoimidoyl group —COOR$^4$, —CON(R$^5$)R$^6$, —N(R$^5$)R$^6$, —CH$_2$COOR$^4$, —CH$_2$N(R$^5$)R$^6$ or —CH$_2$CON(R$^5$)R$^6$ (wherein R$^4$, R$^5$ and R$^6$ are as defined above), s is an integer of from 1 to 3), p is an integer of from 0 to 3, and each of q and r, which may be the same or different, is an integer of from 0 to 5, provided that q and r are not simultaneously 0 and q+r≦6; or a pharmaceutically acceptable salt or ester thereof, and a pharmaceutically acceptable carrier or diluent; with the proviso that when A is =N$^+$(R$^7$)R$^8$, R$^1$ is a negative charge.

* * * * *